US012637411B2

(12) United States Patent
Manfredi et al.

(10) Patent No.: US 12,637,411 B2
(45) Date of Patent: May 26, 2026

(54) STRUCTURALLY MODIFIED OPIOIDS FOR PREVENTION AND TREATMENT OF DISEASES AND CONDITIONS

(71) Applicants: University of Padova, Padua (IT); MGGM LLC, New York, NY (US); Institute for Research in Biomedicine, Bellinzona (CH)

(72) Inventors: Paolo L. Manfredi, Miami Beach, FL (US); Charles E. Inturrisi, New York, NY (US); Andrea Mattarei, Perarolo di Vigonza (IT); Sara De Martin, Vigonza (IT); Jacopo Sgrignani, Almenno San Salvatore (IT); Andrea Cavalli, Zurich (CH)

(73) Assignees: MGGM LLC, Kerhonkson, NY (US); University of Padova, Padua (IT)

( * ) Notice: Subject to any disclaimer, the term of this patent is extended or adjusted under 35 U.S.C. 154(b) by 0 days.

(21) Appl. No.: 17/426,187

(22) PCT Filed: Oct. 10, 2019

(86) PCT No.: PCT/US2019/055590

§ 371 (c)(1),
(2) Date: Jul. 28, 2021

(87) PCT Pub. No.: WO2020/159587

PCT Pub. Date: Aug. 6, 2020

(65) Prior Publication Data

US 2022/0112153 A1 Apr. 14, 2022

Related U.S. Application Data

(60) Provisional application No. 62/798,709, filed on Jan. 30, 2019.

(51) Int. Cl.

| | |
|---|---|
| ***C07C 225/16*** | (2006.01) |
| ***C07C 225/18*** | (2006.01) |
| ***C07C 229/34*** | (2006.01) |
| ***C07C 323/29*** | (2006.01) |
| ***C07D 207/09*** | (2006.01) |
| ***C07D 209/14*** | (2006.01) |
| ***C07D 233/64*** | (2006.01) |
| ***C07D 295/135*** | (2006.01) |
| ***C07D 317/58*** | (2006.01) |
| ***C07D 319/06*** | (2006.01) |
| ***C07D 333/28*** | (2006.01) |

(52) U.S. Cl.

CPC .......... *C07C 225/16* (2013.01); *C07C 225/18* (2013.01); *C07C 229/34* (2013.01); *C07C 323/29* (2013.01); *C07D 207/09* (2013.01); *C07D 209/14* (2013.01); *C07D 233/64* (2013.01); *C07D 295/135* (2013.01); *C07D 317/58* (2013.01); *C07D 319/06* (2013.01); *C07D 333/28* (2013.01); *C07B 2200/05* (2013.01)

(58) Field of Classification Search

CPC .................................................... C07C 225/16
See application file for complete search history.

(56) References Cited

U.S. PATENT DOCUMENTS

| | | | | |
|---|---|---|---|---|
| 4,048,211 | A | 9/1977 | Barnett | |
| 4,596,807 | A | 6/1986 | Crosby | |
| 5,189,054 | A | 2/1993 | Salituro et al. | |
| 5,593,876 | A | 1/1997 | Stamler et al. | |
| 5,883,115 | A | 3/1999 | Santus et al. | |
| 6,008,258 | A | 12/1999 | Inturrisi | |
| 6,143,933 | A * | 11/2000 | Scheinmann ......... | C12P 41/004 564/317 |
| 6,242,456 | B1 | 6/2001 | Shuster et al. | |
| 9,212,128 | B2 | 12/2015 | Ismail et al. | |
| 9,468,611 | B2 | 10/2016 | Manfredi et al. | |
| 9,855,226 | B2 | 1/2018 | Manfredi et al. | |
| 10,040,752 | B2 | 8/2018 | Mkrtchyan et al. | |
| 2006/0167032 | A1 | 7/2006 | Galer et al. | |

(Continued)

FOREIGN PATENT DOCUMENTS

| | | | |
|---|---|---|---|
| WO | 9715294 | A1 | 5/1997 |
| WO | 199745551 | A1 | 12/1997 |

(Continued)

OTHER PUBLICATIONS

Pasternak and Pan "Mu Opioids and Their Receptors: Evolution of a Concept" Pharmacological Reviews 65:1257-1317, Oct. 2013.*
Shim "Consensus 3D Model of μ-Opioid Receptor Ligand Efficacy Based on a Quantitative Conformationally Sampled Pharmacophore." Journal of Physical Chemistry B, 2011, 115(22), 7487-7496.*
Lattanza "Synthesis and Biological Evaluation of 14-Alkoxymorphinans. 22.1 Influence of the 14-Alkoxy Group and the Substitution in Position 5 in 14-Alkoxymorphinan-6-ones on in Vitro and in Vivo Activities" J. Med. Chem. 2005, 48, 3372-3378.*
Dupre "Analgesics. I. Esters and ketones derived from α-amino-ω-cyano-ω,ω-diarylalkanes." Journal of the Chemical Society 1949, 500-10.*

(Continued)

*Primary Examiner* — David K O'Dell
(74) *Attorney, Agent, or Firm* — Wood Herron & Evans LLP

(57) ABSTRACT

Aspects of the present invention are directed to structurally modified opioids (SMOs) that result in improved modulating activity at the NMDAR and improved PK and PD parameters over existing drugs with NMDAR modulating activity. The structural modifications of an opioid or opioid enantiomer that result in the SMOs can be obtained by starting the synthetic process de novo; by modifying the synthetic process for the opioid at any intermediate step during the synthesis of the racemate or of one enantiomer; or by modifying the structure of the opioid or opioid enantiomer after the synthesis. The nitric acid ester substitutions are of particular relevance, especially when associated to deuterated substitutions and/or halogen substitutions.

1 Claim, 13 Drawing Sheets

(56) References Cited

U.S. PATENT DOCUMENTS

| | | | |
|---|---|---|---|
| 2008/0200370 | A1 | 8/2008 | Tseng |
| 2008/0234352 | A1 | 9/2008 | Fischer et al. |
| 2009/0156817 | A1 | 6/2009 | Wang et al. |
| 2009/0185998 | A1 | 7/2009 | Veronese et al. |
| 2010/0261906 | A1 | 10/2010 | Haar, Jr. et al. |
| 2012/0128683 | A1 | 5/2012 | Shantha |
| 2012/0208747 | A1 | 8/2012 | Kim et al. |
| 2014/0037721 | A1 | 2/2014 | Liang et al. |
| 2014/0088155 | A1 | 3/2014 | Manfredi et al. |
| 2014/0350302 | A1 | 11/2014 | Ismail et al. |
| 2015/0152081 | A1 | 6/2015 | Kandula |
| 2015/0374684 | A1 | 12/2015 | Javitt |
| 2016/0235691 | A1 | 8/2016 | Mironer |
| 2017/0029432 | A1 | 2/2017 | Trawick et al. |
| 2017/0057909 | A1 | 3/2017 | Mkrtchyan et al. |
| 2018/0214395 | A1 | 8/2018 | Manfredi et al. |
| 2018/0221396 | A1 | 8/2018 | Chadeayne |
| 2020/0277250 | A1 | 9/2020 | Safaei-Ghomi et al. |

FOREIGN PATENT DOCUMENTS

| | | | |
|---|---|---|---|
| WO | 9831358 | A1 | 7/1998 |
| WO | 9849970 | A1 | 11/1998 |
| WO | 2005072705 | A1 | 8/2005 |
| WO | 2009092324 | A1 | 7/2009 |
| WO | 2012014109 | A1 | 2/2012 |
| WO | 2013077720 | A1 | 5/2013 |
| WO | 2013168000 | A1 | 11/2013 |
| WO | 2014052427 | A1 | 4/2014 |
| WO | 2015192772 | A1 | 12/2015 |
| WO | 2016103274 | A1 | 6/2016 |
| WO | 2016118741 | A1 | 7/2016 |
| WO | 2016191763 | A2 | 12/2016 |
| WO | 2017035224 | A1 | 3/2017 |
| WO | 2017035225 | A1 | 3/2017 |
| WO | 2017035524 | A1 | 3/2017 |
| WO | 2018144551 | A2 | 8/2018 |
| WO | 2018216018 | A1 | 11/2018 |
| WO | 201952545 | A1 | 3/2019 |
| WO | 2020159587 | A1 | 8/2020 |
| WO | 2020181194 | A1 | 9/2020 |

OTHER PUBLICATIONS

Aceto "Dependence studies of new compounds in the rhesus monkey, rat and mouse" NIDA Research Monograph, 76 (Probl. Drug Depend., 1986), 392-447.*

Kepler "Preparation of methadone and some congeners labeled with tritium in the aromatic ring" Journal of Labelled Compounds and Radiopharmaceuticals, 19(2), 271-82 1982.*

Brizer, DA, Hartman N, Sweeney J, Millman RB. Effect of methadone plus neuroleptics on treatment-resistant chronic paranoid schizophrenia. Am J Psychiatry. Sep. 1985; 142(9):1106-7.

Broglio K. Randomization in Clinical Trials: Permuted Blocks and Stratification. JAMA. 2018;319(21):2223-2224.

Brown RT, Nicholas CR, Cozzi NV, Gassman MC, Cooper KM, Muller D, Thomas CD, Hetzel SJ, Henriquez KM, Ribaudo AS, Hutson PR. Pharmacokinetics of Escalating Doses of Oral Psilocybin in Healthy Adults. Clin Pharmacokinet. Dec. 2017;56 (12):1543-1554.

Bruce, RD. The marketing of methadone: how an effective medication became unpopular. Int J Drug Policy. Nov. 2013;24(6):e89-e90.

Brunoni, AR et al., Decreased brain-derived neurotrophic factor plasma levels in psoriasis patients. Braz J Med Biol Res. Aug. 2015; 48(8):711-4.

Cacabelos R, Takeda M, Winblad B. The glutamatergic system and neurodegeneration in dementia: preventive strategies in Alzheimer's disease. Int J Geriatr Psychiatry. Jan. 1999;14(1):3-47.

Cai, X, et al. The association between brain-derived neurotrophic factor gene polymorphism and migraine: a meta-analysis. J Headache Pain. 2017; 18(1): 13.

Callahan RJ, Au JD, Paul M, Liu C, Yost CS. Functional inhibition by methadone of N-methyl-D-aspartate receptors expressed in Xenopus oocytes: stereospecific and subunit effects. Anesth Analg. 2004;98(3).

Canadian Office Action in Canadian Patent Application No. 2,893,238, dated Dec. 5, 2019, 5 pgs.

Canadian Office Action in Canadian Patent Application No. 2,893,238, dated Oct. 11, 2018, 6 pgs.

Canitano et al. ("Glutamatergic agents in Autism spectrum disorders: current trends", Research in Autism Spectrum Disorders, 2014, vol. 8, pp. 255-265), (Year: 2014).

Canitano et al. ("Glutannatergic agents in Autism spectrum disorders: current trends", Research in Autism Spectrum Disorders, 2014, vol. 8, pp. 255-265), (Year: 2014).

Capuron L, et al. Interferon-alpha-induced changes in tryptophan metabolism: relationship to depression and paroxetine treatment, Biol. Psychiatry. 2003, 54:906-914.

Carroll, FI and Carlezon WA. Development of Kappa Opioid Receptor Antagonists. Journal of medicinal chemistry. 2013; 56(6):2178-2195.

Casy, A. F., The steric factor in medicinal chemistry; dissymetric probes of pharmacological receptors (Opioid ligands part 2): pp. 503-548. 1993. Plenum Press.

Celiker, H et al., Neuroprotective Effects of Memantine in the Retina of Glaucomatous Rats: An Electron Microscopic Study. J Ophthalmic Vis Res. Apr.-Jun. 2016; 11(2):174-82.

Chen, Huei-Sheng Vincent et al., The chemical biology of clinically tolerated NMDA receptor antagonists. Journal of Neurochemistry, 2006, 97, 1611-1626.

Cheng, A, Hou Y, Mattson MP. Mitochondria and neuroplasticity. ASN Neuro. Oct. 4, 2010;2(5).

Chinese Office Action in Chinese Patent Application No. 201880020508.4, dated Apr. 6, 2022, 9 pgs.

Chinese Office Action in Chinese Patent Application No. 201880020508.4, dated Nov. 2, 2022 (English translation included), 6 pgs.

Chisu, V et al., Testosterone induces neuroprotection from oxidative stress. Effects on catalase activity and 3-nitro-L-tyrosine incorporation into alpha-tubulin in a mouse neuroblastoma cell line. Arch Ital Biol. May 2006; 144(2):63-73.

Chou R, Cruciani RA, Fiellin DA, Compton P, Farrar JT, Haigney MC, Inturrisi C et al. Methadone safety: a clinical practice guideline from the American Pain Society and College on Problems of Drug Dependence, in collaboration with the Heart Rhythm Society. J Pain. 2014; 15(4):321-337.

Cleveland WS. Robust locally weighted regression and smoothing scatterplots. J Am Stat Assoc. 1979;74(368):829-836.

Codd, E.E. et al., "Serotonin and Norepinephrine Uptake Inhibiting Activity of Centrally Acting Analgesics: Structural Determinants and Role in Antinociception," JPET 1995; 274(3):1263-1270.

Colognesi et al., Depression and Cognitive Impairment—Extrahepatic Manifestations of NAFLD and NASH, Biomedicines 2020, 8, 229.

Compston, A, Coles A (Apr. 2002). "Multiple sclerosis". Lancet. 359 (9313):1221-31.

Corona, G et al., Testosterone supplementation and body composition: results from a meta-analysis of observational studies. J Endocrinol Invest. Sep. 2016; 39(9):967-81.

Coskunoglu, A. et al., Evidence of associations between brain-derived neurotrophic factor (BDNF) serum levels and gene polymorphisms with tinnitus. Noise Health. May-Jun. 2017; 19(88):140-148.

Cowan, A., Geller EB, Adler MW. Differential effects of opioids on flurothyl seizure thresholds in rats. NIDA Res Monogr 1979; 27:198-204.

Coyle, JT. NMDA Receptor and Schizophrenia: A Brief History. Schizophrenia Bulletin vol. 38 No. 5 pp. 920-926, 2012.

Dan, B. Angelman syndrome: Current understanding and research prospects. Epilepsia, 2009; 50:2331-2339.

Davis, A.M. et al., "d-Methadone Blocks Morphine Tolerance and N-Methyl-D-Aspartate-Induced Hyperalgesia," J Pharma and Exper Therap, 1999;289:1048-1053.

Daws at al., Increased global integration in the brain after psilocybin therapy for depression. Nature Medicine, 2022.

(56) References Cited

OTHER PUBLICATIONS

Dayalu, P and Teener JW. Stiff Person Syndrome and Other Anti-GAD-Associated Neurologic Disorders. Semin Neurol. Nov. 2012; 32(5):544-9.
De Carvalho LP, Bochet P, Rossier J. The endogenous agonist quinolinic acid and the non endogenous homoquinolinic acid discriminate between NMDAR2 receptor subunit. Neurochem. Int. 1996; 28:445-452.
De Conno, F, Groff L, Brunelli C, Zecca E, Ventafridda V, Ripamonti Clinical experience with oral methadone administration in the treatment of pain in 196 advanced cancer patients C.J Clin Oncol. Oct. 1996; 14 (10):2836-42.
De Martin S, Vitolo O, Bernstein G, Alimonti A, Traversa S, Inturrisi CE, Manfredi PL, The NMDAR Antagonist Dextromethadone Increases Plasma BDNF Levels in Healthy Volunteers Undergoing a 14-Day In-Patient Phase 1 Study, ACNP 57th Annual Meeting: Poster Session II. Neuropsychopharmacol. 43, 228-382 (2018).
Delyfer, MN et al., Evidence for glutamate-mediated excitotoxic mechanisms during photoreceptor degeneration in the rd1 mouse retina. Mol Vis. Sep. 1, 2005; 11:688-96.
Den Boer, M et al., Hepatic steatosis: a mediator of the metabolic syndrome. Lessons from animal models. Arterioscler Thromb Vasc Biol. Apr. 2004; 24(4):644-9. Epub 2004.
Desseilles et al., Massachusetts General Hospital SAFER Criteria for Clinical Trials and Research. Harvard Review of Psychiatry. Psychopharmacology, Sep.-Oct. 2013; 21(5):1-6.
Dickman KG, Youssef JG, Mathew SM, Said SI. Ionotropic glutamate receptors in lungs and airways: molecular basis for glutamate toxicity. Am J Respir Cell Mol Biol. 2004;30(2):139-144.
Djupesland PG, Mahmoud RA, Messina JC. Accessing the brain: the nose may know the way. J Cereb Blood Flow Metab. 2013;33(5):793-794.
Doble, The pharmacology and mechanism of action of riluzole. Neurology. Dec. 1996; 47(6 Suppl 4):S233-41.
Drago, F et al., Effects of opiates and opioids on intraocular pressure of rabbits and humans. 1985 Clin Exp Pharmacol Physiol. Mar.-Apr. 1985; 12(2):107-13.
Drug Enforcement Administration. Diversion Control Division. Drug & Chemical Evaluation Section. Methadone. Jul. 19, 2019.
Duchen, MR. Mitochondria, calcium-dependent neuronal death and neurodegenerative disease. Pflugers Arch. 2012: 464(1):111-121.
Eap CB, Cuendet C, Baumann P. Binding of d-methadone, I-methadone, and dl-methadone to proteins in plasma of healthy volunteers: role of the variants of alpha1-acid glycoprotein. Clin Pharmacol Ther. Mar. 1990;47(3):338-46.
Egan, MF, et al. The BDNF val66met polymorphism affects activity-dependent secretion of BDNF and human memory and hippocampal function. Cell. 2003; 112:257-269.
Eleti, S. Drugs in Alzheimer's disease Dementia: An overview of current pharmacological management and future directions. Psychiatr Danub. Sep. 2016;28(Suppl-1):136-140.
Kuner T, Schoepfer R. Multiple structural elements determine subunit specificity of Mg2+ block in NMDA receptor channels. J Neurosci. 1996;16(11):3549-3558.
Kussius CL et al., Agonist-specific Gating of NMDA Receptors, Channels (Austin). Author manuscript; available in PMC Aug. 5, 2011.
Kvam TM, Stewart LH, Andreassen OA. Psychedelic drugs in the treatment of anxiety, depression and addiction. Tidsskr Nor Laegeforen. Nov. 12, 2018;138(18).
Lke, NJ et al., Leigh syndrome: neuropathology and pathogenesis. J Neuropathol Exp Neurol. Jun. 2015; 74(6):482-92.
Leach K, Sexton PM and Christopoulos A, Allosteric GPCR modulators: taking advantage of permissive receptor pharmacology, Trends Pharmacol. Sci. 28: 382-389, 2007.
Leung JC, Marphis T, Craver RD, Silverstein DM. Altered NMDA receptor expression in renal toxicity: Protection with a receptor antagonist. Kidney Int. 2004;66(1):167-176.
Levinson, I, Galynker II, Rosenthal RN. Methadone withdrawal psychosis. J Clin Psychiatry. Feb. 1995; 56(2):73-6.
Li N, Lee B, Liu RJ, et al. mTOR-dependent synapse formation underlies the rapid antidepressant effects of NMDA antagonists. Science. 2010;329(5994):959-964.
Li, W. and Pozzo-Miller L. BDNF deregulation in Rett syndrome. Neuropharmacology 2014:76.
Lindelof, K, Bendtsen L. Memantine for prophylaxis of chronic tension-type headache—a double-blind, randomized, crossover clinical trial. Cephalalgia. Mar. 2009, 29(3):314-21.
Liu, Miao et al., Inhibition of NMDAR Reduces Bladder Hypertrophy and Improves Bladder Function in Cyclophosphamide Induced Cystitis J Urol. May 2015; 193(5): 1676-1683.
Liu, S, Cui J, Niu Z, Yi M, Zhang X, Che F, Ma X. Do obsessive-compulsive disorder and Tourette syndrome share a common susceptibility gene? An association study of the BDNF Val66Met polymorphism in the Chinese Han population. World J Biol Psychiatry. 2015; 16(8):602-9.
Liu, Z. et al., Glutamate release predicts ongoing myocardial ischemia of rat hearts. Scand J Clin Lab Invest. Apr. 19, 2010; 70(3):217-24.
Liu. J. et al. Signaling Defects in iPSC-Derived Fragile X Premutation Neurons. Hum Mol Genet 21, 3795-3805 (2012).
Loix S, De Kock M, and Henin P (2011) The anti-inflammatory effects of ketamine: state of the art. Acta Anaesthesiol Belg 62:47-58.
Loureiro CM, Shuhama R, Fachim HA, Menezes PR, Del-Ben CM, Louzada-Junior P. Low plasma concentrations of N-methyl-D-aspartate receptor subunits as a possible biomarker for psychosis. Schizophr Res. 2018;202:55-63.
Lovelace MD, Varney B, Sundaram G, et al. Recent evidence for an expanded role of the kynurenine pathway of tryptophan metabolism in neurological diseases. Neuropharmacology. 2017;112(Pt B):373-388.
Lugo-Huitron R, Ugalde Muniz P, Pineda B, Pedraza-Chaverri J, Rios C, Perez-de la Cruz V. Quinolinic acid: an endogenous neurotoxin with multiple targets. Oxid Med Cell Longev. 2013;2013:104024.
Lutz PE, Kieffer BL. Opioid receptors: distinct roles in mood disorders. Trends Neurosci. 2013;36(3):195-206.
Ly C et al., Psychedelics Promote Structural and Functional Neural Plasticity, Cell Rep. Jun. 12, 2018; 23(11):3170-3182.
López-Valdes, HE, Andrew N. Clarkson, Yan Ao, Andrew C. Charles, S. Thomas Carmichael, Michael V. Sofroniew, and K.C. Brennan. Memantine enhances recovery from stroke. Stroke. Jul. 2014; 45(7):2093-2100.
Ma et al., Excessive activation of NMDA receptors in the pathogenesis of multiple peripheral organs via mitochondrial dysfunction, oxidative stress, and inflammation. SN Comprehensive Clinical Medicine (2020) 2:551-569.
Mackay JP, Nassrallah WB, Raymond LA. Cause or compensation?-Altered neuronal Ca2+ handling in Huntington's disease. CNS Neurosci Ther. 2018;24(4):301-310.
Maderuelo. Cristina, Aranzazu Zarzuelo, Jose M Lanao. Critical factors in the release of drugs from sustained release hydrophilic matrices. J. Control. Release, 154 (1) (2011), pp. 2-19.
Maes M, et al. Depressive and anxiety symptoms in the early puerperium are related to increased degradation of tryptophan into kynurenine, a phenomenon which is related to immune activation. Life Sci. 2002; 71:1837-1848.
Magdalon, J et al. "Dysfunctional mTORC1 Signaling: A Convergent Mechanism between Syndromic and Nonsyndromic Forms of Autism Spectrum Disorder?" Ed. Merlin G. Butler. International Journal of Molecular Sciences 18.3 (2017): 659. PMC. Web. Aug. 21, 2017.
Mahachoklertwattana, P et al., N-methyl-D-aspartate (NMDA) receptors mediate the release of gonadotropin-releasing hormone (GnRH) by NMDA in a hypothalamic GnRH neuronal cell line (GT1-1). Endocrinology. Mar. 1994; 134(3):1023-30.
Mahaling, DU et al., Comparison of lipid profile in different grades of non-alcoholic fatty liver disease diagnosed on ultrasound. Asian Pac J Trop Biomed. Nov. 2013; 3(11):907-912.
Maneckjee R, Minna JD. Characterization of methadone receptor subtypes present in human brain and lung tissues. Life Sci. 1997;61(22).

(56) References Cited

OTHER PUBLICATIONS

Manfredi, PL and Houde RW. Prescribing Methadone, A Unique Analgesic. J Supp Oncology 2003. 1(3):216-219.
Manfredi, PL et al., "Intravenous methadone for cancer pain unrelieved by morphine and hydromorphone: clinical observations," Pain 1997;70:99-101.
Manfredi, PL et al., "Methadone Analgesia in Cancer Pain Patients on Chronic Methadone Maintenance Therapy," J Pain Sympt Manag 2001;21(2):169-174.
Manfredi, PL, Breuer B, Wallenstein S, Stegmann M, Bottomley G and Libow L. Opioid Treatment for Agitation in Patients with Advanced Dementia. Int J Ger Psy 2003; 18:700-705.
Manfredi, PL, Breuer BB, Meier DM and Libow L. Pain Assessment in Elderly Patients with Severe Dementia. J Pain Sympt Manag 2003; 25(1):48-52.
Manfredi, PL, Foley KM, Payne R, Inturrisi CE and Houde R. Parenteral Methadone: an Essential Medication for the Treatment of Pain. J Pain Sympt Manage 2003; 26:687-8.
Manfredi, PL, Gonzales GR and Payne R. Reversible spastic paraparesis induced by high-dose intravenous methadone. J Pain. Feb. 2001; 2(1):77-79.
Manfredi, PL, Shreier G, Ling T. Cancer Pain. In Pappagallo M., ed. The Neurological Basis of Pain. McGraw-Hill. Dec. 2004.
Manfredi, PL. Methadone for cancer pain. [Letter]. Pain 1998; 77:103-104.
Manfredi, PL. Opioids versus antidepressants in postherpetic neuralgia: A randomized placebo-controlled trial. [Letter]. Neurology. Neurology. Mar. 25, 2003; 60(6):1052-3.
Mannaioni G, Lanzi C, Lotti M, et al. Methadone Dose Adjustments, Plasma R-Methadone Levels and Therapeutic Outcome of Heroin Users: A Randomized Clinical Trial. Eur Addict Res. 2018;24(1):9-18.
Marco S, Giralt A, Petrovic MM, et al. Suppressing aberrant GluN3A expression rescues synaptic and behavioral impairments in Huntington's disease models. Nat Med. 2013;19(8):1030-1038.
Marimuthu, P, Varadarajan S, Krishnan M, Shanmugam S, Kunjuraman G, Ravinder JR, Arumugam B, Alex D, Swaminathan P. Evaluating the efficacy of memantine on improving cognitive functions in epileptic patients receiving anti-epileptic drugs: A double-blind placebo-controlled clinical trial (Phase IIIb pilot study). Ann Indian Acad Neurol. Jul.-Sep. 2016; 19(3):344-50.
Marmor, M et al., Coronary artery disease and opioid use. Am J Cardiol. May 15, 2004; 93(10):1295-7.
Martin, HGS and Yu Tian W. Blocking the Deadly Effects of the NMDA Receptor in Stroke. Cell 140, Jan. 22, 2010.
Martins, LB, Duarte H, Ferreira AV, Rocha NP, Teixeira AL, Domingues RB. Migraine is associated with altered levels of neurotrophins. Neurosci Lett. Feb. 5, 2015; 587:6-10.
Marvanova, M. et al. The Neuroprotective Agent Memantine Induces Brain-Derived Neurotrophic Factor and trkB Receptor Expression in Rat Brain. Molecular and Cellular Neuroscience 2001; 18:247-258.
Matsui A, Williams JT. Activation of μ-opioid receptors and block of KIR3 potassium channels and NMDA receptor conductance by I- and d-methadone in rat locus coeruleus. Br J Pharmacol. 2010;161(6):1403-1413.
Mayo Clinic Autism Spectrum Disorder (2018 <https://www.nnayoclinic.org/diseases-conditions/autisnn-spectrum-disorder/> symptoms-causes/syc-20352928?p=1). (Year: 2018).
Mazinani, R, Nejati S, Khodaei M. Effects of memantine added to risperidone on the symptoms of schizophrenia: A randomized double-blind, placebo-controlled clinical trial. Psychiatry Res. Jan. 2017; 247:291-295.
Ahmed, A. et al., Pseudobulbar affect: prevalence and management. Therapeutics and Clinical Risk Management 2013;9:483-489.
Banerjee, A, Larsen RS, Philpot BD, Paulsen O. Roles of Presynaptic NMDA Receptors in Neurotransmission and Plasticity. Trends in Neurosciences, 2015, vol. 39, Issue 1.
Brachman, RA, McGowan JC, Perusini JN, et al. Ketamine as a Prophylactic Against Stress-Induced Depressive-like Behavior. Biol Psychiatry. 2015;79(9):776-786.
Chen, Huei-Sheng Vincent and Lipton, Stuart A., The chemical biology of clinically tolerated NMDA receptor antagonists. Journal of Neurochemistry, 2006, 97, 1611-1626.
Codd, EE, Shank RP, Schupsky JJ, Raffa RB. Serotonin and norepinephrine uptake inhibiting activity of centrally acting analgesics: structural determinants and role in antinociception. J Pharmacol Exp Ther. Sep. 1995;274(3):1263-70.
Du, J. et al., Glutamate in peripheral organs: Biology and pharmacology. European Journal of Pharmacology 784(2016) 42-48.
Frank, RAW et al., Hierarchical organization and genetically separable subfamilies of PSD95 postsynaptic supercomplexes. J Neurochem. Aug. 2017;142(4):504-511.
Hansen, KB, Yi F, Perszyk RE, Furukawa H, Wollmuth LP, Gibb AJ, Traynelis SF. Structure, function, and allosteric modulation of NMDA receptors. J Gen Physiol. Aug. 6, 2018;150(8):1081-1105.
Horrigan, FT, et al., Methadone block of K+ current in squid giant fiber lobe neurons. J Gen Physiol. Feb. 1996;107(2):243-60.
International Search Report and Written Opinion in International Patent Application No. PCT/US2019/055590, dated Mar. 13, 2020, 11 pgs.
Inturrisi, CE. NMDA receptors, nitric oxide and opioid tolerance. Regulatory Peptides, 1994, vol. 54, Issue 1.
Lee, Chia-Hsueh et al., NMDA receptor structures reveal subunit arrangement and pore architecture, Nature. Jul. 10, 2014, 511(7508):191-197.
Lee, Ming-Chak et al., Characterisation of the Expression of NMDA Receptors in Human Astrocytes. PLoS One, Nov. 2010, vol. 5, Issue 11, e14123, 11 pgs.
Limapichat, W. et al., Key Binding Interactions for Memantine in the NMDA Receptor, ACS Chemical Neuroscience, 2013, 4, 255-260.
Lomize, M. et al., OPM database and PPM web server: resources for positioning of proteins in membranes, Nucleic Acids Research, 2012, 40, D370-D376.
Low, Chian-Ming et al., New Insights into the Not-So-New NR3 Subunits of N-Methyl-D-aspartate Receptor: Localization, Structure, and Function. Mol Pharmacol 78:1-11, 2010.
Lowe, Stephen L; Wong, Conrad J; Witcher, Jennifer. Safety, tolerability, and pharmacokinetic evaluation of single? and multiple? ascending doses of a novel kappa opioid receptor antagonist. The Journal of Clinical Pharmacology, Sep. 2014, vol. 54, Issue 9.
Nakamura, T. et al., Protein S-Nitrosylation as a Therapeutic Target for Neurodegenerative Diseases. Trends in Pharmacological Sciences, Jan. 2016, vol. 37, No. 1, pp. 73-84.
Patrizi, A, Picard N, Simon AJ, Gunner G, Centofante E, Andrews NA, Fagiolini M. Chronic Administration of the N-Methyl-D-Aspartate Receptor Antagonist Ketamine Improves Rett Syndrome Phenotype. Biol Psychiatry. May 1, 2016;79(9):755-64.
Pubchem. CID 10072. Mar. 26, 2005, pp. 1-19. Retrieved from the Internet <URL: <https://pubchem.ncbi.nlm.nih.gov/compound/10072>>; p. 2, formula.
Pubchem. CID 426183. Mar. 26, 2005, pp. 1-9. Retrieved from the Internet <URL: https://pubchem.ncbl.nlm.nih.gov/compound/426183>>; p. 2, formula.
Pubchem. CID 44795. Aug. 8, 2005, pp. 1-10. Retrieved from the Internet <URL: <https://pubchem.ncbi.nlm.nih.gov/compound/44795>>; p. 2, formula.
Pubchem. CID 62408. Aug. 8, 2005, pp. 1-10. Retrieved from the Internet <URL: https://pubchem.ncanlm.nlh.gov/compound/62408>; p. 2, formula.
Pubchem. CID 643985. Jun. 1, 2005, pp. 1-22. Retrieved from the Internet <URL: <https://pubchem.ncbi.nim.nih.gov/compound/643985>>; p. 2, formula.
Pubchem. CID 9648. Mar. 26, 2005, pp. 1-21. Retrieved from the Internet <URL: <https://pubchem.ncbi.nlm.nih.gov/compound/9648>>; p. 2, formula.
Wulff, H, Castle NA, Pardo LA. Voltage-gated potassium channels as therapeutic targets. Nat Rev Drug Discov Dec. 2009;8(12):982-1001.

(56) References Cited

OTHER PUBLICATIONS

Zanos, P, Moaddel R, Morris PJ, Riggs LM, Highland JN, Georgiou P, Pereira EFR, Albuquerque EX, Thomas CJ, Zarate CA Jr, Gould TD. Ketamine and Ketamine Metabolite Pharmacology: Insights into Therapeutic Mechanisms. Pharmacol Rev. Jul. 2018;70(3):621-660.

Zhou, SF. Polymorphism of human cytochrome P450 2D6 and its clinical significance: Part II. Clin Pharmacokinet. 48:761-804, 2009.

Sanacora, G. et al., "Subtype-Specific Alterations of y-Aminobutyric Acid and Glutamate in Patients with Major Depression," Arch Gen Psychiatry 2004;61:705-713.

Sanchack, KE, Thomas CA. Autism Spectrum Disorder: Primary Care Principles. Am Fam Physician. Dec. 15, 2016; 94(12):972-979.

Santiago-Palma, J, Khojainova N, Kornick C, Fischberg DJ, Primavera LH, Payne R and Manfredi P. Intravenous methadone in the management of chronic cancer pain: safe and effective starting doses when substituting methadone for fentanyl. Cancer 2001; 92(7):1919-1925.

Sava A, Formaggio E, Carignani C, Andreetta F, Bettini E, Griffante C. NMDA-induced ERK signalling is mediated by NR2B subunit in rat cortical neurons and switches from positive to negative depending on stage of development. Neuropharmacology. 2012;62(2):925-932.

Schmidt, KG, Bergert H, Funk RH. Neurodegenerative diseases of the retina and potential for protection and recovery. Curr Neuropharmacol. Jun. 2008; 6(2):164-78.

Schuster, R. et al., Elevated methylation and decreased serum concentrations of BDNF in patients in levomethadone compared to diamorphine maintenance treatment. Eur Arch Psychiatry Clin Neurosci 2017; 267:33-40.

Schwarcz R, Bruno JP, Muchowski PJ, Wu HQ. Kynurenines in the mammalian brain: when physiology meets pathology. Nat Rev Neurosci. 2012;13(7):465-477.

Schwarcz R, Stone TW. The kynurenine pathway and the brain: challenges, controversies and promises. Neuropharmacology. 2017;112(Pt B):237-247.

Scirica, BM et al., Effect of ranolazine, an antianginal agent with novel electrophysiological properties, on the incidence of arrhythmias in patients with non-ST-segment elevation acute coronary syndrome: results from the Metabolic Efficiency with Ranolazine for Less Ischemia in Non-ST-Elevation Acute Coronary Syndrome-Thrombolysis in Myocardial Infarction 36 (MERLIN-TIMI 36) randomized controlled trial. Circulation. 2007; 116:1647-1652.

Scott CC, Robbins EB, Chen KK: Pharmacologic comparison of the optical isomers of methadone. J Pharm Exp Ther. 1948; 93:282-286.

Seltzman, H. H. et al., "The Preparation of Tritium Labeled Methadone and Its Metabolites," Journal of Labeled Compounds and Radiopharmaceuticals (1981) 18(9):1365-1377.

Shafti, SS et al., Amelioration of deficit syndrome of schizophrenia by norepinephrine reuptake inhibitor. Ther Adv Psychopharmacol 2015, vol. 5(5):263-270.

Shaiova, L, Berger, A., Blinderman, C.D., Bruera, E., Davis, M. P., Derby, S., Inturrisi, C., Kalman, J., Mehta, D., Pappagallo, M., Perlov, E.: Consensus guideline on parenteral methadone use in pain and palliative care. Palliat. Support Care, 6:165-176, 2008.

Sheets L. Excessive activation of ionotropic glutamate receptors induces apoptotic hair-cell death independent of afferent and efferent innervation. Sci Rep. 2017;7:41102. Published Jan. 23, 2017.

Shimoyama, N. et al., "d-Methadone Is Antinociceptive in the Rat Formalin Test," J Pharma and Exper Therap 1997;283:648-652.

Silver, N. et al., "A 10-year, longitudinal assessment of dopamine agonists and methadone in the treatment of restless legs syndrome," Sleep Medicine, Elsevier, Amsterdam, NI (November 5. 2010) 12(5):440-444.

Skolnick, P. et al., "Adaptation of N-Methyl-D-Aspartate (NMDA) Receptors following Antidepressant Treatment: Implications for the Pharmacotherapy of Depression," Pharmacopsychiatry 1996;29(1):23-26.

Skowronska K, Obara-Michlewska M, Zielinska M, Albrecht J. NMDA Receptors in Astrocytes: In Search for Roles in Neurotransmission and Astrocytic Homeostasis. Int J Mol Sci. 2019;20(2):309.

Slominski, AT. On the Role of the Endogenous Opioid System in Regulating Epidermal Homeostasis. Journal of Investigative Dermatology. 2015; 135:333-334.

Smith, DE et al., Rapamycin and Interleukin-1b Impair Brain-derived Neurotrophic Factor-dependent Neuron Survival by Modulating Autophagy. Jul. 25, 2014 The Journal of Biological Chemistry 289, 20615-20629.

Snyder, F.R., "Methadone and Acetylmethadol: Systematic Versus Differential Effects on Affective States," Pharmacology Biochemistry and Behavior 1986;25(1):310 (Abstract).

Soyka M, Zingg C. Feasability and safety of transfer from racemic methadone to (R)-methadone in primary care: clinical results from an open study. World J Biol Psychiatry. 2009;10(3):217-24.

Soyka, M, Limmer C, Lehnert R, Koller G, Martin G, Küfner H, Kagerer S, Haberthur A. A comparison of cognitive function in patients under maintenance treatment with heroin, methadone, or buprenorphine and healthy controls: an open pilot study. Am J Drug Alcohol Abuse. Nov. 2011; 37(6):497-508.

Sprenger, T, Seifert CL, Miederer M, Valet M, Tölle TR. Successful prophylactic treatment of chronic cluster headache with low-dose levomethadone. J Neurol. Nov. 2008; 255(11):1832-3.

Stanley, BG et al., Lateral hypothalamic NMDA receptors and glutamate as physiological mediators of eating and weight control. Am J Physiol. Feb. 1996; 270(2 Pt 2): R443-9.

Stanne, TM, Åberg ND, Nilsson S, Jood K, Blomstrand C, Andreasson U, Blennow K, Zetterberg H, Isgaard J, Svensson J, Jern C.Low Circulating Acute Brain-Derived Neurotrophic Factor Levels Are Associated With Poor Long-Term Functional Outcome After Ischemic Stroke. Stroke. Jul. 2016; 47(7):1943-5.

Stern P, Behe P, Schoepfer R, Colquhoun D. Single-channel conductances of NMDA receptors expressed from cloned CDNAs: comparison with native receptors. Proc Biol Sci. 1992;250(1329):271-277.

Steuer H, Jaworski A, Elger B, et al. Functional characterization and comparison of the outer blood-retina barrier and the blood-brain barrier. Invest Ophthalmol Vis Sci. 2005;46(3):1047-1053.

Stillman, MJ. Testosterone replacement therapy for treatment refractory cluster headache. Headache. Jun. 2006; 46(6):925-33.

Stringer M, Makina MK, Milesa J, Morleya LS, d-Morphine, but not I-morphine, has low micromolar affinity for the non-competitive N-methyl-D-aspartate site in rat forebrain: Possible clinical implications for the management of neuropathic pain, Neuroscience Letters 295 (2000) 21-24.

Strupp, M, Kremmyda O, Brandt T. Pharmacotherapy of vestibular disorders and nystagmus. Semin Neurol. Jul. 2013; 33(3):286-96.

Studerus E, Kometer M, Hasler F, Vollenweider FX. Acute, subacute and long-term subjective effects of psilocybin in healthy humans: a pooled analysis of experimental studies. J Psychopharmacol. Nov. 2011;25(11):1434-52.

Sullivan, DA et al., Androgen deficiency, Meibomian gland dysfunction, and evaporative dry eye. Ann N Y Acad Sci. Jun. 2002; 966:211-22.

Sun, HM et al. Methadone maintenance treatment program reduces criminal activity and improves social well-being of drug users in China: a systematic review and meta-analysis. BMJ Open. Jan. 8, 2015;5(1).

Sun, X et al., Increasing glutamate promotes ischemia-reperfusion-induced ventricular arrhythmias in rats in vivo. Pharmacology. 2014; 93(1-2):4-9.

Sutter, M, Walter M, Dürsteler KM, Strasser J, Vogel M. Psychosis after Switch in Opioid Maintenance Agonist and Risperidone-Induced Pisa Syndrome: Two Critical Incidents in the Treatment of a Patient with Dual Diagnosis. J Dual Diagn. Dec. 9, 2016:0.

Swanger SA and Traynelis SF. Synaptic Receptor Diversity Revealed Across Space and Time. Trends in Neurosciences, Aug. 2018, vol. 41, No. 8:763-765.

Taiwanese Office Action in Taiwanese Patent Application No. 107108987, dated Feb. 11, 2022, 8 pgs. (English translation included).

(56) References Cited

OTHER PUBLICATIONS

Takagi Y, Aruga E.New Opioid Options in Japan—Methadone, Tapentadol and Hydromorphone]. Gan To Kagaku Ryoho. Feb. 2018;45(2):205-211.

Takei, N et al., Brain-Derived Neurotrophic Factor Induces Mammalian Target of Rapamycin-Dependent Local Activation of Translation Machinery and Protein Synthesis in Neuronal Dendrites. The Journal of Neuroscience, Nov. 3, 2004 24(44):9760-9769.

Talka, R. et al. Methadone is a Non-Competitive Antagonist at the alpha462 and alpha3* Nicotinic Acetylcholine Receptors and an Agonist at the alpha7 Nicotinic Acetylcholine Receptor, Basic & Clinical Pharmacology & Toxicology, 2015, 116, 321-328.

Tapia-Arancibia, L, Aliaga E, Silhol M, Arancibia S. New insights into brain BDNF function in normal aging and Alzheimer disease. Brain Research Reviews 2008. 59(1):201-20.

Tauboll, E et al., Interactions between hormones and epilepsy. Seizure. May 2015; 28:3-11.

Teng H, Cai W, Zhou L, Zhang J, Liu Q, Wang Y, et al. (2010) Evolutionary Mode and Functional Divergence of Vertebrate NMDA Receptor Subunit 2 Genes. PLoS One 5(10).

Tennant, F. S. Jr., "(−)-a-Acetylmethadol for Treatment of Chronic Pain Patients who Abuse Opioids," Drug and Alcohol Dependence 1983;12:243-247.

Terenius, L., "A Rapid Assay of Affinity for the Narcotic Receptor in Rat Brain: Application to Methadone Analogues," Acta pharmacol. et toxicol. (1974) 34:88-91.

Tonacci, A, Borghini A, Mercuri A, Pioggia G, Andreassi MG. Brain-derived neurotrophic factor (Val66Met) polymorphism and olfactory ability in young adults. J Biomed Sci. Aug. 7, 2013; 20:57. doi: 10.1186/1423-0127-20-57.

Tornoe CW, Garnett CE, Wang Y, Florian J, Li M, Gobburu JV. Creation of a knowledge management system for QT analyses. J Clin Pharmacol. 2011;51(7):1035-1042.

Toskulkao T, Pornchai R, Akkarapatumwong V, Vatanatunyakum S, Govitrapong P. Alteration of lymphocyte opioid receptors in methadone maintenance subjects. Neurochem Int. 2010;56(2):285-290.

Traynor, K. FDA approves edaravone for amyotrophic lateral sclerosis. Am J Health Syst Pharm. Jun. 15, 2017; 74(12):868.

International Search Report and Written Opinion in International Patent Application No. PCT/US2022/035255, dated Sep. 26, 2022, 10 pgs.

International Search Report in International Patent Application No. PCT/US2018/016159, mailed Jul. 20, 2018, 12 pgs.

Inturrisi, C.E. et al., Pharmacokinetics and pharmacodynamics of methadone in patients with chronic pain. Clin. Pharm. Therap. 41:392-401, 1987.

Inturrisi, C.E., "Opioid Analgesic Therapy in Cancer Pain," Advances in Pain Research and Therapy (Foley, K.M. et al., Eds.) 1990;16:133-154.

Inturrisi, C.E., "Pharmacology of methadone and its isomers," Minerva Anestesiologica 2005;71:435-437.

Inturrisi, C.E., Portenoy, R.K., Max, M.B., Colburn, W.A. and Foley, K.M. Pharmacokinetic pharmacodynamic relationships of methadone infusions in patients with cancer pain. Clin. Pharmacol. Ther. 47:565 577, 1990.

Inturrisi, C.E., Verebely K. The levels of methadone in the plasma in methadone maintenance. Clin Pharmacol Ther. 1972;13(5):633-637.

Isbell H, Eisenman AJ: The addiction liability of some drugs of the methadone series. J Pharmacol Exp Ther. 1948;93:305-313.

Iseri, PK et al., The effect of memantine in harmaline-induced tremor and neurodegeneration. Neuropharmacology. Sep. 2011; 61(4):715-23.

Ishibashi, H et al. Tool-use learning induces BDNF expression in a selective portion of monkey anterior parietal cortex. Brain Res Mol Brain Res. 2002; 102:110-112.

Ishikawa, I, Shinno H, Ando N, Mori T, Nakamura Y. The effect of memantine on sleep architecture and psychiatric symptoms in patients with Alzheimer's disease. Acta Neuropsychiatr. Jun. 2016; 28(3):157-64.

Isidori, AM, Balercia G, Calogero AE, Corona G, Ferlin A, Francavilla S, Santi D, Maggi M.Outcomes of androgen replacement therapy in adult male hypogonadism: recommendations from the Italian society of endocrinology. J Endocrinol Invest. Jan. 2015; 38(1):103-12.

Ito, Y, Shimazawa M, Inokuchi Y, Fukumitsu H, Furukawa S, Araie M, Hara H. Degenerative alterations in the visual pathway after NMDA-induced retinal damage in mice. Brain Res. May 30, 2008; 1212:89-101.

Iwaszkiewicz, KS et al., Targeting peripheral opioid receptors to promote analgesic and anti-inflammatory actions. Front Pharmacol 2013; 4:132-137.

Japanese Office Action in Japanese Patent Application No. 2019-562230, dated Jan. 31, 2022, 5 pgs. (English language translation only).

Johnson MW, Griffiths RR, Hendricks PS, Henningfield JE. The abuse potential of medical psilocybin according to the 8 factors of the Controlled Substances Act. Neuropharmacology. Nov. 2018;142:143-166.

Jolliet-Riant P, Boukef MF, Duché JC, Simon N, Tillement JP. The genetic variant A of human alpha 1-acid glycoprotein limits the blood to brain transfer of drugs it binds. Life Sci. 1998;62(14):PL219-PL226.

Judd, LL, Janowsky DS, Segal DS, Parker DC, Huey LY. Behavioral effects of methadone in schizophrenic patients. Am J Psychiatry. Feb. 1981; 138(2):243-5.

Kalemenev, SV, Zubareva OE, Sizov VV, Lavrent'eva VV, Lukomskaya NY, Kim KK, Zaitsev AV, Magazanik LG. Memantine attenuates cognitive impairments after status epilepticus induced in a lithium-pilocarpine model. Dokl Biol Sci. Sep. 2016; 470(1):224-227.

Kalev-Zylinska ML, Green TN, Morel-Kopp MC, et al. N-methyl-D-aspartate receptors amplify activation and aggregation of human platelets. Thromb Res. 2014;133(5):837-847.

Kandel, ER (Editor), James H. Schwartz (Editor), Thomas M. Jessell (Editor), Steven A. Siegelbaum (Editor), A. J. Hudspeth (Editor). Principles of Neural Science, Fifth Edition, 2013.

Kang J, Jiang L, Goldman SA, Nedergaard M. Astrocyte-mediated potentiation of inhibitory synaptic transmission. Nat Neurosci. 1998;1(8):683-692.

Kargbo, Psilocybin Therapeutic Research: The Present and Future Paradigm, ACS Medicinal Chemistry Letters, Mar. 2, 2020, vol. 11, pp. 399-402.

Karlsen et al., The EASL-Lancet Liver Commission: protecting the next generation of Europeans against liver disease complications and premature mortality. Lancet 2022; 399: 61-116.

Karolewicz B, Stockmeier CA, Ordway GA. Elevated levels of the NR2C subunit of the NMDA receptor in the locus coeruleus in depression. Neuropsychopharmacology. 2005;30(8):1557-1567.

Katchman, AN et al., Influence of opioid agonists on cardiac human ether-a-go-go-related gene K(+) currents. J Pharmacol Exp Ther. Nov. 2002; 303(2):688-94.

Kempton MJ, Salvador Z, Munafò MR, Geddes JR, Simmons A, Frangou S, Williams SC (2011), "Structural neuroimaging studies in major depressive disorder. Meta-analysis and comparison with bipolar disorder", Archives of General Psychiatry, 68(7):675-690.

Kenakin T, Strachan RT. PAM-Antagonists: A Better Way to Block Pathological Receptor Signaling? Trends Pharmacol Sci. 2018;39(8):748-765.

Kenakin TP, Biased signalling and allosteric machines: new vistas and challenges for drug discovery, Br. J. Pharmacol. 165: 1659-1669, 2012.

Kenakin TP, Overview of receptor interaction of agonists and antagonists, Curr. Protoc. Pharmacol. Chapter 4: Unit 4.1, 2008.

Kernan WN, Viscoli CM, Makuch RW, Brass LM, Horwitz RI. Stratified randomization for clinical trials. J Clin Epidemiol. 1999;52(1):19-26.

Khazaie, H, Najafi F, Ghadami MR, Azami A, Nasouri M, Tahmasian M, Khaledi-Paveh B. Addict Health. Sleep Disorders in Methadone Maintenance Treatment Volunteers and Opium-dependent Patients. Apr. 2016; 8(2):84-89.

Khogali, SE et al., Is glutamine beneficial in ischemic heart disease? Nutrition. Feb. 2002; 18(2):123-6.

(56) References Cited

OTHER PUBLICATIONS

Kiang, C-H. et al., "Determination of Acetylmethadol and Metabolites by Use of High-Performance Liquid Chromatography," Journal of Chromatography (1981) 222:81-93.
Kim, HK, Isaacs-Trepanier C, Elmi N, Rapoport SI, Andreazza AC. Mitochondrial dysfunction and lipid peroxidation in rat frontal cortex by chronic NMDA administration can be partially prevented by lithium treatment. J Psychiatr Res. May 2016; 76:59-65.
Kishi T, Matsunaga S, Iwata N. A Meta-Analysis of Memantine for Depression. J Alzheimers Dis. 2017;57(1):113-121. doi:10.3233/JAD-161251.
Kishi T, Matsunaga S, Oya K, Nomura I, Ikuta T, Iwata N. Memantine for Alzheimer's Disease: An Updated Systematic Review and Meta-analysis. J Alzheimers Dis. 2017;60(2):401-425. doi: 10.3233/JAD-170424. PMID: 28922160.
Koch A, Bonus M, Gohlke H, Klöcker N. Isoform-specific Inhibition of N-methyl-D-aspartate Receptors by Bile Salts. Sci Rep. Jul. 1, 20191;9(1):10068.
Konitsiotis, S, Tsironis C, Kiortsis DN, Evangelou A. Effects of N-methyl-D-aspartate receptor antagonism on neuroleptic-induced orofacial dyskinesias. Psychopharmacology (Berl) 2006; 185(3):369-77.
Korde, AS, Maragos WF. Direct exposure to N-methyl-D-aspartate alters mitochondrial function. Neurosci Lett. Jun. 3, 2016; 623:47-51.
Korgaonkar MS, Goldstein-Piekarski AN, Fornito A, Williams LM. Intrinsic connectomes are a predictive biomarker of remission in major depressive disorder, Mol Psychiatry, Nov. 6, 2019.
Kornick, CA et al., QTc interval prolongation associated with intravenous methadone. Pain. Oct. 2003; 105(3):499-506.
Kotermanski SE, Johnson JW. Mg2+ imparts NMDA receptor subtype selectivity to the Alzheimer's drug memantine. J Neurosci. 2009;29(9):2774-2779.
Kovac, JR et al., Testosterone supplementation therapy in the treatment of patients with metabolic syndrome. Postgrad Med. Nov. 2014; 126(7):149-56.
Kraus, C., Kadriu, B., Lanzenberger, R. et al. Prognosis and improved outcomes in major depression: a review. Transl Psychiatry 9, 127 (2019).
Kristensen K, Christensen CB, Christrup LL. The mu1, mu2, delta, kappa opioid receptor binding profiles of methadone stereoisomers and morphine. Life Sci. 1995;56(2):p. L45-p. L50.
Kritis, AA, Stamoula EG, Paniskaki KA, Vavilis TD. Researching glutamate-induced cytotoxicity in different cell lines: a comparative/collective analysis/study. Front Cell Neurosci. Mar. 17, 2015; 9:91.
Krystal, J.H. et al., "NMDA Agonists and Antagonists as Probes of Glutamatergic Dysfunction and Pharmacotherapies in Neuropsychiatric Disorders," Harv Rev Psych 1999;7(3):125-143.
Ksiazek-Winiarek, DJ, Szpakowski P, Glabinski A. Neural Plasticity in Multiple Sclerosis: The Functional and Molecular Background. Neural Plast. 2015; 2015:307175.
Kubryak OV, Umriukhin AE, Emeljanova IN, et al. Increased β-endorphin level in blood plasma as an indicator of positive response to depression treatment. Bull Exp Biol Med. 2012;153(5):758-760.
Grilo LS, Carrupt PA, Abriel H. Stereoselective Inhibition of the hERG1 Potassium Channel. Front Pharmacol. Nov. 22, 2010;1:137.
Gross, ER et al., Acute methadone treatment reduces myocardial infarct size via the delta-opioid receptor in rats during reperfusion. Anesth Analg. Nov. 2009; 109(5):1395-402.
Gruber, S. A. et al., "Methadone maintenance Improves Cognitive Performance After Two Months of Treatment," Experimental and Clinical Psychopharmacology (May 2006) 14(2):157-164.
Gudin, JA, Laitman A, Nalamachu S. Opioid Related Endocrinopathy. Pain Med. Oct. 2015; 16 Suppl 1:S9-15.
Guillemin GJ, Quinolinic acid: neurotoxicity, Febs J. 2012;279(8):1355.
Gutwinski S, Schoofs N, Stuke H, Riemer TG, Wiers CE, Bermpohl F. Opioid tolerance in methadone maintenance treatment: comparison of methadone and levomethadone in long-term treatment. Harm Reduct J. Feb. 16, 2016;13:7.
Gören, MZ et al., F. Cardiovascular responses to NMDA injected into nuclei of hypothalamus or amygdala in conscious rats. Pharmacology. Nov. 2000; 61(4):257-62.
Hackos DH, Hanson JE, Diverse models of NMDA receptor positive allosteric modulation: Mechanisms and consequences, Neuropharmacology, 2017, 112 (Pt A), 34-45.
Haddadi, NS et al., Peripheral NMDA Receptor/NO System Blockage Inhibits Itch Responses Induced by Chloroquine in Mice. Acta Derm Venereol. May 8, 2017; 97(5):571-577.
Halberstadt AL, Geyer MA. Multiple receptors contribute to the behavioral effects of indoleamine hallucinogens. Neuropharmacology. 2011;61(3): 364-381.
Hall, J, Thomas KL, Everitt BJ. Rapid and selective induction of BDNF expression in the hippocampus during contextual learning. Nat Neurosci. 2000; 3:533-535.
Halperin JJ, Heyes MP. Neuroactive kynurenines in Lyme borreliosis, Neurology. 1992;42(1):43-50.
Hama R, Bennett CL. The mechanisms of sudden-onset type adverse reactions to oseltamivir. Acta Neurol Scand. 2017;135(2):148-160.
Han, JC. Rare Syndromes and Common Variants of the Brain-Derived Neurotrophic Factor Gene in Human Obesity. Prog Mol Biol Transl Sci. 2016.
Hanania T, Manfredi P, Inturrisi C, Vitolo OV. The N-methyl-D-aspartate receptor antagonist d-methadone acutely improves depressive-like behavior in the forced swim test performance of rats Exp Clin Psychopharmacol. 2019;10.1037.
Hani, AJ, Mikati HM, Mikati MA. Genetics of pediatric epilepsy. Pediatr Clin North Am. Jun. 2015; 62(3):703-22.
Hansen K et al., Structure, function, and allosteric modulation of NMDA receptors, Rockefeller University Press, J. Gen. Physiol. 2018 vol. 150 No. 8, 1081-1105.
Hanson E. et al., Tonic Activation of GluN2C/GluN2D-Containing NMDA Receptors by Ambient Glutamate Facilitates Cortical Interneuron Maturation, The Journal of Neuroscience, May 8, 2019 39(19):3611-3626.
Hashimoto, K, Koizumi H, Nakazato M, Shimizu E, Iyo M. Role of brain-derived neurotrophic factor in eating disorders: recent findings and its pathophysiological implications. Prog Neuropsychopharmacol Biol Psychiatry. May 2005; 29(4):499-504.
Hashimoto, K; Tomitaka, S; Narita, N; Minabe, Y; Iyo, M; Fukui, S (1996) "Induction of heat shock protein HSP-70 in rat retrosplenial cortex following administration of dextromethorphan". Environmental Toxicology and Pharmacology. 1(4):235-239.
He L, Kim J, Ou C, McFadden W, van Rijn RM, Whistler JL. Methadone antinociception is dependent on peripheral opioid receptors. J Pain. 2009;10(4):369-379.
Heberlein, A. et al. Association of testosterone and BDNF serum levels with craving during alcohol withdrawal. Alcohol 54 (2016) 67-72.
Heinrich, H, Grunitz J, Stonawski V, Frey S, Wahl S,, Albrecht B, Goecke TW, Beckmann MW, Kornhuber J, Fasching PA, Moll GH, Eichler A. Attention, cognitive control and motivation in ADHD: Linking event-related brain potentials and DNA methylation patterns in boys at early school age. Scientific Reports 7, Article No. 3823 (2017).
Henningfield J, Apseloff G, Gorodestsky C, et al. No meaningful opioid abuse liability of REL-1017 (esmethadone; d-methadone), a rapid-acting antidepressant in clinical development: A human abuse potential study. Neuropsychopharmacology. 2021;46(Suppl 1):p. 315.
Henriques, A, Pitzer C and Schneider A. Neurotrophic growth factors for the treatment of amyotrophic lateral sclerosis: where do we stand? Frontiers in Neuroscience, Jun. 2010 vol. 4 Art 32.
Henssler J, Heinz A, Brandt L, Bschor T. Antidepressant Withdrawal and Rebound Phenomena. Dtsch Arztebl Int. 2019;116(20):355-361.
Hermanussen, M, Tresguerres JA. A new anti-obesity drug treatment: first clinical evidence that, antagonising glutamate-gated Ca2+ ion channels with memantine normalises binge-eating disorders. Econ Hum Biol. Jul. 2005; 3(2):329-37.
Hermes, G, Nagy D, Waterson M, Zsarnovszky A, Varela L, Hajos M, Horvath TL. Role of mitochondrial uncoupling protein-2 (UCP2)

(56) References Cited

OTHER PUBLICATIONS in higher brain functions, neuronal plasticity and network oscillation. Mol Metab. Apr. 9, 2016; 5(6):415-21.
Hervé F, Duché JC, d'Athis P, Marché C, Barré J, Tillement JP, Binding of disopyramide, methadone, dipyridamole, chlorpromazine, lignocaine and progesterone to the two main genetic variants of human alpha1-acid glycoprotein: evidence for drug-binding differences between the variants and for the presence of two separate drug-binding sites on alpha1-acid glycoprotein. Pharmacogenetics. 1996;6(5):403-415.
Herzog, AG. Psychoneuroendocrine aspects of temporolimbic epilepsy. Part II: Epilepsy and reproductive steroids. Psychosomatics. Mar.Apr. 1999; 40(2):102-8.
Hiratsuka M, Takekuma Y, Endo N, Narahara K, Hamdy SI, Kishikawa Y, Matsuura M, Agatsuma Y, Inoue T, Mizugaki M. Allele and genotype frequencies of CYP2B6 and CYP3A5 in the Japanese population. Eur J Clin Pharmacol. Sep. 2002;58(6):417-21.
Ho PS, Yen CH, Chen CY, Huang SY, Liang CS. Changes in cytokine and chemokine expression distinguish dysthymic disorder from major depression and healthy controls. Psychiatry Res. Feb. 2017;248:20-27.
Horrigan, FT and Gilly WF: Methadone block of K+ current in squid giant fiber lobe neurons. J Gen Physiol. Feb. 1, 1996; 107(2):243-260.
Hough C, Morford A, Epel E, Lindqvist D, Saverio Bersani F, Jain F, Mahan L, Ross R, Burke H, Mellon S, Wolkowitz O, Victor Reus V. Pre-Treatment Allostatic Load and Metabolic Dysregulation Predict Antidepressant Response in Major Depressive Disorder. Biological Psychiatry vol. 81, Issue 10, Supplement, May 15, 2017, pp. S405-S406.
Houston, M. The role of magnesium in hypertension and cardiovascular disease. J Clin Hypertens (Greenwich). Nov. 2011; 13(11):843-7.
Howard DM, Adams MJ, Clarke TK, Hafferty JD, Gibson J, Shirali M, et al. (Mar. 2019), "Genome-wide meta-analysis of depression identifies 102 independent variants and highlights the importance of the prefrontal brain regions", Nature Neuroscience, 22 (3): 343-352.
Howell, N. Leber hereditary optic neuropathy: respiratory chain dysfunction and degeneration of the optic nerve. 1988 Vis Res 38:1495-1504.
Huang, L, Bocek M, Jordan JK, Sheehan AH. Memantine for the prevention of primary headache disorders. Ann Pharmacother. Nov. 2014; 48(11):1507-11.
Huang, Y, Dreyfus CF. The role of growth factors as a therapeutic approach to demyelinating disease. Exp Neurol. Sep. 2016; 283(Pt B):531-40.
Hurvich CM, Simonoff JS, and Tsai CL. Smoothing parameter selection in nonparametric regression using an improved Akaike Information Criterion. J R Stat Soc Series B Stat Methodol. 1998;60(2):271-293.
Hutchinson MR, Somogyi AA. (S)-(+)-methadone is more immunosuppressive than the potent analgesic (R)-(−)-methadone. Int Immunopharmacol. 2004;4(12):1525-1530.
Iijima et al. "Studies in the (+)-morphinan series. 4. A markedly improved synthesis of (+)-morphine" Journal of Organic Chemistry. Mar. 1, 1978 (Mar. 1, 1978) vol. 43, p. 1462-1463; p. 1462, col. 1.
Iizuka, A, Nakamura K, Hirai H. Long-term oral administration of the NMDA receptor antagonist memantine extends life span in spinocerebellar ataxia type 1 knock-in mice. Neurosci Lett. Apr. 10, 20150 592:37-41.
Imam, L, Hannan SA. Noise-induced hearing loss: a modern epidemic? Br J Hosp Med (Lond). May 2, 2017; 78(5):286-290.
Indian First Examination Report in Indian Patent Application No. 201917033638, dated Mar. 24, 2021, 10 pgs.
International Search Report and Written Opinion in International Patent Application No. PCT/US2013/061639, mailed Nov. 26, 2013, 12 pgs.
International Search Report and Written Opinion in International Patent Application No. PCT/US2020/067498, dated Mar. 30, 2021, 14 pgs.
International Search Report and Written Opinion in International Patent Application No. PCT/US2021/023882, mailed Jul. 28, 2021, 9 pgs.
International Search Report and Written Opinion in International Patent Application No. PCT/US2022/023950, dated Jul. 13, 2022, 11 pgs.
International Search Report and Written Opinion in International Patent Application No. PCT/US2022/028559, mailed Jul. 25, 2022, 9 pgs.
Office Action in U.S. Appl. No. 15/204,052, dated May 3, 2017, 9 pgs.
Office Action in U.S. Appl. No. 15/884,915, dated Aug. 6, 2019, 11 pgs.
Office Action in U.S. Appl. No. 15/884,915, dated Feb. 7, 2022, 13 pgs.
Office Action in U.S. Appl. No. 15/884,915, dated Jun. 24, 2021, 11 pgs.
Office Action in U.S. Appl. No. 15/884,915, dated Mar. 14, 2019, 11 pgs.
Office Action in U.S. Appl. No. 15/884,915, dated Mar. 19, 2020, 12 pgs.
Office Action in U.S. Appl. No. 15/884,915, dated Nov. 8, 2022, 17 pgs.
Office Action in U.S. Appl. No. 15/884,915, dated Oct. 22, 2020, 14 pgs.
Olivan-Blázquez, B, Herrera-Mercadal P, Puebla-Guedea M, Pérez-Yus MC, Andrés E, Fayed N, López-Del-Hoyo Y, Magallon R, Roca M, Garcia-Campayo J. Efficacy of memantine in the treatment of fibromyalgia: A double-blind, randomised, controlled trial with 6-month follow-up. Pain. Dec. 2014; 155(12):2517-25.
Olney JW, Labruyere J, Price MT (1989) "Pathological Changes Induced in Cerebrocortical Neurons by Phencyclidine and Related Drugs". Science. 244:1360-1362.
Olsen, G.D., Wendel, H.A., Livermore, J.D., Leger, R.M., Lynn, R.K. and Gerber, N., Clinical effects and pharmacokinetics of racemic methadone and its optical isomers, Clin. Pharmacol. Ther., 21 (1976) 147-157.
Ondo, W. G., "Methadone for Refractory Restless Legs Syndrome,." Movement Disorders: Official Journal of the Movement Disorder Society (Mar. 2005) 20(3):345-348.
Ortiz-López, L, González-Olvera JJ, Vega-Rivera NM, Garcia-Anaya M, Carapia-Hernández AK, Velázquez-Escobar JC, Ramírez-Rodriguez GB. Human neural stem/progenitor cells derived from the olfactory epithelium express the TrkB receptor and migrate in response to BDNF. Neuroscience. Jul. 4, 2017; 355:84-100.
Paoletti, P. et al., NMDA receptor subunit diversity: impact on receptor properties, synaptic plasticity and disease. Nature Reviews Neuroscience 14, 383-400 (2013).
Papakostas GI, Fava M. Predictors, moderators, and mediators (correlates) of treatment outcome in major depressive disorder. Dialogues Clin Neurosci. 2008;10(4):439-451.
Partial International Search Report in International Patent Application No. PCT/US2018/016159, mailed May 7, 2018, 2 pgs.
Pasternak GW, Pan YX. Mu opioids and their receptors: evolution of a concept. Pharmacol Rev. 2013;65 (4):1257-1317. Published Sep. 27, 2013.
Patel, AV et al., Lingual and palatal gustatory afferents each depend on both BDNF and NT-4, but the dependence is greater for lingual than palatal afferents. J Comp Neurol. Aug. 15, 2010; 518(16):3290-301.
Patrizi, A et al., Chronic Administration of the N-Methyl-D-Aspartate Receptor Antagonist Ketamine Improves Rett Syndrome Phenotype. Biol Psychiatry. May 1, 2016; 79(9):755-64.
Peeters M, Romieu P, Maurice T, Su TP, Maloteaux JM, Hermans E. Involvement of the sigma1 receptor in the modulation of dopaminergic transmission by amantadine, The European Journal of Neuroscience 2004. 19(8):2212-20.
Pellissier, LP et al., m opioid receptor, social behaviour and autism spectrum disorder: reward matters. Br J Pharmacol. Apr. 3, 2017 doi: 10.1111/bph. 13808. [Epub ahead of print].

(56) References Cited

OTHER PUBLICATIONS

Pereverseff RS, Beshai S, Dimova M. First episode indices associated with lifetime chronicity of depression among formerly depressed participants: an exploratory study [published online ahead of print, May 10, 2017] [published correction appears in J Ment Health. Dec. 2018;27(6):604]. J Ment Health. 2017;1-7.
Peter, S, Manousaridis K, Boesch S, Mennel S. Memantine for optic nerve atrophy in Friedreich's Ataxia. Article in German. Ophthalmologe. Aug. 2016; 113(8):704-7.
Peyman, GA et al. Effects of morphine on corneal sensitivity and epithelial wound healing: implications for topical ophthalmic analgesia. Br J Ophthalmol. Feb. 1994; 78(2):138-141.
Pfister et al. NASH limits anti-tumour surveillance in immunotherapy-treated HCC. Nature 2021; 592: 450-456.
Pietersen, HG et al., Glutamate metabolism of the heart during coronary artery bypass grafting. Clin Nutr. Apr. 1998; 17(2):73-5.
Pochwat B, Palucha-Poniewiera A, Szewczyk B, Pilc A, Nowak G. NMDA antagonists under investigation for the treatment of major depressive disorder. Expert Opin Investig Drugs. 2014.
Pontius, A. A., Overwhelming Remembrance of Things Past: Proust Portrays Limbic Kindling by External Stimulus-Literary Genius Can Presage Neurobiological Patterns of Puzzling Behavior. Psychological Reports, 73(2), 1993, pp. 615-621.
Povysheva NV, Johnson JW. Tonic NMDA receptor-mediated current in prefrontal cortical pyramidal cells and fast-spiking interneurons. J Neurophysiol. 2012;107(8):2232-2243.
Prentice, H, Modi JP, Wu JY. Mechanisms of Neuronal Protection against Excitotoxicity, Endoplasmic Reticulum Stress, and Mitochondrial Dysfunction in Stroke and Neurodegenerative Diseases. Oxid Med Cell Longev. 2015.
Prokopova, B, Hlavacova N, Vlcek M, Penesova A, Grunnerova L, Garafova A, Turcani P, Kollar B, Jezova D. Early cognitive impairment along with decreased stress-induced BDNF in male and female patients with newly diagnosed multiple sclerosis. J Neuroimmunol. Jan. 15, 2017; 302:34-40.
Ragguett RM, Rong C, Rosenblat JD, Ho RC, Mcintyre RS. Pharmacodynamic and pharmacokinetic evaluation of buprenorphine + samidorphan for the treatment of major depressive disorder. Expert Opin Drug Metab Toxicol. 2018, 14(4):475-482.
Raison CL, et al. CSF concentrations of brain tryptophan and kynurenines during immune stimulation with IFN-alpha: relationship to CNS immune responses and depression, Mol. Psychiatry. 2010, 15:393-403.
Ramírez LA, Pérez-Padilla EA, Garcia-Oscos F, Salgado H, Atzori M, Pineda JC. A new theory of depression based on the serotonin/kynurenine relationship and the hypothalamic-pituitary-adrenal axis, Biomedica. 2018;38(3):437-450. Published Sep. 1, 2018.
Rasika, S et al., BDNF Mediates the Effects of Testosterone on the Survival of New Neurons in an Adult Brain. Proc Natl Acad Sci U S A. Aug. 16, 1994; 91(17):7854-8.
Reddy, DS. Anticonvulsant activity of the testosterone-derived neurosteroid 3alpha-androstanediol. Neuroreport. Mar. 1, 2004; 15(3):515-8.
Ribeiro, S, Schmidt AP, Schmidt SR. Opioids for treating nonmalignant chronic pain: the role of methadone. Rev Bras Anestesiol. Sep. 2002; 52(5):644-51.
Rickli A, Liakoni E, Hoener MC, Liechti ME. Opioid-induced inhibition of the human 5-HT and noradrenaline transporters in vitro: link to clinical reports of serotonin syndrome. Br J Pharmacol. 2018;175(3):532-543.
Riva, V, Battaglia M, Nobile M, Cattaneo F, Lazazzera C, Mascheretti S, Giorda R, Mérette C, Émond C, Maziade M, Marino C. GRIN2B predicts attention problems among disadvantaged children. Eur Child Adolesc Psychiatry. Jul. 2015; 24(7):827-36.
Roberts, A. C. et al. Downregulation of NR3A-containing NMDARs is required for synapse maturation and memory consolidation. Neuron 63, 342-356 (2009).
Rodríguez-Muñoz M, Sánchez-Blázquez P, Vicente-Sánchez A, Berrocoso E, Garzón J. The mu-opioid receptor and the NMDA receptor associate in PAG neurons: implications in pain control. Neuropsychopharmacology. 2012;37(2):338-349.
Roffey, P, Mikhail M, Thangathurai D. NMDA receptor blockade prevents nitroglycerin-induced headaches. Headache. Jul.-Aug. 2001; 41(7):733.
Rojas-Corrales, MO, Gibert-Rahola J, Mico JA. Role of atypical opiates in OCD. Experimental approach through the study of 5-HT2A/C receptor-mediated behavior. Psychopharmacology (Berl). Feb. 2007; 190(2):221-31.
Rosanoff, A. Magnesium and hypertension. Clin Calcium. Feb. 2005; 15(2):255-60.
Rosini, F, Federighi P, Pretegiani E, Piu P, Leigh RJ, Serra A, Federico A, Rufa A. Ocular-motor profile and effects of memantine in a familial form of adult cerebellar ataxia with slow saccades and square wave saccadic intrusions. PLOS One. Jul. 22, 2013; 8(7).
Rottach, KG, Schaner BM, Kirch MH, Zivotofsky AZ, Teufel LM, Gallwitz T, Messer T. Restless legs syndrome as side effect of second generation antidepressants. J Psychiatr Res. 2009 43(1):70-5.
Rush AJ, Trivedi MH, Wisniewski SR, Nierenberg AA, Stewart JW, Warden D, et al. Acute and longer-term outcomes in depressed outpatients requiring one or several treatment steps: a STAR*D report. Am J Psychiatry. 2006;163:1905-17.
Saint-Mont U. Randomization Does Not Help Much, Comparability Does. PLoS One. 2015;10(7):e0132102. Published Jul. 20, 2015.
Sala, G. Antioxidants Partially Restore Glutamate Transport Defect in Leber Hereditary Optic Neuropathy Cybrids. Journal of Neuroscience Research 2008, 86:3331-3337.
Sanacora, G et al., Ketamine: Promising Path or False Prophecy in the Development of Novel Therapeutics for Mood Disorders?, Neuropsychopharmacology (2015) 40, 259-267.
Trenkwalder, C, Hening WA, Montagna P, Oertel WH, Allen RP, Walters AS, Costa J, Stiasny-Kolster K, Sampaio C. Treatment of restless legs syndrome: an evidence-based review and implications for clinical practice. Mov Disord. Dec. 15, 2008; 23(16):2267-302.
Trujillo KA, Akil H. Inhibition of morphine tolerance and dependence by the NMDA receptor antagonist MK-801. Science. 1991;251(4989):85-87.
Trujillo KA. Are NMDA receptors involved in opiate-induced neural and behavioral plasticity? A review of preclinical studies. Psychopharmacology (Berl). 2000;151(2-3):121-141.
Trullas, R. et al., "Functional antagonists at the NMDA receptor complex exhibit antidepressant actions," Eur J Pharmacol 1990;185:1-10.
Tsai, MC, Huang TL. Brain-derived neurotrophic factor (BDNF) and oxidative stress in heroin-dependent male patients undergoing methadone maintenance treatment. Psychiatry Res. Dec. 27, 2016; 249:46-50.
Tung, KH et al. Contrasting cardiovascular properties of the μ-opioid agonists morphine and methadone in the rat. Eur J Pharmacol Sep. 5, 2015; 762:372-81.
Turana, Y, Ranakusuma TA, Purba JS, Amir N, Ahmad SA, Machfoed MH, Handayani YS, Asmarinah, Waspadji S. Enhancing Diagnostic Accuracy of aMCI in the Elderly: Combination of Olfactory Test, Pupillary Response Test, BDNF Plasma Level, and APOE Genotype. Int J Alzheimers Dis. 2014; 2014:912586.
Tyler, MP, Hongjie Y, Eric DM et al. GRIN2A mutation and early-onset epileptic encephalopathy: personalized therapy with memantine. Annals of Clinical and Translational Neurology 2014; 1(3):190-198.
Jranagase, A, Katsunuma S, Doi K, Nibu K. BDNF expression in olfactory bulb and epithelium during regeneration of olfactory epithelium. Neurosci Lett. May 10, 2012; 516(1):45-9.
Vaupel, D. Bruce et al., "I-a-Acetylmethadol, I-a-Acetyl-N-normethadol, and I-a-Acetyl-N,N-dinormethadol: Comparisons with Morphone and Methadone in Suppression of the Opioid Withdrawal Syndrome in the Dog," The Journal of Pharmacology and Experimental Therapeutics (1997) 283(2):833-842.
Vink, R. Magnesium in the CNS: recent advances and developments. Magnes Res. Mar. 1, 2016; 29(3):95-101.
Vuong, C et al., The effects of opioids and opioid analogs on animal and human endocrine systems. Endocr Rev. Feb. 2010; 31(1):98-132.

(56) References Cited

OTHER PUBLICATIONS

Vogelin, E, Baker JM, Gates J, Dixit V, Constantinescu MA, Jones NF. Effects of local continuous release of brain derived neurotrophic factor (BDNF) on peripheral nerve regeneration in a rat model. Exp Neurol. Jun. 2006; 199(2):348-53.

Wang J, Hajizadeh N, Moore EE, et al. Tissue Plasminogen Activator ((PA) Treatment for COVID-19 Associated Acute Respiratory Distress Syndrome (ARDS): A Case Series [published online ahead of print, Apr. 8, 2020]. J Thromb Haemost. 2020;10.1111/jth.14828.

Wang, GY, Kydd R, Russell BR. Auditory event-related potentials in methadone substituted opiate users. J Psychopharmacol. Sep. 2015; 29(9):983-95.

Wang, GY, Wouldes TA, Kydd R, Jensen M, Russell BR. Neuropsychological performance of methadone-maintained opiate users. J Psychopharmacol. Aug. 2014; 28(8):789-99.

Wang, GY, Wouldes TA, Russell BR. Methadone maintenance treatment and cognitive function: a systematic review. Curr Drug Abuse Rev. Sep. 2013; 6(3):220-30.

Wang, Y et al. Associations between cognitive impairment and motor dysfunction in Parkinson's disease. Brain and Behavior. 2017; 7(6).

Wang, Yiwei, Hailong Liu, Yongzhong Lin, Guangming Liu, Hongwei Chu, Pengyao Zhao, Xiaohan Yang, Tiezheng Zheng, Ming Fan, Xuezhong Zhou, Jun Meng & Changkai Sun. Network-Based Approach to Identify Potential Targets and Drugs that Promote Neuroprotection and Neurorepair in Acute Ischemic Stroke, Nature Scientific Reports, Jan. 2017.

Watanabe, M. et al. (1992) Developmental changes in distribution of NMDA receptor channel subunit mRNAs. Neuroreport 3, 1138-1140.

Welters A, Lammert E, Mayatepek E, Meissner T. Need for Better Diabetes Treatment: The Therapeutic Potential of NMDA Receptor Antagonists. Bessere Diabetesmedikamente sind erforderlich: therapeutisches Potenzial von NMDAR Antagonisten. Klin Padiatr. 2017;229(1):14-20.

White, HD et al., Treatment of pain in fibromyalgia patients with testosterone gel: Pharmacokinetics and clinical response. Int Immunopharmacol. Aug. 2015; 27(2):249-56.

Wickramatilake, CM et al., Association of serum testosterone with lipid abnormalities in patients with angiographically proven coronary artery disease. Indian J Endocrinol Metab. Nov.-Dec. 2013; 17(6):1061-1065.

Willi, TS, Honer WG, Thornton AE, Gicas K, Procyshyn RM, Vila-Rodriguez F, Panenka WJ, Aleksic A, Leonova O1, Jones AA1, MacEwan GW, Barr AM. Factors affecting severity of positive and negative symptoms of psychosis in a polysubstance using population with psychostimulant dependence. Psychiatry Res. Jun. 30, 2016; 240:336-42.

Williams NR, Heifets BD, Blasey C, et al. Attenuation of Antidepressant Effects of Ketamine by Opioid Receptor Antagonism. Am J Psychiatry. 2018;175(12):1205-1215.

Winter CA, Flataker L. Antitussive Action of d-Isomethadone and d-Methadone in Dogs. Proc Soc Exp Biol Med. 1952;81(2):463-465.

Wissel PS, Denke M, Inturrisi CE. A comparison of the effects of a macrobiotic diet and a Western diet on drug metabolism and plasma lipids in man. Eur J Clin Pharmacol. 1987;33(4):403-407.

Wolfensberger, TJ. Macular Edema—Rationale for Therapy. Dev Ophthalmol. 2017; 58:74-86.

Written Opinion in International Patent Application No. PCT/US2018/016159, mailed Jul. 20, 2018, 23 pgs.

Wu et al. "dextro-Morphine attenuates the morphine-produced conditioned place preference via the sigma1 receptor activation in the rat" HHS Public Access. May 21, 2008 (May 21, 2008) <<https://www.nclatnim.nih.govipmc/articles/PMC1936970/?report=classic>> p. 1-11.

Wulff, H et al., Voltage-gated potassium channels as therapeutic drug targets. Nat Rev Drug Discov. Dec. 2009; 8(12):982-1001.

Xiao, Y. et al., "Blockade of Rat a3b4 Nicotinic Receptor Function by Methadone, Its Metabolites, and Structural Analogs," Journal of Pharmacology and Experimental Therapeutics, American Society for Pharmacology and Experimental Therapeutics, US (Oct. 1, 2001) 299(1)366-371.

Yamakura T, Mori H, Masaki H, Shimoji K, Mishina M. Different sensitivities of NMDA receptor channel subtypes to non-competitive antagonists. Neuroreport. 1993;4(6):687-690.

Yang, JC, Rodriguez A, Royston A, Niu YQ, Merve Avar, Ryan Brill, Christa Simon, Jim Grigsby, Randi J. Hagerman, and Olichney JM. Memantine Improves Attentional Processes in Fragile X-Associated Tremor/Ataxia Syndrome: Electrophysiological Evidence from a Randomized Controlled Trial. Sci Rep. 2016; 6:217-19.

Yanik, M et al., Reduced serum brain-derived neurotrophic factor in patients with first onset vitiligo. Neuropsychiatr Dis Treat. Dec. 12, 2014; 10:2361-7.

Yeap, BB. Hormonal changes and their impact on cognition and mental health of ageing men. Maturitas. Oct. 2014; 79(2):227-35.

Yeung, A.W., W. Wu, M. Freewan, R. Stocker, N.J. King, and S.R. Thomas. 2012. Flavivirus infection induces indoleamine 2,3-dioxygenase in human monocyte-derived macrophages via tumor necrosis factor and NF-KB. Journal of Leukocyte Biology 91: 657-666.

Yilmaz, A. et al., "Prolonged effect of an anesthetic dose of ketamine on behavioral despair," Pharmacol Biochem Behav 2002;71:341-344.

Zagon, IS et al., Naltrexone, an opioid antagonist, facilitates reepithelialization of the cornea in diabetic rat. Invest Ophthalmol Vis Sci. Jan. 2000; 41(1):73-81.

Zajecka JM, Stanford AD, Memisoglu A, Martin WF, Pathak S. Buprenorphine/samidorphan combination for the adjunctive treatment of major depressive disorder: results of a phase III clinical trial (FORWARD-3). Neuropsychiatr Dis Treat. 2019;15:795-808. Published Apr. 4, 2019.

Zarate, C. A., Jr. et al., "A Randomized Trial of an N-methyl-D-aspartate Antagonist in Treatment-Resistant Major Depression," Arch Gen Psy 2006;63:856-864.

Zgliczynski, S et al., Effect of testosterone replacement therapy on lipids and lipoproteins in hypogonadal and elderly men. Atherosclerosis. Mar. 1996; 121(1):35-43.

Zhang H, Largent-Milnes TM, Vanderah TW. Glial neuroimmune signaling in opioid reward. Brain Res Bull. 2020;155:102-111.

Zhang, G and Stackman RS Jr. The role of serotonin 5-HT2A receptors in memory and cognition. Front. Pharmacol., Oct. 2015 vol. 6, article 225.

Zhang, N et al., The relationship between endogenous testosterone and lipid profile in middle-aged and elderly Chinese men. European Journal of Endocrinology. (2014) 170:487-494.

Zhu X, Ye G, Wang Z, Luo J, Hao X. Sub-anesthetic doses of ketamine exert antidepressant-like effects and upregulate the expression of glutamate transporters in the hippocampus of rats. Neurosci Lett. 2017;639:132-137.

Zott B, Simon MM, Hong W, et al. A vicious cycle of β amyloid-dependent neuronal hyperactivation. Science. 2019;365(6453):559-565.

Iijima, I. et al., Studies in the (+)-morphinan series. 5. Synthesis and biological properties of (+)-naloxone, J Med Chem. Apr. 1978;21(4):398-400.

McDole, B, Isgor C, Pare C, Guthrie K. BDNF over-expression increases olfactory bulb granule cell dendritic spine density in vivo. Neuroscience. Sep. 24, 2015; 304:146-60.

McGee MA, Abdel-Rahman AA. N-Methyl-D-Aspartate Receptor Signaling and Function in Cardiovascular Tissues. J Cardiovasc Pharmacol. 2016;68(2):97-105.

McLennan, Y et al., Fragile X Syndrome. Curr Genomics. May 2011; 12(3):216-224.

Mealing GA, Lanthorn TH, Murray CL, Small DL, Morley P. Differences in degree of trapping of low-affinity uncompetitive N-methyl-D-aspartic acid receptor antagonists with similar kinetics of block. J Pharmacol Exp Ther. 1999;288(1):204-210.

Mealing GA, Lanthorn TH, Small DL, et al. Structural modifications to an N-methyl-D-aspartate receptor antagonist result in large differences in trapping block. J Pharmacol Exp Ther. 2001;297(3):906-914.

(56) References Cited

OTHER PUBLICATIONS

Meisner, Falko et al. for the German Competence Network HIV/AIDS. Memantine Upregulates BDNF and Prevents Dopamine Deficits in SIV-Infected Macaques: A Novel Pharmacological Action of Memantine. Neuropsychopharmacology (2008) 33, 2228-2236.
Meuldijk, R, Colon EJ. Methadone treatment of Tourette's disorder. Am J Psychiatry. Jan. 1992; 149(1):139-40.
Mexican Office Action in Mexican Patent Application No. MX/a/2019/009038, dated Jul. 14, 2022, 6 pgs.
Mexican Office Action in Mexican Patent Application No. MX/a/2019/009038, dated Mar. 2, 2022, 5 pgs. (English language translation).
Miglio G, Varsaldi F, Lombardi G. Human T lymphocytes express N-methyl-D-aspartate receptors functionally active in controlling T cell activation. Biochem Biophys Res Commun. 2005;338(4):1875-1883.
Milenkovic VM, Stanton EH, Nothdurfter C, Rupprecht R, Wetzel CH, The Role of Chemokines in the Pathophysiology of Major Depressive Disorder, Int J Mol Sci. 2019; 20(9):2283.
Mischoulon, D et al., Randomized, proof-of-concept trial of low dose naltrexone for patients with breakthrough symptoms of major depressive disorder on antidepressants. J Affect Disord. Jan. 15, 2017; 208:6-14.
Mitchell, T.B. et al., "Subjective and physiological responses among racemic-methadone maintenace patients in relation to relative (S)-vs. (R)-methadone exposure," Br J Clin Pharmacol 2004;58(6):609-617.
Mohammadi, MR, Mohammadzadeh S, Akhondzadeh S. Memantine versus Methylphenidate in Children and Adolescents with Attention Deficit Hyperactivity Disorder: A Double-Blind, Randomized Clinical Trial.Iran J Psychiatry. Apr. 2015; 10(2):106-14.
Molassiotis, A, Smith JA, Bennett MI, Blackhall F, Taylor D, Zavery B, Harle A, Booton R, Rankin EM, Lloyd-Williams M, Morice AH. Clinical expert guidelines for the management of cough in lung cancer: report of a UK task group on cough. Cough. Oct. 6, 2010; 6:9.
Monaghan DT, Jane DE. Pharmacology of NMDA Receptors. In: Van Dongen AM, editor. Biology of the NMDA Receptor. Boca Raton (FL): CRC Press/Taylor & Francis; 2009. Chapter 12.
Monaghan DT, Larsen H. NR1 and NR2 subunit contributions to N-methyl-D-aspartate receptor channel blocker pharmacology. J Pharmacol Exp Ther. 1997;280(2):614-620.
Monyer, H. et al. (1994) Developmental and regional expression in the rat brain and functional properties of four NMDA receptors. Neuron 12, 529-540.
Moore JX, Chaudhary N, Akinyemiju T. Metabolic Syndrome Prevalence by Race/Ethnicity and Sex in the United States, National Health and Nutrition Examination Survey, 1988-2012. Prev Chronic Dis 2017;14:160287.
Moravcova et al., The effect of oleic and palmitic acid on induction of steatosis and cytotoxicity on rat hepatocytes in primary culture. Physiol Res 2015;64(Suppl 5):S627-36.
Morley, JE. Pharmacologic Options for the Treatment of Sarcopenia. Calcif Tissue Int. Apr. 2016; 98(4):319-3.
Morley, JS, Watt JW, Wells JC, Miles JB, Finnegan MJ, Leng G. Methadone in pain uncontrolled by morphine. Lancet. Nov. 13, 1993; 342(8881):1243.
Morrison, KE et al., Distinct profiles of social skill in adults with autism spectrum disorder and schizophrenia. Autism Res. May 2017; 10(5):878-887.
Morrison, RS, Carney MT and Manfredi PL. Pain Management. In: Rosenthal RA, Zenilman ME, Katlic MR, eds. Principles and Practice of Geriatric Surgery. New York: Springer; 2001:160-173.
Moryl, N et al., A phase I study of D-methadone in patients with chronic pain, Journal of Opioid Management 12:1, Jan./Feb. 2016.
Moryl, N, Santiago-Palma J, Kornick C, Derby S, Fischberg D, Payne R, Manfredi P. Pitfalls of opioid rotation: substituting another opioid for methadone in patients with cancer pain. Pain 2002; 96(3):325-328.
Moryl, N. et al., "Pitfalls of opioid rotation: substituting another opioid for methadone in patients with cancer pain," Pain 2002;96(3):325-328.
Moryl, N et al., A Phase I/II Study of D-Methadone in Patients with Chronic Pain—Therapeutic/Diagnostic Protocol, Memorial Sloan-Kettering Cancer Center (2008) IRB#: 01-017A(12):1-28.
Moryl, N; Cristina Tamasdan; Dana Tarcatu; Howard T. Thaler; Denise Correa; Richard Steingart; Richard Payne; Eugenie Obbens. A phase I study of d-methadone in patients with chronic pain. Journal of Opioid Management 2016:12(1):47-55.
Moser T, Starr A. Auditory neuropathy—neural and synaptic mechanisms. Nat Rev Neurol. 2016;12(3):135-149.
Muehlmann, AM, Devine DP. Glutamate-mediated neuroplasticity in an animal model of self-injurious behaviour. Behav Brain Res. May 16, 2008; 189(1):32-40.
Naidu, PSI, Kulkarni SK. Excitatory mechanisms in neuroleptic-induced vacuous chewing movements (VCMs): possible involvement of calcium and nitric oxide. Behav Pharmacol. Jun. 2001; 12(3):209-16.
Nam et al., Activation of Astrocytic μ-Opioid Receptor Causes Conditioned Place Preference, 2019; Cell Reports 28, 1154-1166.
Nam MH, Han KS, Lee J, et al. Expression of μ-Opioid Receptor in CA1 Hippocampal Astrocytes. Exp Neurobiol. 2018;27(2):120-128.
Napoli, I. et al., The fragile X syndrome protein represses activity-dependent translation through CYFIP1, a new 4E-BP. Cell, 2008, 134(6):1042-1054.
Nardelli P, Powers R, Cope TC, Rich MM. Increasing motor neuron excitability to treat weakness in sepsis. Ann Neurol. 2017;82(6):961-971.
Narita M, Hashimoto K, Amano T, et al. Post-synaptic action of morphine on glutamatergic neuronal transmission related to the descending antinociceptive pathway in the rat thalamus. J Neurochem. 2008;104(2):469-478.
Navarrete M, Cuartero MI, Palenzuela R, et al. Astrocytic p38alpha MAPK drives NMDA receptor-dependent long-term depression and modulates long-term memory. Nat Commun. 2019;10(1):2968.
Nelson, Jr., Shawn Daniel. "Synthesis and rapid biological annotation of single-enantiomer small molecules", Doctoral dissertation, 2018, Harvard University, Graduate School of Arts & Sciences. pg <http://Sciences.pg>. 44 para 1 to p. 45, para 1.
Nicholls, DG, Budd SL. Neuronal excitotoxicity: the role of mitochondria. Biofactors. 1998; 8(3-4):287-99.
Nichols, DE et al., "Improvements to the Synthesis of Psilocybin and a Facile Method for Preparing the O-Acetyl Prodrug of Psilocin" Chemistry 1999(6):935-938, 10.1055/s-1999-3490.
Nicoll RA. A Brief History of Long-Term Potentiation. Neuron. 2017;93(2):281-290.
Nicolodi, M, Del Bianco PL, Sicuteri F. Modulation of excitatory amino acids pathway: a possible therapeutic approach to chronic daily headache associated with analgesic drugs abuse. Int J Clin Pharmacol Res. 1997; 17(2-3):97-100.
Nicolodi, M, Sicuteri F. Exploration of NMDA receptors in migraine: therapeutic and theoretic implications. Int J Clin Pharmacol Res. 1995; 15(5-6):181-9.
Noel, Peter R et General Practitioner Research Panel. "The sulphone analogue of d-methadone: Assessment of antitussive activity in general practice", British Journal of Diseases of the Chest. 1963, vol. 57 No 1. p. 48-52.
Noruzzadeh, R, Modabbernia A, Aghamollaii V, Ghaffarpour M, Harirchian MH, Salahi S, Nikbakht N, Noruzi N, Tafakhori A. Memantine for Prophylactic Treatment of Migraine Without Aura: A Randomized Double-Blind Placebo-Controlled Study. Headache. Jan. 2016; 56(1):95-103.
Office Action in Australian Patent Application No. 2013323645, dated Jul. 19, 2017, 4 pgs.
Office Action in U.S. Appl. No. 13/803,375, dated Apr. 9, 2015, 16 pgs.
Office Action in U.S. Appl. No. 13/803,375, dated Feb. 11, 2016, 12 pgs.
Office Action in U.S. Appl. No. 13/803,375, dated Jun. 2, 2016, 6 pgs.

(56) References Cited

OTHER PUBLICATIONS

"Coronavirus, i tossicodipendenti sembrano immuni: l'ipotesi degli esperti di Villa Maraini-Cri" II Messaggero, May 4, 2020, Caltagirone Editore.
Abe, Koji et al. "Confirmatory Double-Blind, Parallel-Group, Placebo-Controlled Study of Efficacy and Safety of Edaravone (MCI-186) in Amyotrophic Lateral Sclerosis Patients." Amyotrophic Lateral Sclerosis & Frontotemporal Degeneration 15.7-8 (2014): 610-617.
Abramson FP. Methadone plasma protein binding: alterations in cancer and displacement from alpha1-acid glycoprotein. Clin Pharmacol Ther. 1982;32(5):652-658.
Ahmed, A and Simmons Z. Pseudobulbar affect: prevalence and management. Therapeutics and Clinical Risk Management 2013; 9:483-489.
Allen, RP, Barker PB, Horská DA, Earley CJ. Thalamic glutamate/glutamine in restless legs syndrome. Neurology 2013; 80:2028-2034.
Almatroudi, A. et al., "Combined adminsitration of buprenorphine and naltrexone produces antidepressant-like effects in mice," Journal of Psychopharmacology (2015) 29(7):812-821.
Alsemari, A. Hypogonadism and neurological diseases. Neurol Sci. May 2013; 34(5):629-38.
Andreassen, CS, Jakobsen J, Flyvbjerg A, Andersen H. Expression of neurotrophic factors in diabetic muscle-relation to neuropathy and muscle strength. Brain. Oct. 2009; 132 (Pt 10):2724-33.
Andreassen, OA, Aamo, TO and Jorgensen, HA. Inhibition by memantine of the development of persistent oral dyskinesias induced by long-term haloperidol treatment of rats. British Journal of Phamacology. 1996; 119:751-757.
Andreassen, OA, Waage J, Finsen B, Jørgensen HA. Memantine attenuates the increase in striatal preproenkephalin mRNA expression and development of haloperidol-induced persistent oral dyskinesias in rats. Brain Res. 2003; 24; 994(2):188-92.
Anitha, M, Nandhu MS, Anju TR, Jes P, Paulose CS. Targeting glutamate mediated excitotoxicity in Huntington's disease: neural progenitors and partial glutamate antagonist—memantine. Med Hypotheses. Jan. 2011; 76(1):138-40.
Arnone D, Mcintosh AM, Ebmeier KP, Munafò MR, Anderson IM (2012). "Magnetic resonance imaging studies in unipolar depression: systematic review and meta-regression analyses". European Neuropsychopharmacology. 22 (1):1-16.
Asp, L., A.S. Johansson, A. Mann, B. Owe-Larsson, E.M. Urbanska, T. Kocki, M. Kegel, G. Engberg, G.B. Lundkvist, and H. Karlsson. 2011. Effects of pro-inflammatory cytokines on expression of kynurenine pathway enzymes in human dermal fibroblasts. Journal of Inflammation 8: 25.
Attems, J et al., Olfaction and Aging: A Mini-Review. Gerontology. 2015; 61(6):485-90.
Australian Office Action in Australian Patent Application No. 2013323645, dated Jul. 19, 2017, 4 pgs.
Axelrod, FB. Familial dysautonomia. Muscle & Nerve 2004; 29(3):352-363.
Bach, TV, Pan J, Kirstein A, Grief CJ, Grossman D. Use of Methadone as an Adjuvant Medication to Low-Dose Opioids for Neuropathic Pain in the Frail Elderly: A Case Series. J Palliat Med. Dec. 2016; 19(12):1351-1355.
Bai, X, Zhang C, Chen A, Liu W, Li J, Sun Q, Wang H. Protective Effect of Edaravone on Glutamate-Induced Neurotoxicity in Spiral Ganglion Neurons. Neural Plast 2016; Article ID 4034218, 10 pgs.
Banaschewski T., Becker K., Scherag S., Franke B. & Coghil, D. Molecular genetics of attention-deficit/hyperactivity disorder. an overview. Eur. Child Adolesc. Psychiatry 19, 237-257 (2010).
Banke TG, Traynelis SF. Activation of NR1/NR2B NMDA receptors. Nat Neurosci. 2003;6(2):144-152.
Bannai H, Niwa F, Sherwood MW, Shrivastava AN, Arizono M, Miyamoto A, Sugiura K, Lévi S, Triller A, Mikoshiba K. Bidirectional control of synaptic GABAAR clustering by glutamate and calcium. Cell reports. Dec. 29, 2015;13(12):2768-80.
Bart, G et al., Methadone and the QTc Interval: Paucity of Clinically Significant Factors in a Retrospective Cohort. Journal of Addiction Medicine 2017. 11(6):489-493.
Bartus, RT, Bétourné A, Basile A, Peterson BL, Glass J, Boulis NM. Beta2-Adrenoceptor agonists as novel, safe and potentially effective therapies for Amyotrophic lateral sclerosis (ALS) Neurobiology of Disease 85 (2016) 11-24.
Bathina, S. et al., "Brain-derived neurotrophic factor and its clinical implications," Arch Med Sci 2015; 11, 6: 1164-1178.
Bathina, S. et al., BDNF protects pancreatic b cells (RIN5F) against cytotoxic action of alloxan, streptozotocin, doxorubicin and benzo(a)pyrene in vitro. Metabolism. May 2016; 65(5):667-84.
Bauer, J, Werner A, Kohl W, Kugel H, Shushakova A, Pedersen A, Ohrmann P.Hyperactivity and impulsivity in adult attention-deficit/hyperactivity disorder is related to glutamatergic dysfunction in the anterior cingulate cortex. World J Biol Psychiatry. Dec. 15, 2016:1-9.
Beal MF, Kowall NW, Ellison DW, Mazurek MF, Swartz KJ, Martin JB. Replication of the neurochemical characteristics of Huntington's disease by quinolinic acid. Nature. 1986;321(6066):168-171.
Beckett, A. H., and N. J. Harper. "162. Configurational studies in synthetic analgesics: the synthesis of (−)-methadone from D-(−)-alanine." Journal of the Chemical Society (Resumed) (1957): 858-861.
Benedek IH, Blouin RA, McNamara PJ. Serum protein binding and the role of increased alpha1-acid glycoprotein in moderately obese male subjects. Br J Clin Pharmacol. 1984;18(6):941-946.
Berken, GH, Stone MM, Stone SK. Methadone in schizophrenic rage: a case study. Am J Psychiatry. Feb. 1978; 135(2):248-9.
Berman, EF, Adler MW. The anticonvulsant effect of opioids and opioid peptides against maximal electroshock seizures in rats. Neuropharmacology. Mar. 1984; 23(3):367-71.
Berman, R.M. et al., "Antidepressant Effects of Ketamine in Depressed Patients," Biol. Psych. 2000;47:351-354.
Bernstein G, Davis K, Mills C, Wang L, McDonnell M, Oldenhof J, et al. Characterization of the safety and pharmacokinetic profile of D-methadone, a novel N-methyl-D-aspartate receptor antagonist in healthy, opioid-naive subjects: results of two phase 1 studies. J Clin Psychopharmacol. 2019;39:226-37.
Berretta N, Jones RS. Tonic facilitation of glutamate release by presynaptic N-methyl-D-aspartate autoreceptors in the entorhinal cortex. Neuroscience 1996; 75:339-344.
Bezprozvanny, I, Klockgether T. Therapeutic prospects for spinocerebellar ataxia type 2 and 3.Drugs Future. Dec. 2009; 34(12).
Biederman, J., Monuteaux, M. C., Mick, E., Spencer, T., Wilens, T. E., Silva, J. M., et al. (2006). Young adult outcome of attention deficit hyperactivity disorder: a controlled 10-year follow-up study. Psychological Medicine, 36(167-179).
Bikbova, G et al., Neuronal Changes in the Diabetic Cornea: Perspectives for Neuroprotection. Biomed Res Int. 2016; Article ID 5140823, 8 pgs.
Binder, DK, Scharfman HE. Brain-derived neurotrophic factor. Growth Factors. Sep. 2004; 22(3):123-31.
Bisaga, A. et al., "Therapeutic potential of NMDA receptor antagonists in the treatment of alcohol and substance use disorders," Exp Opin Invest Drugs 2009;9(10):2233-2248.
Blanke ML, VanDongen AM. Constitutive activation of the N-methyl-D-aspartate receptor via cleft-spanning disulfide bonds. J Biol Chem. 2008;283(31):21519-21529.
Blasco, H et al., The Glutamate Hypothesis in ALS: Pathophysiology and Drug Development. Curr Med Chem. 2014; 21(31):3551-75.
Blue, ME et al., Development of amino acid receptors in frontal cortex from girls with Rett syndrome. Annals of Neurology 1999; 45(4):541-5.
Blyumin, E. V. et al. "Construction of Three Contiguous Tertiary Stereocenters From Aziridines in One Step", Organic Letters, 2007, vol. 9(23), pp. 4677-4680. abstract; p. 4678, Scheme 1; p. 4679, Table 1, entry 1; p. 4680, col. 2, para 2.
Borzelleca, J. F. et al., "Toxicological Evaluation of μ-Agonists. Part II: 9-12, Assessment of Toxicity Following 30 Days of Repeated

(56) References Cited

OTHER PUBLICATIONS

Oral Dosing of Male and Female Rats with Levo-alpha-noracetylmethadol HCI (NorLAAM)," Journal of Applied Toxicology (1995) 15(5):339-355.

Botez, MI, Botez-Marquard T, Elie R, Pedraza OL, Goyette K, Lalonde R.Amantadine hydrochloride treatment in heredodegenerative ataxias: a double blind study. J Neurol Neurosurg Psychiatry. Sep. 1996; 61(3):259-64.

Bouvier G, Bidoret C, Casado M, Paoletti P. Presynaptic NMDA receptors: Roles and rules. Neuroscience. 2015;311:322-340.

Boyer, P.A. et al., "Chronic Administration of Imipramine and Citalopram Alters the Expression of NMDA Receptor Subunit mRNAs in Mouse Brain: A Quantitative In Situ Hybridization Study," J Mol Neurosci 1998;10:219-233.

Bozic M, Valdivielso JM. The potential of targeting NMDA receptors outside the CNS. Expert Opin Ther Targets. 2015;19(3):399-413.

Braidy N, Grant R, Adams S, Brew BJ, Guillemin GJ. Mechanism for quinolinic acid cytotoxicity in human astrocytes and neurons. Neurotox Res. 2009;16(1):77-86.

Brennan, BP, Roberts JL, Fogarty KV, Reynolds KA, Jonas JM, Hudson JI. Memantine in the treatment of binge eating disorder: an open-label, prospective trial. Int J Eat Disord. 2008 41(6):520-6.

Bernstein, G. et al., Characterization of the Safety and Pharmacokinetic Profile of D-Methadone, a Novel N-Methyl-D-Aspartate Receptor Antagonist in Healthy, Opioid-Naive Subjects: Results of Two Phase 1 Studies J Clin Psychopharmacol. May/Jun. 2019;39(3):226-237.

Elkader, A.K. et al., "Major Depressive Disorder and Patient Satisfaction in Relation to Methadone Pharmacokinetics and Pharmacodynamics in Stabilized Methadone Maintenance Patients," Journal of Clinical Psychopharmacology 2009;29(1):77-81.

Elnagar MR, Walls AB, Helal GK, Hamada FM, Thomsen MS, Jensen AA. Probing the putative alpha7 nAChR/NMDAR complex in human and murine cortex and hippocampus: Different degrees of complex formation in healthy and Alzheimer brain tissue. PLoS One. 2017;12(12):e0189513. Published Dec. 20, 2017.

Elvira et al., Covalent Polymer-Drug Conjugates, Molecules, Jan. 31, 2005, vol. 10, pp. 114-125.

Erhardt S, Lim CK, Linderholm KR, et al. Connecting inflammation with glutamate agonism in suicidality. Neuropsychopharmacology. 2013;38(5):743-752.

Erickson, KI, Prakash RS, Voss MW, Chaddock L, Heo S, McLaren M, Pence BD, Martin SA, Vieira VJ, Woods JA, McAuley E, Kramer AF. Brain-derived neurotrophic factor is associated with age-related decline in hippocampal volume. The Journal of Neuroscience 2010. 30(15):5368-75.

Esfahani, MR et al., Memantine for axonal loss of optic neuritis. Graefes Arch Clin Exp Ophthalmol. Jun. 2012; 250(6):863-9.

Estienne, MJ, Barb CR.Modulation of growth hormone, luteinizing hormone, and testosterone secretion by excitatory amino acids in boars. Reprod Biol. Mar. 2002; 2(1):13-24.

European extended Search Report in European Patent Application No. 19913054.3, dated Sep. 23, 2022, 5 pgs.

European Official Action in European Patent Application No. 18706021.5, dated Jan. 4, 2022, 4 pgs.

Euser, AG. Cipolla MJ. Magnesium sulfate for the treatment of eclampsia: a brief review. Stroke. Apr. 2009; 40(4):1169-75.

Fakhri, A, Pakseresht S, Haghdoost MR, Hekmatkhah N, Torkashvand M, Ghorbanzadeh B. Memantine Enhances the Effect of Olanzapine in Patients with Schizophrenia: A Randomized, Placebo-Controlled Study. Acta Med Iran. Nov. 2016; 54(11):696-703.

Farinelli, I, De Filippis S, Coloprisco G, Missori S, Martelletti P. Future drugs for migraine. Intern Emerg Med. Oct. 2009; 4(5):367-73.

Fava M, Freeman MP, Flynn M, et al. Double-blind, placebo-controlled, dose-ranging trial of intravenous ketamine as adjunctive therapy in treatment-resistant depression (TRD) Mol Psychiatry 2018.

Fava M, Stahl S, Pani L, De Martin S, Pappagallo M, Guidetti C, Alimonti A, Bettini E, Mangano RM, Wessel T, de Somer M, Caron J, Vitolo OV, DiGuglielmo GR, Gilbert A, Mehta H, Kearney M, Mattarei A, Gentilucci M, Folli F, Traversa S, Inturrisi CE, Manfredi PL. REL-1017 (Esmethadone) as Adjunctive Treatment in Patients With Major Depressive Disorder: A Phase 2a Randomized Double-Blind Trial. Am J Psychiatry. Feb. 2022; 179(2):122-131.

Feinberg, DT, Hartman N. Methadone and schizophrenia. [Letter]. Am J Psychiatry. Dec. 1991; 148(12):1750-1.

Fellin T, Pascual O, Gobbo S, Pozzan T, Haydon PG, Carmignoto G. Neuronal synchrony mediated by astrocytic glutamate through activation of extrasynaptic NMDA receptors [published correction appears in Neuron. Jan. 6, 2005;45(1):177]. Neuron. 2004;43(5):729-743.

Fernandes, C. et al., Development of a PEGylated-Based Platform for E!cient Delivery of Dietary Antioxidants Across the Blood-Brain Barrier, Bioconjugate Chem, 2018, 29, 1677-1689.

Fernandez CA, Smith C, Yang W, et al. Concordance of DMET plus genotyping results with those of orthogonal genotyping methods. Clin Pharmacol Ther. 2012;92:360-365.

Finsterer, J. Mitochondrial disorders, cognitive impairment and dementia. J Neurol Sci. Aug. 15, 2009; 283(1-2):143-8.

Fjelldal, M. F., "Properties of glutamate receptor subunit GluN2B antagonists and effects of prenatal opioid exposure—studies in chicken and rat," Sep. 2019, pp. 1-68.

Flory, JH, Wiesenthal AC, Thaler HT, Koranteng L, Moryl N. Methadone Use and the Risk of Hypoglycemia for Inpatients with Cancer Pain. Journal of pain and symptom management. 2016; 51(1):79-87.

Fogaça MV, Fukumoto K, Franklin T, et al. N-Methyl-D-aspartate receptor antagonist d-methadone produces rapid, mTORC1-dependent antidepressant effects. Neuropsychopharmacology. 2019;44(13):2230-2238.

Forcelli PA, Turner JR, Lee BG, et al. Anxiolytic- and antidepressant-like effects of the methadone metabolite 2-ethyl-5-methyl-3,3-diphenyl-1-pyrroline (EMDP). Neuropharmacology. 2016; Sep. 12, 2015.

Foster DJR, Somogyi AA, White JM, et al. Population pharmacokinetics of (R)-, (S)- and rac-methadone in methadone maintenance patients. Br J Clin Pharmacol. 2004;57:742-755.

Fraser, HF et al., Human pharmacology and addictiveness of certain dextroisomers of synthetic analgesics, United Nations Office on Drugs and Crime, of the National Institute of Mental Health, Addiction Research Center, U.S. Public Health Service, Lexington, Ky, Jan. 1, 1962, pp. 25-35.

Fraysse, B, Nagi SM, Boher B et al. Ca2+ overload and mithocondrial permeability transition pore activation in living delta-sarcoglycan-deficient cardiomyocites. Am J Physiol 2010; 299 (3): 1158-1166.

Froimowitz, M., "Conformation-Activity Study of Methadone and Related Compounds," J. Med. Chem. (1982) 25:689-696.

Frontera, JL, Cervino AS, Jungblut LD, Paz DA. Brain-derived neurotrophic factor (BDNF) expression in normal and regenerating olfactory epithelium of Xenopus laevis. Ann Anat. Mar. 2015; 198:41-8.

Frye, CA. Effects and mechanisms of progestogens and androgens in ictal activity. Epilepsia. Jul. 2010; 51 Suppl 3:135-40.

Fuziwara, S et al., NMDA-type glutamate receptor is associated with cutaneous barrier homeostasis. J Invest Dermatol. Jun. 2003; 120(6):1023-9.

Gabrielsen, JS et al.,Trends in Testosterone Prescription and Public Health Concerns. Urol Clin North Am. May 2016; 43(2):261-71.

Gannon, M, Che P, Chen Y, Jiao K, Roberson ED, and Wang Q. Noradrenergic dysfunction in Alzheimer's disease. Front Neurosci. 2015; 9:220.

Garnett C, Bonate PL, Dang Q, Ferber G, Huang D, Liu J, et al. Scientific white paper on concentration-QTc modeling. [published correction appears in J Pharmacokinet Pharmacodyn. 2018;45(3):399]. J Pharmacokinet Pharmacodyn. 2018;45(3):383-397.

Garrido MJ, Aguirre C, Trocóniz IF, Marot M, Valle M, Zamacona MK, Calvo R. Alpha1-acid glycoprotein (AAG) and serum protein binding of methadone in heroin addicts with abstinence syndrome. Int J Clin Pharmacol Ther. Jan. 2000;38(1):35-40.

(56) References Cited

OTHER PUBLICATIONS

Garrido MJ, Jiminez R, Gomez E, Calvo R. Influence of plasma-protein binding on analgesic effect of methadone in rats with spontaneous withdrawal. J Pharm Pharmacol. 1996;48(3):281-284.
Gautam S, Ukawala R, Dhoot H, Jain S. Design and characterization of controlled release tablet of metoprolol. J. Pharm. Bioall. Sci., 4 (5) (2012), p. 90.
Gerber JG, Rhodes RJ, Gal J. Stereoselective metabolism of methadone N-demethylation by cytochrome P4502B6 and 2019. Chirality. 2004;16:36-44.
Geremia, NM, Pettersson LM, Hasmatali JC, Hryciw T, Danielsen N, Schreyer DJ, Verge VM. Endogenous BDNF regulates induction of intrinsic neuronal growth programs in injured sensory neurons. Exp Neurol. May 2010; 223(1):128-42.
Ghasemi, M, Schachter SC. The NMDA receptor complex as a therapeutic target in epilepsy: a review. Epilepsy Behav. Dec. 2011; 22(4):617-40.
Gill, SS. and Pulido OM. Glutamate Receptors in Peripheral Tissues: Current Knowledge, Future Research and Implications for Toxicology. Toxicologic Pathology 2001; 29(2):208-223.
Glaser, R, et al., Testosterone pellet implants and migraine headaches: a pilot study. Maturitas. Apr. 2012; 71(4):385-8.
Glass, MJ et al., NMDA Receptor Plasticity in the Hypothalamic Paraventricular Nucleus Contributes to the Elevated Blood Pressure Produced by Angiotensin II. Journal of Neuroscience, 2015, 35(26):9558-9567.
Glue, P, Cape G, Tunnicliff D, Lockhart M, Lam F, Gray A, Hung N, Hung CT, Harland S, Devane J, Howes J, Weis H, Friedhoff L. Switching Opioid-Dependent Patients From Methadone to Morphine: Safety, Tolerability, and Methadone Pharmacokinetics. Clin Pharmacol. Aug. 2016; 56(8):960-5.
Gorman AL et al., The d- and I-isomers of methadone bind to the non-competitive site on the N-methyl-D-aspartate (NMDA) receptor in rat forebrain and spinal cord, Neuroscience Letters 223 (1997) 5-8.
Gorman, A.L. Elliott KJ, Inturrisi CE. The d- and I-isomers of methadone bind to the non-competitive site on the N-methyl-D-aspartate (NMDA) receptor in rat forebrain and spinal cord, Nerurosci Lett 1997. 223:5-8.
Gorman, A.L. et al., The d- and I-isomers of methadone bind to the non-competitive site on the N-methyl-D-aspartate (NMDA) receptor in rat forebrain and spinal cord, Nerurosc iLett, 1997;223:5-8.
Grados, M et al., A selective review of glutamate pharmacological therapy in obsessive-compulsive and related disorders. Psychol Res Behav Manag. 2015; 8:115-131.
Grand T, Abi Gerges S, David M, Diana MA, Paoletti P. Unmasking GluN1/GluN3A excitatory glycine NMDA receptors. Nat Commun. 2018;9(1):4769.
Gregory, CW and Bowen RL. Novel therapeutic strategies for Alzheimer's disease based on the forgotten reproductive hormones. Cell Mol Life Sci. Feb. 2005; 62(3):313-9.
Grevert, P, Masover B, Goldstein A. Failure of Methadone and Levomethadyl Acetate (Levo-Alpha-Acetylmethadol, LAAM) Maintenance to Affect Memory. Arch Gen Psychiatry. Jul. 1977; 34 (7):849-53.

* cited by examiner

STRUCTURALLY MODIFIED OPIOIDS FOR PREVENTION AND TREATMENT OF DISEASES AND CONDITIONS

CROSS-REFERENCE TO RELATED APPLICATIONS

The present application claims priority to, and benefit of the filing date of, U.S. Provisional Patent Application Ser. No. 62/798,709, filed Jan. 30, 2019, the disclosure of which is hereby incorporated herein by reference in its entirety.

FIELD OF THE INVENTION

The present invention is generally related to the development of structurally modified opioids for the prevention and treatment of various diseases and conditions.

BACKGROUND OF THE INVENTION

This section is intended to introduce the reader to various aspects of art that may be related to various aspects of the present invention, which are described and/or claimed below. This discussion is believed to be helpful in providing the reader with background information to facilitate a better understanding of various aspects of the present invention. Accordingly, it should be understood that these statements are to be read in this light, and not as admissions of prior art.

The present inventors have previously disclosed that certain pharmaceutical compounds presently classified among the opioids and opioid enantiomers, including those with minimal or no clinically-relevant opioid agonist activity, alone or in combination with other drugs, including opioid antagonists, may be useful for the treatment of certain diseases and conditions (see U.S. Pat. Nos. 6,008,258, 9,468,611, and International Patent Application No. PCT/US2018/016159).

N-methyl-D-aspartate receptors (NMDARs) are increasingly recognized as potential therapeutic targets for a multiplicity of human diseases caused by genetic or environmental factors, or a combination of genetic plus environmental (G+E) factors. However, a single NMDAR antagonist/modulator will likely not be effective for the multiplicity of diseases implicated in NMDAR dysfunction.

SUMMARY OF THE INVENTION

Certain exemplary aspects of the invention are set forth below. It should be understood that these aspects are presented merely to provide the reader with a brief summary of certain forms the invention might take and that these aspects are not intended to limit the scope of the invention. Indeed, the invention may encompass a variety of aspects that may not be explicitly set forth below.

In one aspect of the invention, the present inventors now disclose that by modifying the structure of opioid drugs and their enantiomers, novel drugs (referred to herein as Structurally Modified Opioids or SMOs) can be designed and synthesized, those novel drugs having unique pharmacokinetic (PK) and pharmacodynamic (PD) properties with potentially safe and effective therapeutic actions, including actions at glutamate receptors, including NMDARs, and including differential actions at NMDAR subtypes, for the treatment and prevention of various diseases and conditions, including novel drugs for the improvement of cognitive and social skills.

In another aspect of the invention, the structural modification of an opioid or opioid enantiomer can be obtained: (a) by starting the synthetic process de novo; (b) by modifying the synthetic process for the opioid at any intermediate step during the synthesis of the racemate or of one enantiomer; or (c) by modifying the structure of the opioid or opioid enantiomer after the synthesis.

NMDARs may be the potential therapeutic targets of SMOs as described herein. In that regard; NMDARs are increasingly recognized as potential therapeutic targets for a multiplicity of human diseases caused by genetic or environmental factors, or a combination of genetic plus environmental (G+E) factors. Further, as described above, a single NMDAR antagonist/modulator will likely not be effective for the multiplicity of diseases implicated in NMDAR dysfunction. However, it is now disclosed by the present inventors that newly designed molecules (SMOs) may be useful for select diseases and conditions by targeting preferentially select cellular populations, cellular sites, brain areas, specific diseases, disease stages, conditions, and select periods of the subject's lifespan. The SMOs may be optimized for pharmacokinetic (PK) parameters (such as optimal lipid solubility for reaching select brain areas and/or select receptor subtypes and receptor sites in the CNS) or changes in metabolic parameters that may alter drug half-life, including half-life in select patient populations. Further, the SMOs may be optimized for pharmacodynamic (PD) parameters such as actions at select NMDARs domains and sites (such as the trans-membrane domain and the PCP site of NMDARs and or the extracellular domain and the NO site of NMDARs). And the SMOs may be optimized for certain NMDAR subtypes (e.g., NR1, NR2A-D, NR3A-B as detailed below), and potentially optimized for other select actions at different receptors (other than NMDARs) and transporters as detailed below.

Other aspects of the present invention may include or be directed to compounds such as those of Formulae I-VII, below:

A compound having a structure analogue to dextromethadone according to formula I:

(I)

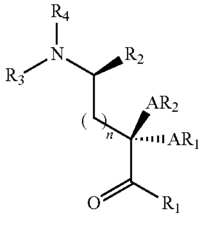

wherein $R_1$ is selected from the group consisting of alkyl, aryl, $C_3$-$C_{12}$ cycloalkyl, or heterocyclyl, any of which are optionally substituted at one or more positions by deuterium, halogen, alkyl, hydroxy, alkoxy, aryl, aryloxy, heterocyclyl, nitro, nitric acid ester;

$AR_1$ is selected from the group consisting of aryl or heterocyclyl, any of which are optionally substituted at one or more positions by deuterium, halogen, alkyl, hydroxy, alkoxy, aryl, aryloxy, heterocyclyl, nitro, nitric acid ester;

$AR_2$ is selected from the group consisting of aryl or heterocyclyl, any of which are optionally substituted at one or more positions by deuterium, halogen, alkyl, hydroxy, alkoxy, aryl, aryloxy, heterocyclyl, nitro, nitric acid ester;

$R_2$ is hydrogen, deuterium or selected from the group consisting of alkyl, aryl, $C_3$-$C_{12}$ cycloalkyl, or heterocyclyl, any of which are optionally substituted at one or more positions by deuterium, halogen, alkyl, hydroxy, alkoxy, aryl, aryloxy, heterocyclyl, nitro, nitric acid ester;

$R_3$ is alkyl optionally substituted at one or more positions by deuterium, halogen, hydroxy, alkoxy, nitric acid ester;

$R_4$ is alkyl optionally substituted at one or more positions by deuterium, halogen, hydroxy, alkoxy, nitric acid ester; and n is comprised between 1 and 4.

A compound having a structure analogue to levopropoxyphene according to formula II:

(II)

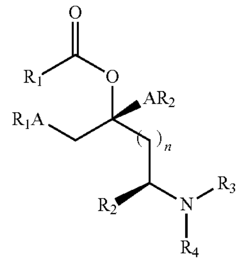

wherein $R_1$ is selected from the group consisting of alkyl, aryl, $C_3$-$C_{12}$ cycloalkyl, or heterocyclyl, any of which are optionally substituted at one or more positions by deuterium, halogen, alkyl, hydroxy, alkoxy, aryl, aryloxy, heterocyclyl, nitro, nitric acid ester;

$AR_1$ is selected from the group consisting of aryl or heterocyclyl, any of which are optionally substituted at one or more positions by deuterium, halogen, alkyl, hydroxy, alkoxy, aryl, aryloxy, heterocyclyl, nitro, nitric acid ester;

$AR_2$ is selected from the group consisting of aryl or heterocyclyl, any of which are optionally substituted at one or more positions by deuterium, halogen, alkyl, hydroxy, alkoxy, aryl, aryloxy, heterocyclyl, nitro, nitric acid ester;

$R_2$ is hydrogen, deuterium or selected from the group consisting of alkyl, aryl, $C_3$-$C_{12}$ cycloalkyl, or heterocyclyl, any of which are optionally substituted at one or more positions by deuterium, halogen, alkyl, hydroxy, alkoxy, aryl, aryloxy, heterocyclyl, nitro, nitric acid ester;

$R_3$ is alkyl optionally substituted at one or more positions by deuterium, halogen, hydroxy, alkoxy, nitric acid ester;

$R_4$ is alkyl optionally substituted at one or more positions by deuterium, halogen, hydroxy, alkoxy, nitric acid ester; and n is comprised between 1 and 4.

A compound having a structure analogue to dextroisomethadone according to formula III:

(III)

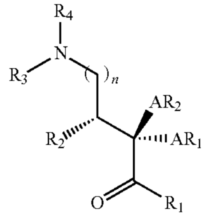

wherein $R_1$ is selected from the group consisting of alkyl, aryl, $C_3$-$C_{12}$ cycloalkyl, or heterocyclyl, any of which are optionally substituted at one or more positions by deuterium, halogen, alkyl, hydroxy, alkoxy, aryl, aryloxy, heterocyclyl, nitro, nitric acid ester;

$AR_1$ is selected from the group consisting of aryl or heterocyclyl, any of which, are optionally substituted at one or more positions by deuterium, halogen, alkyl, hydroxy, alkoxy, aryl, aryloxy, heterocyclyl, nitro, nitric acid ester;

$AR_2$ is selected from the group consisting of aryl or heterocyclyl, any of which are optionally substituted at one or more positions by deuterium, halogen, alkyl, hydroxy, alkoxy, aryl, aryloxy, heterocyclyl, nitro, nitric acid ester;

$R_2$ is hydrogen, deuterium or selected from the group consisting of alkyl, aryl, $C_3$-$C_{12}$ cycloalkyl, or heterocyclyl, any of which are optionally substituted at one or more positions by deuterium, halogen, alkyl, hydroxy, alkoxy, aryl, aryloxy, heterocyclyl, nitro, nitric acid ester;

$R_3$ is alkyl optionally substituted at one or more positions by deuterium, halogen, hydroxy, alkoxy, nitric acid ester;

$R_4$ is alkyl optionally substituted at one or more positions by deuterium, halogen, hydroxy, alkoxy, nitric acid ester; and n is comprised between 1 and 4.

A compound having a structure analogue to levomoramide according to formula IV:

(IV)

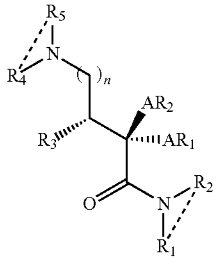

wherein $NR_1R_2$ is optionally cyclized through $C_3$-$C_{12}$ cycloalkyl, or heterocyclyl, any of which are optionally substituted at one or more positions by deuterium, halogen, alkyl, hydroxy, alkoxy, aryl, aryloxy, heterocyclyl, nitro, nitric acid ester;

If $NR_1R_2$ is not cyclized $R_1$ is selected from the group consisting of alkyl, aryl, $C_3$-$C_{12}$ cycloalkyl, or heterocyclyl, any of which are optionally substituted at one or more positions by deuterium, halogen, alkyl, hydroxy, alkoxy, aryl, aryloxy, heterocyclyl, nitro, nitric acid ester. $R_2$ is hydrogen, deuterium or selected from the group consisting of alkyl, aryl, $C_3$-$C_{12}$ cycloalkyl, or heterocyclyl, any of which are optionally substituted at one or more positions by deuterium, halogen, alkyl, hydroxy, alkoxy, aryl, aryloxy, heterocyclyl, nitro, nitric acid ester;

$AR_1$ is selected from the group consisting of aryl or heterocyclyl, any of which are optionally substituted at one or more positions by deuterium, halogen, alkyl, hydroxy, alkoxy, aryl, aryloxy, heterocyclyl, nitro, nitric acid ester;

$AR_2$ is selected from the group consisting of aryl or heterocyclyl, any of which are optionally substituted at one or more positions by deuterium, halogen, alkyl, hydroxy, alkoxy, aryl, aryloxy; heterocyclyl, nitro, nitric acid ester;

$R_3$ is hydrogen; or selected from the group consisting of alkyl, aryl, $C_3$-$C_{12}$ cycloalkyl, or heterocyclyl, any of which are optionally substituted at one or more positions by deuterium, halogen, alkyl, hydroxy, alkoxy, aryl, aryloxy, heterocyclyl, nitro, nitric acid ester;

$NR_4R_5$ is optionally cyclized through $C_3$-$C_{12}$ cycloalkyl, or heterocyclyl, any of which are optionally substituted at one or more positions by deuterium, halogen, alkyl, hydroxy, alkoxy, aryl, aryloxy, heterocyclyl, nitro, nitric acid ester;

If $NR_1R_2$ is not cyclized $R_1$ is selected from the group consisting of alkyl, aryl, $C_3$-$C_{12}$ cycloalkyl, or heterocyclyl, any of which are optionally substituted at one or more positions by deuterium, halogen, alkyl, hydroxy, alkoxy, aryl, aryloxy, heterocyclyl, nitro, nitric acid ester. $R_2$ is hydrogen, deuterium or selected from the group consisting of alkyl, aryl, $C_3$-$C_{12}$ cycloalkyl, or heterocyclyl, any of which are optionally substituted at one or more positions by deuterium, halogen, alkyl, hydroxy, alkoxy, aryl, aryloxy, heterocyclyl, nitro, nitric acid ester; and n is comprised between 1 and 4.

A compound having a structure analogue to N-methyl-dextromethadone according to formula V:

(V)

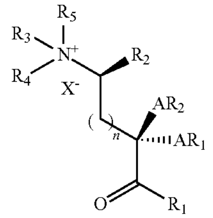

wherein $R_1$ is selected from the group consisting of alkyl, aryl, $C_3$-$C_{12}$ cycloalkyl, or heterocyclyl, any of which are optionally substituted at one or more positions by deuterium, halogen, alkyl, hydroxy, alkoxy, aryl, aryloxy, heterocyclyl, nitro, nitric acid ester;

$AR_1$ is selected from the group consisting of aryl or heterocyclyl, any of which are optionally substituted at one or more positions by deuterium, halogen, alkyl, hydroxy, alkoxy, aryl, aryloxy, heterocyclyl, nitro, nitric acid ester;

$AR_2$ is selected from the group consisting of aryl or heterocyclyl, any of which are optionally substituted at one or more positions by deuterium, halogen, alkyl, hydroxy, alkoxy, aryl, aryloxy, heterocyclyl, nitro, nitric acid ester;

$R_2$ is hydrogen, deuterium or selected from the group consisting of alkyl, aryl, $C_3$-$C_{12}$ cycloalkyl, or heterocyclyl, any of which are optionally substituted at one or more positions by deuterium, halogen, alkyl, hydroxy, alkoxy, aryl, aryloxy, heterocyclyl, nitro, nitric acid ester;

$R_3$ is alkyl optionally substituted at one or more positions by deuterium, halogen, hydroxy, alkoxy, nitric acid ester;

$R_4$ is alkyl optionally substituted at one or more positions by deuterium, halogen, hydroxy, alkoxy, nitric acid ester;

$R_5$ is alkyl optionally substituted at one or more positions by deuterium, halogen, hydroxy, alkoxy, nitric acid ester;

$X^-$ is the nitrogen-counter-ion; and n is comprised between 1 and 4.

A compound having a structure analogue to levorphanol according to formula VI:

(VI)

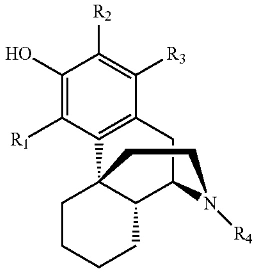

wherein $R_1$ is hydrogen, deuterium, halogen, hydroxyl, nitro, nitric acid ester or selected from the group consisting of alkyl, alkoxy, aryl, aryloxy, heterocyclyl, any of which are optionally substituted at one or more positions by deuterium, halogen, alkyl, hydroxy, alkoxy, aryl, aryloxy, heterocyclyl, nitro, nitric acid ester;

$R_2$ is hydrogen, deuterium, halogen, hydroxyl, nitro, nitric acid ester or selected from the group consisting of alkyl, alkoxy, aryl, aryloxy, heterocyclyl, any of which are optionally substituted at one or more positions by deuterium, halogen, alkyl, hydroxy, alkoxy, aryl, aryloxy, heterocyclyl, nitro, nitric acid ester;

$R_3$ is hydrogen, deuterium, halogen, hydroxyl, nitro, nitric acid ester or selected from the group consisting of alkyl, alkoxy, aryl, aryloxy, heterocyclyl, any of which are optionally substituted at one or more positions by deuterium, halogen, alkyl, hydroxy, alkoxy, aryl, aryloxy, heterocyclyl, nitro, nitric acid ester; and $R_4$ is hydrogen or selected from the group consisting of alkyl, alkoxy, aryl, aryloxy, heterocyclyl, any of which are optionally substituted at one or more positions by deuterium, halogen, alkyl, hydroxy, alkoxy, aryl, aryloxy, heterocyclyl, nitro, nitric acid ester.

A compound having a structure analogue to dextromethorphan or dextrorphan according to formula VII:

(VII)

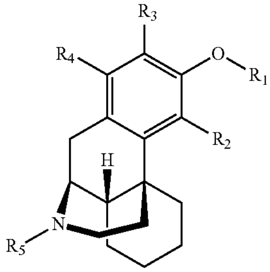

wherein $R_1$ is hydrogen, nitric acid ester or selected from the group consisting of alkyl, alkoxy, aryl, aryloxy, heterocyclyl, any of which are optionally substituted at one or more positions by deuterium, halogen, alkyl, hydroxy, alkoxy, aryl, aryloxy, heterocyclyl, nitro, nitric acid ester;

$R_2$ is hydrogen, deuterium, halogen, hydroxyl, nitro, nitric acid ester or selected from the group consisting of alkyl, alkoxy, aryl, aryloxy, heterocyclyl, any of which are optionally substituted at one or more positions by deuterium, halogen, alkyl, hydroxy, alkoxy, aryl, aryloxy, heterocyclyl, nitro, nitric acid ester;

$R_3$ is hydrogen, deuterium, halogen, hydroxyl, nitro, nitric acid ester or selected from the group consisting of alkyl, alkoxy, aryl, aryloxy, heterocyclyl, any of which are optionally substituted at one or more positions by deuterium, halogen, alkyl, hydroxy, alkoxy, aryl, aryloxy, heterocyclyl, nitro, nitric acid ester;

$R_4$ is hydrogen, deuterium, halogen, hydroxyl, nitro, nitric acid ester or selected from the group consisting of alkyl, alkoxy, aryl, aryloxy, heterocyclyl, any of which are optionally substituted at one or more positions by deuterium, halogen, alkyl, hydroxy, alkoxy, aryl, aryloxy, heterocyclyl, nitro, nitric acid ester; and $R_5$ is hydrogen or selected from the group consisting of alkyl, alkoxy, aryl, aryloxy, heterocyclyl, any of which are optionally substituted at one or more positions by deuterium, halogen, alkyl, hydroxy, alkoxy, aryl, aryloxy, heterocyclyl, nitro, nitric acid ester.

General examples of such compounds also include: Dextromethadone fluoro-derivatives (—F), including fluoro-dextromethadones; Dextromethadone nitro derivatives (—$NO_2$), including nitro-dextromethadones; Dextromethadone fluoro-nitro-derivatives, including fluoro-nitro-dextromethadones; and Deuterated dextromethadone derivatives modified as above for dextromethadone (Deuterated dextromethadone fluoro-derivatives (—F), including fluoro-dextromethadones; Deuterated dextromethadone nitro derivatives (—$NO_2$), including nitro-dextromethadones; and Deuterated dextromethadone fluoro-nitro-derivatives, including fluoro-nitro-dextromethadones).

General examples of such compounds may also include Dextroisomethadone derivatives, including: Dextroisomethadone fluoro derivatives, including fluoro-dextroisomethadones; Dextroisomethadone nitro derivative, including nitro-dextroisomethadones; Dextromethadone fluoro-nitro-derivatives, including fluoro-nitro-dextromethadones; and Deuterated dextroisomethadone derivatives modified as above for dextroisomethadone.

General examples of such compounds may also include N-methyl-dextromethadone derivatives, including: N-methyl-dextromethadone fluoro-derivatives, including fluoro-N-methyl-dextromethadones; N-methyl-dextromethadone nitro derivatives, including nitro-N-methyl-dextromethadones; N-methyl-dextromethadone fluoro-nitro-derivatives, including fluoro-nitro-N-methyl-dextromethadones; and Deuterated N-methyl-dextromethadone derivatives modified as above for N-methyl-dextromethadone.

General examples of such compounds may also include Levomoramide derivatives, including: Levomoramide fluoro-derivatives, including fluoro-levomoramides; Levomoramide nitro derivatives, including nitro-levomoramides; Levomoramide fluoro-nitro-derivatives, including fluoro-nitro-levomoramides; and Deuterated levomoramide derivatives modified as above for levomoramide General examples of such compounds may also include Levopropoxyphene derivatives, including: Levopropoxyphene fluoro-derivatives, including fluoro-levopropoxyphenes; Levopropoxyphene nitro derivatives, including nitro-levopropoxyphenes; Levopropoxyphene fluoro-nitro-derivatives, including fluoro-nitro-levopropoxyphenes; and Deuterated levopropoxyphene derivatives modified as above for levopropoxyphene.

General examples of such compounds may also include Levorphanol derivatives, including: Levorphanol-fluoro-derivatives, including fluoro-levorphanols; Levorphanol-nitro derivatives, including nitro-levorphanols; Levorphanol fluoro-nitro-derivatives, including fluoro-nitro-levorphanols; and Deuterated levorphanol derivatives modified as above for levorphanol.

General examples of such compounds may also include Dextromethorphan and dextrorphan derivatives, including: Dextromethorphan and dextrorphan-fluoro-derivatives, including fluoro-dextromethorphan and nitro-dextrorphan; Dextromethorphan and dextrorphan-nitro derivatives, including nitro-dextromethorphan and nitro-dextrorphan; Dextromethorphan and dextrorphan fluoro-nitro-derivatives, including fluoro dextromethorphan and fluoro-nitro-dextrorphan; and Deuterated dextromethorphan and deuterated dextrorphan derivatives modified as above for dextromethorphan and dextrorphan.

BRIEF DESCRIPTION OF THE DRAWINGS

The accompanying drawings, which are incorporated in and constitute a part of this specification, illustrate embodiments of the invention and, together with the general description of the invention given above and the detailed description of the embodiments given below, serve to explain the principles of the present invention.

In FIG. 2A, a schedule for administration and testing rats is shown, where administered d-methadone or ketamine and then subjected to various tests. FIG. 2B shows rats tested in FUST 24 hr later. FIG. 2C shows rats tested for locomotor activity (LMA) 2 days later. FIG. 2D shows the rats tested for NSFT 72 hr later. And FIG. 2E represents home cage feeding. The results are the mean±S.E.M. FUST: One-way ANOVA, $F_{3,42}=3.26$, $p=0.031$; Fisher's LSD: Veh x Met, $p=0.025$; Veh x Ket, $p=0.046$; n=9-12/group. NSFT: One-way ANOVA, $F_{3,27}=4.87$, $p=0.008$; Fisher's LSD: Veh x Met, $p=0.035$; Veh x Ket, $p=0.005$; n=7-8/group.

FIG. 3A shows time-course for the CUS protocol, drug dosing, and behavioral analysis. D-methadone and ketamine prevented the behavioral effects of CUS in FIG. 3B [sucrose preference test (SPT) (F3, 45=2.99)], FIG. 3C [FUST (F3,46=5.43)], and FIG. 3D [NSFT (F3,46=6.79)]. No difference was found for water sniffing or (FIG. 3E) home cage food consumption. Results are the mean±S.E.M., n=9-15/group. $P<0.05$, One-Way ANOVA and Duncan posthoc test.

FIG. 6 shows cell viability of ARPE-19 cells after treatment with the NMDAR agonist L-glutamate alone (1 mM L-Glu) or in combination with the NMDAR antagonists MK-801 (1 mM L-Glu+MK-801) and REL-1017 (1 mM L-Glu+REL-1017). ** $P<0.01$ vs vehicle (one-way ANOVA followed by Dunnett's post hoc test). The concentration of dextromethadone (Rel-1017) in all experiments is 30 microMolar.

In FIGS. 8A-8D, the marked cell nuclei appear white, while the immunofluorescence of p65 appears in greyscale.

DETAILED DESCRIPTION

Figure 1:
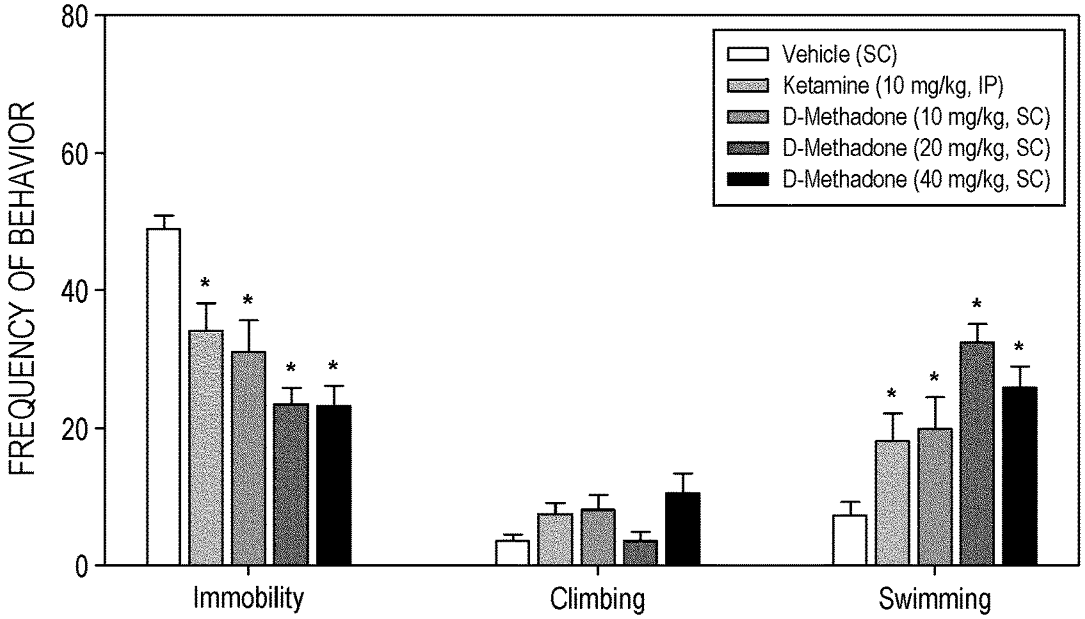
FIG. 1 shows the effects of ketamine and d-methadone on immobility, climbing and swimming counts in a Forced Swim Test ("FST"). Data represent mean±SEM. For immobility: *p=0.0034 for ketamine, 0.0007 for d-methadone 10 mg/kg, and <0.0001 for d-methadone 20 and 40 mg/kg compared to vehicle group, ANOVA. For climbing: *p<0.05 for d-methadone 40 mg/kg vs. vehicle. For swimming: *p<0.05 for ketamine and d-methadone 10 mg/kg, <0.0001 for d-methadone 20 mg/kg, and 0.0003 for d-methadone 40 mg/kg vs. vehicle, ANOVA.

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

For the purposes of this disclosure, the present inventors define "diseases" as human and veterinary diseases and conditions in their different stages, from preclinical stages to advanced stages, (including symptoms and signs of diseases, including prodromes and other manifestations of diseases), and aging (including accelerated aging and diseases due to physical and chemical factors, including environmental factors, toxins, and drugs, foods and lack of nutrients and vitamins).

For the purposes of this disclosure, the present inventors define "conditions" as cognitive underperformance relatively to the individual's potential and goals and deficits in social skills relatively to the individual's potential and goals and deficits I special senses relatively to the individual's potential and goals.

For the purposes of this disclosure, the present inventors define "treatment" as treatment and prevention and amelioration of diseases and conditions.

For the purposes of this disclosure, the present inventors define "Structurally Modified Opioids" (SMOs), the compositions-of-matter object of this disclosure, as new active pharmaceutical ingredients designed or derived from structural modifications of opioids, including modifications of molecules at any intermediate step of opioid synthesis.

For the purposes of this disclosure, the present inventors define as "opioids" synthetic and natural drugs that bind to opioid receptors, including agonists, partial agonists and antagonists, including opioid enantiomers, including especially opioids and opioid enantiomers with minimal or no clinically-relevant opioid agonist activity at doses that exert other pharmacological actions, e.g., NMDAR modulation, and including especially enantiomers with ion channel modulating activity, including especially modulators of N-methyl-D-aspartate receptors (NMDARs) and other ion channels, and including especially opioids and opioid enantiomers with minimal or no clinically relevant opioid activity with actions at other Nervous System (NS) receptors and transporters, including those resulting in changes in neurotransmitters such as serotonin, NE, DA, GABA, or changes in neurotrophic factors such as BDNF, or changes in synaptic proteins, such as PD95, GluR1, synapsin, NMDAR1 and including especially novel compounds with actions at both, NMDARs and nitric oxide pathways.

As described above, in one aspect of the invention, the present inventors now disclose that by modifying the structure of opioid drugs and their enantiomers, novel drugs (referred to herein as Structurally Modified Opioids or SMOs) can be designed and synthesized, those novel drugs having unique pharmacokinetic (PK) and pharmacodynamic (PD) properties with potentially safe and effective therapeutic actions including actions at glutamate receptors, including NMDARs and including differential actions at NMDAR subtypes, for the treatment and prevention of various diseases and conditions, including drugs for the improvement of cognitive and social skills.

In another aspect of the invention, the structural modification of an opioid or opioid enantiomer can be obtained: (a) by starting the synthetic process de novo; (b) by modifying the synthetic process for the opioid at any intermediate step during the synthesis of the racemate or of one enantiomer; or (c) by modifying the structure of the opioid or opioid enantiomer after the synthesis.

NMDARs may be the potential therapeutic targets of SMOs as described herein. In that regard, NMDARs are increasingly recognized as potential therapeutic targets for a multiplicity of human diseases caused by genetic or environmental factors, or a combination of genetic plus environmental (G+E) factors. Further, as described above, a single NMDAR antagonist/modulator will likely not be effective for the multiplicity of diseases implicated in NMDAR dysfunction. However, it is now disclosed by the present inventors that newly designed molecules (SMOs) may be useful for select diseases and conditions by targeting preferentially select cellular populations, cellular sites, brain areas, specific diseases, disease stages, conditions, and select periods of the subject's lifespan. The SMOs may be optimized for pharmacokinetic (PK) parameters (such as optimal lipid solubility for reaching select brain areas and/or select receptor sites in the CNS) or changes in metabolic parameters that may alter drug half-life, including half-life in select patient populations. Further, the SMOs may be optimized for pharmacodynamic (PD) parameters such as actions at select NMDARs domains and sites (such as the trans-membrane domain and the PCP site of NMDARs and or the extracellular domain and the NO site of NMDARs). And the SMOs may be optimized for certain NMDAR subtypes (e.g., NR1, NR2A-D, NR3A-B as detailed below), and potentially optimized for other select actions at different receptors (other than NMDARs) and transporters as detailed below.

The NMDAR in its tetrameric form is formed by more than 3000 amino acids. The protein complex is surrounded by extracellular medium, cytoplasm, and by the cellular membrane [depending on the region/domain of the NMDAR: amino-terminal domain (AMT), agonist binding domain (ABD), trans-membrane domain (TMD), carboxyl-terminal domain (CTD)]. The complex structure of this tetrameric allosteric system, and the multiplicity of variables it entails, including variations in subunits of NMDARs, [NR1, NR2A-D, NR3A-B, coded by seven distinct genes with genetic and epigenetic variances, including alternative splicing variants (NR1 comprehends 8 different splice variant isoforms), and SNPs of subunits], render the NMDAR a potential culprit for a multiplicity of diseases and a target for a multiplicity of different drugs. The differences in spatial (brain areas and circuits and neuronal sub-populations and non-neuronal cells, including astrocytes, or even extra CNS cellular populations expressing NMDARs) and temporal (age related) NMDAR and NMDAR subtype expression, the location of NMDARs on cell membranes (presynaptic and/or postsynaptic and synaptic and/or extra synaptic), the absolute number of NMDARs on the cell membrane (which varies among patients and diseases and or conditions and during development and across the lifespan and disease course of patients), the number of open and closed NMDA channels at a given time, the timing of the open and closed state during physiologic activity, during pathologic activity and during the block caused by a toxin or drug, the length of time the channel remains in the open state or closed state after activation or deactivation during physiologic conditions, pathologic conditions (including modulating effects by protons and pH, including desensitization from prolonged exposure to agonist/co-agonist and including effects on the receptor mediated by $Mg^{2+}$, $Zn^{2+}$, $Ca^{2+}$, NO, etc., or after modulation by a drug or a toxin, including endogenous toxins (e.g., quinolinic acid) or food (e.g., polyamine rich foods, alcohol), including excessive amounts of neurotransmitters (e.g., glutamate), the different effects of its open and closed state in specific cell membrane areas and within specific neuronal and astrocytic populations and in specific areas of the brain (or even extra CNS), and spatial (within particular brain areas or even outside the brain), and functional (within different cellular populations), and temporal (age related) variations in subunits, and the multiplicity of binding sites on the receptor tetrameric complex for agonists (glutamate/NMDA), co-agonists (glycine and d-serine) and modulators [(Mg and NO protons, $Zn^{2+}$ (blockers), and polyamines (activators)], and drugs (aminoglycosides, cisplatin) and toxins (domoic acid) and antibodies (NMDAR encephalitis), the multiplicity and variance of electric events that influence the NMDAR activity (changes in membrane potential), including minimal events, and their biochemical pathological and physiological consequences, and the events (including biochemical events) mediated by ion currents, especially $Ca^{2+}$, can all be differentially influenced by new chemical entities-(SMOs), specifically designed and optimized for modulation of NMDARs, with the potential for becoming new drugs.

These potential drugs (SMOs) are likely to have different effects in different cellular populations (including regulating the inhibitory function of certain inter-neurons that may be hyperactive or hypoactive and play a role in diseases like depression or restless leg syndrome and other diseases such as neurodevelopmental or neurodegenerative diseases), and different effects based on the inter-individual genetically determined variances in receptors, or variances in physiological and pathological states (neurodevelopmental diseases) or simply predisposition to certain diseases in the presence of certain environmental factors (G+E), variances in molecular structure of receptors and finally in the dysregulation and damage of NMDARs under pathological conditions (human diseases, including CNS degenerative diseases, including those caused by environmental factors (toxins), medical treatments and aging or even foods, for example polyamine rich foods or alcohol or lack of certain nutrients and vitamins) with consequential alterations in membrane potentials, biochemical responses including enzymatic cascades, and signaling cascades like Ras-ERK and their consequences, triggered by altered ionic currents through the NMDA receptor pore, including $Ca^{2+}$. These are all factors that highlight the multiplicity of roles and the complexity of the NMDARs in physiological and pathological states but also their importance and potential for becoming viable therapeutic targets for new safe and effective drugs, especially novel drugs with unique PK and PD characteristics that may be selective or simply safer and or more effective for specific diseases (Hansen K B, Yi F, Perszyk R E, Furukawa H, Wollmuth L P, Gibb A J, Traynelis S F. Structure, function, and allosteric modulation of NMDA receptors. J Gen Physiol. 2018 Aug. 6; 150(8): 1081-1105. doi: 10.1085/jgp.201812032. Epub 2018 Jul. 23. Review).

Channel Pore Blockers

Even subtle structural differences among different NMDAR blockers/modulators, including structural differences among drugs acting at the same domain (trans-membrane domain) and site (PCP site) of the NMDAR, such as for example, amantadine and memantine or PCP and ketamine, may alter their pharmacokinetic (PK) and their pharmacodynamic (PD) properties, including differential activity at receptor subtypes, and thus novel drugs (including drugs SMOs, drugs with similar but not identical chemical structure compared to opioids and opioid enantiomers) might offer potential advantages for select diseases and conditions and select patient populations. These advantages (or disadvantages) might originate even from subtle structural differences within very similar molecules. These structural molecular modifications might result in changes in PK and PD (and thus alter for example the effects on any of the NMDAR variables described above) resulting in effects that might be advantageous for subpopulations of patients.

Amantadine is FDA approved for Parkinson disease, while memantine, structurally very similar to amantadine but with a higher affinity for NR1-NR2B NMDAR subtype relatively to the NR1-NR2A subtype, is FDA approved for Alzheimer's disease (advanced and late stages only); dextromethorphan (in combination with quinidine, to off-set PK shortcomings due to its very short half-life) is FDA approved for patients with emotional lability secondary to pseudobulbar palsy; ketamine is approved as an anesthetic and is in current use for the treatment of depression in many specialized clinics in the USA, including clinics affiliated with Harvard Medical School. Ketamine's levo-enantiomer, esketamine, was recently granted FDA approval for use in depression. All of these drugs are thought to exert their therapeutic effects on the above listed very specific diseases and conditions through NMDAR modulation of dysfunctional, hyperactive receptors. Despite their putative action at a common domain and site of the NMDAR (trans-membrane domain and PCP site), with similar micromolar affinities, these drugs display different PK and PD profiles, and this holds true also for drugs with very similar structures, such as memantine and amantadine or PCP and ketamine. These PK/PD differences are likely to explain their select effectiveness for one but not another disease or indication associated with NMDAR dysfunction, including effectiveness in a particular stage of the same diseases and not another stage, as seen with memantine when used for the treatment of Alzheimer's disease.

Furthermore, among the NMDAR antagonists in current clinical use (amantadine for Parkinson disease, memantine for Alzheimer's disease, dextromethorphan for pseudobulbar palsy and ketamine for anesthesia and depression)—all of which appear to work at the same site (or in close proximity to each other) within the inner channel of the NMDAR, in proximity with the $Mg^{2+}$ site, at the so called PCP site, located within the trans-membrane portion of the NMDAR, with similar affinities in the micromolar range—indications differ widely. While dysfunctional NMDARs may be present in a multiplicity of diseases, including the diseases cited above and those listed in International Patent Application No. PCT/US2018/016159, the extent of dysfunction, the NMDAR location on cell membranes, on cell types, within specific cellular population and circuits and brain areas (or any of the variables listed above), are likely to differ substantially among different diseases and are likely to be influenced differentially by different drugs; and even within the same indication, the stage of the disease might determine the effectiveness or lack of effectiveness of the same drug (as indicated above, memantine is approved for moderate and severe Alzheimer's disease but did not show effectiveness for mild Alzheimer's disease). Also, amantadine and memantine are structurally very similar but their indications and effects are different. Along the same lines, a modification of the PCP molecule originated ketamine and the difference in "trapping, onset, offset" between these two drugs determine the clinical usefulness of ketamine and the lack of clinical indications and toxicity of PCP (Zanos P, Moaddel R, Morris P J, Riggs L M, Highland J N, Georgiou P, Pereira E F R, Albuquerque E X, Thomas C J, Zarate C A Jr, Gould T D. Ketamine and Ketamine Metabolite Pharmacology: Insights into Therapeutic Mechanisms. Pharmacol Rev. 2018 July; 70(3):621-660).

Thus, the NMDAR complex can be differentially influenced by drugs acting not only at different binding sites of the receptor but it can also be influenced differentially by drugs acting at the putative same site (PCP site) or in its close proximity with similar but not identical mechanisms and affinities, differences in onset/offset/trapping and differential affinities for specific NMDAR subtypes.

This premise underscores a great potential in the area of discovery of novel NMDAR antagonists because the unique PK and PD characteristics specific to the novel molecule will result in different actions and effects on cells. These actions and effects (e.g., blocking/modulating actions at the NMDARs), including their mechanisms (e.g., uncompetitive), may thus potentially prove beneficial for targeting specific diseases and disease stages. Furthermore, certain novel drugs disclosed by the present inventors (SMOs) are likely to exert other effects at sites different from NMDARs, as is the case for dextromethadone, and these effects might also be beneficial for specific diseases and patients (the "other effects" for dextromethadone are detailed below as examples for the potential "other effects" for SMOs).

Potential for NMDAR Modulation by Select Drugs in the Opioid Family

Select opioids and their enantiomers have NMDAR modulating effects and may potentially target specific diseases and conditions associated with NMDAR dysfunction, as disclosed by the inventors in Patent Application No. PCT/US2018/016159. Dextromethorphan, the d-isomer of the racemate racemethorphan is presently the only example of an opioid enantiomer with NMDAR blocking action and weak or clinically negligible opioidergic activity that is FDA approved, in combination with quinidine, for a specific neurologic indication, the treatment of emotional lability in pseudobulbar palsy. The development and approval of dextromethorphan in combination with quinidine (a drug with several drawbacks as detailed below) for a very specific indication (emotional lability in pseudobulbar palsy) is an example of the clinical usefulness of specific NMDAR modulators for specific indications, underscoring the unmet need for library of drugs with clinically tolerated NMDAR modulating effects and favorable PK and PD profiles in order to target select disease. Synthetic opioids have been designed and synthesized for optimal targeting of opioid receptors. By modifying the structure of select opioid drugs the present inventors are now for the first time optimizing the structure of opioid drugs for targeting NMDARs and NMDAR subtypes. In order to avoid or minimize effects of opioidergic drugs mediated by opioid receptors, opioid enantiomers with little or no opioid activity have previously been selected for development as NMDAR antagonists (see U.S. Pat. Nos. 6,008,258; 9,468,611; International Patent Application No. PCT/US2018/016159). While the opioid effects appear to be stereospecific, the NMDAR blocking effects are generally not stereospecific, allowing the choice of the lesser opioidergic enantiomer for development as a novel potential NMDAR modulator for a specific disease. The combination of opioids with opioid antagonists has also been proposed for opioidergic drugs with NMDAR antagonism, such as levorphanol, (International Patent Application No. PCT/US2018/016159), in order to block opioid effects while maintaining NMDAR modulating effects. While select opioid and opioid enantiomer drugs may potentially target diseases caused by NMDAR dysfunction, novel modifications of their structure (as proposed in this application for SMOs) will potentially result in new molecular entities that maintain certain NMDAR modulating properties while displaying favorable PK parameters (e.g., enhanced liposolubility or favorable metabolic parameters) and PD parameters (e.g., optimization of the SAR at NMDARs) advantageous for specific diseases, conditions and or patient populations.

As previously disclosed in the present inventors' International Patent Application No. PCT/US2018/016159, dextromethorphan has a very short half-life and may be ineffective for many disorders and patient subpopulations when used as a single agent. However, dextromethorphan was combined with quinidine to circumvent the very short half-life of dextromethorphan alone and found to be effective in pseudobulbar palsy (Ahmed A. et al., Pseudobulbar affect: prevalence and management. Therapeutics and Clinical Risk Management 2013; 9:483-489). And so, the US Food and Drug Administration (FDA) has approved dextromethorphan HBr and quinidine sulfate 20 mg/10 mg capsules (Nuedexta®; Avanir Pharmaceuticals, Inc) as the first treatment for pseudobulbar affect (PBA). Unfortunately, quinidine carries potentially fatal risks of arrhythmias and thrombocytopenia rendering Nuedexta® a weak candidate for further development for treatment of other disorders. In addition, dextromethorphan has an active metabolite and is subject to a CYP2D6 genetic polymorphism that results in variable pharmacokinetics and response in the population (Zhou S F. Polymorphism of human cytochrome P450 2D6 and its clinical significance: part II. Clin Pharmacokinet. 48:761-804, 2009). These are disadvantages compared to dextromethadone and potentially compared to its derivatives with NMDAR antagonism, and compared to other opioid drugs disclosed in International Patent Application No. PCT/US2018/016159 and their derivatives, including SMOs, disclosed in the present application, and including a structural modified dextromethorphan molecule: modifications of the dextromethorphan molecule, similar to the modifications outlined below for SMOs, may change its PK and PD profile and render the new modified drugs safe and effective for select conditions.

As disclosed above, the inventors have been performing preclinical (in vitro and in vivo) and clinical development work with racemic methadone and its isomers, in particular with dextromethadone, for over two decades. Dextromethadone [d-methadone; (+)-methadone); S-methadone] is one of the two opioid enantiomers of the racemate, dl-methadone (methadone). The methadone racemate dl-methadone has been in clinical use for over 60 years for the treatment of pain and opioid addiction. Dextromethadone a novel NMDA antagonist, currently undergoing development for a multiplicity of clinical indications, has clinically negligible opioid effects and favorable PK and PD profiles, as discovered by the inventors in phase 1 clinical studies (Bernstein G, Davis K, Mills C, Wang L, McDonnell M, Oldenhof J, Inturrisi C, Manfredi P L, Vitolo O V. Characterization of the Safety and Pharmacokinetic Profile of D-Methadone, a Novel N-Methyl-D-Aspartate Receptor Antagonist in Healthy, Opioid-Naive Subjects: Results of Two Phase 1 Studies J Clin Psychopharmacol. 2019 May/June; 39(3): 226-237) and as disclosed in International Patent Application No. PCT/US2018/016159. While dextromethadone might prove itself useful for the treatment of one or more diseases, one or more structural modifications of the dextromethadone molecule and the structural modification of other select opioids disclosed in the present applications (SMOs) might render the PK/PD parameters of the resulting new chemical entities more favorable for specific diseases and conditions and offer PK and PD advantages over dextromethadone and other available NMDAR antagonists and potentially useful for different patient populations and for select diseases.

NMDAR Dysfunction Including Glutamate Excitotoxicity

Excitotoxicity is cellular damage caused by excessive extracellular glutamate (the main excitatory amino acid) resulting in excessive activation of NMDARs (and other ionotropic glutamate-activated membrane receptors such as AMPA receptors and kainate receptors). Importantly, NMDAR hyperactivity can also occur in the presence of normal glutamate levels if NMDARs are over-stimulated not by glutamate but for example by endogenous toxins (such as quinolinic acid) or by exogenous toxins (aminoglycoside toxicity is an example of hyper-stimulation of NMDARs conducive to damage to a select cellular population, the of hair cells in the inner ear, and consequential hair cell loss and deafness at physiologic glutamate levels; dietary polyamines may also cause NMDAR hyperstimulation). Other toxins, including autoantibodies, as is the case in NMDAR encephalitis, may cause NMDAR hyperstimulation in the presence of physiologic glutamate levels and potentially cause toxicity in select neuronal populations and neuronal circuits and cause diseases in normal and or genetically vulnerable patients. This is a point to be taken into account when considering that dysfunction of the NMDAR is implicated in a multiplicity of diseases. Even when the disease is clearly caused by a genetic mutation, hereditary or sporadic, the mechanism for cellular damage can be hyper-activation of NMDARs, even in face of physiologic glutamate levels. SMOs might therefore represent a potential treatment for a multiplicity of diseases and a select SMO may be selective for a certain genetic disease and or for disease caused by environmental factors (e.g., disease caused by exposure to toxins, including medical treatments, or even diseases caused by lack of select nutrients) or probably more commonly, a disease caused by genetic factors (predisposition to NMDAR toxicity)+environmental factors (toxins or lack of select nutrients) thus falling into the G+E paradigm cited above.

In its mildest form, NMDAR hyperactivity, caused by excessive glutamate or by another cause, might be limited to temporary synaptic malfunction or dendritic loss or other minor abnormalities (e.g., dendritic pruning defect), which might represent reversible conditions. This concept of reversible NMDAR related toxicity has important therapeutic and preventive implications, for conditions such as normal aging of neuronal populations or diseases and conditions like depression, ADHD, PTSD, anxiety disorders including SAD, RLS, temporary cognitive impairment and many other diseases and conditions where neuronal irreversible damage or death, while possibly present in severe forms, might not be a driving factor. These are diseases where alteration of neuronal function or neuronal circuitry prevail as the main pathogenetic mechanism as opposed to diseases where actual neuronal loss appears more prominent (e.g., Alzheimer's disease, Parkinson disease, ALS et cetera). As mentioned above, even potentially "reversible" NMDAR related toxicity might also progress towards the triggering of apoptotic cascades with irreversible neuronal damage and death, such as in a multiplicity of neurodevelopmental and in neurodegenerative diseases, underscoring the potential of NMDAR modulators in secondary prevention of diseases and conditions.

In the classic excitotoxicity paradigm, in the context of acute conditions, such as trauma and ischemia, a sudden release of excessive glutamate can cause excitotoxicity in the surrounding tissue and amplify acute necrosis and cell death from the primary event. Glutamate is the most important excitatory neurotransmitter and is responsible for over 90% of excitatory communications among neurons. Glutamate is mostly intracellular, where it is internalized into synaptic vesicles. The brain contains approximately 10 mMol of intracellular glutamate and 0.6 microM of extracellular glutamate. The physiologic extracellular concentration during excitatory neuronal communications may be as high as 1 mM but this high extracellular concentration only lasts for a few msec under physiological conditions. The activation of the NMDAR—the opening of the channel—triggered under physiological conditions by glutamate lasts longer than the pulse stimulation from glutamate, tens to hundreds of mSec. In other words, the NMDAR channel remains open for longer than the time it takes for the extracellular glutamate to decay to resting levels. The toxic extracellular concentration of extracellular glutamate can be as low as 2-4 microM if the exposure is prolonged, and thus the resting synaptic physiological concentration (0.6 microM) is close to the concentration that is toxic for cells, while the intracellular "reserve" of glutamate very high (10 mM). This very high content of intracellular glutamate content poses high potential for damage of surrounding neurons in case of excessive release of glutamate (excitotoxicity). As stated above, NMDARs can also be overactive when brain glutamate is at physiologic levels and thus NMDAR blockers and modulators can also be therapeutic when glutamate is at physiologic concentrations and NMDARs are dysregulated for reasons other than excessive glutamate (e.g., select toxins).

Glutamate mediated physiologic neuronal activity intervenes in many sensory, motor and association physiologic neuronal pathways and thus is essential for normal NS functioning, including sensory (including special senses such as vision, hearing, olfaction and taste) and motor activities. Additionally, by intervening in neuronal plasticity mediated by NMDARs and other ionotropic glutamate receptors (AMPA and kainate receptors), glutamate is essential for LTP, LTD, experience determined synaptic refinement, which are essential for proper development, and thus memory formation, learning, mood setting and ultimately thinking and behavior. Finally, by influencing neuronal activity and survival, e.g., via modulation of BDNF or modulation of synaptic proteins, as previously shown by the inventors, or by other mechanisms, NMDARs are also likely to influence the function, trophism and aging not only of the nervous system, but the trophism and aging of all organs and systems, because proper neuronal functioning influences function, trophism and aging of all other tissues, organs and systems through innervation. Additionally, NMDAR also serve important functions on extra CNS cells (Jie Du, Xiao-Hui Li, Yuan-Jian Li. Glutamate in peripheral organs: Biology and pharmacology. European Journal of Pharmacology 784 (2016) 42-48) with implications on treatment of diseases secondary to NMDAR dysfunction in cells that are not part of the nervous system. The intentional design of new molecules (in the case of this disclosure, new SMOs) with little or no CNS penetration, e.g., polarized or larger molecules that cannot cross the blood brain barrier, and thus are devoid of potential CNS effects, may be conducive to the development of new drugs for the treatment of disorders caused by dysfunction of NMDARs outside of the CNS.

The present inventors performed an experiment demonstrating the presence of NMDARs on retinal epithelial pigment cells. The present inventors then demonstrated the susceptibility of these cells to glutamate induced toxicity and toxicity from inflammatory mediators, and finally the present inventors showed that the NMDAR modulator dextromethadone prevents toxicity in these cells (see the Example section, below). These new data underscore the potential for SMOs for treating diseases originating from dysfunctional NMDARs situated outside the CNS.

The NMDAR is a positive allosteric system requiring the balanced binding of an agonist (glutamate) a co-agonist (glycine or d-serine), modulating factors such as $Zn^+$, NO, protons (pH), polyamines, and the contribution of a regulatory physiologic channel blocker ($Mg^{2+}$) for proper functioning.

The NMDAR tetramer complex is assembled from seven different protein subtypes. NR1 is mandatory and required for membrane expression; NR2 A-D, and NR3 A-B are the other subtypes. These seven proteins are coded by seven distinct genes with differential expression depending on regional (different NMDA subtypes in different brain areas, neuronal populations, neuronal circuits) and temporal factors (for example, NR3A expression is relatively higher at younger ages and decreases toward adulthood, whereas NR3B expression gradually increases over development.

NR1 protein does not fluctuate much across different ages; NR2A and NR2B also exhibit differential expression at different stages of development). Furthermore, NR2B may be more prominent at extra synaptic locations and thus its presence may render cells more vulnerable to excitotoxicity (the preferential block by memantine of this receptor subtype, NR1-NR2B complex, may render this drug particularly apt in preventing excitotoxicity in certain diseases). The NMDAR expressing NR2C and NR2D and NR3A and NR3B may be more resistant to the magnesium block and thus may be active (open channel) even when neurons are in the hyperpolarized state compared to NR1-NR2A and NR1-NR2B and tri-heterotetramers NR1-NR2A-NR2B complexes that require the voltage gated expulsion of $Mg^{2+}$ for activation (opening of the channel pore), mediated via AMPARs. NR3 NMDAR subtypes, which are resistant to the magnesium block and less permeant to $Ca^{2+}$, may intervene during minimal synaptic events and influence regulation of dendritic proteins and thus synapse plasticity. Furthermore, only glycine is required for activation of NR3 NMDARs while glutamate and NMDA do not act as agonists at these receptors and thus the MR3 bearing receptors, while still classified among NMDARs because of their structural similarities with other NMDAR subtypes, are functionally distinct because of their lack of activation by NMDA, resistance to $Mg^{2+}$ block and relative impermeability to $Ca^{2+}$. Also, MK-801 and memantine are less active at NR3A-B compared to their activity in blocking channels containing NR2 subunits (Chian-Ming Low and Karen Siaw-Ling WeeNew Insights into the Not-So-New NR3 Subunits of N-Methyl-D-aspartate Receptor: Localization, Structure, and Function. Mol Pharmacol 78:1-11, 2010). While most SMOs are more likely to act at NMDAR with the NR2 subunits, it is also possible that select SMOs may instead target NMDARs with NR3A-B subunits or the mixed NR1-NR2/NR3 tri-heterotetramers subtypes and thus they may potentially help define the role of the N3A-B receptor subtypes in disease and as therapeutic targets for SMOs.

Because of the NMDARs widespread presence and their essential role in virtually all physiological NS activities (and many extra nervous system activities), it is not surprising that competitive agonist and co-agonists interfere too strongly and/or too widely and too unpredictably with normal physiologic activities and thus cannot be clinically tolerated because of side effects. It is also not surprising that competitive agonist and co-agonists should bear NMDAR effects that cannot be predicted and tuned (modulated) for treatment of select diseases. High affinity NMDA channel blockers are also poor candidates as therapeutic agents because they have the potential for remaining trapped within the channel and result in a persistent block that results in severe side effects. The designer drug MK-801 (dizocilpine) may induce coma; the illicit drug phencyclidine (PCP; "angel dust") causes hallucinations. Ketamine, an FDA approved anesthetic derived from PCP, is a low-affinity NMDAR uncompetitive antagonist with a faster "off rate" compared to dizocilpine and PCP, resulting in lesser "trapping"; however, ketamine it is likely to remain a bit too long within the channel for clinical tolerability outside of anesthetic indications or select psychiatric indications. In fact, ketamine determines clinical effects such as sedation and dissociation, which can be advantageous for anesthetic indications (for anesthesia ketamine is used in higher doses compared to the doses that are used for depression). These ketamine effects (sedation and dissociation) remain however unwanted when the indication is, for example, major depressive disorder and not anesthesia; in select cases, e.g., severe cases of treatment resistant depression, sedation and dissociation may be acceptable side effects, if short lived as is the case with intranasal esketamine, recently approved by the FDA for certain patients with depression. Once the NMDAR antagonist/modulator binds to its target binding site within the receptor, it should be released shortly thereafter—without being trapped in the pore of the NMDAR complex and thus this release should happen within a reasonable amount of time—"off rate" (offset)—otherwise it will remain within the channel too long and interfere with physiologic activities (learning, memory formation etc.) and cause sedation and psychotomimetic side effects. MK-801, PCP, and ketamine are subject to "trapping" at decreasing rates: 100% MK-801, 98% PCP and 86% ketamine (Zanos et al. 2018). The timing of the NMDAR antagonists for entering the open channel is also a point to consider: when the channel opens for only a few msec during normal phasic physiological activities, for example for LTP during memory formation and during learning, it would be preferable that the drug should not enter the open channel, so the "on rate" (onset), the time it takes for the drug to enter the open channel, should be closer to 1 second (several hundred msec) rather than only a few tens of msec, the timing of physiologic activity. Thus, NMDAR modulators have a narrow window for both the "on rate"—onset—[should not be too fast (side effects) or too slow (ineffective)] and the "off rate"—offset—[should also not be too fast (ineffective, magnesium-like block) or too slow (side effects, MK-801 and PCP type block)]. Other factors may also come into play, such as the dose and the serum drug level (as exemplified by the different dosages of ketamine for anesthesia and depression) and the clinical indication and the stage of the disease within the same clinical indication (e.g., memantine is effective for moderate and advanced Alzheimer's but not for mild Alzheimer's). Ketamine at higher doses for anesthesia and at lower doses for depression is an example of the differential clinical uses of the same drug for different indications, even within a narrow therapeutic window. Another less common form of narrow therapeutic window may be referred not to the dosage but to the stage of disease: while the NMDA receptor block characteristics of memantine—with its on rate of 1 second and its off rate close to 5 seconds—might render this drug useful for moderate to severe Alzheimer's, its actions were not found effective for mild Alzheimer's where a drug with slightly different onset and offset actions might instead be effective.

The ideal NMDAR modulator candidate is likely to be a different drug for different diseases, and even a different drug for different stages of the same disease, and may also differ in specific patient subpopulations and for the age of the patient. Each novel SMO drug, by offering different PK and PD characteristics, may offer advantages for specific diseases and conditions and patient populations. More lipophilic drugs may preferentially target NMDARs more difficult to reach, such as those parts of super-complexes (see details below) and therefore among the SMOs disclosed in this application, tri-halogen compounds or fluoro-derivatives may be especially advantageous in certain diseases or patient sub-populations where super-complexes are affected. The selection of a specific indication for a particular SMO is likely to become increasingly better defined while moving from the initial phases of development of the new drugs, starting from the design of novel unique chemical formulas that among other features must also take into account drug polarity and molecular size for Blood Brain Barrier (BBB) crossing and preferential targeting of select brain areas and specific SAR for NMDAR (this can be seen below in the library of newly designed compounds discussed and described as "Design, Molecular Modeling, Synthesis and Testing of Structurally Modified Opioids with NMDAR Modulating Activity").

Design, Molecular Modeling, Synthesis, and Testing of Structurally Modified Opioids with NMDAR Modulating Activity In order to optimize the chemical structure of SMOs for their activity at NMDARs, including differential activity at NMDAR subtypes that may be preferentially modulated or blocked for targeting specific diseases and conditions triggered, maintained or worsened by dysfunctional NMDARs, the present inventors designed a first set of SMOs, new chemical entities, optimized for their structure activity relationship (SAR) with the NMDAR based on the known NMDAR affinities of select opioid drugs and ongoing in-silico testing for newly designed SMOs. In addition to PD parameters related to SAR with NMDARs, SMOs are optimized for PK parameters such as enhanced liposolubility. New mechanisms of potential additional sites of NMDAR block were also considered in the design of SMOs, e.g., in the case of nitro-derivatives of opioids and opioid enantiomers and in particular of nitro-derivatives of dextromethadone: as detailed in the application SMO nitro-derivatives may have additional NMDA modulating actions by interfacing with the amino-terminal domain of NMDA receptors. The present inventors then proceeded to test these compounds in a new computational model developed ad hoc of the NMDAR trans-membrane domain (in silico static+dynamic modeling) for affinity towards the putative PCP binding site of the NMDAR. The in silico ranking (static and dynamic), in addition to directly selecting SMOs by determining the putative ligand/receptor affinities that aid in prioritizing the synthesis of SMOs designated for further testing, generates information on the SAR and thus also aids in the design of additional SMOs optimized for NMDAR channel blocking activity.

Different lipophilic gradients will determine differential binding to CNS NMDARs that may be more or less accessible, e.g., NMDARs that are part of super-complexes might be less accessible to less lipophilic molecules. Of note dextromethadone increased PD95 levels in a rat model of depression (as detailed below, and in FIG. 4B); PD95 proteins are essential for the formation of supercomplexes containing NMDARs. The present inventors have also designed compounds that do not cross the BBB for targeting peripheral NMDARs while purposefully sparing NMDAR located in the CNS; these compounds will be tested for clinical indications where the dysfunctional NMDARs are primarily located outside of the CNS. Aside from lipophilic gradients, molecular weight of the SMOs, their synthetic feasibility, and their putative stability, were all considered in the design of these new molecules (SMOs) and in the development plan for new clinically safe SMOs optimized for selective NMDAR activity.

As mentioned above and throughout the application a subset of SMOs were designed to introduce a nitric ester group resulting in nitro-SMOs in order to potentially modulate NMDA receptor activity by S-nitrosylation of the sulfhydryl group of the cysteine residue on its N-terminus (or extracellular amino-domain of the NMDAR). As described above, this might result in differential PD effects at the level of the open channel of the NMDAR in the extracellular domain rather than solely in the trans-membrane domain of the NMDAR as it might be the case for dextromethadone and other non-nitro-SMOs. Nitrosylation may also provide protection against reactive nitrogen species (RNS) as described above in the application, thus providing additional means of cellular protection, aside for the action on the open channel of NMDARs and thus offering additional therapeutic properties.

Once the synthetic work of SMOs selected on the basis of in silico results is done, results from electrophysiological studies from the different sets of SMOs, aside from informing on NMDAR blocking activity of each compound, including differential affinity for NMDARs subtypes, will also provide additional insight into the SAR of additional new agents in order to design follow-up generations of NMDARs blockers by further modifications of the section of the molecule of the SMOs most relevant for the NMDAR block.

Figure 10:
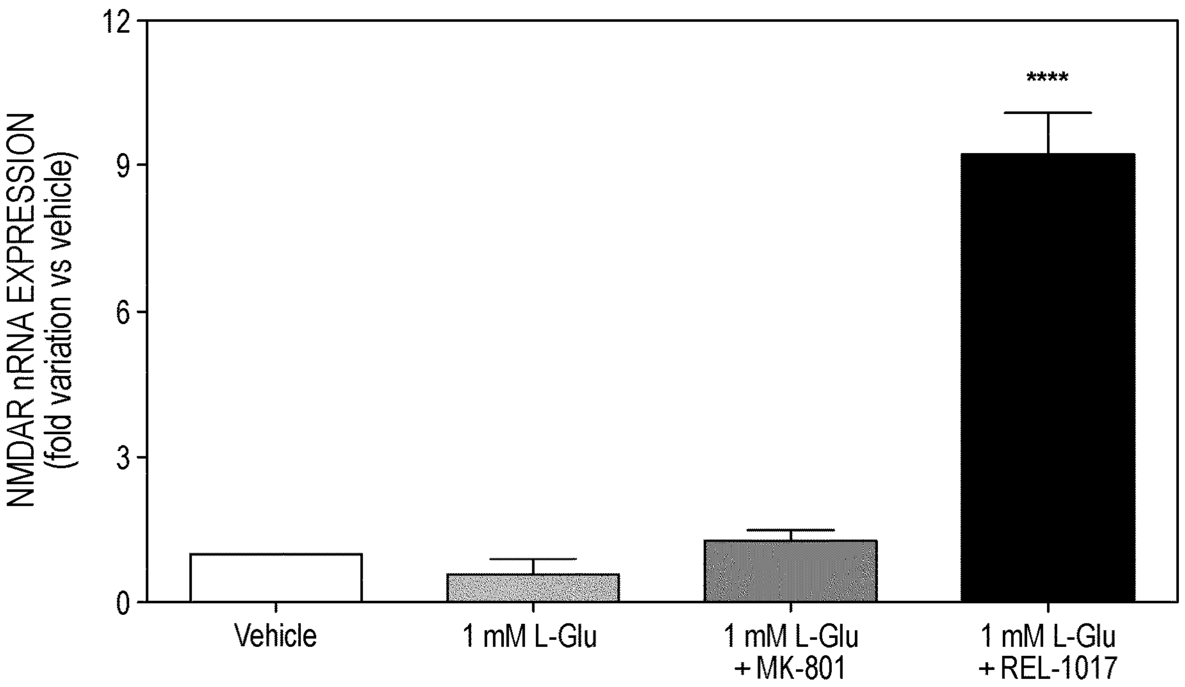
FIG. 10 shows relative quantification of NMDAR1 gene expression in ARPE-19 cells after the following treatment conditions: L-glutamate (1 mM L-Glu), pretreatment was performed with MK-801 (1 mM L-Glu+MK-801) or REL-1017 (1 mM L-Glu+REL-1017). ****$P<0.0001$ vs vehicle (one-way ANOVA followed by Dunnett's post hoc test).

Fluoro-derivatives, nitro-derivatives and fluoro-nitro-derivatives and deuterated fluoro-derivatives, deuterated nitro-derivatives and deuterated fluoro-nitro-derivatives are of particular interest for optimization of SAR with the NMDAR, because of the potential for improving PK parameters (especially for fluoro-derivatives) and because of additional NMDAR modulating mechanisms and prevention of RNS cellular damage (especially for nitro-derivatives). The present inventors have already shown that select deuterated dextromethadone molecules may act preferentially at select NMDAR receptor subtypes (GluN1-GluN2B tetramers) and that dextromethadone increases PD95, an essential component of supercomplexes at the post-synaptic density containing NMDARs. The inventors also showed that dextromethadone increases GluR1 (FIG. 4B), in vivo, and mRNA for NMDAR1, in vitro, (FIG. 10). The expression of both receptors, AMPAR and NMDAR is thus potentially modulated by dextromethadone. In addition to fluoro-derivatives, nitro-derivatives and fluoro-nitro-derivatives, the molecules obtained by combining deuteration with fluoro and nitroderivatives are of particular interest for this disclosure.

In addition to the extensive work on dextromethadone, this disclosure also focuses on other opioid enantiomers of interest such as dextroisomethadone, levomoramide, levopropoxyphene, levorphanol, dextromethorphan and N-methyl-dextromethadone by characterizing the NMDAR affinities of these compounds in a newly developed ad hoc molecular model of the trans-membrane domain of the NMDAR and by designing structural modifications of these opioids followed by further in-silico testing and then proceeding with the development plan outlined above for dextromethadone (further in silico testing with improved definition of SAR, synthesis of the molecules, electrophysiological testing, in vitro and in vivo testing and again improved definition of SAR and design of additional new molecules).

In general, then, the following formulae (Formulae I-VII, below) are examples of the newly designed compounds associated with the present invention. Those compounds are as follows:

A compound having a structure analogue to dextromethadone according to formula I:

(I)

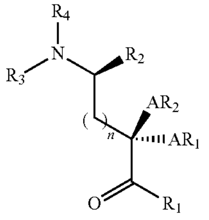

wherein $R_1$ is selected from the group consisting of alkyl, aryl, $C_3$-$C_{12}$ cycloalkyl, or heterocyclyl, any of which are optionally substituted at one or more positions by deuterium, halogen, alkyl, hydroxy, alkoxy, aryl, aryloxy, heterocyclyl, nitro, nitric acid ester;

$AR_1$ is selected from the group consisting of aryl or heterocyclyl, any of which are optionally substituted at one or more positions by deuterium, halogen, alkyl, hydroxy, alkoxy, aryl, aryloxy, heterocyclyl, nitro, nitric acid ester;

$AR_2$ is selected from the group consisting of aryl or heterocyclyl, any of which are optionally substituted at one or more positions by deuterium, halogen, alkyl, hydroxy, alkoxy, aryl, aryloxy, heterocyclyl, nitro, nitric acid ester;

$R_2$ is hydrogen, deuterium or selected from the group consisting of alkyl, aryl, $C_3$-$C_{12}$ cycloalkyl, or heterocyclyl, any of which are optionally substituted at one or more positions by deuterium, halogen, alkyl, hydroxy, alkoxy, aryl, aryloxy, heterocyclyl, nitro, nitric acid ester;

$R_3$ is alkyl optionally substituted at one or more positions by deuterium, halogen, hydroxy, alkoxy, nitric acid ester;

$R_4$ is alkyl optionally substituted at one or more positions by deuterium, halogen, hydroxy, alkoxy, nitric acid ester; and n is comprised between 1 and 4.

A compound having a structure analogue to levopropoxyphene according to formula II:

(II)

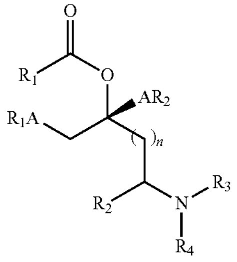

wherein $R_1$ is selected from the group consisting of alkyl, aryl, $C_3$-$C_{12}$ cycloalkyl, or heterocyclyl, any of which are optionally substituted at one or more positions by deuterium, halogen, alkyl, hydroxy, alkoxy, aryl, aryloxy, heterocyclyl, nitro, nitric acid ester;

$AR_1$ is selected from the group consisting of aryl or heterocyclyl, any of which are optionally substituted at one or more positions by deuterium, halogen, alkyl, hydroxy, alkoxy, aryl, aryloxy, heterocyclyl, nitro, nitric acid ester;

$AR_2$ is selected from the group consisting of aryl or heterocyclyl, any of which are optionally substituted at one or more positions by deuterium, halogen, alkyl, hydroxy, alkoxy, aryl, aryloxy, heterocyclyl, nitro, nitric acid ester;

$R_2$ is hydrogen, deuterium or selected from the group consisting of alkyl, aryl, $C_3$-$C_{12}$ cycloalkyl, or heterocyclyl, any of which are optionally substituted at one or more positions by deuterium, halogen, alkyl, hydroxy, alkoxy, aryl, aryloxy, heterocyclyl, nitro, nitric acid ester;

$R_3$ is alkyl optionally substituted at one or more positions by deuterium, halogen, hydroxy, alkoxy, nitric acid ester;

$R_4$ is alkyl optionally substituted at one or more positions by deuterium, halogen, hydroxy, alkoxy, nitric acid ester; and n is comprised between 1 and 4.

A compound having a structure analogue to dextroisomethadone according to formula III:

(III)

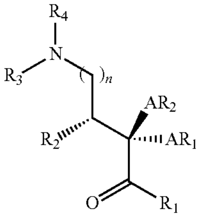

wherein $R_1$ is selected from the group consisting of alkyl, aryl, $C_3$-$C_{12}$ cycloalkyl, or heterocyclyl, any of which are optionally substituted at one or more positions by deuterium, halogen, alkyl, hydroxy, alkoxy, aryl, aryloxy, heterocyclyl, nitro, nitric acid ester;

$AR_1$ is selected from the group consisting of aryl or heterocyclyl, any of which are optionally substituted at one or more positions by deuterium, halogen, alkyl, hydroxy, alkoxy, aryl, aryloxy, heterocyclyl, nitro, nitric acid ester;

$AR_2$ is selected from the group consisting of aryl or heterocyclyl, any of which are optionally substituted at one or more positions by deuterium, halogen, alkyl, hydroxy, alkoxy, aryl, aryloxy, heterocyclyl, nitro, nitric acid ester;

$R_2$ is hydrogen, deuterium or selected from the group consisting of alkyl, aryl, $C_3$-$C_{12}$ cycloalkyl, or heterocyclyl, any of which are optionally substituted at one or more positions by deuterium, halogen, alkyl, hydroxy, alkoxy, aryl, aryloxy, heterocyclyl, nitro, nitric acid ester;

$R_3$ is alkyl optionally substituted at one or more positions by deuterium, halogen, hydroxy, alkoxy, nitric acid ester;

$R_4$ is alkyl optionally substituted at one or more positions by deuterium, halogen, hydroxy, alkoxy, nitric acid ester; and n is comprised between 1 and 4.

A compound having a structure analogue to levomoramide according to formula IV:

(IV)

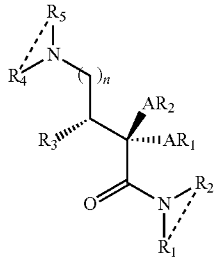

wherein $NR_1R_2$ is optionally cyclized through $C_3$-$C_{12}$ cycloalkyl, or heterocyclyl, any of which are optionally substituted at one or more positions by deuterium, halogen, alkyl, hydroxy, alkoxy, aryl, aryloxy, heterocyclyl, nitro, nitric acid ester;

If $NR_1R_2$ is not cyclized $R_1$ is selected from the group consisting of alkyl, aryl, $C_3$-$C_{12}$ cycloalkyl, or heterocyclyl, any of which are optionally substituted at one or more positions by deuterium, halogen, alkyl, hydroxy, alkoxy, aryl, aryloxy, heterocyclyl, nitro, nitric acid ester. $R_2$ is hydrogen, deuterium or selected from the group consisting of alkyl, aryl, $C_3$-$C_{12}$ cycloalkyl, or heterocyclyl, any of which are optionally substituted at one or more positions by deuterium, halogen, alkyl, hydroxy, alkoxy, aryl, aryloxy, heterocyclyl, nitro, nitric acid ester;

$AR_1$ is selected from the group consisting of aryl or heterocyclyl, any of which are optionally substituted at one or more positions by deuterium, halogen, alkyl, hydroxy, alkoxy, aryl, aryloxy, heterocyclyl, nitro, nitric acid ester;

$AR_2$ is selected from the group consisting of aryl or heterocyclyl, any of which are optionally substituted at one or more positions by deuterium, halogen, alkyl, hydroxy, alkoxy, aryl, aryloxy, heterocyclyl, nitro, nitric acid ester;

$R_3$ is hydrogen; or selected from the group consisting of alkyl, aryl, $C_3$-$C_{12}$ cycloalkyl, or heterocyclyl, any of which are optionally substituted at one or more positions by deuterium, halogen, alkyl, hydroxy, alkoxy, aryl, aryloxy, heterocyclyl, nitro, nitric acid ester;

$NR_4R_5$ is optionally cyclized through $C_3$-$C_{12}$ cycloalkyl, or heterocyclyl, any of which are optionally substituted at one or more positions by deuterium, halogen, alkyl, hydroxy, alkoxy, aryl, aryloxy, heterocyclyl, nitro, nitric acid ester;

If $NR_1R_2$ is not cyclized $R_1$ is selected from the group consisting of alkyl, aryl, $C_3$-$C_{12}$ cycloalkyl, or heterocyclyl, any of which are optionally substituted at one or more positions by deuterium, halogen, alkyl, hydroxy, alkoxy, aryl, aryloxy, heterocyclyl, nitro, nitric acid ester. $R_2$ is hydrogen, deuterium or selected from the group consisting of alkyl, aryl, $C_3$-$C_{12}$ cycloalkyl, or heterocyclyl, any of which are optionally substituted at one or more positions by deuterium, halogen, alkyl, hydroxy, alkoxy, aryl, aryloxy, heterocyclyl, nitro, nitric acid ester; and n is comprised between 1 and 4.

A compound having a structure analogue to N-methyl-dextromethadone according to formula V:

(V)

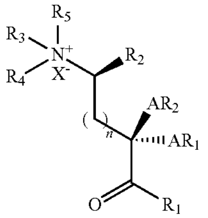

wherein $R_1$ is selected from the group consisting of alkyl, aryl, $C_3$-$C_{12}$ cycloalkyl, or heterocyclyl, any of which are optionally substituted at one or more positions by deuterium, halogen, alkyl, hydroxy, alkoxy, aryl, aryloxy, heterocyclyl, nitro, nitric acid ester;

$AR_1$ is selected from the group consisting of aryl or heterocyclyl, any of which are optionally substituted at one or more positions by deuterium, halogen, alkyl, hydroxy, alkoxy, aryl, aryloxy, heterocyclyl, nitro, nitric acid ester;

$AR_2$ is selected from the group consisting of aryl or heterocyclyl, any of which are optionally substituted at one or more positions by deuterium, halogen, alkyl, hydroxy, alkoxy, aryl, aryloxy, heterocyclyl, nitro, nitric acid ester;

$R_2$ is hydrogen, deuterium or selected from the group consisting of alkyl, aryl, $C_3$-$C_{12}$ cycloalkyl, or heterocyclyl, any of which are optionally substituted at one or more positions by deuterium, halogen, alkyl, hydroxy, alkoxy, aryl, aryloxy, heterocyclyl, nitro, nitric acid ester;

$R_3$ is alkyl optionally substituted at one or more positions by deuterium, halogen, hydroxy, alkoxy, nitric acid ester;

$R_4$ is alkyl optionally substituted at one or more positions by deuterium, halogen, hydroxy, alkoxy, nitric acid ester;

$R_5$ is alkyl optionally substituted at one or more positions by deuterium, halogen, hydroxy, alkoxy, nitric acid ester;

$X^-$ is the nitrogen-counter-ion; and n is comprised between 1 and 4.

A compound having a structure analogue to levorphanol according to formula VI:

(VI)

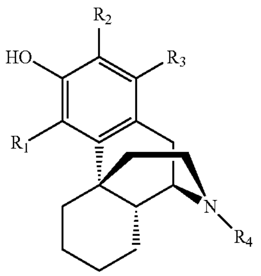

wherein $R_1$ is hydrogen, deuterium, halogen, hydroxyl, nitro, nitric acid ester or selected from the group consisting of alkyl, alkoxy, aryl, aryloxy, heterocyclyl, any of which are optionally substituted at one or more positions by deuterium, halogen, alkyl, hydroxy, alkoxy, aryl, aryloxy, heterocyclyl, nitro, nitric acid ester;

$R_2$ is hydrogen, deuterium, halogen, hydroxyl, nitro, nitric acid ester or selected from the group consisting of alkyl, alkoxy, aryl, aryloxy, heterocyclyl, any of which are optionally substituted at one or more positions by deuterium, halogen, alkyl, hydroxy, alkoxy, aryl, aryloxy, heterocyclyl, nitro, nitric acid ester;

$R_3$ is hydrogen, deuterium, halogen, hydroxyl, nitro, nitric acid ester or selected from the group consisting of alkyl, alkoxy, aryl, aryloxy, heterocyclyl, any of which are optionally substituted at one or more positions by deuterium, halogen, alkyl, hydroxy, alkoxy, aryl, aryloxy, heterocyclyl, nitro, nitric acid ester; and $R_4$ is hydrogen or selected from the group consisting of alkyl, alkoxy, aryl, aryloxy, heterocyclyl, any of which are optionally substituted at one or more positions by deuterium, halogen, alkyl, hydroxy, alkoxy, aryl, aryloxy, heterocyclyl, nitro, nitric acid ester.

A compound having a structure analogue to dextromethorphan or dextrorphan according to formula VII:

(VII)

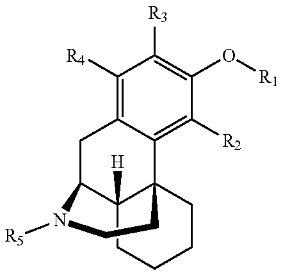

wherein $R_1$ is hydrogen, nitric acid ester or selected from the group consisting of alkyl, alkoxy, aryl, aryloxy, heterocyclyl, any of which are optionally substituted at one or more positions by deuterium, halogen, alkyl, hydroxy, alkoxy, aryl, aryloxy, heterocyclyl, nitro, nitric acid ester;

$R_2$ is hydrogen, deuterium, halogen, hydroxyl, nitro, nitric acid ester or selected from the group consisting of alkyl, alkoxy, aryl, aryloxy, heterocyclyl, any of which are optionally substituted at one or more positions by deuterium, halogen, alkyl, hydroxy, alkoxy, aryl, aryloxy, heterocyclyl, nitro, nitric acid ester;

$R_3$ is hydrogen, deuterium, halogen, hydroxyl, nitro, nitric acid ester or selected from the group consisting of alkyl, alkoxy, aryl, aryloxy, heterocyclyl, any of which are optionally substituted at one or more positions by deuterium, halogen, alkyl, hydroxy, alkoxy, aryl, aryloxy, heterocyclyl, nitro, nitric acid ester;

$R_4$ is hydrogen, deuterium, halogen, hydroxyl, nitro, nitric acid ester or selected from the group consisting of alkyl, alkoxy, aryl, aryloxy, heterocyclyl, any of which are optionally substituted at one or more positions by deuterium, halogen, alkyl, hydroxy, alkoxy, aryl, aryloxy, heterocyclyl, nitro, nitric acid ester; and $R_5$ is hydrogen or selected from the group consisting of alkyl, alkoxy, aryl, aryloxy, heterocyclyl, any of which are optionally substituted at one or more positions by deuterium, halogen, alkyl, hydroxy, alkoxy, aryl, aryloxy, heterocyclyl, nitro, nitric acid ester.

Further, for all SMOs, including those listed above with formulas I-VII and for all listed substitutions the nitric acid ester substitutions are of relevance especially when associated to deuterated substitutions and/or halogen substitutions.

TABLE 1a

| List of first set of designed SMOs tested in the in silico molecular model of the trans-membrane domain of the NR1-NR2B subtype of the closed NMDAR |
|---|
| 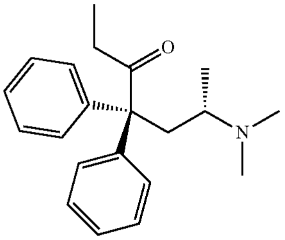<br>DMD<br>Chemical Formula: $C_{21}H_{27}NO$<br>Molecular Weight: 309,45300 |
| 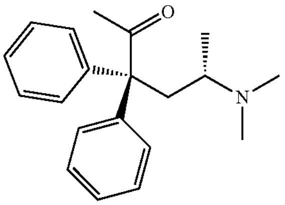<br>DMD1<br>Chemical Formula: $C_{20}H_{25}NO$<br>Molecular Weight: 295,42600 |
| 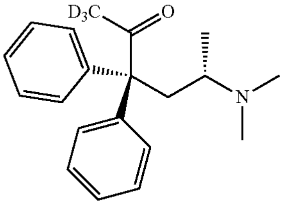<br>DMD2<br>Chemical Formula: $C_{20}H_{22}D_3NO$<br>Molecular Weight: 298,44431 |
| 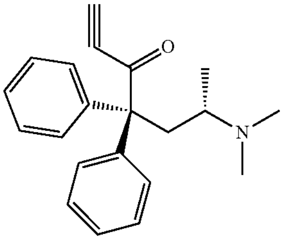<br>DMD3<br>Chemical Formula: $C_{21}H_{23}NO$<br>Molecular Weight: 305,42100 |

TABLE 1a-continued

List of first set of designed SMOs tested in the in silico molecular model of the trans-membrane domain of the NR1-NR2B subtype of the closed NMDAR

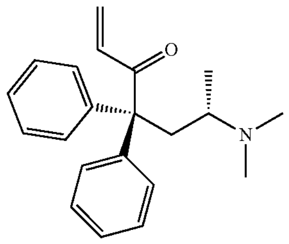

DMD4
Chemical Formula: $C_{21}H_{25}NO$
Molecular Weight: 307,43700

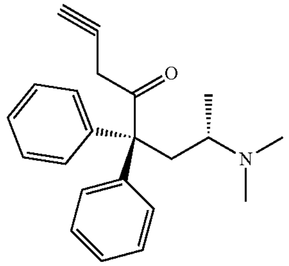

DMD5
Chemical Formula: $C_{22}H_{25}NO$
Molecular Weight: 319,44800

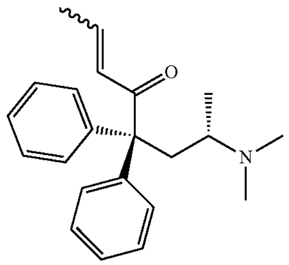

DMD6
Chemical Formula: $C_{22}H_{27}NO$
Molecular Weight: 321,46400

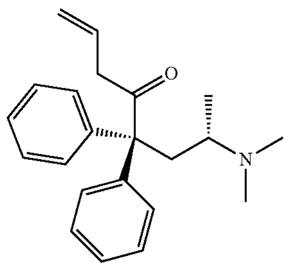

DMD7
Chemical Formula: $C_{22}H_{27}NO$
Molecular Weight: 321,46400

TABLE 1a-continued

List of first set of designed SMOs tested in the in silico molecular model of the trans-membrane domain of the NR1-NR2B subtype of the closed NMDAR

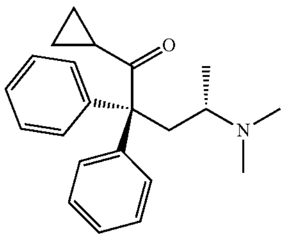

DMD8
Chemical Formula: $C_{22}H_{27}NO$
Molecular Weight: 321,46400

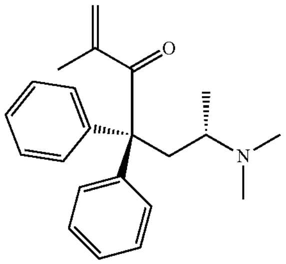

DMD9
Chemical Formula: $C_{22}H_{27}NO$
Molecular Weight: 321,46400

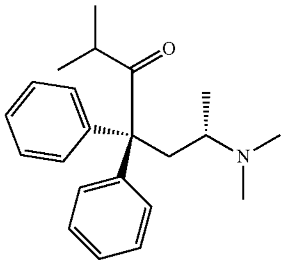

DMD10
Chemical Formula: $C_{22}H_{29}NO$
Molecular Weight: 323,48000

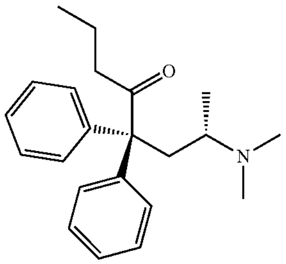

DMD11
Chemical Formula: $C_{22}H_{29}NO$
Molecular Weight: 323,48000

TABLE 1a-continued

List of first set of designed SMOs tested in the in silico molecular model of the trans-membrane domain of the NR1-NR2B subtype of the closed NMDAR

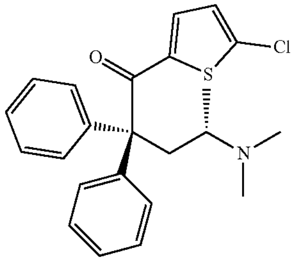

DMD12
Chemical Formula: $C_{23}H_{24}ClNOS$
Molecular Weight: 397,96100

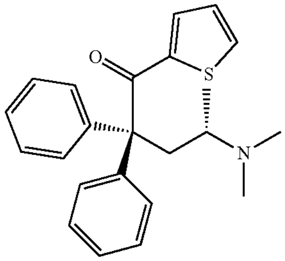

DMD13
Chemical Formula: $C_{23}H_{25}NOS$
Molecular Weight: 363,51900

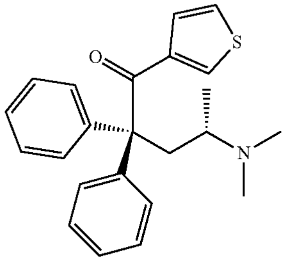

DMD14
Chemical Formula: $C_{23}H_{25}NOS$
Molecular Weight: 363,51900

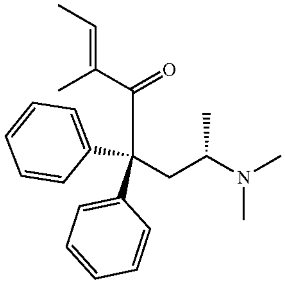

DMD15
Chemical Formula: $C_{23}H_{29}NO$
Molecular Weight: 335,49100

TABLE 1a-continued

List of first set of designed SMOs tested in the in silico molecular model of the trans-membrane domain of the NR1-NR2B subtype of the closed NMDAR

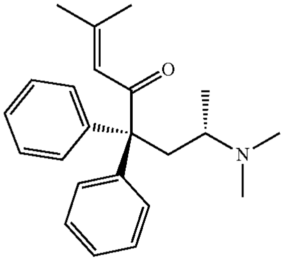

DMD16
Chemical Formula: $C_{23}H_{29}NO$
Molecular Weight: 335,49100

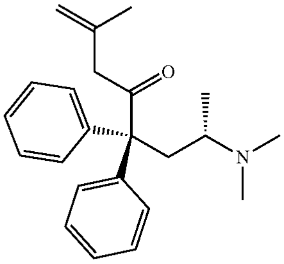

DMD17
Chemical Formula: $C_{23}H_{29}NO$
Molecular Weight: 335,49100

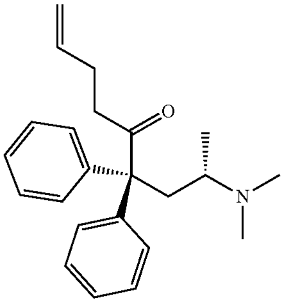

DMD18
Chemical Formula: $C_{23}H_{29}NO$
Molecular Weight: 335,49100

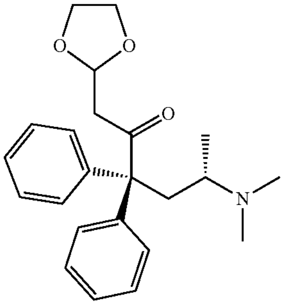

DMD19
Chemical Formula: $C_{23}H_{29}NO_3$
Molecular Weight: 367,48900

TABLE 1a-continued

| List of first set of designed SMOs tested in the in silico molecular model of the trans-membrane domain of the NR1-NR2B subtype of the closed NMDAR |
| --- |
| 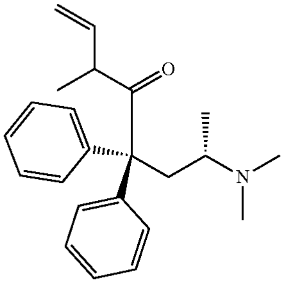<br>DMD20<br>Chemical Formula: $C_{23}H_{29}NO$<br>Molecular Weight: 335,49100 |
| 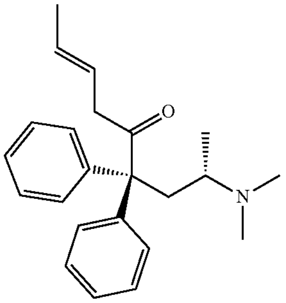<br>DMD21<br>Chemical Formula: $C_{23}H_{29}NO$<br>Molecular Weight: 335,49100 |
| 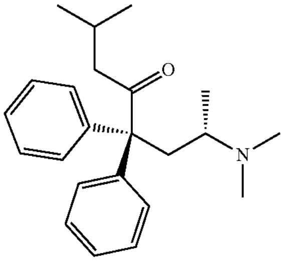<br>DMD22<br>Chemical Formula: $C_{23}H_{31}NO$<br>Molecular Weight: 337,50700 |
| 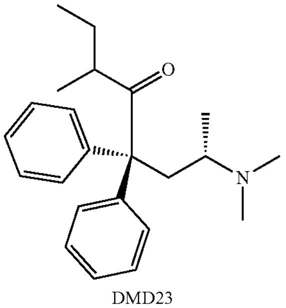<br>DMD23<br>Chemical Formula: $C_{23}H_{31}NO$<br>Molecular Weight: 337,50700 |
| 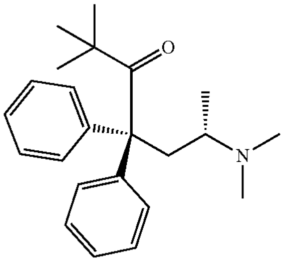<br>DMD24<br>Chemical Formula: $C_{23}H_{31}NO$<br>Molecular Weight: 337,50700 |
| 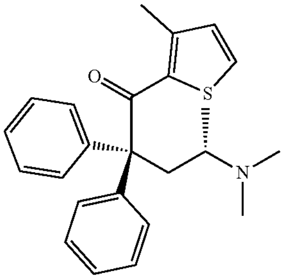<br>DMD25<br>Chemical Formula: $C_{24}H_{27}NOS$<br>Molecular Weight: 377,54600 |
| 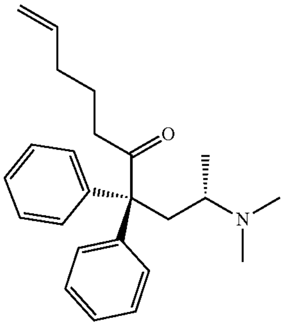<br>DMD26<br>Chemical Formula: $C_{24}H_{31}NO$<br>Molecular Weight: 349,51800 |
| 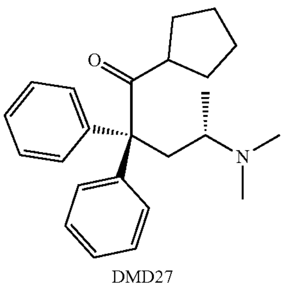<br>DMD27<br>Chemical Formula: $C_{24}H_{31}NO$<br>Molecular Weight: 349,51800 |

TABLE 1a-continued

List of first set of designed SMOs tested in the in silico molecular model of the trans-membrane domain of the NR1-NR2B subtype of the closed NMDAR

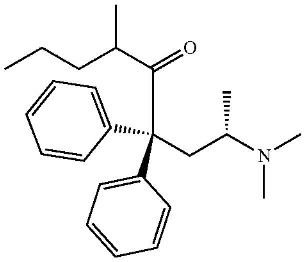

DMD28
Chemical Formula: $C_{24}H_{33}NO$
Molecular Weight: 351,53400

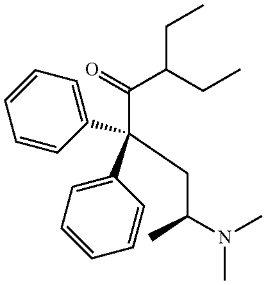

DMD29
Chemical Formula: $C_{24}H_{33}NO$
Molecular Weight: 351,53400

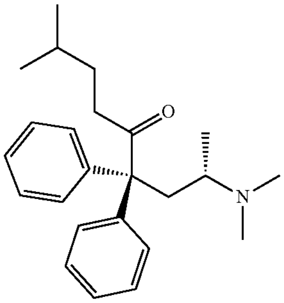

DMD30
Chemical Formula: $C_{24}H_{33}NO$
Molecular Weight: 351,53400

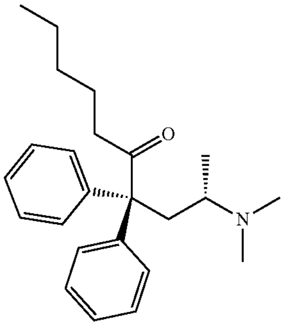

DMD31
Chemical Formula: $C_{24}H_{33}NO$
Molecular Weight: 351,53400

TABLE 1a-continued

List of first set of designed SMOs tested in the in silico molecular model of the trans-membrane domain of the NR1-NR2B subtype of the closed NMDAR

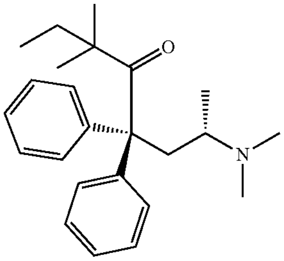

DMD32
Chemical Formula: $C_{24}H_{33}NO$
Molecular Weight: 351,53400

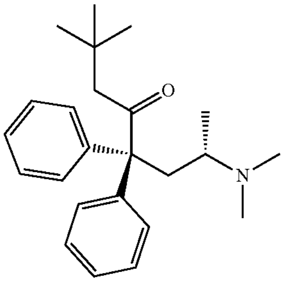

DMD33
Chemical Formula: $C_{24}H_{33}NO$
Molecular Weight: 351,53400

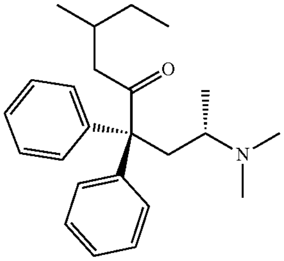

DMD34
Chemical Formula: $C_{24}H_{33}NO$
Molecular Weight: 351,53400

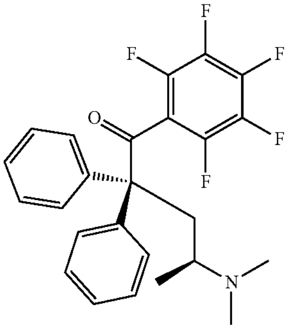

DMD35
Chemical Formula: $C_{25}H_{22}F_5NO$
Molecular Weight: 447,44902

TABLE 1a-continued

| List of first set of designed SMOs tested in the in silico molecular model of the trans-membrane domain of the NR1-NR2B subtype of the closed NMDAR |
|---|
| 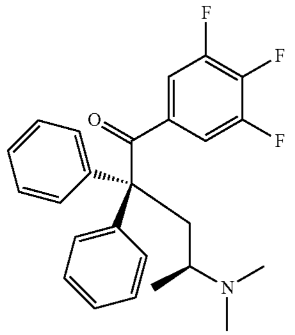 DMD36 Chemical Formula: $C_{25}H_{24}F_3NO$ Molecular Weight: 411,46821 |
| 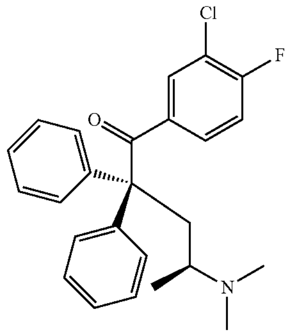 DMD37 Chemical Formula: $C_{25}H_{25}ClFNO$ Molecular Weight: 409,92940 |
| 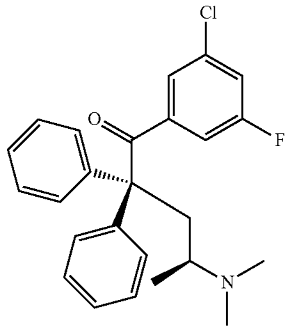 DMD38 Chemical Formula: $C_{25}H_{25}ClFNO$ Molecular Weight: 409,92940 |

TABLE 1a-continued

| List of first set of designed SMOs tested in the in silico molecular model of the trans-membrane domain of the NR1-NR2B subtype of the closed NMDAR |
|---|
| 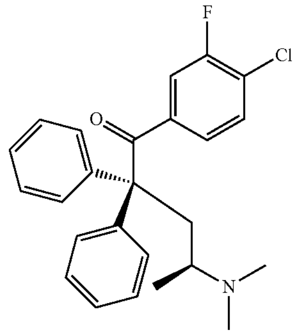 DMD39 Chemical Formula: $C_{25}H_{25}ClFNO$ Molecular Weight: 409,92940 |
| 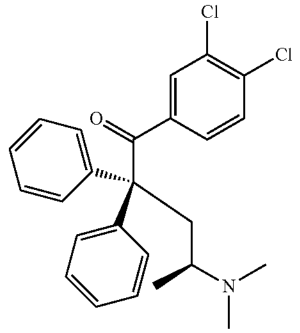 DMD40 Chemical Formula: $C_{25}H_{25}Cl_2NO$ Molecular Weight: 426,38100 |
| 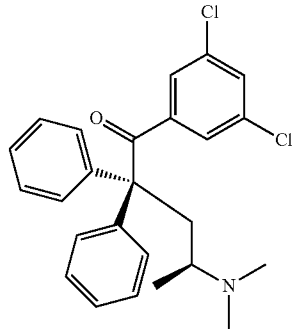 DMD41 Chemical Formula: $C_{25}H_{25}Cl_2NO$ Molecular Weight: 426,38100 |

TABLE 1a-continued

List of first set of designed SMOs tested in the in silico molecular model of the trans-membrane domain of the NR1-NR2B subtype of the closed NMDAR

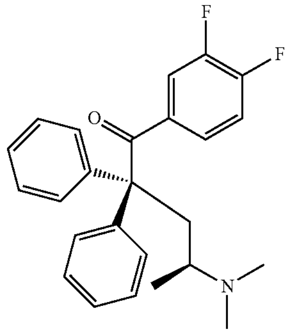

DMD42
Chemical Formula: $C_{25}H_{25}F_2NO$
Molecular Weight: 393,47781

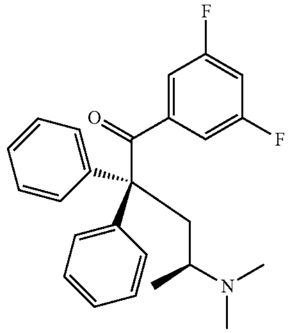

DMD43
Chemical Formula: $C_{25}H_{25}F_2NO$
Molecular Weight: 393,47781

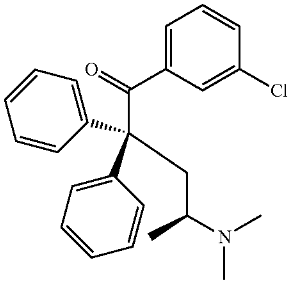

DMD44
Chemical Formula: $C_{25}H_{26}ClNO$
Molecular Weight: 391,93900

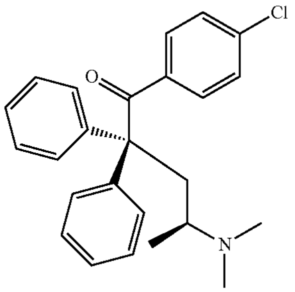

DMD45
Chemical Formula: $C_{25}H_{26}ClNO$
Molecular Weight: 391,93900

TABLE 1a-continued

List of first set of designed SMOs tested in the in silico molecular model of the trans-membrane domain of the NR1-NR2B subtype of the closed NMDAR

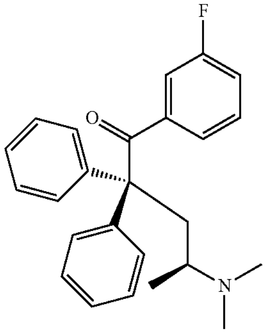

DMD46
Chemical Formula: $C_{25}H_{26}FNO$
Molecular Weight: 375,48740

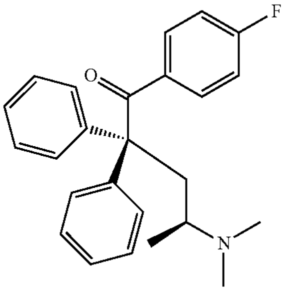

DMD47
Chemical Formula: $C_{25}H_{26}FNO$
Molecular Weight: 375,48740

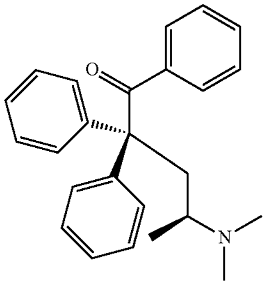

DMD48
Chemical Formula: $C_{25}H_{27}NO$
Molecular Weight: 357,49700

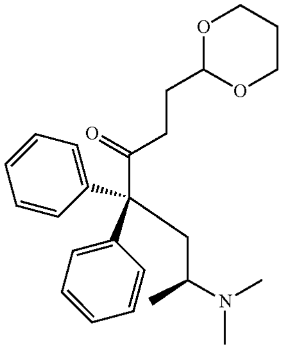

DMD49
Chemical Formula: $C_{25}H_{33}NO_3$
Molecular Weight: 395,54300

TABLE 1a-continued

List of first set of designed SMOs tested in the in silico molecular model of the trans-membrane domain of the NR1-NR2B subtype of the closed NMDAR

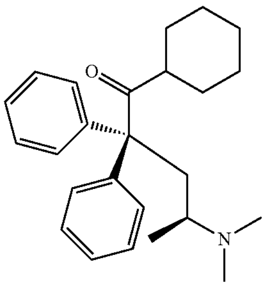

DMD50
Chemical Formula: $C_{25}H_{33}NO$
Molecular Weight: 363,54500

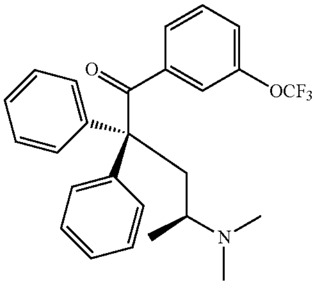

DMD51
Chemical Formula: $C_{26}H_{26}F_3NO_2$
Molecular Weight: 441,49421

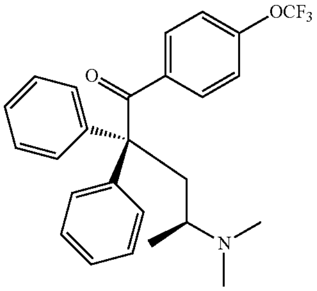

DMD52
Chemical Formula: $C_{26}H_{26}F_3NO_2$
Molecular Weight: 441,49421

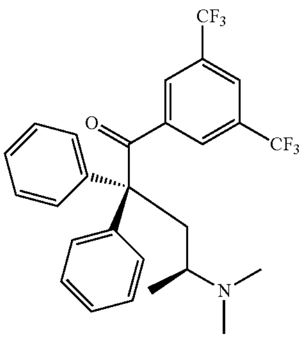

DMD53
Chemical Formula: $C_{27}H_{25}F_6NO$
Molecular Weight: 493,49342

TABLE 1a-continued

List of first set of designed SMOs tested in the in silico molecular model of the trans-membrane domain of the NR1-NR2B subtype of the closed NMDAR

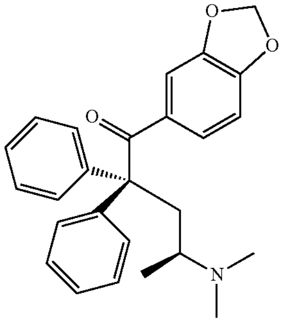

DMD54
Chemical Formula: $C_{26}H_{27}NO_3$
Molecular Weight: 401,50600

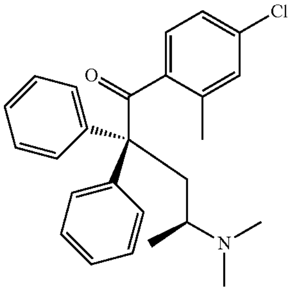

DMD55
Chemical Formula: $C_{26}H_{28}ClNO$
Molecular Weight: 405,96600

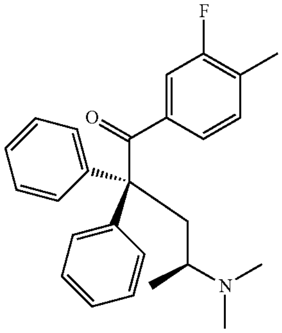

DMD56
Chemical Formula: $C_{26}H_{28}FNO$
Molecular Weight: 389,51440

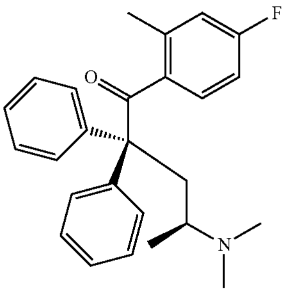

DMD57
Chemical Formula: $C_{26}H_{28}FNO$
Molecular Weight: 389,51440

TABLE 1a-continued

| List of first set of designed SMOs tested in the in silico molecular model of the trans-membrane domain of the NR1-NR2B subtype of the closed NMDAR |
| --- |
| 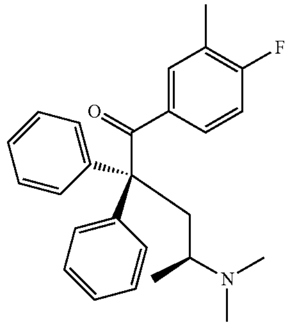<br>DMD58<br>Chemical Formula: $C_{26}H_{28}FNO$<br>Molecular Weight: 389,51440 |
| 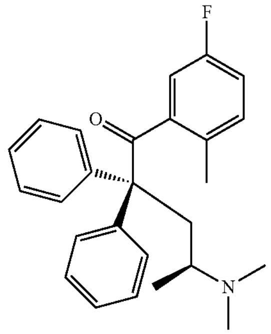<br>DMD59<br>Chemical Formula: $C_{26}H_{28}FNO$<br>Molecular Weight: 389,51440 |
| 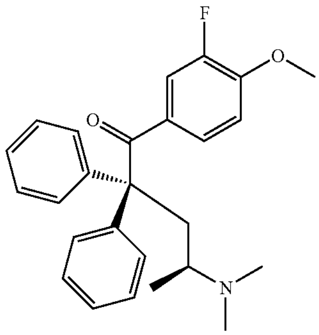<br>DMD60<br>Chemical Formula: $C_{26}H_{28}FNO_2$<br>Molecular Weight: 405,51340 |

TABLE 1a-continued

| List of first set of designed SMOs tested in the in silico molecular model of the trans-membrane domain of the NR1-NR2B subtype of the closed NMDAR |
| --- |
| 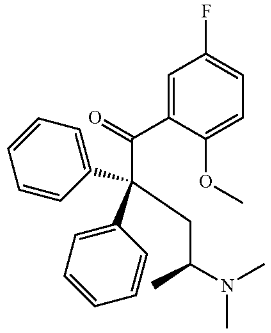<br>DMD61<br>Chemical Formula: $C_{26}H_{28}FNO_2$<br>Molecular Weight: 405,51340 |
| 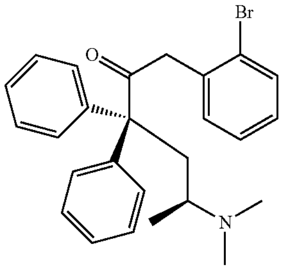<br>DMD62<br>Chemical Formula: $C_{26}H_{28}BrNO$<br>Molecular Weight: 450,42000 |
| 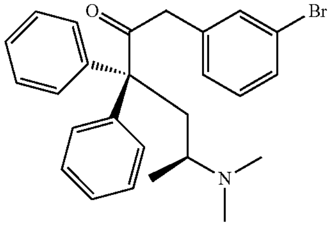<br>DMD63<br>Chemical Formula: $C_{26}H_{28}BrNO$<br>Molecular Weight: 450,42000 |
| 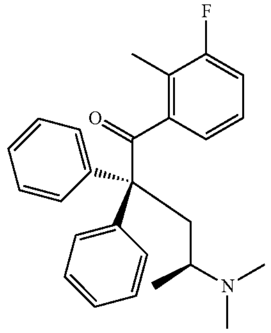<br>DMD64<br>Chemical Formula: $C_{26}H_{28}FNO$<br>Molecular Weight: 389,51440 |

TABLE 1a-continued

| List of first set of designed SMOs tested in the in silico molecular model of the trans-membrane domain of the NR1-NR2B subtype of the closed NMDAR |
|---|
| 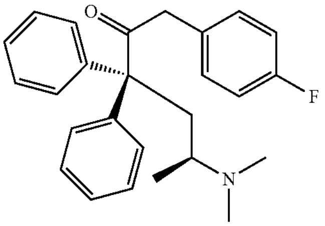<br>DMD65<br>Chemical Formula: $C_{26}H_{28}FNO$<br>Molecular Weight: 389,51440 |
| 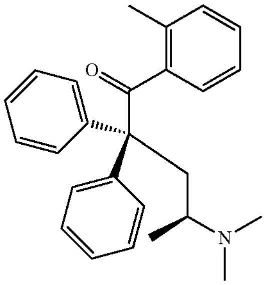<br>DMD66<br>Chemical Formula: $C_{26}H_{29}NO$<br>Molecular Weight: 371,52400 |
| 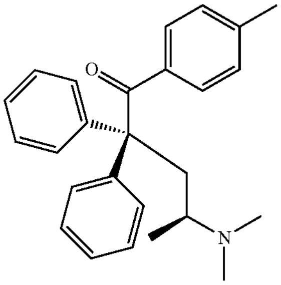<br>DMD67<br>Chemical Formula: $C_{26}H_{29}NO$<br>Molecular Weight: 371,52400 |
| 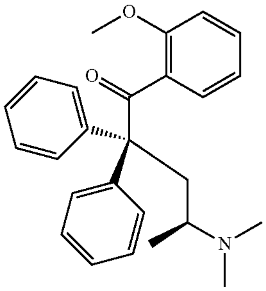<br>DMD68<br>Chemical Formula: $C_{26}H_{29}NO_2$<br>Molecular Weight: 387,52300 |

TABLE 1a-continued

| List of first set of designed SMOs tested in the in silico molecular model of the trans-membrane domain of the NR1-NR2B subtype of the closed NMDAR |
|---|
| 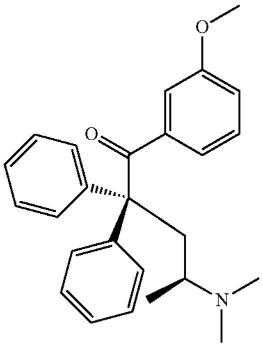<br>DMD69<br>Chemical Formula: $C_{26}H_{29}NO_2$<br>Molecular Weight: 387,52300 |
| 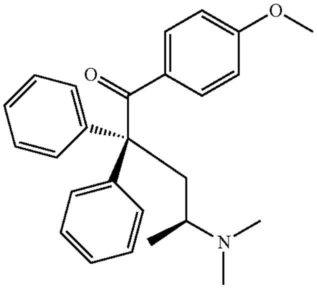<br>DMD70<br>Chemical Formula: $C_{26}H_{29}NO_2$<br>Molecular Weight: 387,52300 |
| 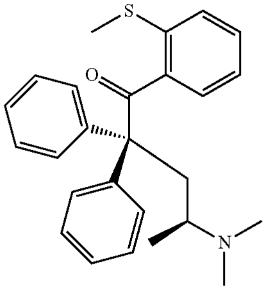<br>DMD71<br>Chemical Formula: $C_{26}H_{29}NOS$<br>Molecular Weight: 403,58400 |
| 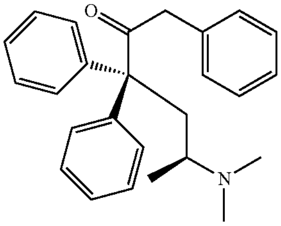<br>DMD72<br>Chemical Formula: $C_{26}H_{29}NO$<br>Molecular Weight: 371,52400 |

TABLE 1a-continued

List of first set of designed SMOs tested in the in silico molecular model of the trans-membrane domain of the NR1-NR2B subtype of the closed NMDAR

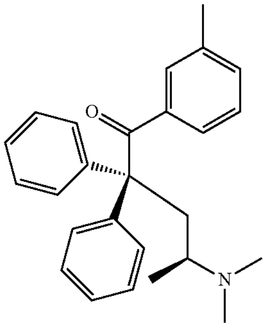

DMD73
Chemical Formula: $C_{26}H_{29}NO$
Molecular Weight: 371,52400

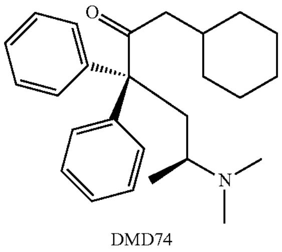

DMD74
Chemical Formula: $C_{26}H_{35}NO$
Molecular Weight: 377,57200

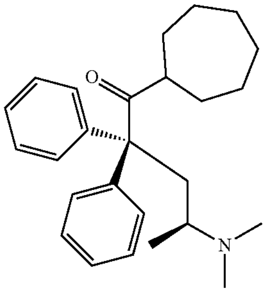

DMD75
Chemical Formula: $C_{26}H_{35}NO$
Molecular Weight: 377,57200

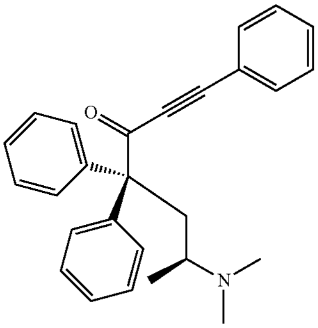

DMD76
Chemical Formula: $C_{27}H_{27}NO$
Molecular Weight: 381,51900

TABLE 1a-continued

List of first set of designed SMOs tested in the in silico molecular model of the trans-membrane domain of the NR1-NR2B subtype of the closed NMDAR

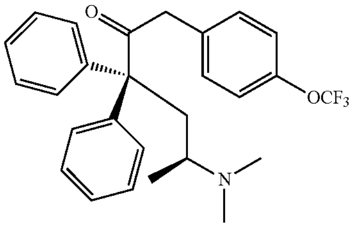

DMD77
Chemical Formula: $C_{27}H_{28}F_3NO_2$
Molecular Weight: 455,52121

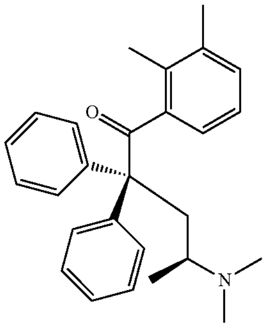

DMD78
Chemical Formula: $C_{27}H_{31}NO$
Molecular Weight: 385,55100

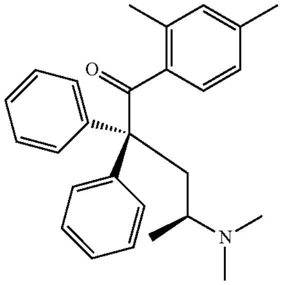

DMD79
Chemical Formula: $C_{27}H_{31}NO$
Molecular Weight: 385,55100

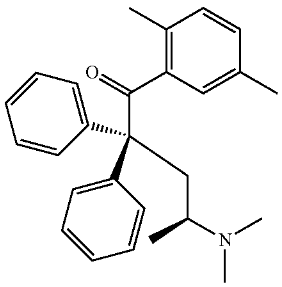

DMD80
Chemical Formula: $C_{27}H_{31}NO$
Molecular Weight: 385,55100

TABLE 1a-continued

List of first set of designed SMOs tested in the in silico molecular model of the trans-membrane domain of the NR1-NR2B subtype of the closed NMDAR

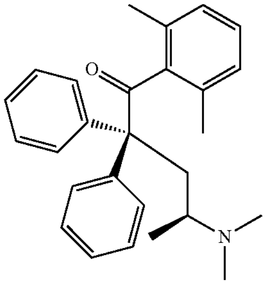

DMD81
Chemical Formula: $C_{27}H_{31}NO$
Molecular Weight: 385,55100

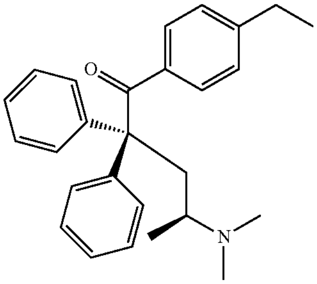

DMD82
Chemical Formula: $C_{27}H_{31}NO$
Molecular Weight: 385,55100

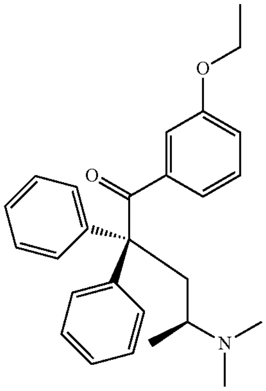

DMD83
Chemical Formula: $C_{27}H_{31}NO_2$
Molecular Weight: 401,55000

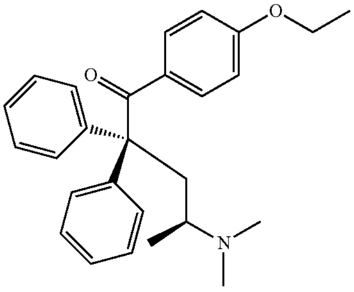

DMD84
Chemical Formula: $C_{27}H_{31}NO_2$
Molecular Weight: 401,55000

TABLE 1a-continued

List of first set of designed SMOs tested in the in silico molecular model of the trans-membrane domain of the NR1-NR2B subtype of the closed NMDAR

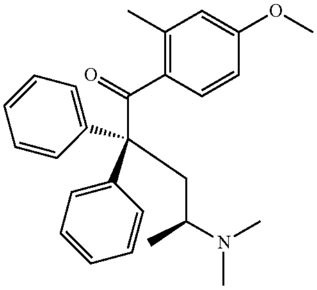

DMD85
Chemical Formula: $C_{27}H_{31}NO_2$
Molecular Weight: 401,55000

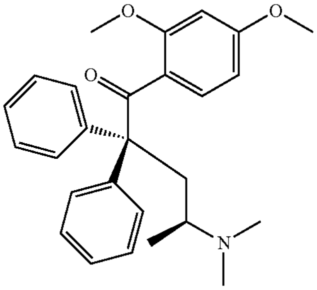

DMD86
Chemical Formula: $C_{27}H_{31}NO_3$
Molecular Weight: 417,54900

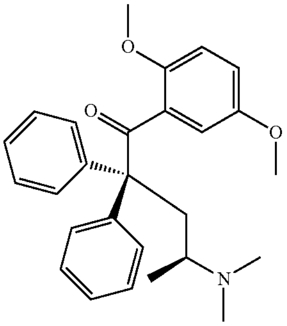

DMD87
Chemical Formula: $C_{27}H_{31}NO_3$
Molecular Weight: 417,54900

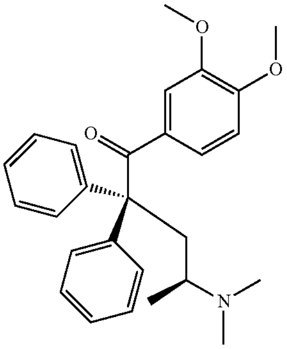

DMD88
Chemical Formula: $C_{27}H_{31}NO_3$
Molecular Weight: 417,54900

TABLE 1a-continued

| List of first set of designed SMOs tested in the in silico molecular model of the trans-membrane domain of the NR1-NR2B subtype of the closed NMDAR |
| --- |
| 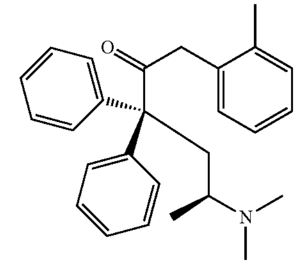<br>DMD89<br>Chemical Formula: $C_{27}H_{31}NO$<br>Molecular Weight: 385,55100 |
| 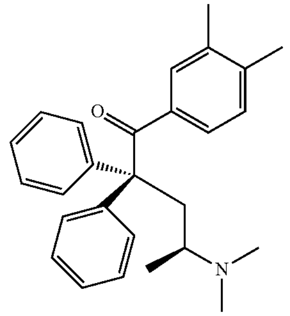<br>DMD90<br>Chemical Formula: $C_{27}H_{31}NO$<br>Molecular Weight: 385,55100 |
| 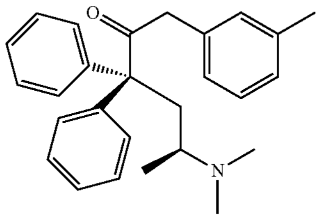<br>DMD91<br>Chemical Formula: $C_{27}H_{31}NO$<br>Molecular Weight: 385,55100 |
| 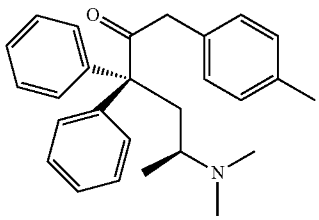<br>DMD92<br>Chemical Formula: $C_{27}H_{31}NO$<br>Molecular Weight: 385,55100 |

TABLE 1a-continued

| List of first set of designed SMOs tested in the in silico molecular model of the trans-membrane domain of the NR1-NR2B subtype of the closed NMDAR |
| --- |
| 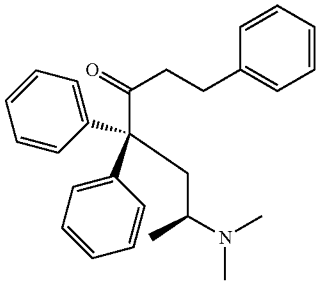<br>DMD93<br>Chemical Formula: $C_{27}H_{31}NO$<br>Molecular Weight: 385,55100 |
| 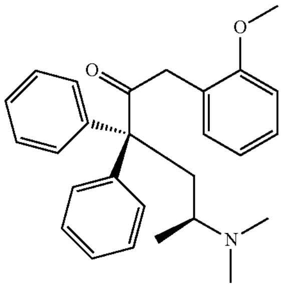<br>DMD94<br>Chemical Formula: $C_{27}H_{31}NO_2$<br>Molecular Weight: 401,55000 |
| 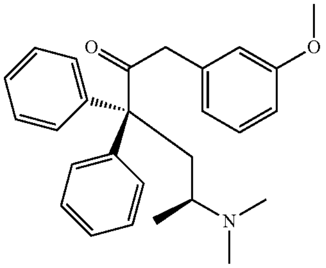<br>DMD95<br>Chemical Formula: $C_{27}H_{31}NO_2$<br>Molecular Weight: 401,55000 |
| 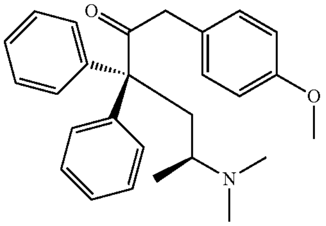<br>DMD96<br>Chemical Formula: $C_{27}H_{31}NO_2$<br>Molecular Weight: 401,55000 |

TABLE 1a-continued

List of first set of designed SMOs tested in the in silico molecular model of the trans-membrane domain of the NR1-NR2B subtype of the closed NMDAR

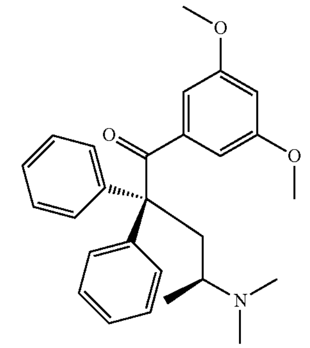

DMD97
Chemical Formula: $C_{27}H_{31}NO_3$
Molecular Weight: 417,54900

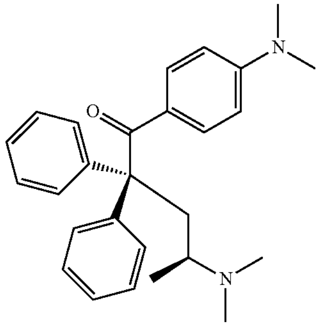

DMD98
Chemical Formula: $C_{27}H_{32}N_2O$
Molecular Weight: 400,56600

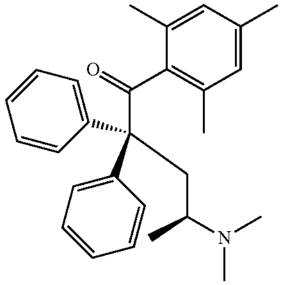

DMD99
Chemical Formula: $C_{28}H_{33}NO$
Molecular Weight: 399,57800

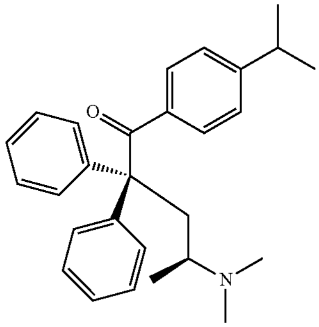

DMD100
Chemical Formula: $C_{28}H_{33}NO$
Molecular Weight: 399,57800

TABLE 1a-continued

List of first set of designed SMOs tested in the in silico molecular model of the trans-membrane domain of the NR1-NR2B subtype of the closed NMDAR

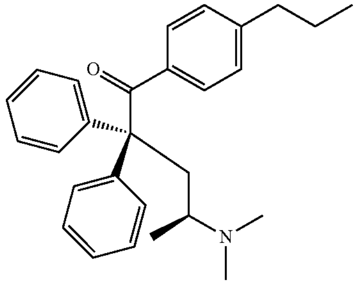

DMD101
Chemical Formula: $C_{28}H_{33}NO$
Molecular Weight: 399,57800

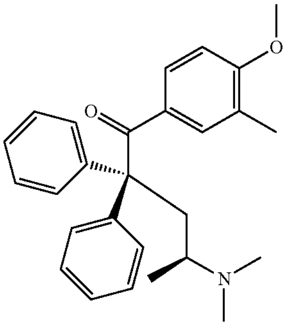

DMD102
Chemical Formula: $C_{28}H_{33}NO_2$
Molecular Weight: 415,57700

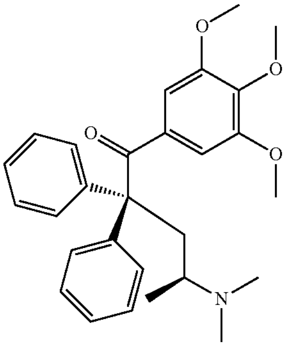

DMD103
Chemical Formula: $C_{28}H_{33}NO_4$
Molecular Weight: 447,57500

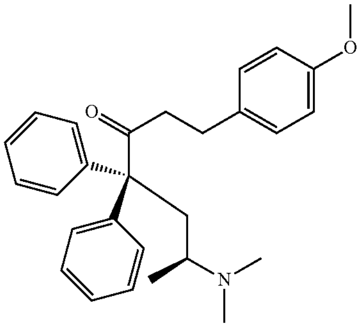

DMD104
Chemical Formula: $C_{28}H_{33}NO_2$
Molecular Weight: 415,57700

TABLE 1a-continued

List of first set of designed SMOs tested in the in silico molecular model of the trans-membrane domain of the NR1-NR2B subtype of the closed NMDAR

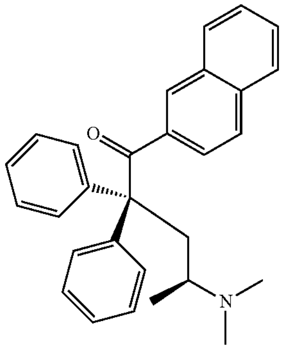

DMD105
Chemical Formula: $C_{29}H_{29}NO$
Molecular Weight: 407,55700

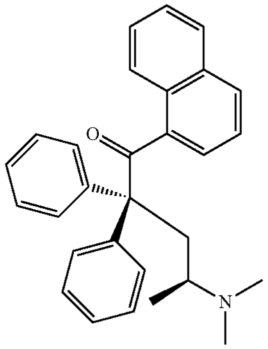

DMD106
Chemical Formula: $C_{29}H_{29}NO$
Molecular Weight: 407,55700

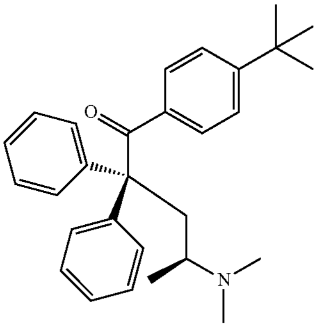

DMD107
Chemical Formula: $C_{29}H_{35}NO$
Molecular Weight: 413,60500

TABLE 1a-continued

List of first set of designed SMOs tested in the in silico molecular model of the trans-membrane domain of the NR1-NR2B subtype of the closed NMDAR

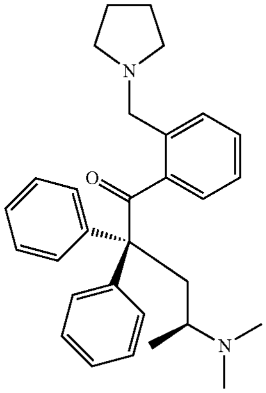

DMD108
Chemical Formula: $C_{30}H_{36}N_2O$
Molecular Weight: 440,63100

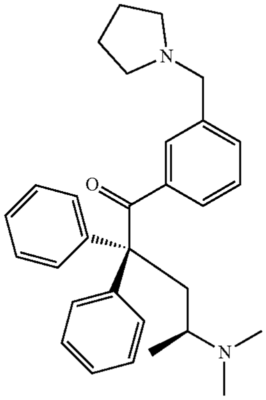

DMD109
Chemical Formula: $C_{30}H_{36}N_2O$
Molecular Weight: 440,63100

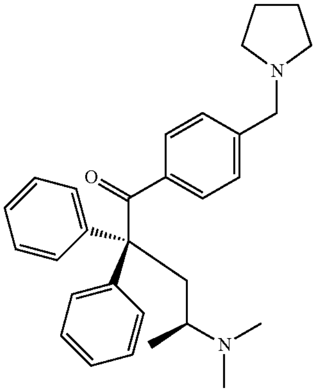

DMD110
Chemical Formula: $C_{30}H_{36}N_2O$
Molecular Weight: 440,63100

TABLE 1a-continued

List of first set of designed SMOs tested in the in silico molecular model of the trans-membrane domain of the NR1-NR2B subtype of the closed NMDAR

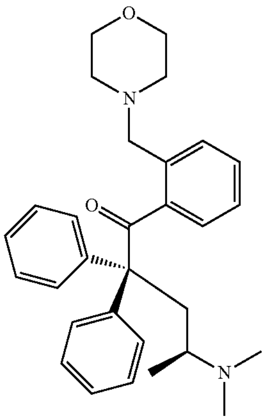

DMD111
Chemical Formula: $C_{30}H_{36}N_2O_2$
Molecular Weight: 456,63000

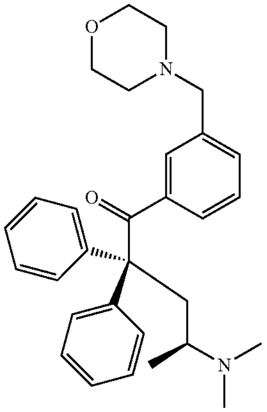

DMD112
Chemical Formula: $C_{30}H_{36}N_2O_2$
Molecular Weight: 456,63000

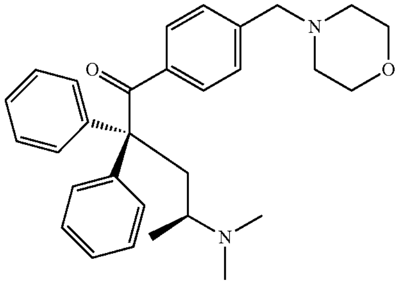

DMD113
Chemical Formula: $C_{30}H_{36}N_2O_2$
Molecular Weight: 456,63000

TABLE 1a-continued

List of first set of designed SMOs tested in the in silico molecular model of the trans-membrane domain of the NR1-NR2B subtype of the closed NMDAR

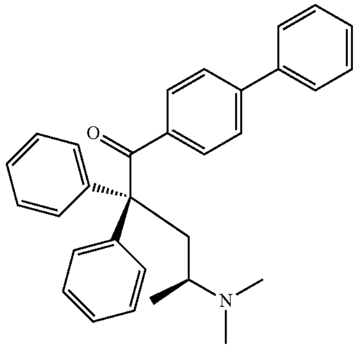

DMD114
Chemical Formula: $C_{31}H_{31}NO$
Molecular Weight: 433,59500

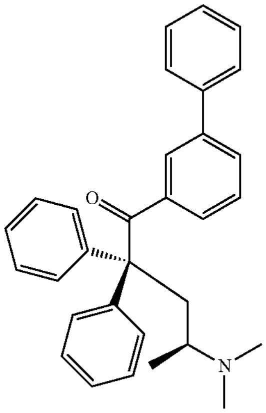

DMD115
Chemical Formula: $C_{31}H_{31}NO$
Molecular Weight: 433,59500

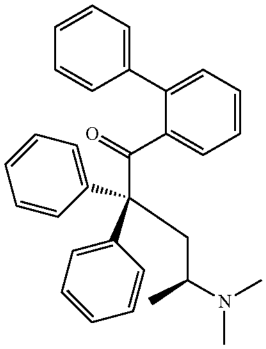

DMD116
Chemical Formula: $C_{31}H_{31}NO$
Molecular Weight: 433,59500

TABLE 1a-continued

List of first set of designed SMOs tested in the in silico molecular model of the trans-membrane domain of the NR1-NR2B subtype of the closed NMDAR

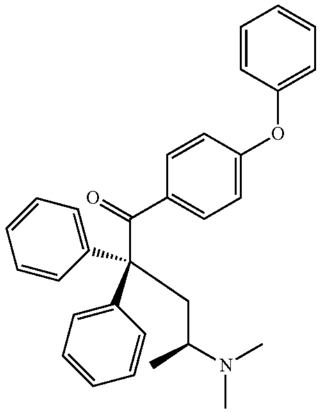

DMD117
Chemical Formula: $C_{31}H_{31}NO_2$
Molecular Weight: 449,59400

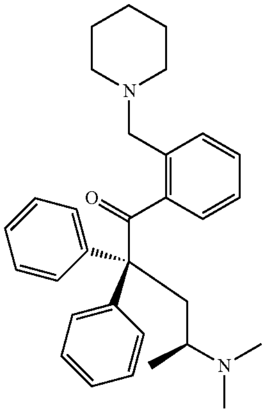

DMD118
Chemical Formula: $C_{31}H_{38}N_2O$
Molecular Weight: 454,65800

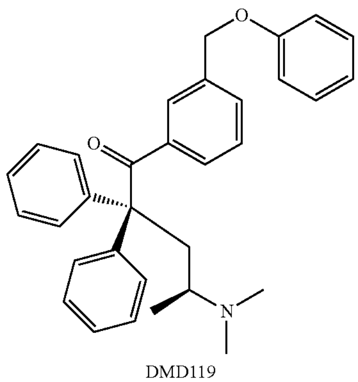

DMD119
Chemical Formula: $C_{32}H_{33}NO_2$
Molecular Weight: 463,62100

TABLE 1a-continued

List of first set of designed SMOs tested in the in silico molecular model of the trans-membrane domain of the NR1-NR2B subtype of the closed NMDAR

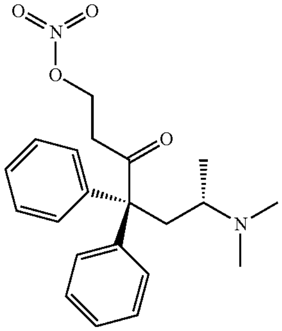

Nitro-DMD1
Chemical Formula: $C_{21}H_{26}N_2O_4$
Molecular Weight: 370,44900

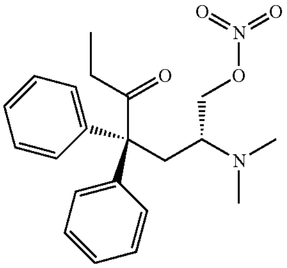

Nitro-DMD2
Chemical Formula: $C_{21}H_{26}N_2O_4$
Molecular Weight: 370,44900

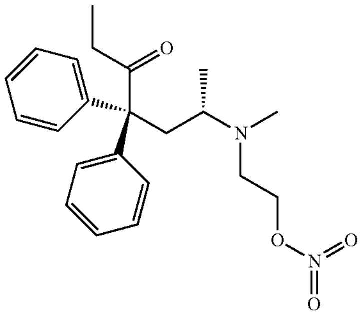

Nitro-DMD3
Chemical Formula: $C_{22}H_{28}N_2O_4$
Molecular Weight: 384,47600

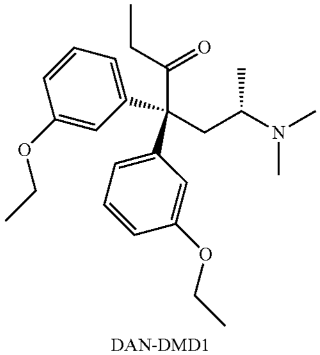

DAN-DMD1
Chemical Formula: $C_{25}H_{35}NO_3$
Molecular Weight: 397,55900

TABLE 1a-continued

List of first set of designed SMOs tested in the in silico molecular model of the trans-membrane domain of the NR1-NR2B subtype of the closed NMDAR

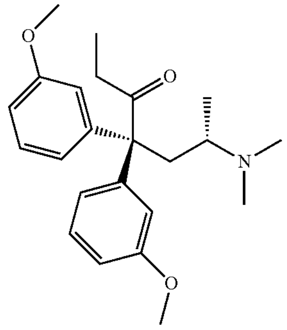

DAN-DMD2
Chemical Formula: $C_{23}H_{31}NO_3$
Molecular Weight: 369,50500

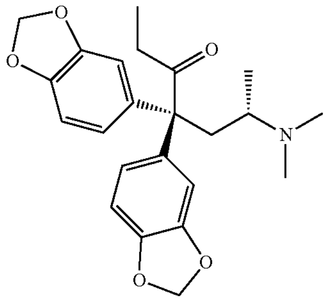

DAN-DMD3
Chemical Formula: $C_{23}H_{27}NO_5$
Molecular Weight: 397,47100

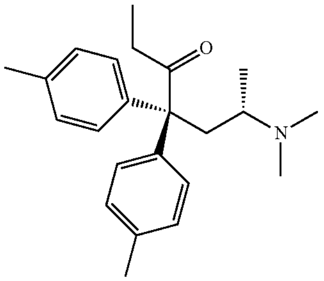

DAN-DMD4
Chemical Formula: $C_{23}H_{31}NO_3$
Molecular Weight: 369,50500

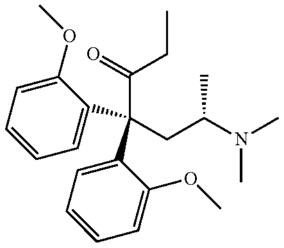

DAN-DMD5
Chemical Formula: $C_{23}H_{31}NO_3$
Molecular Weight: 337,50700

TABLE 1a-continued

List of first set of designed SMOs tested in the in silico molecular model of the trans-membrane domain of the NR1-NR2B subtype of the closed NMDAR

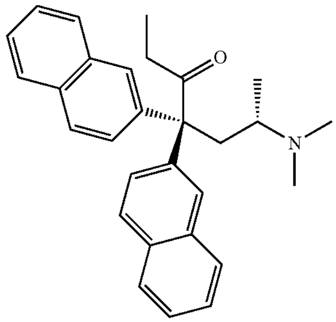

DAN-DMD6
Chemical Formula: $C_{29}H_{31}NO$
Molecular Weight: 409,57300

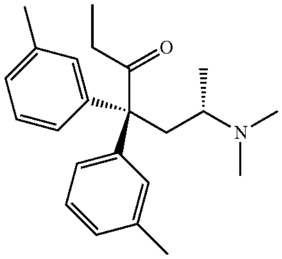

DAN-DMD7
Chemical Formula: $C_{23}H_{31}NO$
Molecular Weight: 337,50700

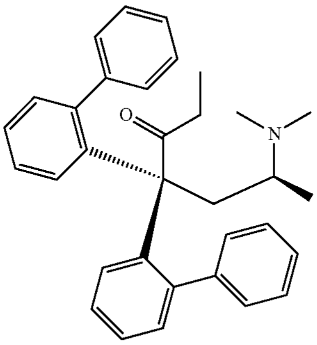

DAN-DMD8
Chemical Formula: $C_{33}H_{35}NO$
Molecular Weight: 461,64900

TABLE 1a-continued

| List of first set of designed SMOs tested in the in silico molecular model of the trans-membrane domain of the NR1-NR2B subtype of the closed NMDAR |
|---|
| 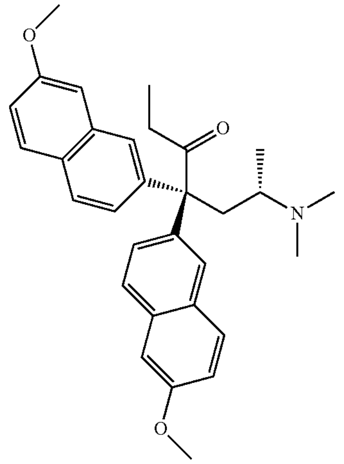 [SMILES: CCC(=O)[C@@](C[C@H](C)N(C)C)(c1ccc2cc(OC)ccc2c1)c1ccc2ccc(OC)cc2c1] DAN-DMD9 Chemical Formula: $C_{31}H_{35}NO_3$ Molecular Weight: 469,62500 |
| 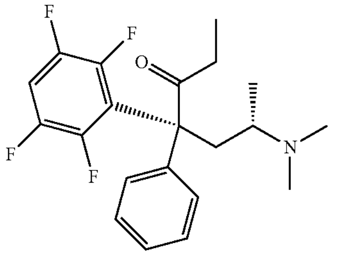 [SMILES: CCC(=O)[C@@](C[C@H](C)N(C)C)(c1ccccc1)c1c(F)c(F)cc(F)c1F] DAN-DMD10 Chemical Formula: $C_{21}H_{23}F_4NO$ Molecular Weight: 381,41461 |
| 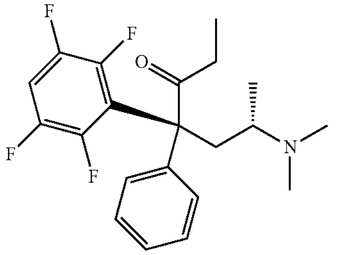 [SMILES: CCC(=O)[C@](C[C@H](C)N(C)C)(c1ccccc1)c1c(F)c(F)cc(F)c1F] DAN-DMD11 Chemical Formula: $C_{21}H_{23}F_4NO$ Molecular Weight: 381,41461 |
| 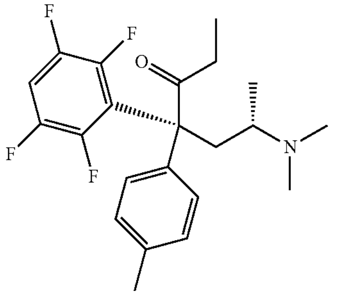 [SMILES: CCC(=O)[C@@](C[C@H](C)N(C)C)(c1ccc(C)cc1)c1c(F)c(F)cc(F)c1F] DAN-DMD12 Chemical Formula: $C_{22}H_{25}F_4NO$ Molecular Weight: 395,44161 |

TABLE 1a-continued

| List of first set of designed SMOs tested in the in silico molecular model of the trans-membrane domain of the NR1-NR2B subtype of the closed NMDAR |
|---|
| 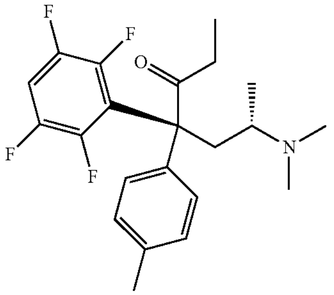 [SMILES: CCC(=O)[C@](C[C@H](C)N(C)C)(c1ccc(C)cc1)c1c(F)c(F)cc(F)c1F] DAN-DMD13 Chemical Formula: $C_{22}H_{25}F_4NO$ Molecular Weight: 395,44161 |
| 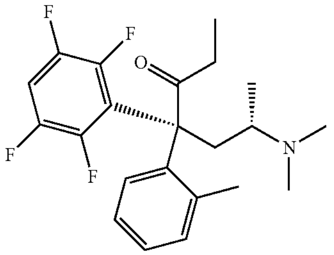 [SMILES: CCC(=O)[C@@](C[C@H](C)N(C)C)(c1ccccc1C)c1c(F)c(F)cc(F)c1F] DAN-DMD14 Chemical Formula: $C_{22}H_{25}F_4NO$ Molecular Weight: 395,44161 |
| 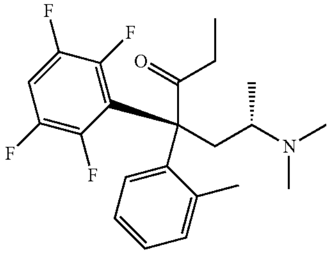 [SMILES: CCC(=O)[C@](C[C@H](C)N(C)C)(c1ccccc1C)c1c(F)c(F)cc(F)c1F] DAN-DMD15 Chemical Formula: $C_{22}H_{25}F_4NO$ Molecular Weight: 395,44161 |
| 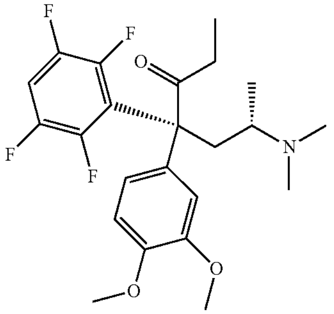 [SMILES: CCC(=O)[C@@](C[C@H](C)N(C)C)(c1ccc(OC)c(OC)c1)c1c(F)c(F)cc(F)c1F] DAN-DMD16 Chemical Formula: $C_{23}H_{27}F_4NO_3$ Molecular Weight: 441,46661 |

TABLE 1a-continued

| List of first set of designed SMOs tested in the in silico molecular model of the trans-membrane domain of the NR1-NR2B subtype of the closed NMDAR |
|---|
| 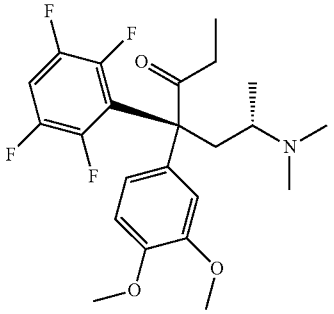 [SMILES: CCC(=O)[C@](C[C@H](C)N(C)C)(c1ccc(OC)c(OC)c1)c1c(F)c(F)cc(F)c1F] DAN-DMD17 Chemical Formula: $C_{23}H_{27}F_4NO_3$ Molecular Weight: 441,46661 |
| 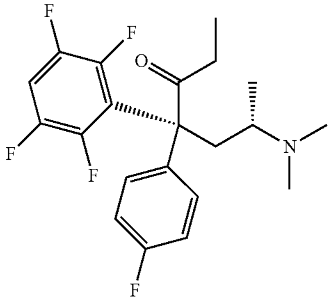 [SMILES: CCC(=O)[C@@](C[C@H](C)N(C)C)(c1ccc(F)cc1)c1c(F)c(F)cc(F)c1F] DAN-DMD18 Chemical Formula: $C_{21}H_{22}F_5NO$ Molecular Weight: 399,40502 |
| 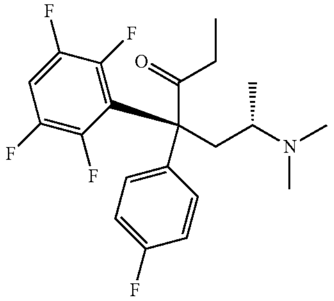 [SMILES: CCC(=O)[C@](C[C@H](C)N(C)C)(c1ccc(F)cc1)c1c(F)c(F)cc(F)c1F] DAN-DMD19 Chemical Formula: $C_{21}H_{22}F_5NO$ Molecular Weight: 399,40502 |
| 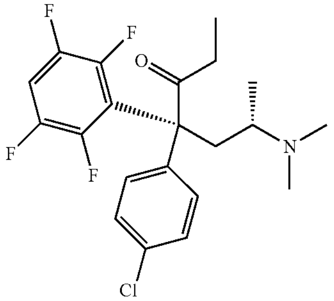 [SMILES: CCC(=O)[C@@](C[C@H](C)N(C)C)(c1ccc(Cl)cc1)c1c(F)c(F)cc(F)c1F] DAN-DMD20 Chemical Formula: $C_{21}H_{22}ClF_4NO$ Molecular Weight: 415,85661 |

TABLE 1a-continued

| List of first set of designed SMOs tested in the in silico molecular model of the trans-membrane domain of the NR1-NR2B subtype of the closed NMDAR |
|---|
| 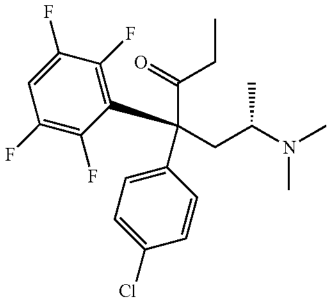 [SMILES: CCC(=O)[C@](C[C@H](C)N(C)C)(c1ccc(Cl)cc1)c1c(F)c(F)cc(F)c1F] DAN-DMD21 Chemical Formula: $C_{21}H_{22}ClF_4NO$ Molecular Weight: 415,85661 |
| 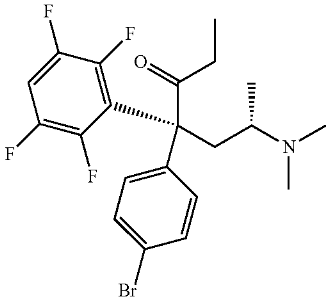 [SMILES: CCC(=O)[C@@](C[C@H](C)N(C)C)(c1ccc(Br)cc1)c1c(F)c(F)cc(F)c1F] DAN-DMD22 Chemical Formula: $C_{21}H_{22}BrF_4NO$ Molecular Weight: 460,31061 |
| 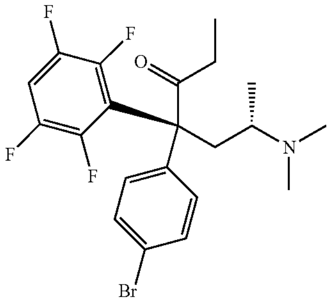 [SMILES: CCC(=O)[C@](C[C@H](C)N(C)C)(c1ccc(Br)cc1)c1c(F)c(F)cc(F)c1F] DAN-DMD23 Chemical Formula: $C_{21}H_{22}BrF_4NO$ Molecular Weight: 460,31061 |
| 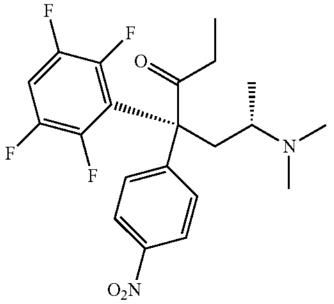 [SMILES: CCC(=O)[C@@](C[C@H](C)N(C)C)(c1ccc([N+](=O)[O-])cc1)c1c(F)c(F)cc(F)c1F] DAN-DMD24 Chemical Formula: $C_{21}H_{22}F_4N_2O_3$ Molecular Weight: 426,41161 |

TABLE 1a-continued

| List of first set of designed SMOs tested in the in silico molecular model of the trans-membrane domain of the NR1-NR2B subtype of the closed NMDAR |
|---|

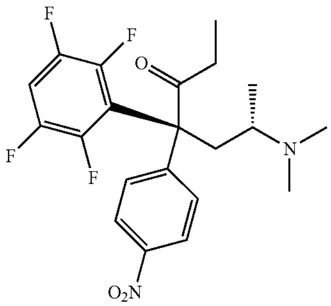 [SMILES: CCC(=O)[C@](C[C@H](C)N(C)C)(c1ccc([N+](=O)[O-])cc1)c1c(F)c(F)cc(F)c1F]

DAN-DMD25
Chemical Formula: $C_{21}H_{22}F_4N_2O_3$
Molecular Weight: 426,41161

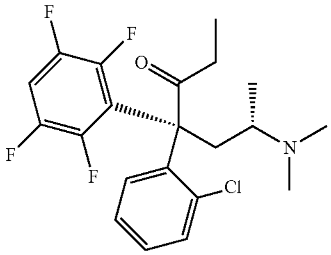 [SMILES: CCC(=O)[C@@](C[C@H](C)N(C)C)(c1ccccc1Cl)c1c(F)c(F)cc(F)c1F]

DAN-DMD26
Chemical Formula: $C_{21}H_{22}ClF_4NO$
Molecular Weight: 415,85661

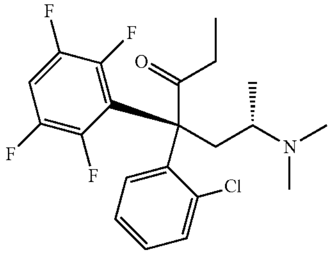 [SMILES: CCC(=O)[C@](C[C@H](C)N(C)C)(c1ccccc1Cl)c1c(F)c(F)cc(F)c1F]

DAN-DMD27
Chemical Formula: $C_{21}H_{22}ClF_4NO$
Molecular Weight: 415,85661

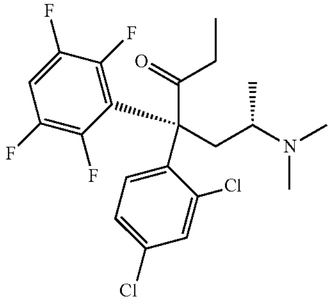 [SMILES: CCC(=O)[C@@](C[C@H](C)N(C)C)(c1ccc(Cl)cc1Cl)c1c(F)c(F)cc(F)c1F]

DAN-DMD28
Chemical Formula: $C_{21}H_{21}Cl_2F_4NO$
Molecular Weight: 450,29861

TABLE 1a-continued

List of first set of designed SMOs tested in the in silico molecular model of the trans-membrane domain of the NR1-NR2B subtype of the closed NMDAR

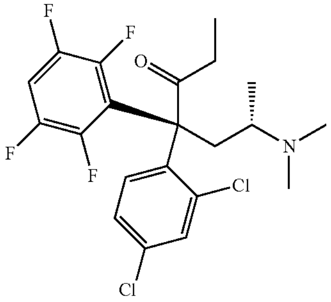 [SMILES: CCC(=O)[C@](C[C@H](C)N(C)C)(c1ccc(Cl)cc1Cl)c1c(F)c(F)cc(F)c1F]

DAN-DMD29
Chemical Formula: $C_{21}H_{21}Cl_2F_4NO$
Molecular Weight: 450,29861

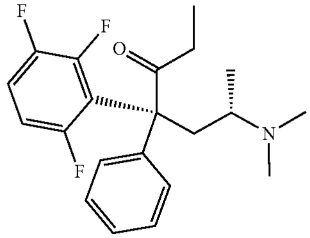 [SMILES: CCC(=O)[C@@](C[C@H](C)N(C)C)(c1ccccc1)c1c(F)ccc(F)c1F]

DAN-DMD30
Chemical Formula: $C_{21}H_{24}F_3NO$
Molecular Weight: 363,42421

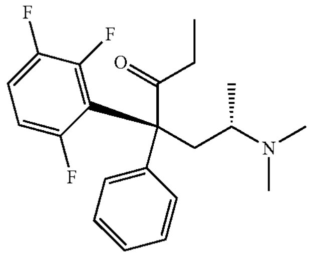 [SMILES: CCC(=O)[C@](C[C@H](C)N(C)C)(c1ccccc1)c1c(F)ccc(F)c1F]

DAN-DMD31
Chemical Formula: $C_{21}H_{25}F_2NO$
Molecular Weight: 345,43381

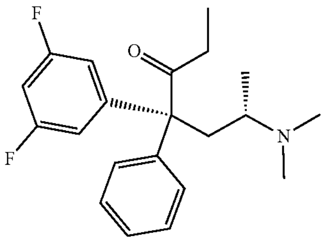 [SMILES: CCC(=O)[C@@](C[C@H](C)N(C)C)(c1ccccc1)c1cc(F)cc(F)c1]

DAN-DMD32
Chemical Formula: $C_{21}H_{25}F_2NO$
Molecular Weight: 345,43381

TABLE 1a-continued

| List of first set of designed SMOs tested in the in silico molecular model of the trans-membrane domain of the NR1-NR2B subtype of the closed NMDAR |
| --- |

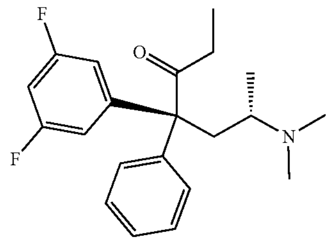 [SMILES: CCC(=O)[C@](C[C@H](C)N(C)C)(c1ccccc1)c1cc(F)cc(F)c1]

DAN-DMD33
Chemical Formula: $C_{21}H_{24}F_3NO$
Molecular Weight: 363,42421

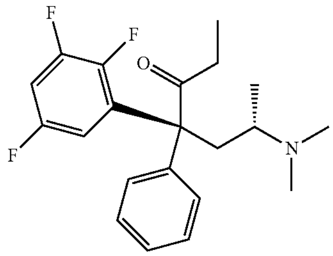 [SMILES: CCC(=O)[C@](C[C@H](C)N(C)C)(c1ccccc1)c1cc(F)cc(F)c1F]

DAN-DMD34
Chemical Formula: $C_{21}H_{24}BrF_2NO$
Molecular Weight: 424,32981

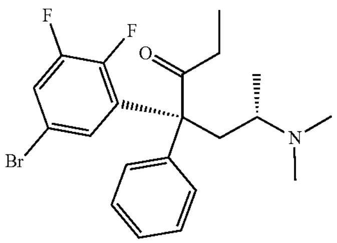 [SMILES: CCC(=O)[C@@](C[C@H](C)N(C)C)(c1ccccc1)c1cc(Br)cc(F)c1F]

DAN-DMD35
Chemical Formula: $C_{21}H_{24}BrF_2NO$
Molecular Weight: 424,32981

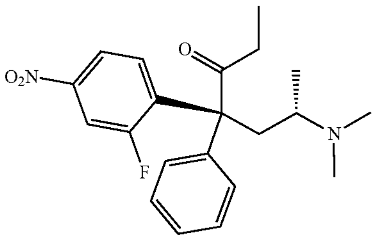 [SMILES: CCC(=O)[C@](C[C@H](C)N(C)C)(c1ccccc1)c1ccc([N+](=O)[O-])cc1F]

DAN-DMD36
Chemical Formula: $C_{21}H_{25}FN_2O_3$
Molecular Weight: 372,44040

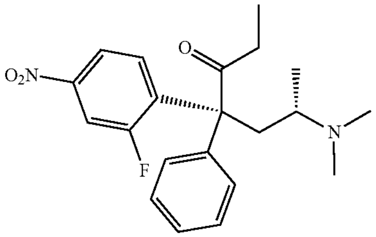 [SMILES: CCC(=O)[C@@](C[C@H](C)N(C)C)(c1ccccc1)c1ccc([N+](=O)[O-])cc1F]

DAN-DMD37
Chemical Formula: $C_{21}H_{25}FN_2O_3$
Molecular Weight: 372,44040

TABLE 1a-continued

| List of first set of designed SMOs tested in the in silico molecular model of the trans-membrane domain of the NR1-NR2B subtype of the closed NMDAR |
| --- |

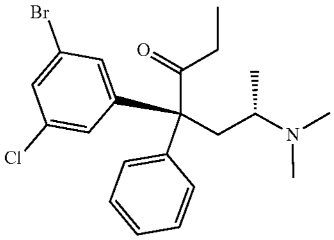 [SMILES: CCC(=O)[C@](C[C@H](C)N(C)C)(c1ccccc1)c1cc(Cl)cc(Br)c1]

DAN-DMD38
Chemical Formula: $C_{21}H_{25}BrClNO$
Molecular Weight: 422,79100

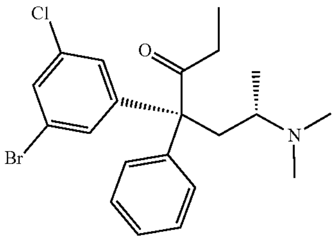 [SMILES: CCC(=O)[C@@](C[C@H](C)N(C)C)(c1ccccc1)c1cc(Cl)cc(Br)c1]

DAN-DMD39
Chemical Formula: $C_{21}H_{25}BrClNO$
Molecular Weight: 422,79100

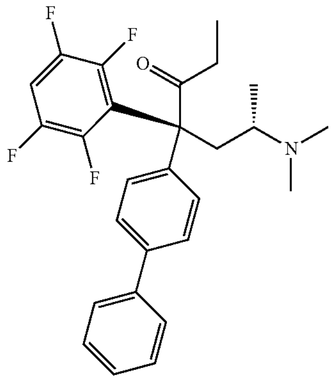

DAN-DMD40
Chemical Formula: $C_{27}H_{27}F_4NO$
Molecular Weight: 457,51261

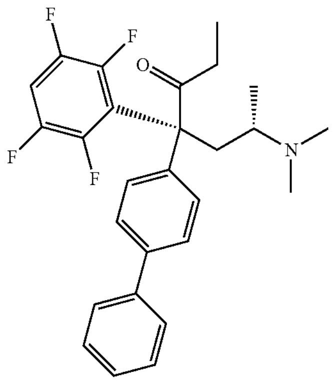 [SMILES: CCC(=O)[C@@](C[C@H](C)N(C)C)(c1ccc(-c2ccccc2)cc1)c1c(F)c(F)cc(F)c1F]

DAN-DMD41
Chemical Formula: $C_{27}H_{27}F_4NO$
Molecular Weight: 457,51261

TABLE 1a-continued

| List of first set of designed SMOs tested in the in silico molecular model of the trans-membrane domain of the NR1-NR2B subtype of the closed NMDAR |
| --- |
| 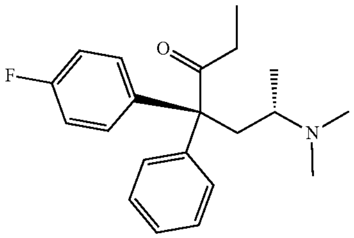 [SMILES: CCC(=O)[C@](C[C@H](C)N(C)C)(c1ccccc1)c1ccc(F)cc1]<br>DAN-DMD42<br>Chemical Formula: $C_{21}H_{26}FNO$<br>Molecular Weight: 327,44340 |
| 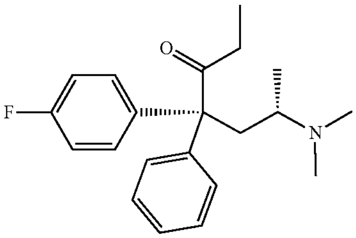 [SMILES: CCC(=O)[C@@](C[C@H](C)N(C)C)(c1ccccc1)c1ccc(F)cc1]<br>DAN-DMD43<br>Chemical Formula: $C_{21}H_{26}FNO$<br>Molecular Weight: 327,44340 |
| 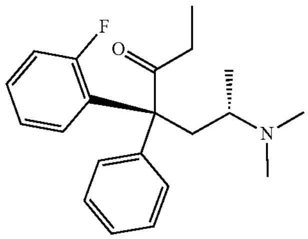 [SMILES: CCC(=O)[C@](C[C@H](C)N(C)C)(c1ccccc1)c1ccccc1F]<br>DAN-DMD44<br>Chemical Formula: $C_{21}H_{26}FNO$<br>Molecular Weight: 327,44340 |
| 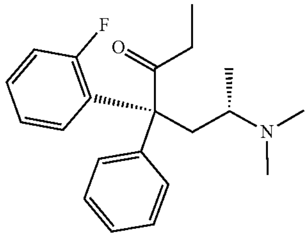 [SMILES: CCC(=O)[C@@](C[C@H](C)N(C)C)(c1ccccc1)c1ccccc1F]<br>DAN-DMD45<br>Chemical Formula: $C_{21}H_{26}FNO$<br>Molecular Weight: 327,44340 |
| 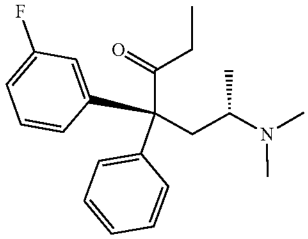 [SMILES: CCC(=O)[C@](C[C@H](C)N(C)C)(c1ccccc1)c1cccc(F)c1]<br>DAN-DMD46<br>Chemical Formula: $C_{21}H_{26}FNO$<br>Molecular Weight: 327,44340 |

TABLE 1a-continued

| List of first set of designed SMOs tested in the in silico molecular model of the trans-membrane domain of the NR1-NR2B subtype of the closed NMDAR |
| --- |
| 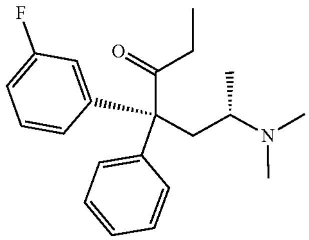 [SMILES: CCC(=O)[C@@](C[C@H](C)N(C)C)(c1ccccc1)c1cccc(F)c1]<br>DAN-DMD47<br>Chemical Formula: $C_{21}H_{26}FNO$<br>Molecular Weight: 327,44340 |
| 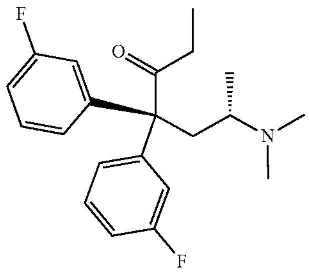<br>DAN-DMD48<br>Chemical Formula: $C_{21}H_{25}F_2NO$<br>Molecular Weight: 345,43381 |
| 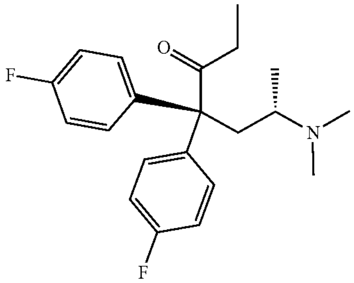<br>DAN-DMD49<br>Chemical Formula: $C_{21}H_{25}F_2NO$<br>Molecular Weight: 345,43381 |
| 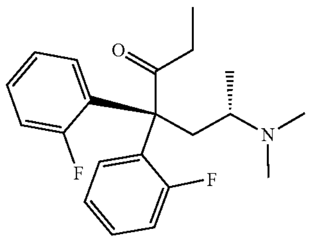<br>DAN-DMD50<br>Chemical Formula: $C_{21}H_{25}F_2NO$<br>Molecular Weight: 345,43381 |

TABLE 1b

List of second set of designed SMOs tested in the in silico molecular model of the trans-membrane domain of the NR1-NR2B subtype of the closed NMDAR

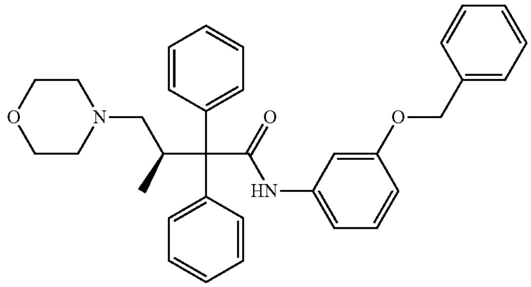 [SMILES: C[C@@H](CN1CCOCC1)C(C(=O)Nc1cccc(OCc2ccccc2)c1)(c1ccccc1)c1ccccc1]

LMA1
Chemical Formula: $C_{34}H_{36}N_2O_3$
Molecular Weight: 520,67300

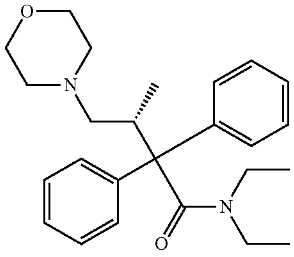 [SMILES: CCN(CC)C(=O)C(c1ccccc1)(c1ccccc1)[C@@H](C)CN1CCOCC1]

LMA2
Chemical Formula: $C_{25}H_{34}N_2O_2$
Molecular Weight: 394,55900

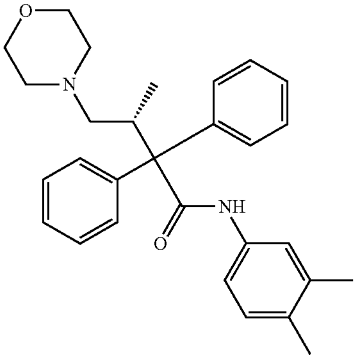 [SMILES: Cc1ccc(NC(=O)C(c2ccccc2)(c2ccccc2)[C@@H](C)CN2CCOCC2)cc1C]

LMA3
Chemical Formula: $C_{29}H_{34}N_2O_2$
Molecular Weight: 442,60300

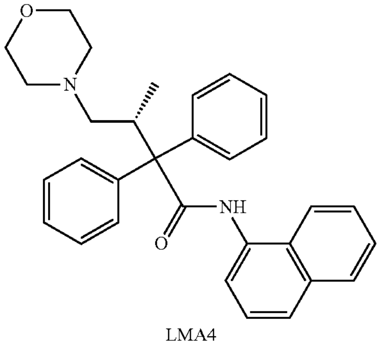

LMA4
Chemical Formula: $C_{31}H_{32}N_2O_2$
Molecular Weight: 464,60900

TABLE 1b-continued

List of second set of designed SMOs tested in the in silico molecular model of the trans-membrane domain of the NR1-NR2B subtype of the closed NMDAR

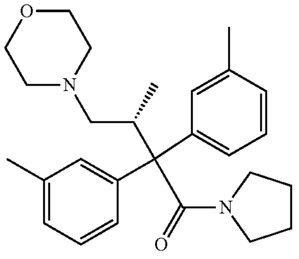 [SMILES: Cc1cccc(C(C(=O)N2CCCC2)(c2cccc(C)c2)[C@@H](C)CN2CCOCC2)c1]

LMA5
Chemical Formula: $C_{27}H_{36}N_2O_2$
Molecular Weight: 420,59700

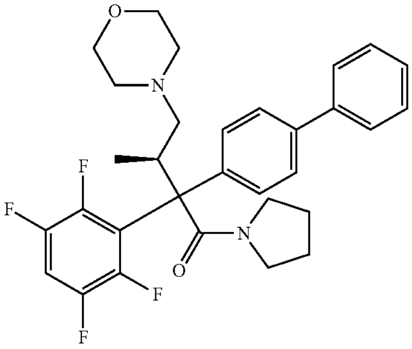 [SMILES: C[C@@H](CN1CCOCC1)C(C(=O)N1CCCC1)(c1ccc(-c2ccccc2)cc1)c1c(F)c(F)cc(F)c1F]

LMA6
Chemical Formula: $C_{31}H_{32}F_4N_2O_2$
Molecular Weight: 540,60261

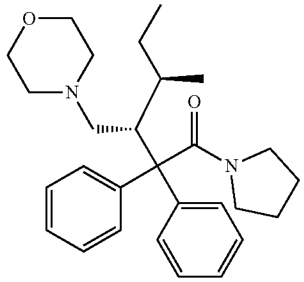 [SMILES: CC[C@@H](C)[C@@H](CN1CCOCC1)C(C(=O)N1CCCC1)(c1ccccc1)c1ccccc1]

LMA7
Chemical Formula: $C_{28}H_{38}N_2O_2$
Molecular Weight: 434,62400

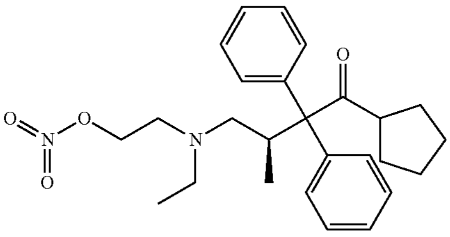 [SMILES: CCN(CCO[N+](=O)[O-])C[C@H](C)C(C(=O)C1CCCC1)(c1ccccc1)c1ccccc1]

LMA8
Chemical Formula: $C_{25}H_{33}N_3O_4$
Molecular Weight: 439,55600

TABLE 1b-continued

| List of second set of designed SMOs tested in the in silico molecular model of the trans-membrane domain of the NR1-NR2B subtype of the closed NMDAR |
|---|
| 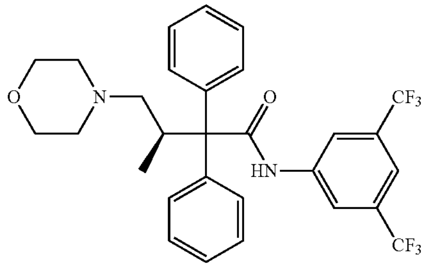 [SMILES: C[C@@H](CN1CCOCC1)C(C(=O)Nc1cc(C(F)(F)F)cc(C(F)(F)F)c1)(c1ccccc1)c1ccccc1] |
| LMA9<br>Chemical Formula: $C_{29}H_{28}F_6N_2O_2$<br>Molecular Weight: 550,54542 |
| 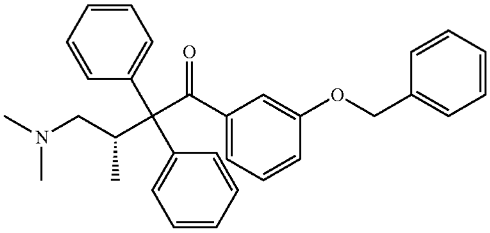 [SMILES: C[C@H](CN(C)C)C(C(=O)c1cccc(OCc2ccccc2)c1)(c1ccccc1)c1ccccc1] |
| DIMD1<br>Chemical Formula: $C_{32}H_{33}NO_2$<br>Molecular Weight: 463,62100 |
| 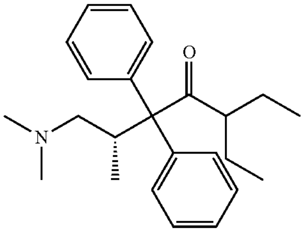 [SMILES: CCC(CC)C(=O)C(c1ccccc1)(c1ccccc1)[C@H](C)CN(C)C] |
| DIMD2<br>Chemical Formula: $C_{24}H_{33}NO$<br>Molecular Weight: 351,53400 |
| 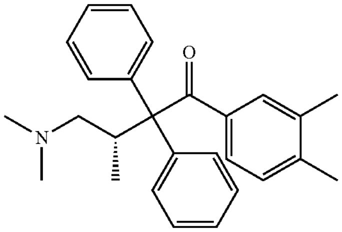 |
| DIMD3<br>Chemical Formula: $C_{27}H_{31}NO$<br>Molecular Weight: 385,55100 |
| 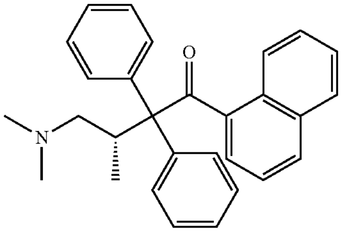 [SMILES: C[C@H](CN(C)C)C(C(=O)c1cccc2ccccc12)(c1ccccc1)c1ccccc1] |
| DIMD4<br>Chemical Formula: $C_{29}H_{29}NO$<br>Molecular Weight: 407,55700 |

TABLE 1b-continued

| List of second set of designed SMOs tested in the in silico molecular model of the trans-membrane domain of the NR1-NR2B subtype of the closed NMDAR |
|---|
| 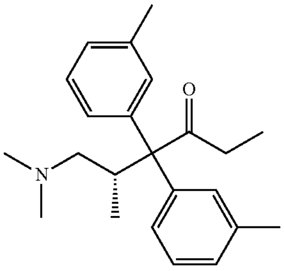 |
| DIMD5<br>Chemical Formula: $C_{23}H_{31}NO$<br>Molecular Weight: 337,50700 |
| 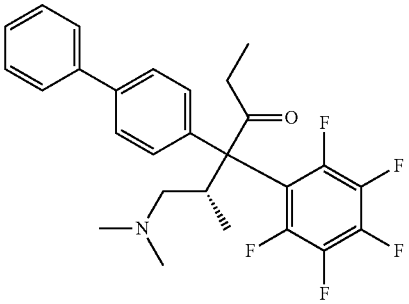 [SMILES: CCC(=O)C(c1ccc(-c2ccccc2)cc1)(c1c(F)c(F)c(F)c(F)c1F)[C@H](C)CN(C)C] |
| DIMD6<br>Chemical Formula: $C_{27}H_{27}F_4NO$<br>Molecular Weight: 457,51261 |
| 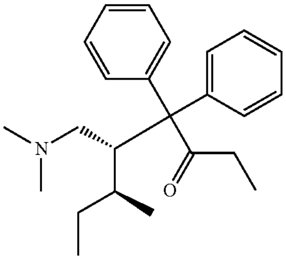 [SMILES: CCC(=O)C(c1ccccc1)(c1ccccc1)[C@@H](CN(C)C)[C@@H](C)CC] |
| DIMD7<br>Chemical Formula: $C_{24}H_{33}NO$<br>Molecular Weight: 351,53400 |
| 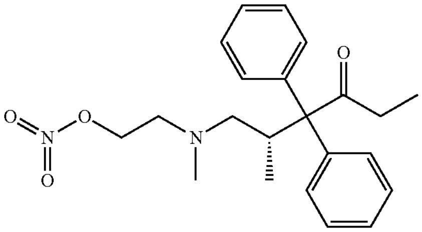 [SMILES: CCC(=O)C(c1ccccc1)(c1ccccc1)[C@H](C)CN(C)CCO[N+](=O)[O-]] |
| DIMD8<br>Chemical Formula: $C_{22}H_{28}N_2O_4$<br>Molecular Weight: 384,47600 |

TABLE 1b-continued

List of second set of designed SMOs tested in the in silico molecular model of the trans-membrane domain of the NR1-NR2B subtype of the closed NMDAR

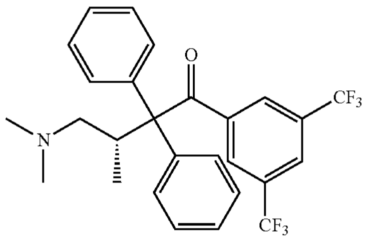 [SMILES: C[C@H](CN(C)C)C(C(=O)c1cc(C(F)(F)F)cc(C(F)(F)F)c1)(c1ccccc1)c1ccccc1]

DIMD9
Chemical Formula: $C_{27}H_{25}F_6NO$
Molecular Weight: 493,49342

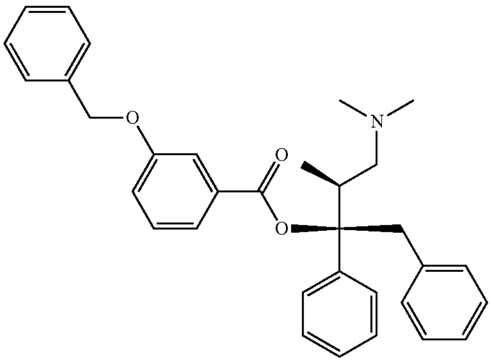 [SMILES: C[C@@H](CN(C)C)[C@@](Cc1ccccc1)(OC(=O)c1cccc(OCc2ccccc2)c1)c1ccccc1]

LPP1
Chemical Formula: $C_{33}H_{35}NO_3$
Molecular Weight: 493,64700

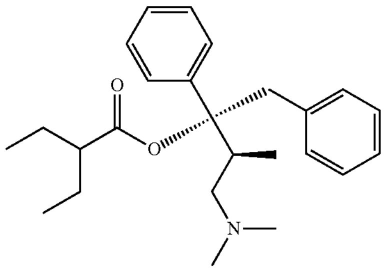 [SMILES: CCC(CC)C(=O)O[C@@](Cc1ccccc1)(c1ccccc1)[C@@H](C)CN(C)C]

LPP2
Chemical Formula: $C_{25}H_{35}NO_2$
Molecular Weight: 381,56000

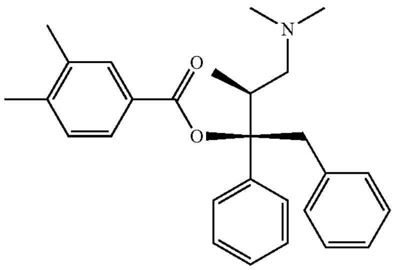 [SMILES: Cc1ccc(C(=O)O[C@@](Cc2ccccc2)(c2ccccc2)[C@@H](C)CN(C)C)cc1C]

LPP3
Chemical Formula: $C_{28}H_{33}NO_2$
Molecular Weight: 415,57700

TABLE 1b-continued

List of second set of designed SMOs tested in the in silico molecular model of the trans-membrane domain of the NR1-NR2B subtype of the closed NMDAR

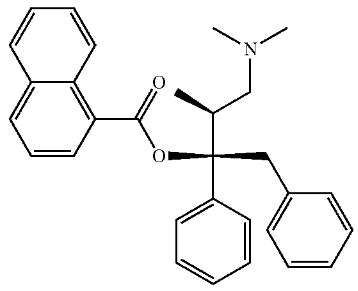 [SMILES: C[C@@H](CN(C)C)[C@@](Cc1ccccc1)(OC(=O)c1cccc2ccccc12)c1ccccc1]

LPP4
Chemical Formula: $C_{30}H_{31}NO_2$
Molecular Weight: 437,58300

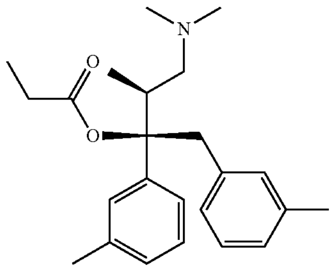 [SMILES: CCC(=O)O[C@@](Cc1cccc(C)c1)(c1cccc(C)c1)[C@@H](C)CN(C)C]

LPP5
Chemical Formula: $C_{24}H_{33}NO_2$
Molecular Weight: 367,53300

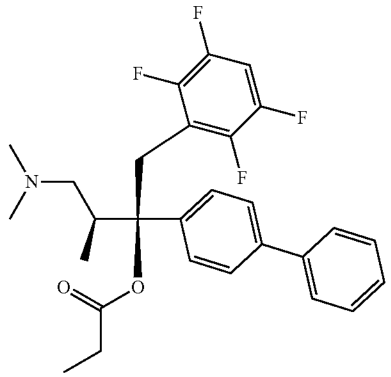 [SMILES: CCC(=O)O[C@@](Cc1c(F)c(F)cc(F)c1F)(c1ccc(-c2ccccc2)cc1)[C@@H](C)CN(C)C]

LPP6
Chemical Formula: $C_{28}H_{29}F_4NO_2$
Molecular Weight: 487,53861

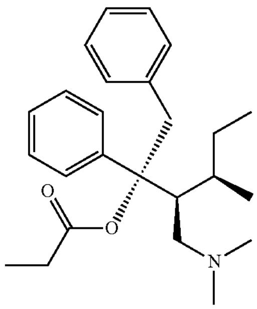 [SMILES: CCC(=O)O[C@@](Cc1ccccc1)(c1ccccc1)[C@H](CN(C)C)[C@H](C)CC]

LPP7
Chemical Formula: $C_{25}H_{35}NO_2$
Molecular Weight: 381,56000

TABLE 1b-continued

| List of second set of designed SMOs tested in the in silico molecular model of the trans-membrane domain of the NR1-NR2B subtype of the closed NMDAR |
|---|
| 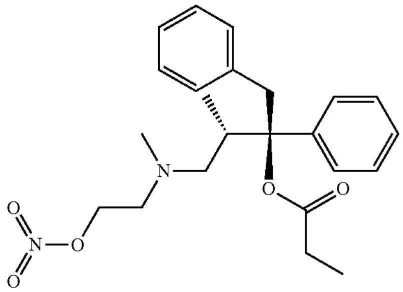 [SMILES: CCC(=O)O[C@@](Cc1ccccc1)(c1ccccc1)[C@@H](C)CN(C)CCO[N+](=O)[O-]]<br>LPP8<br>Chemical Formula: $C_{23}H_{30}N_2O_5$<br>Molecular Weight: 414,50200 |
| 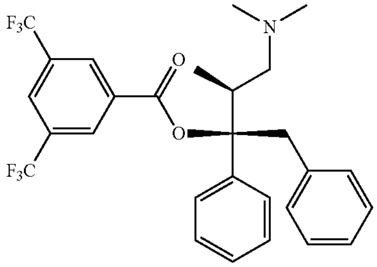 [SMILES: C[C@@H](CN(C)C)[C@@](Cc1ccccc1)(OC(=O)c1cc(C(F)(F)F)cc(C(F)(F)F)c1)c1ccccc1]<br>LPP9<br>Chemical Formula: $C_{28}H_{27}F_6NO_2$<br>Molecular Weight: 523,51942 |
| 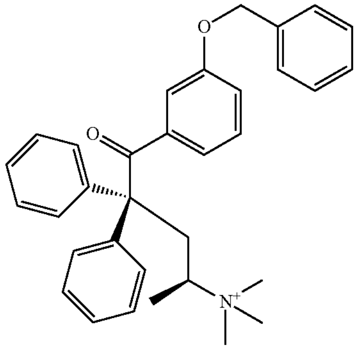<br>NMeDMD1<br>Chemical Formula: $C_{33}H_{36}NO_2^+$<br>Molecular Weight: 478,65545 |
| 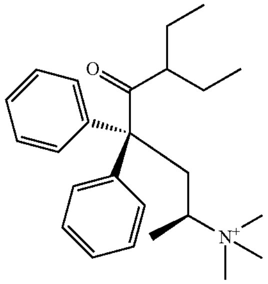<br>NMeDMD2<br>Chemical Formula: $C_{25}H_{36}NO^+$<br>Molecular Weight: 366,56845 |

TABLE 1b-continued

| List of second set of designed SMOs tested in the in silico molecular model of the trans-membrane domain of the NR1-NR2B subtype of the closed NMDAR |
|---|
| 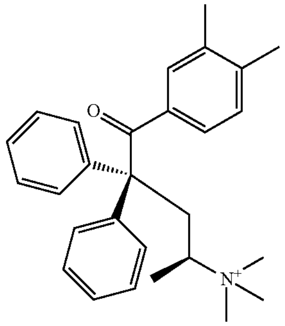<br>NMeDMD3<br>Chemical Formula: $C_{28}H_{34}NO^+$<br>Molecular Weight: 400,58545 |
| 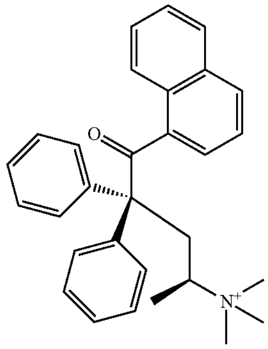<br>NMeDMD4<br>Chemical Formula: $C_{30}H_{32}NO^+$<br>Molecular Weight: 422,59145 |
| 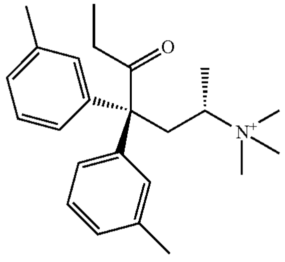<br>NMeDMD5<br>Chemical Formula: $C_{24}H_{34}NO^+$<br>Molecular Weight: 352,54145 |

TABLE 1b-continued

List of second set of designed SMOs tested in the in silico molecular model of the trans-membrane domain of the NR1-NR2B subtype of the closed NMDAR

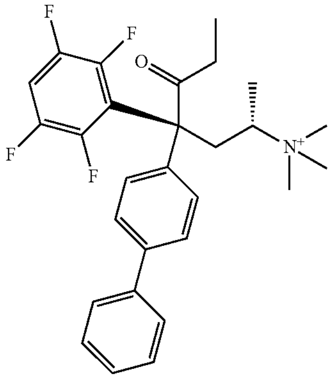 [SMILES: CCC(=O)[C@](C[C@H](C)[N+](C)(C)C)(c1ccc(-c2ccccc2)cc1)c1c(F)c(F)cc(F)c1F]

NMeDMD6
Chemical Formula: $C_{28}H_{30}F_4NO^+$
Molecular Weight: 472,54706

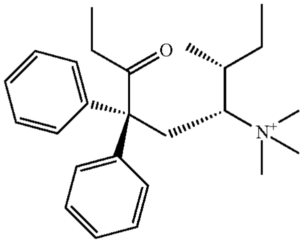

NMeDMD7
Chemical Formula: $C_{25}H_{36}NO^+$
Molecular Weight: 366,56845

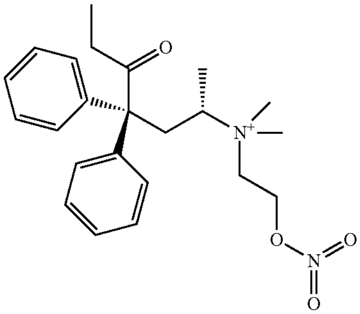

NMeDMD8
Chemical Formula: $C_{23}H_{31}N_2O_4^+$
Molecular Weight: 399,51045

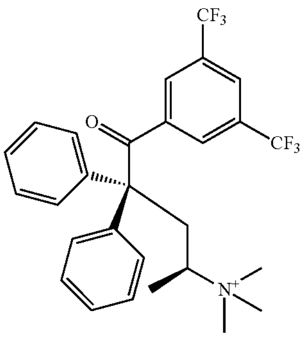

NMeDMD9
Chemical Formula: $C_{28}H_{28}F_6NO^+$
Molecular Weight: 508,52787

TABLE 1b-continued

List of second set of designed SMOs tested in the in silico molecular model of the trans-membrane domain of the NR1-NR2B subtype of the closed NMDAR

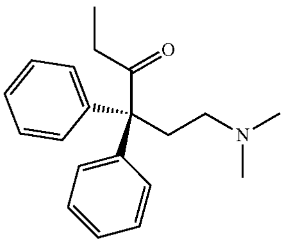

DMD-AA1
Chemical Formula: $C_{20}H_{25}NO$
Molecular Weight: 295,42600

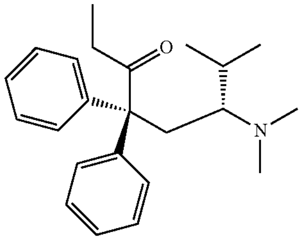

DMD-AA2
Chemical Formula: $C_{23}H_{31}NO$
Molecular Weight: 337,50700

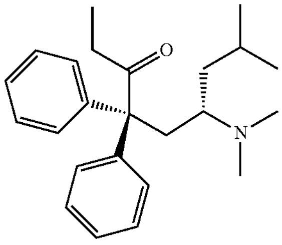

DMD-AA3
Chemical Formula: $C_{24}H_{33}NO$
Molecular Weight: 351,53400

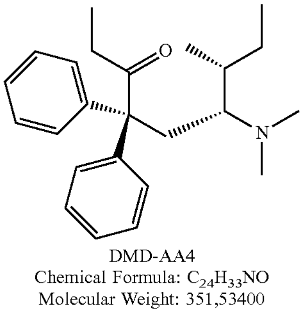

DMD-AA4
Chemical Formula: $C_{24}H_{33}NO$
Molecular Weight: 351,53400

TABLE 1b-continued

| List of second set of designed SMOs tested in the in silico molecular model of the trans-membrane domain of the NR1-NR2B subtype of the closed NMDAR |
|---|

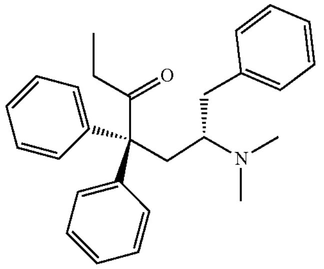

DMD-AA5
Chemical Formula: $C_{27}H_{31}NO$
Molecular Weight: 385,55100

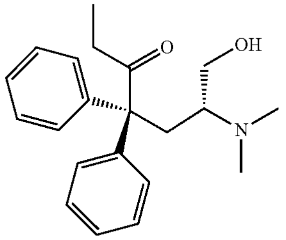

DMD-AA6
Chemical Formula: $C_{21}H_{27}NO_2$
Molecular Weight: 325,45200

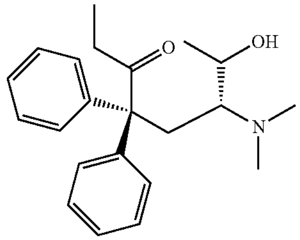

DMD-AA7
Chemical Formula: $C_{22}H_{29}NO_2$
Molecular Weight: 339,47900

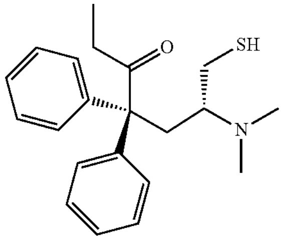

DMD-AA8
Chemical Formula: $C_{21}H_{27}NOS$
Molecular Weight: 341,51300

TABLE 1b-continued

| List of second set of designed SMOs tested in the in silico molecular model of the trans-membrane domain of the NR1-NR2B subtype of the closed NMDAR |
|---|

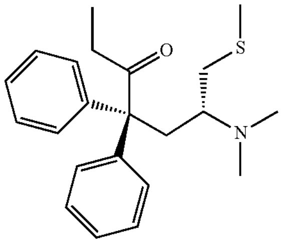

DMD-AA9
Chemical Formula: $C_{22}H_{29}NOS$
Molecular Weight: 355,54000

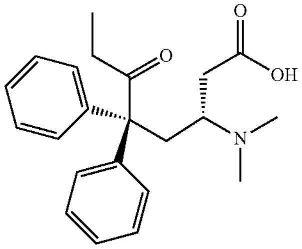

DMD-AA10
Chemical Formula: $C_{22}H_{27}NO_3$
Molecular Weight: 353,46200

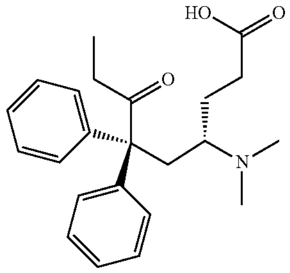

DMD-AA11
Chemical Formula: $C_{23}H_{29}NO_3$
Molecular Weight: 367,48900

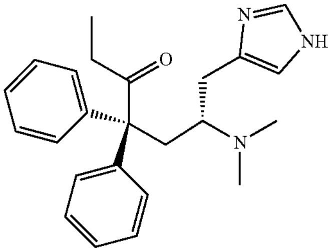

DMD-AA12
Chemical Formula: $C_{24}H_{29}N_3O$
Molecular Weight: 375,51600

TABLE 1b-continued

List of second set of designed SMOs tested in the in silico molecular model of the trans-membrane domain of the NR1-NR2B subtype of the closed NMDAR

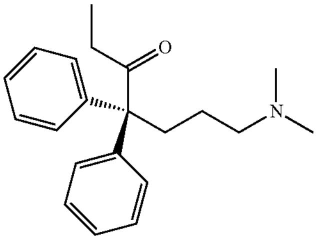

DMD-AA13
Chemical Formula: $C_{21}H_{27}NO$
Molecular Weight: 309,45300

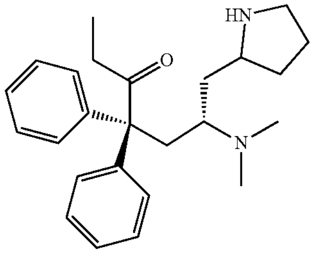

DMD-AA14
Chemical Formula: $C_{25}H_{34}N_2O$
Molecular Weight: 378,56000

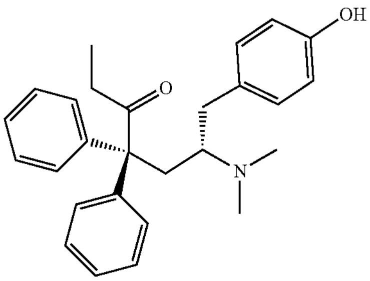

DMD-AA15
Chemical Formula: $C_{27}H_{31}NO_2$
Molecular Weight: 401,55000

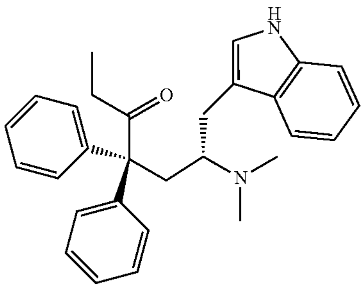

DMD-AA16
Chemical Formula: $C_{29}H_{32}N_2O$
Molecular Weight: 424,58800

Following the design of these molecules, the next steps were the testing of these designer molecules in silico in order to select the best candidates (details of the novel molecular model developed ad hoc and results of testing are discussed below in the section labeled "Molecular Modeling Investigations of Select SMOs Binding to the Trans-Membrane Site of the NMDA Receptor GluN1-GluN2B Tetramer Subtype in its Closed State"), and the synthesis of select molecules, followed by more advanced and specific in vitro and in vivo tests for NMDAR activity, including electro-physiologic testing of NMDARs to characterize relative affinity (methods for which are described in International Patent Application No. PCT/US2018/016159) and testing of mechanism of block (e.g., drugs with uncompetitive type block actions are likely to be safer and more effective because of their selective actions at sites of NMDAR dysfunction and not at sites with physiologic activities). The present inventors have already begun verifying excitotoxicity protection in vitro and are evaluating select SMOs for safety and activity in in vitro experimental models. Finally, after entering into the clinical phases of development, the present inventors will confirm tolerability and effectiveness in human trials, first in healthy volunteers, and then in patients with specific diseases and conditions, as the present inventors are doing with the dextromethadone program, currently in phase 2 clinical development for treatment resistant depression and RLS.

Molecular Modeling Investigations of Select SMOs Binding to the Trans-Membrane Site of the NMDA Receptor GluN1-GluN2B Tetramer Subtype in its Closed State Until recently, because technical limitations in both expression and purification of the trans-membrane proteins of the NMDAR, the structure of the trans-membrane domain of NMDAR had not been characterized at atomistic level. In 2014 Gouaux and co-workers solved the structure of the *Xenopus laevis* GluN1-GluN2B NMDA receptor by X-ray crystallography (Lee, Lu et al. 2014). This structure was obtained in presence of Ro25-6981, a partial agonist, and MK-801, an ion channel blocker, and represents a closed state of the NMDAR. Given the high similarity of this structure with the human sequence, the present inventors used the structure identified by the Protein Data Bank (PDB) code 4TLM as the starting point for the present inventors' computational studies. The present inventors investigated the following drugs shown in Table 2c: (a) putative NMDAR antagonists: levomoramide, d-isomethadone, levopropoxyphene, N-methyl d-methadone; (b) dextromethadone, an established NMDAR antagonist, currently in clinical development for several indications; (c) positive controls (ketamine, memantine, dextromethorphan, amantadine, MK-801, PCP) all known NMDA open channel blockers acting at the PCP site at the trans-membrane domain with known affinities and known clinical effects; the first four drugs are in clinical uses while PCP is a schedule I drug and MK-801 is a high affinity antagonist with severe side effects that impede its clinical use; (d) morphine a drug with negligible NMDAR activity was also tested as a negative control. As seen in table 2 the docking and dynamic scores are in a similar range as those of established NMDAR channel blockers. The present inventors observed that morphine, naloxone and naltrexone (all of which have negligible affinity for the NMDAR) possess a hydrogen donor group, while dextromethorphan and methadone (with known clinically relevant affinity for the NMDAR in the low micromolar range) do not possess this hydrogen donor group. This original observation, together with the novel results of the in-silico testing presented in Annex 2 and the planned patch clamp studies, has greatly aided in the design of novel SMOs with improved SAR for the NMDAR.

Apart from the information shown in Table 2c, Table 2a shows docking results for the first series of newly designed SMOs. And Table 2b shows docking results for the second series of newly designed SMOs.

While NMDAR antagonists acting at the trans-membrane domain of the receptor currently in clinical use are thought to exert their effects by binding to the open NMDAR, for the purpose of this computational model, the present inventors studied the binding to the closed conformation of the channel: clinically effective NMDAR antagonist drugs also bind to the PCP site in the closed state (Zanos et al., 2018) and their "trapping" index in the closed state, a reflection of the relation of "onset" and "offset" time of action, can be an indication of clinical tolerability and effectiveness (Zanos et al., 2018; (Huei-Sheng Vincent Chen and Stuart A. Lipton. The chemical biology of clinically tolerated NMDA receptor antagonists. Journal of Neurochemistry, 2006, 97, 1611-1626)). Effective NMDAR modulators should therefore bind the open channel but also briefly (for a few milliseconds) bind the closed channel ("foot in the door" concept), while avoiding prolonged "trapping". In docking calculations, the ligand is built inside the hosting binding site and therefore the closed conformation is more apt to evaluate the ligand/site interaction: the trajectory of the ligand to the binding site is not considered by the docking calculation.

The computational NMDAR subtype built for this in silico testing is the GluN1-GluN2B tetramer composed by 2 GluN1 subunits and 2 GluN2B subunits. N2B subunits are essential for formation of super-complexes that include NMDARs. As detailed in the application, the inventors discovered that dextromethadone increases levels of PD95, GluR1 in vivo (FIG. 4B) and that in vitro dextromethadone increases mRNA for NMDAR1 (FIG. 10), offering additional insight in the PD and neural plasticity potential of dextromethadone. The carboxy terminal intra-cytoplasmatic tail of GluN2B is essential for NMDA super-complex assembly, together with PD95-PD93 subunits, as discussed above in this application.

To improve the computational efficiency of the present inventors' calculations, only the trans-membrane region of the receptor, where the PCP binding site is located, and where the FDA-approved and clinically tolerated NMDA antagonists also act (dextromethorphan, ketamine/esketamine, amantadine, memantine), and where the present inventors postulate the putative NMDA antagonists opioid enantiomers and their SMOs, object of the present disclosure, act, was included into the simulated models. The goal of this computational portion of the inventors' work is to optimize the structure of select opioids by modifying select portions of their structure key for their binding to the trans-membrane domain of the NMDAR in order to achieve a block of the pore channel when its regulation is needed to prevent or treat select diseases. Each SMO, aside for having unique onset/offset/trapping and unique actions on NMDAR subtypes and variances as described in the application, which may be advantageous for select diseases, will also have unique PK characteristics, which may also offer benefits for select diseases.

Receptor Preparation

First, the receptor was prepared by the 'protein preparation wizard' procedure available in the Schrödinger suite, from Schrödinger of New York, NY (https://www.schrodinger.com/) for molecular modelling.

This procedure automatically assigns the correct protonation state, completes missing side chains or small region, and assigns the correct name to the atoms. Then considering the data available in the Orientations of Proteins in Membranes database (OPM) database, (Lomize et al., 2012) the receptor model was immersed in a membrane model formed by 1-palmitoyl-2-oleoyl-sn-glycero-3-phosphocholine (POPC) molecules.

Docking of Known Drugs

The first attempt to dock the molecules to investigate inside the receptor conformation directly derived from x-ray studies was done using the Glide software (available from Schrödinger, of New York, NY) (https://www.schrodinger.com/glide). During the docking procedure the protein region in which the drug can be positioned was manually defined.

In this case, because of the lacking of a co-crystallized ligand, this region was defined considering the residues identified critical for the memantine binding by Dougherty and co-workers (Limapichat et al., 2013).

The present inventors reduced the van der Waals (VdW) radii of the molecules in order to permit a more 'flexible' adaptation of the molecules to the receptor.

The docking calculations for levopropoxyphene were successful and produced a model of the drug receptor complex, while confirming the potential NMDAR blocking activity of levopropoxyphene.

Then, in order to permit the creation of a site more suitable for drug binding, the levopropoxyphene-receptor complex immersed into the membrane was simulated for 250 ns by Molecular Dynamics (MD) simulations.

The final conformation of the receptor was then used to perform new docking calculations with the same set-up applied initially.

The calculations were successful and structures of the drug receptor complex were obtained for the drugs tested.

Molecular Dynamic (MD) Simulations of the Receptor Drug Complexes

The systems composed by the drug, the receptor and the membrane were then simulated by MD for 1 μsec. The present inventors produced trajectories for the complexes with: l-moramide, d-isometadone, levopropoxyphene, dextromethadone, memantine, ketamine, amantadine, dextromethorphan, PCP, MK-801, morphine. The simulation with the N-methyl d-methadone resulted to be unstable, suggesting a possible difficult binding of this molecule without structural modifications.

Virtual Pre-Screening

The obtained receptor model used to dock I-moramide, d-isometadone, levopropoxyphene, dextromethadone, memantine, ketamine, amantadine, dextromethorphan, PCP, MK-801, morphine was then used to pre-screen the first set of newly designed SMOs and then a second set of SMOs. For this purpose, the 2D chemical structures of the molecules was transformed in 3D models for which all the possible protonation state were calculated. All the ligands were docked inside the receptor and their affinity scored by GlideScore—a specific scoring function for drug-protein interactions, based on the Glide software of Schrödinger, of New York, NY (https://www.schrodinger.com/glide_) and shown in Table 2a (first set of SMOs), Table 2b (second set of SMOs), and table 2c (initial set of select molecules).

TABLE 2a
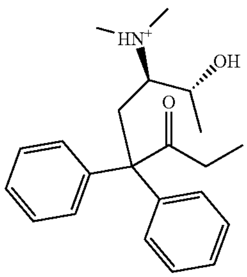 [SMILES: CCC(=O)C(C[C@H]([C@@H](C)O)[NH+](C)C)(c1ccccc1)c1ccccc1]
title: DMD-AA12
glide gscore: −7.885
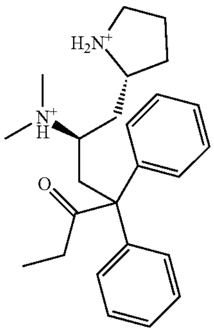
title: DMD-AA14
glide gscore: −7.867
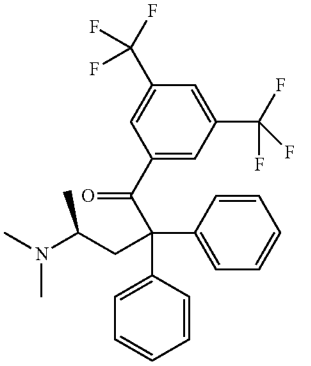 [SMILES: C[C@@H](CC(C(=O)c1cc(C(F)(F)F)cc(C(F)(F)F)c1)(c1ccccc1)c1ccccc1)N(C)C]
title: G55
glide gscore: −7.753
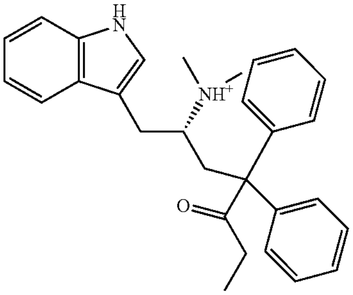 [SMILES: CCC(=O)C(C[C@H](Cc1c[nH]c2ccccc12)[NH+](C)C)(c1ccccc1)c1ccccc1]
title: DMD-AA16
glide gscore: −7.707
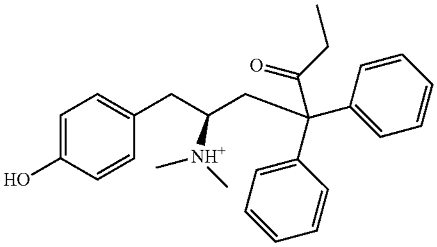 [SMILES: CCC(=O)C(C[C@H](Cc1ccc(O)cc1)[NH+](C)C)(c1ccccc1)c1ccccc1]
title: DMD-AA15
glide gscore: −7.64
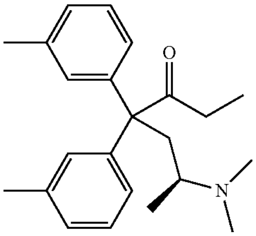
title: DMD7
glide gscore: −7.595
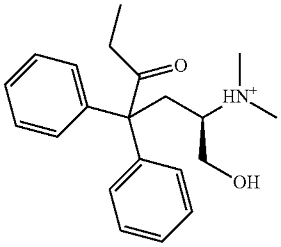 [SMILES: CCC(=O)C(C[C@H](CO)[NH+](C)C)(c1ccccc1)c1ccccc1]
title: DMD-AA5
glide gscore: −7.568
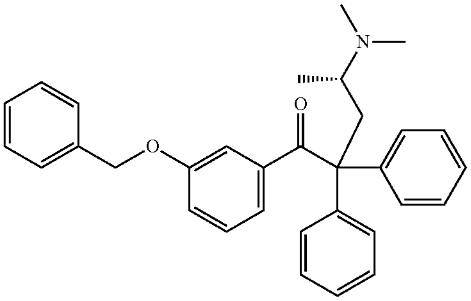 [SMILES: C[C@@H](CC(C(=O)c1cccc(OCc2ccccc2)c1)(c1ccccc1)c1ccccc1)N(C)C]
title: G121
glide gscore: −7.515

TABLE 2a-continued
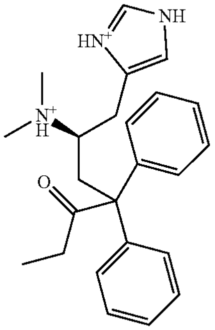
title: DMD-AA10
glide gscore: −7.486
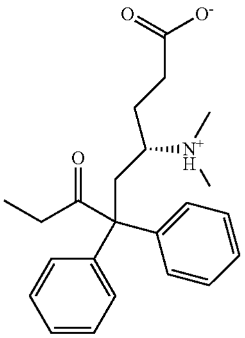
title: DMD-AA9
glide gscore: −7.285
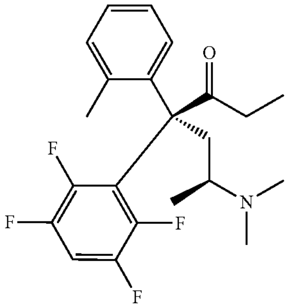 [SMILES: CCC(=O)[C@](C[C@H](C)N(C)C)(c1ccccc1C)c1c(F)c(F)cc(F)c1F]
title: DMD15
glide gscore: −7.273
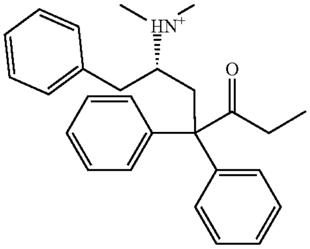 [SMILES: CCC(=O)C(C[C@H](Cc1ccccc1)[NH+](C)C)(c1ccccc1)c1ccccc1]
title: DMD-AA4
glide gscore: −7.257
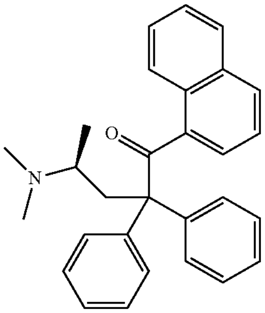 [SMILES: C[C@@H](CC(C(=O)c1cccc2ccccc12)(c1ccccc1)c1ccccc1)N(C)C]
title: G108
glide gscore: −7.249
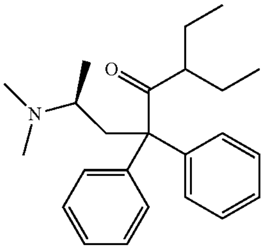 [SMILES: CCC(CC)C(=O)C(C[C@H](C)N(C)C)(c1ccccc1)c1ccccc1]
title: G30
glide gscore: −7.241
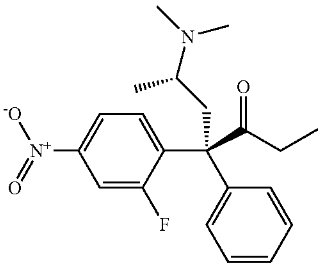
title: DMD37
glide gscore: −7.224
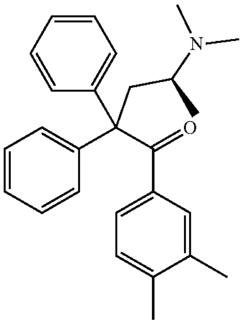 [SMILES: Cc1ccc(C(=O)C(C[C@H](C)N(C)C)(c2ccccc2)c2ccccc2)cc1C]
title: G92
glide gscore: −7.2

TABLE 2a-continued
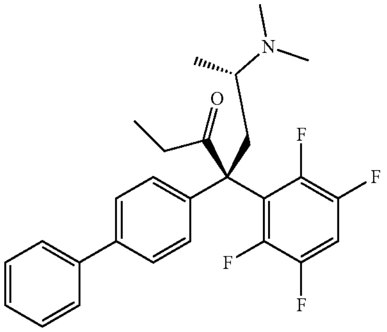 [SMILES: CCC(=O)[C@](C[C@H](C)N(C)C)(c1ccc(-c2ccccc2)cc1)c1c(F)c(F)cc(F)c1F]
title: DMD41
glide gscore: −7.169
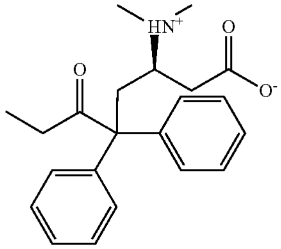 [SMILES: CCC(=O)C(C[C@H](CC(=O)[O-])[NH+](C)C)(c1ccccc1)c1ccccc1]
title: DMD-AA8
glide gscore: −7.165
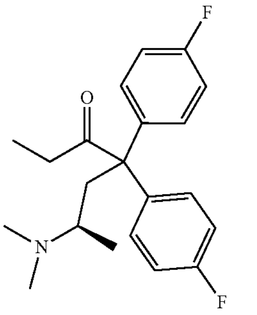 [SMILES: CCC(=O)C(C[C@@H](C)N(C)C)(c1ccc(F)cc1)c1ccc(F)cc1]
title: DMD49
glide gscore: −7.124
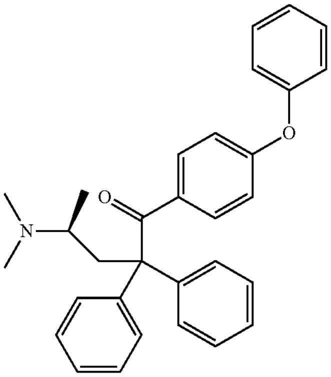 [SMILES: C[C@@H](CC(C(=O)c1ccc(Oc2ccccc2)cc1)(c1ccccc1)c1ccccc1)N(C)C]
title: G119
glide gscore: −7.09
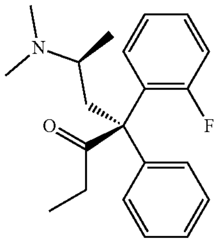 [SMILES: CCC(=O)[C@](C[C@H](C)N(C)C)(c1ccccc1)c1ccccc1F]
title: DMD45
glide gscore: −7.074
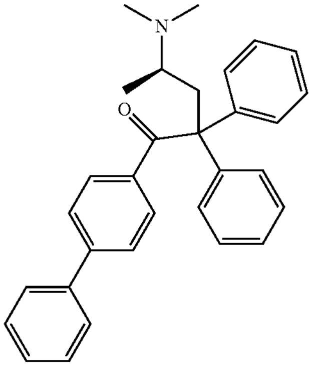 [SMILES: C[C@H](CC(C(=O)c1ccc(-c2ccccc2)cc1)(c1ccccc1)c1ccccc1)N(C)C]
title: G116
glide gscore: −7.067
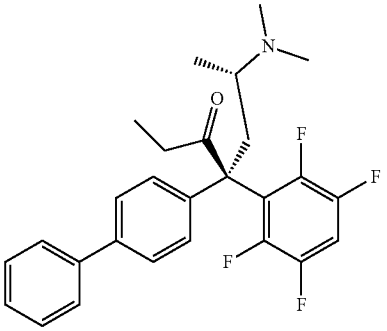 [SMILES: CCC(=O)[C@](C[C@H](C)N(C)C)(c1ccc(-c2ccccc2)cc1)c1c(F)c(F)cc(F)c1F]
title: DMD40
glide gscore: −7.045
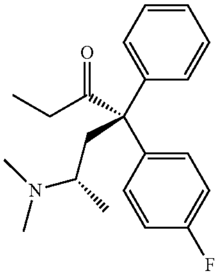 [SMILES: CCC(=O)[C@](C[C@H](C)N(C)C)(c1ccccc1)c1ccc(F)cc1]
title: DMD42
glide gscore: −7.032

TABLE 2a-continued
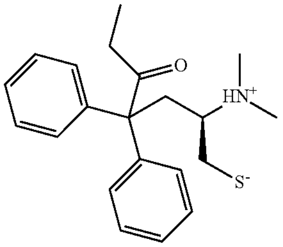 [SMILES: CCC(=O)C(C[C@H](C[S-])[NH+](C)C)(c1ccccc1)c1ccccc1]
title: DMD-AA6
glide gscore: −7.027
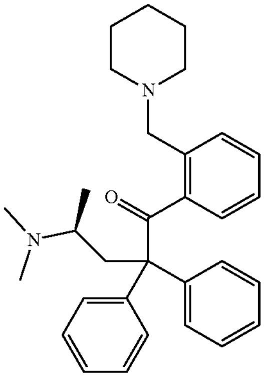 [SMILES: C[C@@H](CC(C(=O)c1ccccc1CN1CCCCC1)(c1ccccc1)c1ccccc1)N(C)C]
title: G120
glide gscore: −7.024
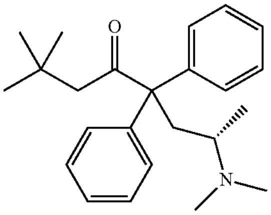 [SMILES: C[C@@H](CC(C(=O)CC(C)(C)C)(c1ccccc1)c1ccccc1)N(C)C]
title: G34
glide gscore: −6.999
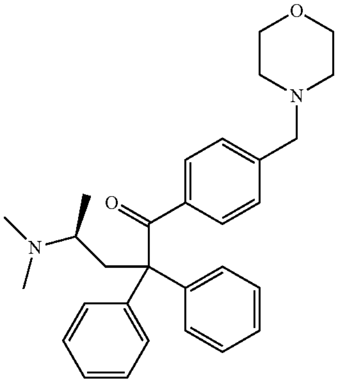 [SMILES: C[C@@H](CC(C(=O)c1ccc(CN2CCOCC2)cc1)(c1ccccc1)c1ccccc1)N(C)C]
title: G115
glide gscore: −6.891
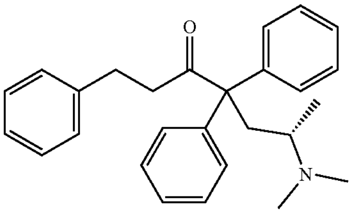 [SMILES: C[C@@H](CC(C(=O)CCc1ccccc1)(c1ccccc1)c1ccccc1)N(C)C]
title: G95
glide gscore: −6.886
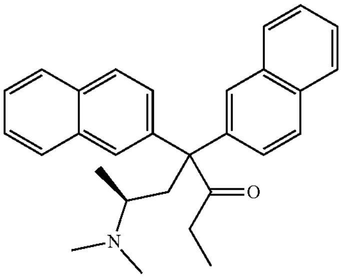 [SMILES: CCC(=O)C(C[C@H](C)N(C)C)(c1ccc2ccccc2c1)c1ccc2ccccc2c1]
title: DMD6
glide gscore: −6.878
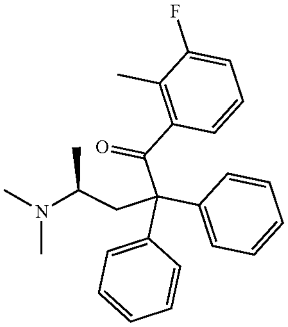 [SMILES: Cc1c(F)cccc1C(=O)C(C[C@H](C)N(C)C)(c1ccccc1)c1ccccc1]
title: G66
glide gscore: −6.874
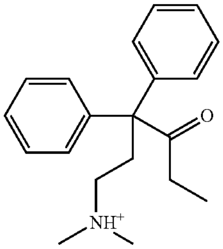 [SMILES: CCC(=O)C(CC[NH+](C)C)(c1ccccc1)c1ccccc1]
title: DMD-AA1
glide gscore: −6.864

TABLE 2a-continued
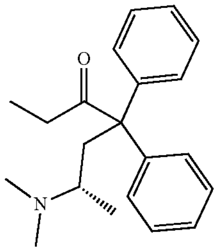 [SMILES: CCC(=O)C(C[C@H](C)N(C)C)(c1ccccc1)c1ccccc1]
title: G1
glide gscore: −6.862
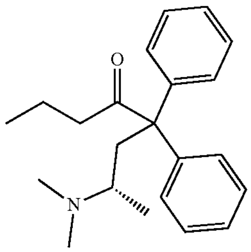 [SMILES: CCCC(=O)C(C[C@H](C)N(C)C)(c1ccccc1)c1ccccc1]
title: G12
glide gscore: −6.861
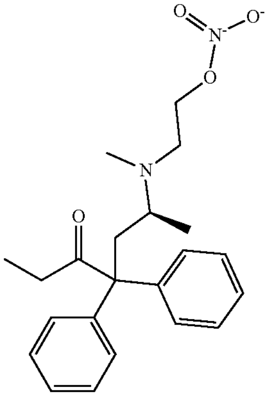
title: G124
glide gscore: −6.853
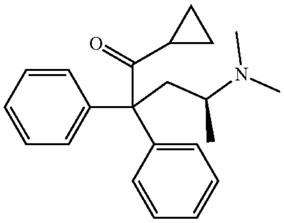 [SMILES: C[C@@H](CC(C(=O)C1CC1)(c1ccccc1)c1ccccc1)N(C)C]
title: G9
glide gscore: −6.847
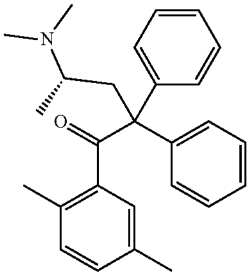 [SMILES: Cc1ccc(C)c(C(=O)C(C[C@H](C)N(C)C)(c2ccccc2)c2ccccc2)c1]
title: G82
glide gscore: −6.837
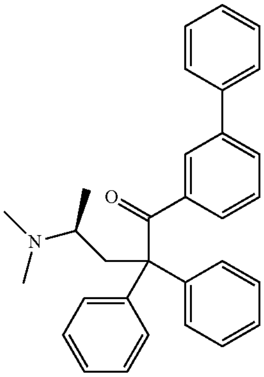 [SMILES: C[C@@H](CC(C(=O)c1cccc(-c2ccccc2)c1)(c1ccccc1)c1ccccc1)N(C)C]
title: G117
glide gscore: −6.835
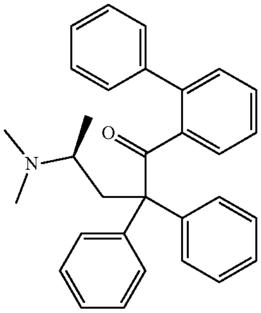 [SMILES: C[C@@H](CC(C(=O)c1ccccc1-c1ccccc1)(c1ccccc1)c1ccccc1)N(C)C]
title: G118
glide gscore: −6.812
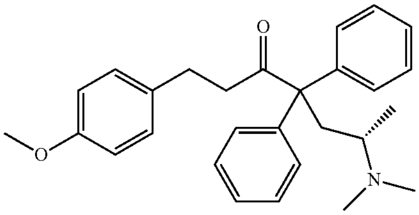
title: G106
glide gscore: −6.803

TABLE 2a-continued
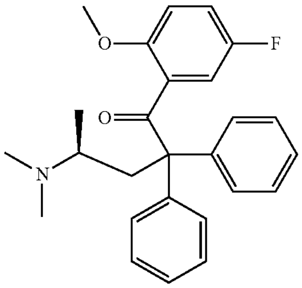 [SMILES: COc1ccc(F)cc1C(=O)C(C[C@H](C)N(C)C)(c1ccccc1)c1ccccc1]
title: G63
glide gscore: −6.799
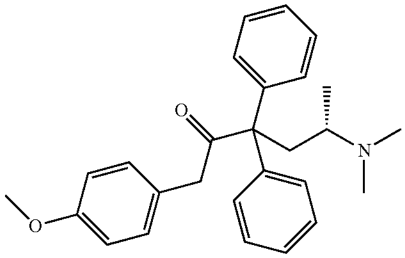
title: G98
glide gscore: −6.799
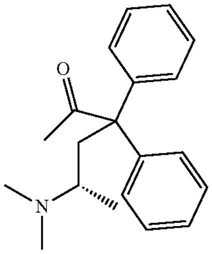 [SMILES: CC(=O)C(C[C@H](C)N(C)C)(c1ccccc1)c1ccccc1]
title: G2
glide gscore: −6.794
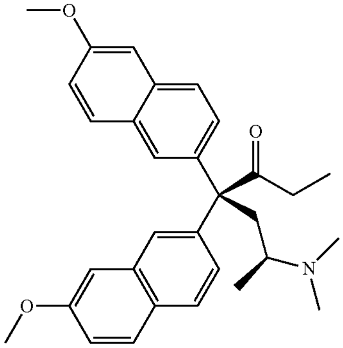
title: DMD9
glide gscore: −6.758
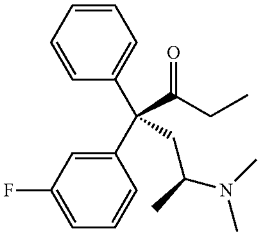 [SMILES: CCC(=O)[C@](C[C@H](C)N(C)C)(c1ccccc1)c1cccc(F)c1]
title: DMD47
glide gscore: −6.757
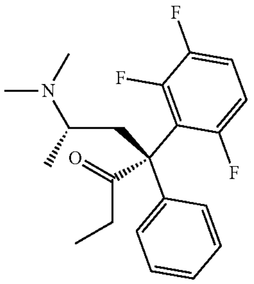 [SMILES: CCC(=O)[C@@](C[C@H](C)N(C)C)(c1ccccc1)c1c(F)ccc(F)c1F]
title: DMD30
glide gscore: −6.737
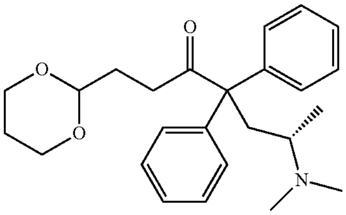 [SMILES: C[C@@H](CC(C(=O)CCC1OCCCO1)(c1ccccc1)c1ccccc1)N(C)C]
title: G50
glide gscore: −6.735
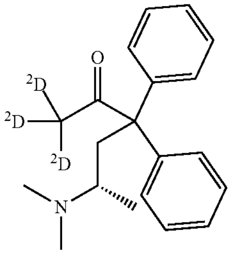 [SMILES: [2H]C([2H])([2H])C(=O)C(C[C@H](C)N(C)C)(c1ccccc1)c1ccccc1]
title: G3
glide gscore: −6.732

TABLE 2a-continued
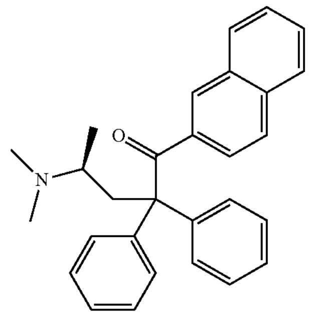 [SMILES: C[C@@H](CC(C(=O)c1ccc2ccccc2c1)(c1ccccc1)c1ccccc1)N(C)C]
title: G107
glide gscore: −6.701
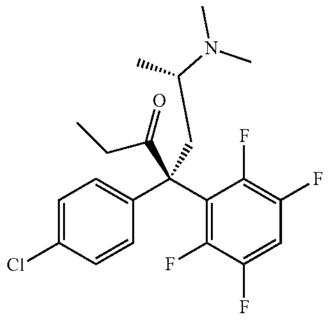 [SMILES: CCC(=O)[C@](C[C@H](C)N(C)C)(c1ccc(Cl)cc1)c1c(F)c(F)cc(F)c1F]
title: DMD21
glide gscore: −6.699
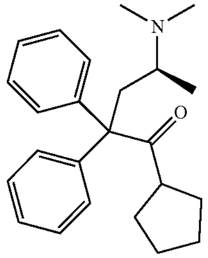 [SMILES: C[C@@H](CC(C(=O)C1CCCC1)(c1ccccc1)c1ccccc1)N(C)C]
title: G28
glide gscore: −6.694
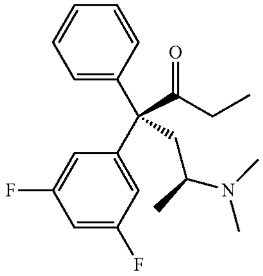 [SMILES: CCC(=O)[C@](C[C@H](C)N(C)C)(c1ccccc1)c1cc(F)cc(F)c1]
title: DMD33
glide gscore: −6.69
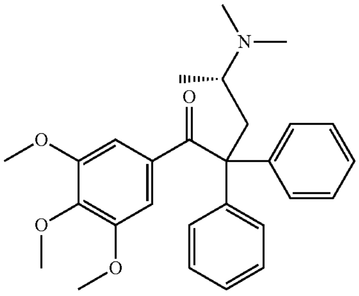 [SMILES: COc1cc(C(=O)C(C[C@H](C)N(C)C)(c2ccccc2)c2ccccc2)cc(OC)c1OC]
title: G105
glide gscore: −6.666
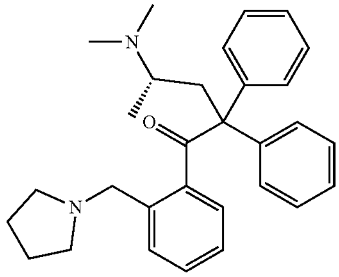 [SMILES: C[C@@H](CC(C(=O)c1ccccc1CN1CCCC1)(c1ccccc1)c1ccccc1)N(C)C]
title: G110
glide gscore: −6.654
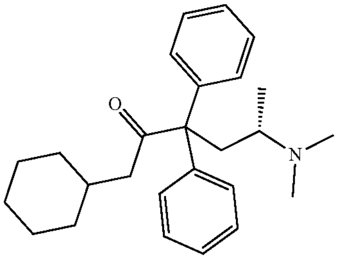 [SMILES: C[C@@H](CC(C(=O)CC1CCCCC1)(c1ccccc1)c1ccccc1)N(C)C]
title: G76
glide gscore: −6.651
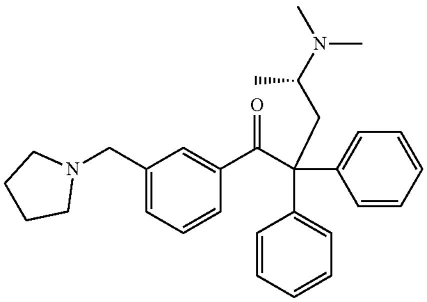 [SMILES: C[C@@H](CC(C(=O)c1cccc(CN2CCCC2)c1)(c1ccccc1)c1ccccc1)N(C)C]
title: G111
glide gscore: −6.633

TABLE 2a-continued
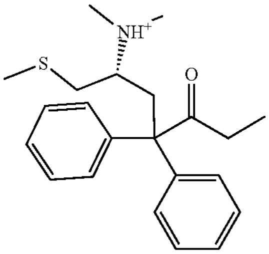 [SMILES: CCC(=O)C(C[C@H](CSC)[NH+](C)C)(c1ccccc1)c1ccccc1]
title: DMD-AA7
glide gscore: −6.623
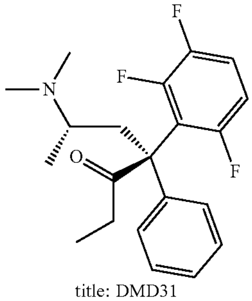
title: DMD31
glide gscore: −6.62
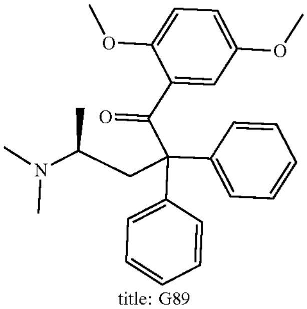
title: G89
glide gscore: −6.615
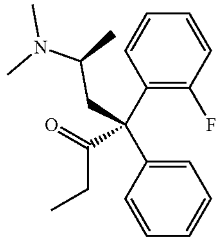 [SMILES: CCC(=O)[C@@](C[C@H](C)N(C)C)(c1ccccc1)c1ccccc1F]
title: DMD44
glide gscore: −6.609
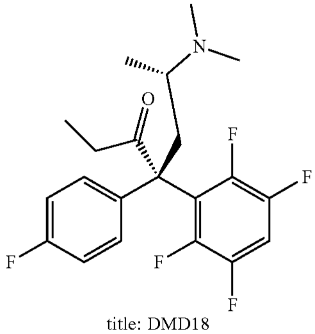
title: DMD18
glide gscore: −6.575
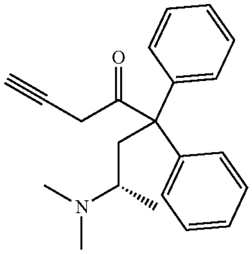 [SMILES: C#CCC(=O)C(C[C@H](C)N(C)C)(c1ccccc1)c1ccccc1]
title: G6
glide gscore: −6.571
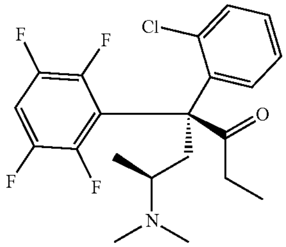 [SMILES: CCC(=O)[C@](C[C@H](C)N(C)C)(c1ccccc1Cl)c1c(F)c(F)cc(F)c1F]
title: DMD27
glide gscore: −6.566
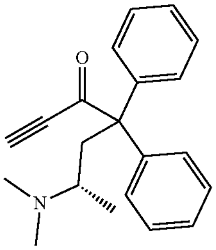 [SMILES: C#CC(=O)C(C[C@H](C)N(C)C)(c1ccccc1)c1ccccc1]
title: G4
glide gscore: −6.566
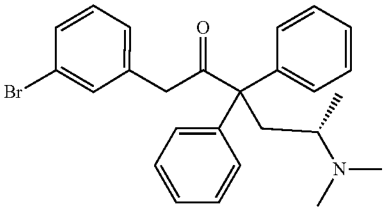 [SMILES: C[C@@H](CC(C(=O)Cc1cccc(Br)c1)(c1ccccc1)c1ccccc1)N(C)C]
title: G65
glide gscore: −6.542
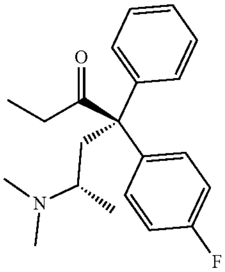 [SMILES: CCC(=O)[C@@](C[C@H](C)N(C)C)(c1ccccc1)c1ccc(F)cc1]
title: DMD43
glide gscore: −6.542

TABLE 2a-continued
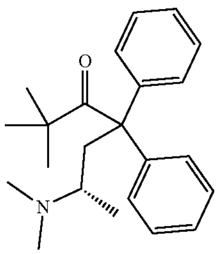 [SMILES: C[C@@H](CC(C(=O)C(C)(C)C)(c1ccccc1)c1ccccc1)N(C)C]
title: G25
glide gscore: −6.523
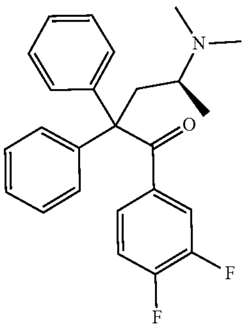 [SMILES: C[C@@H](CC(C(=O)c1ccc(F)c(F)c1)(c1ccccc1)c1ccccc1)N(C)C]
title: G43
glide gscore: −6.501
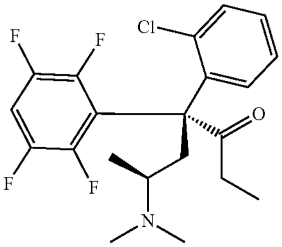 [SMILES: CCC(=O)[C@@](C[C@H](C)N(C)C)(c1ccccc1Cl)c1c(F)c(F)cc(F)c1F]
title: DMD26
glide gscore: −6.499
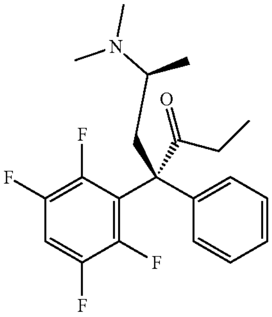 [SMILES: CCC(=O)[C@](C[C@H](C)N(C)C)(c1ccccc1)c1c(F)c(F)cc(F)c1F]
title: DMD11
glide gscore: −6.497
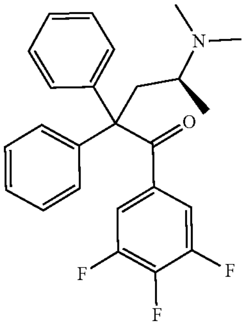 [SMILES: C[C@@H](CC(C(=O)c1cc(F)c(F)c(F)c1)(c1ccccc1)c1ccccc1)N(C)C]
title: G37
glide gscore: −6.492
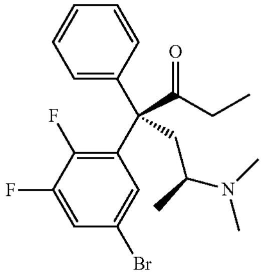 [SMILES: CCC(=O)[C@](C[C@H](C)N(C)C)(c1ccccc1)c1cc(Br)cc(F)c1F]
title: DMD34
glide gscore: −6.48
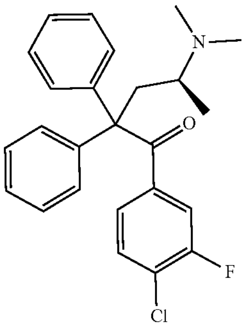 [SMILES: C[C@@H](CC(C(=O)c1ccc(Cl)c(F)c1)(c1ccccc1)c1ccccc1)N(C)C]
title: G40
glide gscore: −6.468
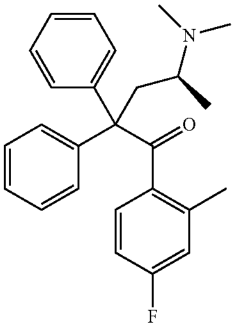 [SMILES: Cc1cc(F)ccc1C(=O)C(C[C@H](C)N(C)C)(c1ccccc1)c1ccccc1]
title: G59
glide gscore: −6.462

TABLE 2a-continued
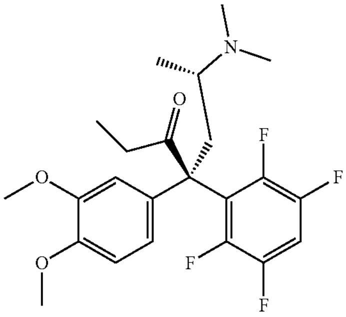 [SMILES: CCC(=O)[C@](C[C@H](C)N(C)C)(c1ccc(OC)c(OC)c1)c1c(F)c(F)cc(F)c1F]
title: DMD17
glide gscore: −6.444
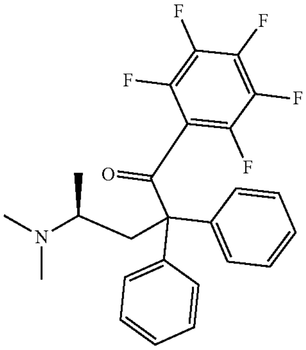 [SMILES: C[C@@H](CC(C(=O)c1c(F)c(F)c(F)c(F)c1F)(c1ccccc1)c1ccccc1)N(C)C]
title: G36
glide gscore: −6.442
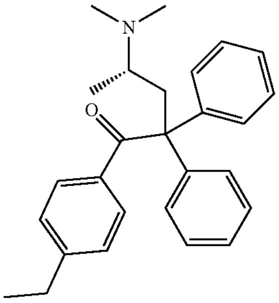 [SMILES: CCc1ccc(C(=O)C(C[C@H](C)N(C)C)(c2ccccc2)c2ccccc2)cc1]
title: G84
glide gscore: −6.442
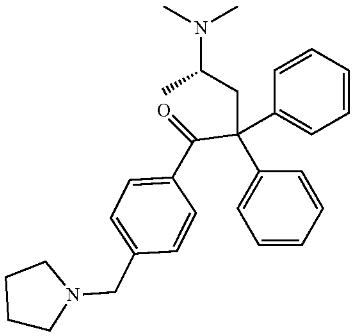 [SMILES: C[C@@H](CC(C(=O)c1ccc(CN2CCCC2)cc1)(c1ccccc1)c1ccccc1)N(C)C]
title: G112
glide gscore: −6.442
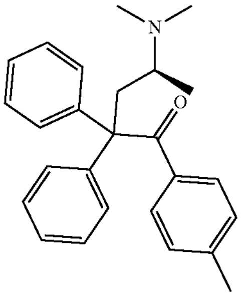 [SMILES: Cc1ccc(C(=O)C(C[C@H](C)N(C)C)(c2ccccc2)c2ccccc2)cc1]
title: G69
glide gscore: −6.432
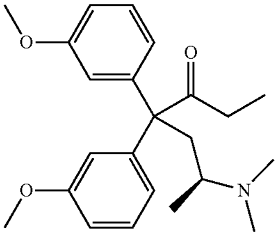
title: DMD2
glide gscore: −6.432
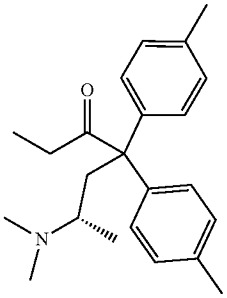
title: DMD4
glide gscore: −6.426
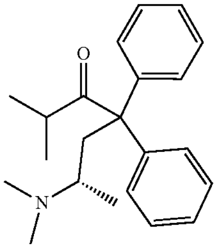 [SMILES: CC(C)C(=O)C(C[C@H](C)N(C)C)(c1ccccc1)c1ccccc1]
title: G11
glide gscore: −6.423

TABLE 2a-continued
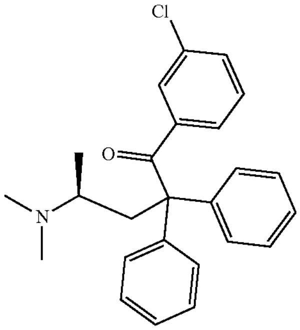 [SMILES: C[C@@H](CC(C(=O)c1cccc(Cl)c1)(c1ccccc1)c1ccccc1)N(C)C]
title: G45
glide gscore: −6.411
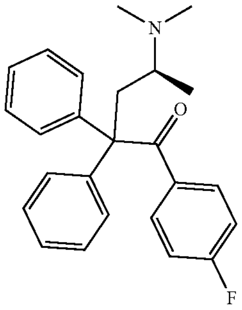 [SMILES: C[C@@H](CC(C(=O)c1ccc(F)cc1)(c1ccccc1)c1ccccc1)N(C)C]
title: G48
glide gscore: −6.4
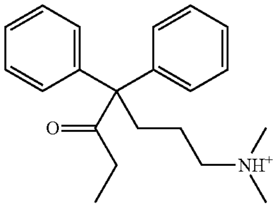 [SMILES: CCC(=O)C(CCC[NH+](C)C)(c1ccccc1)c1ccccc1]
title: DMD-AA13
glide gscore: −6.397
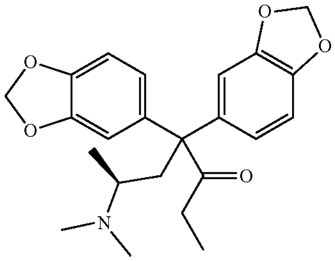 [SMILES: CCC(=O)C(C[C@H](C)N(C)C)(c1ccc2c(c1)OCO2)c1ccc2c(c1)OCO2]
title: DMD3
glide gscore: −6.394
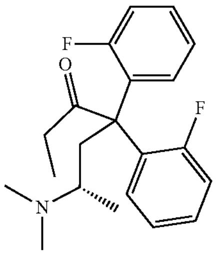 [SMILES: CCC(=O)C(C[C@H](C)N(C)C)(c1ccccc1F)c1ccccc1F]
title: DMD50
glide gscore: −6.369
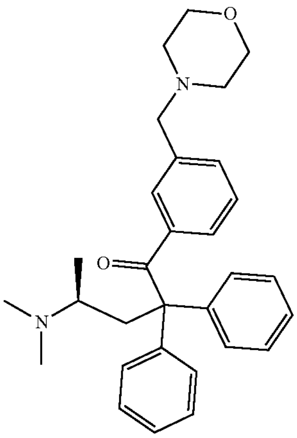 [SMILES: C[C@@H](CC(C(=O)c1cccc(CN2CCOCC2)c1)(c1ccccc1)c1ccccc1)N(C)C]
title: G114
glide gscore: −6.356
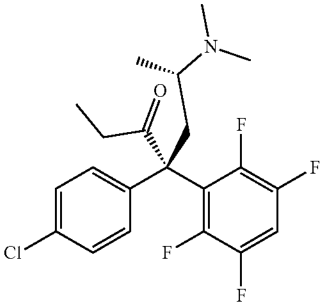 [SMILES: CCC(=O)[C@@](C[C@H](C)N(C)C)(c1ccc(Cl)cc1)c1c(F)c(F)cc(F)c1F]
title: DMD20
glide gscore: −6.344
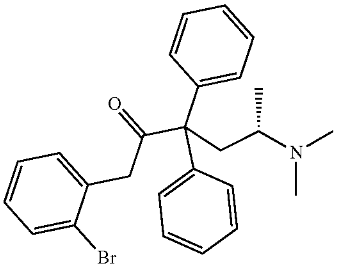 [SMILES: C[C@@H](CC(C(=O)Cc1ccccc1Br)(c1ccccc1)c1ccccc1)N(C)C]
title: G64
glide gscore: −6.341

TABLE 2a-continued
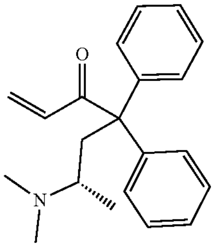 [SMILES: C=CC(=O)C(C[C@H](C)N(C)C)(c1ccccc1)c1ccccc1]
title: G5
glide gscore: −6.329
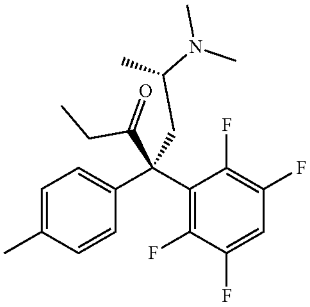 [SMILES: CCC(=O)[C@](C[C@H](C)N(C)C)(c1ccc(C)cc1)c1c(F)c(F)cc(F)c1F]
title: DMD13
glide gscore: −6.329
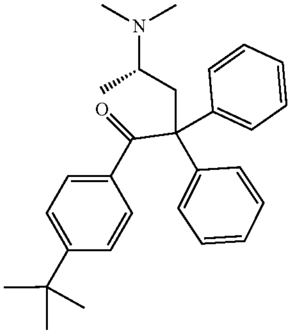 [SMILES: C[C@@H](CC(C(=O)c1ccc(C(C)(C)C)cc1)(c1ccccc1)c1ccccc1)N(C)C]
title: G109
glide gscore: −6.319
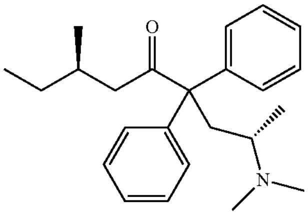 [SMILES: CC[C@@H](C)CC(=O)C(C[C@H](C)N(C)C)(c1ccccc1)c1ccccc1]
title: G35
glide gscore: −6.313
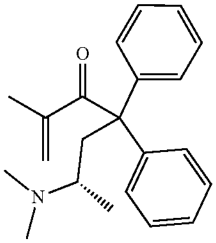 [SMILES: C=C(C)C(=O)C(C[C@H](C)N(C)C)(c1ccccc1)c1ccccc1]
title: G10
glide gscore: −6.307
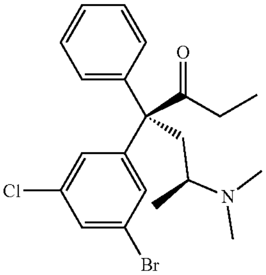 [SMILES: CCC(=O)[C@](C[C@H](C)N(C)C)(c1ccccc1)c1cc(Cl)cc(Br)c1]
title: DMD39
glide gscore: −6.301
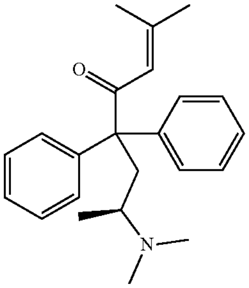 [SMILES: CC(C)=CC(=O)C(C[C@H](C)N(C)C)(c1ccccc1)c1ccccc1]
title: G17
glide gscore: −6.299
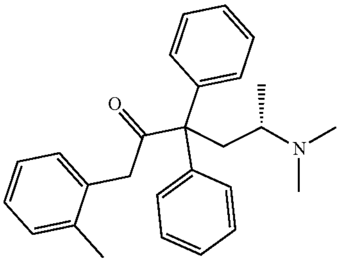 [SMILES: Cc1ccccc1CC(=O)C(C[C@H](C)N(C)C)(c1ccccc1)c1ccccc1]
title: G91
glide gscore: −6.297

TABLE 2a-continued
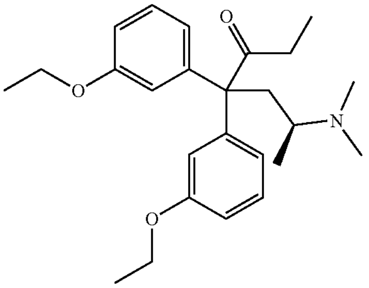 [SMILES: CCOc1cccc(C(C[C@H](C)N(C)C)(C(=O)CC)c2cccc(OCC)c2)c1]
title: DMD1
glide gscore: −6.289
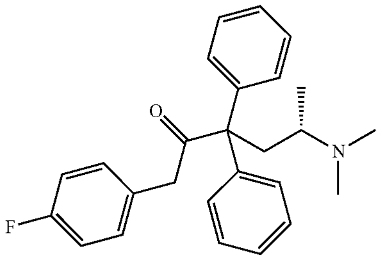 [SMILES: C[C@@H](CC(C(=O)Cc1ccc(F)cc1)(c1ccccc1)c1ccccc1)N(C)C]
title: G67
glide gscore: −6.27
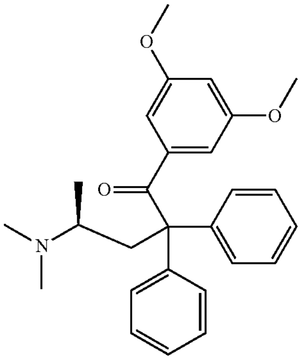
title: G99
glide gscore: −6.266
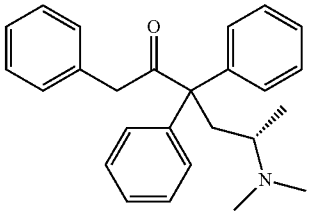 [SMILES: C[C@@H](CC(C(=O)Cc1ccccc1)(c1ccccc1)c1ccccc1)N(C)C]
title: G74
glide gscore: −6.255
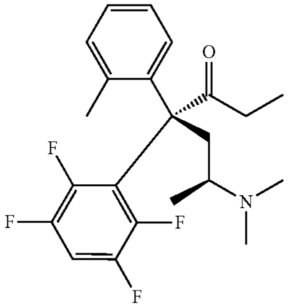 [SMILES: CCC(=O)[C@@](C[C@H](C)N(C)C)(c1ccccc1C)c1c(F)c(F)cc(F)c1F]
title: DMD14
glide gscore: −6.251
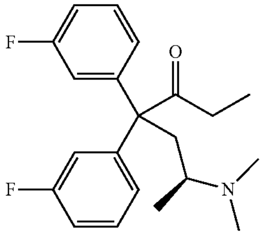 [SMILES: CCC(=O)C(C[C@H](C)N(C)C)(c1cccc(F)c1)c1cccc(F)c1]
title: DMD48
glide gscore: −6.248
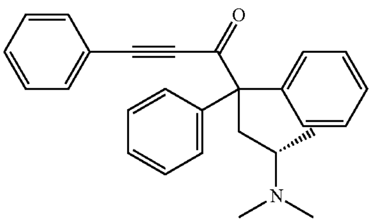 [SMILES: C[C@@H](CC(C(=O)C#Cc1ccccc1)(c1ccccc1)c1ccccc1)N(C)C]
title: G78
glide gscore: −6.241
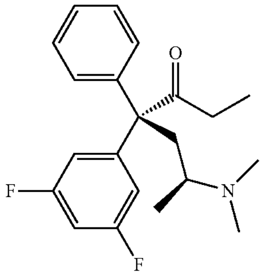 [SMILES: CCC(=O)[C@@](C[C@H](C)N(C)C)(c1ccccc1)c1cc(F)cc(F)c1]
title: DMD46
glide gscore: −6.221

TABLE 2a-continued
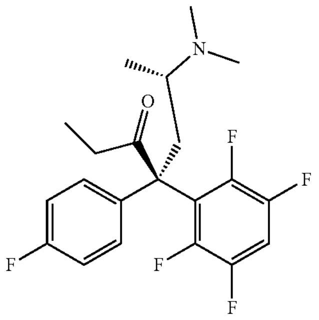 [SMILES: CCC(=O)[C@](C[C@H](C)N(C)C)(c1ccc(F)cc1)c1c(F)c(F)cc(F)c1F]
title: DMD19
glide gscore: −6.22
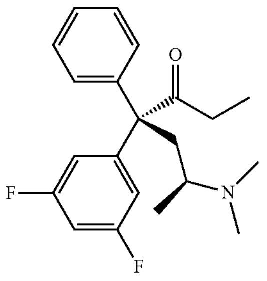 [SMILES: CCC(=O)[C@@](C[C@H](C)N(C)C)(c1ccccc1)c1cc(F)cc(F)c1]
title: DMD32
glide gscore: −6.208
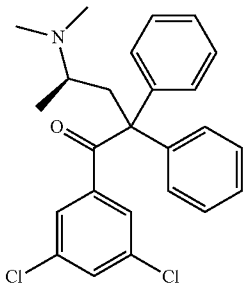 [SMILES: C[C@H](CC(C(=O)c1cc(Cl)cc(Cl)c1)(c1ccccc1)c1ccccc1)N(C)C]
title: G42
glide gscore: −6.203
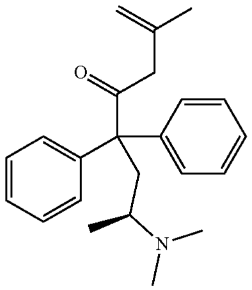 [SMILES: C=C(C)CC(=O)C(C[C@H](C)N(C)C)(c1ccccc1)c1ccccc1]
title: G18
glide gscore: −6.195
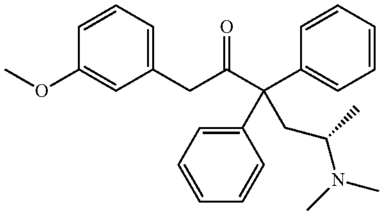
title: G97
glide gscore: −6.193
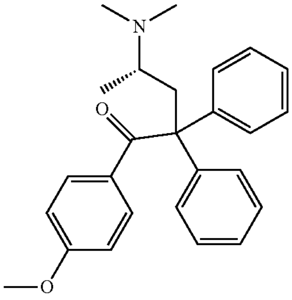 [SMILES: COc1ccc(C(=O)C(C[C@H](C)N(C)C)(c2ccccc2)c2ccccc2)cc1]
title: G72
glide gscore: −6.181
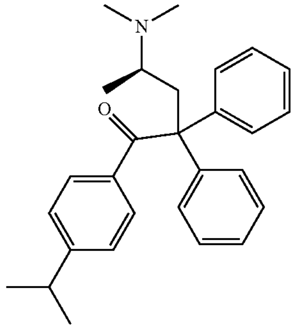 [SMILES: CC(C)c1ccc(C(=O)C(C[C@@H](C)N(C)C)(c2ccccc2)c2ccccc2)cc1]
title: G102
glide gscore: −6.168
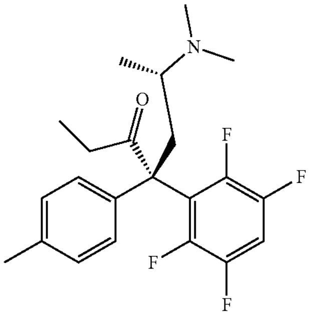 [SMILES: CCC(=O)[C@@](C[C@H](C)N(C)C)(c1ccc(C)cc1)c1c(F)c(F)cc(F)c1F]
title: DMD12
glide gscore: −6.164

TABLE 2a-continued
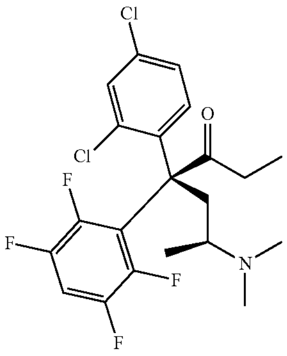 [SMILES: CCC(=O)[C@](C[C@H](C)N(C)C)(c1ccc(Cl)cc1Cl)c1c(F)c(F)cc(F)c1F]
title: DMD28
glide gscore: −6.161
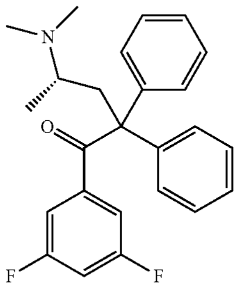
title: G44
glide gscore: −6.157
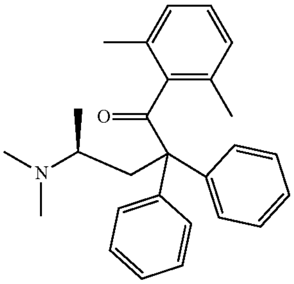 [SMILES: Cc1cccc(C)c1C(=O)C(C[C@H](C)N(C)C)(c1ccccc1)c1ccccc1]
title: G83
glide gscore: −6.156
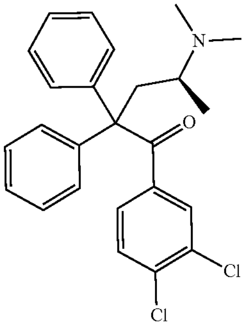 [SMILES: C[C@@H](CC(C(=O)c1ccc(Cl)c(Cl)c1)(c1ccccc1)c1ccccc1)N(C)C]
title: G41
glide gscore: −6.133
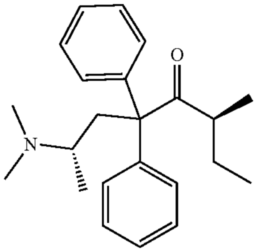 [SMILES: CC[C@H](C)C(=O)C(C[C@H](C)N(C)C)(c1ccccc1)c1ccccc1]
title: G24
glide gscore: −6.125
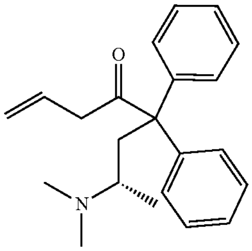 [SMILES: C=CCC(=O)C(C[C@H](C)N(C)C)(c1ccccc1)c1ccccc1]
title: G8
glide gscore: −6.117
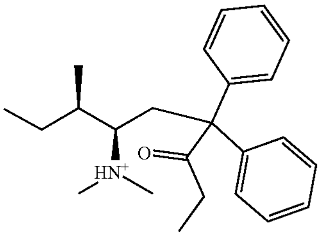 [SMILES: CCC(=O)C(C[C@H]([C@H](C)CC)[NH+](C)C)(c1ccccc1)c1ccccc1]
title: DMD-AA11
glide gscore: −6.111
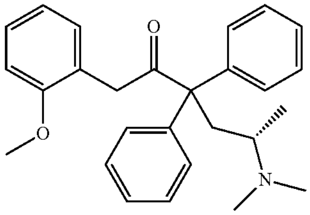 [SMILES: COc1ccccc1CC(=O)C(C[C@H](C)N(C)C)(c1ccccc1)c1ccccc1]
title: G96
glide gscore: −6.09

TABLE 2a-continued
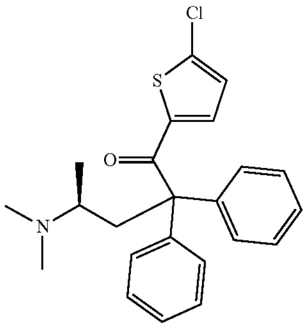 [SMILES: C[C@@H](CC(C(=O)c1ccc(Cl)s1)(c1ccccc1)c1ccccc1)N(C)C]
title: G13
glide gscore: −6.082
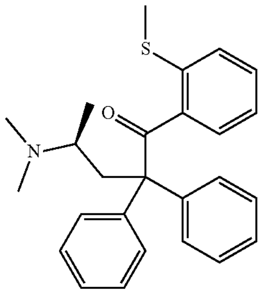
title: G73
glide gscore: −6.079
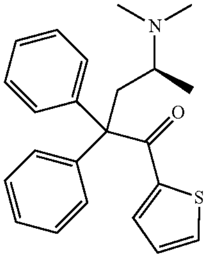 [SMILES: C[C@@H](CC(C(=O)c1cccs1)(c1ccccc1)c1ccccc1)N(C)C]
title: G14
glide gscore: −6.068
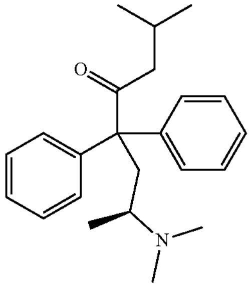 [SMILES: CC(C)CC(=O)C(C[C@H](C)N(C)C)(c1ccccc1)c1ccccc1]
title: G23
glide gscore: −6.064
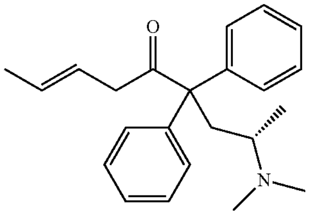 [SMILES: C/C=C/CC(=O)C(C[C@H](C)N(C)C)(c1ccccc1)c1ccccc1]
title: G22
glide gscore: −6.06
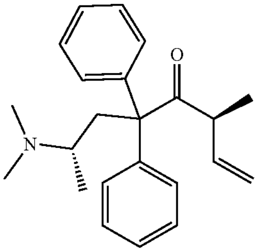 [SMILES: C=C[C@H](C)C(=O)C(C[C@H](C)N(C)C)(c1ccccc1)c1ccccc1]
title: G21
glide gscore: −6.048
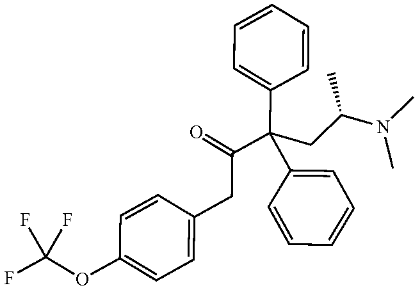 [SMILES: C[C@@H](CC(C(=O)Cc1ccc(OC(F)(F)F)cc1)(c1ccccc1)c1ccccc1)N(C)C]
title: G79
glide gscore: −6.042
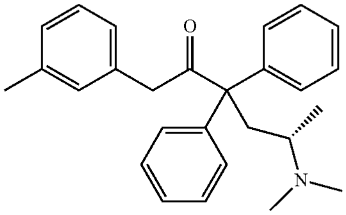
title: G93
glide gscore: −6.024

TABLE 2a-continued
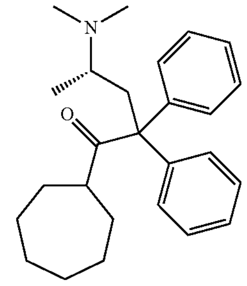 [SMILES: C[C@@H](CC(C(=O)C1CCCCCC1)(c1ccccc1)c1ccccc1)N(C)C]
title: G77
glide gscore: −6.023
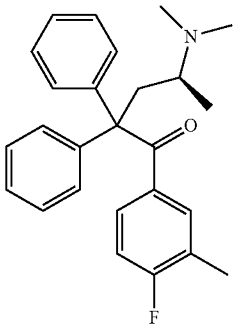 [SMILES: Cc1cc(C(=O)C(C[C@H](C)N(C)C)(c2ccccc2)c2ccccc2)ccc1F]
title: G60
glide gscore: −6.02
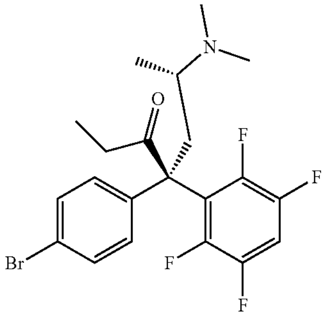
title: DMD23
glide gscore: −6.018
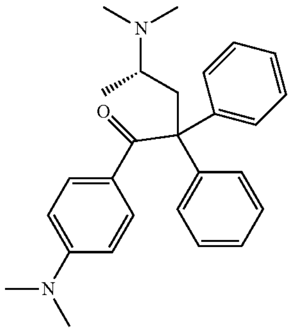 [SMILES: C[C@@H](CC(C(=O)c1ccc(N(C)C)cc1)(c1ccccc1)c1ccccc1)N(C)C]
title: G100
glide gscore: −6.013
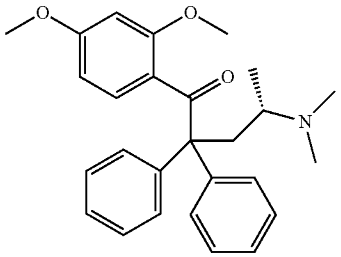
title: G88
glide gscore: −6.013
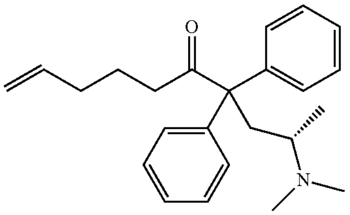 [SMILES: C=CCCCC(=O)C(C[C@H](C)N(C)C)(c1ccccc1)c1ccccc1]
title: G27
glide gscore: −6.002
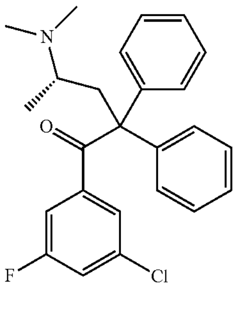 [SMILES: C[C@@H](CC(C(=O)c1cc(F)cc(Cl)c1)(c1ccccc1)c1ccccc1)N(C)C]
title: G39
glide gscore: −5.997
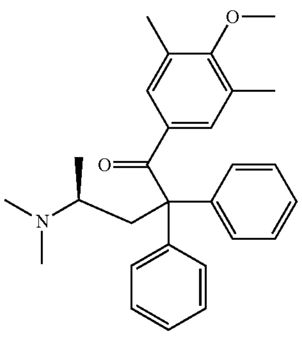 [SMILES: COc1c(C)cc(C(=O)C(C[C@H](C)N(C)C)(c2ccccc2)c2ccccc2)cc1C]
title: G104
glide gscore: −5.996

TABLE 2a-continued
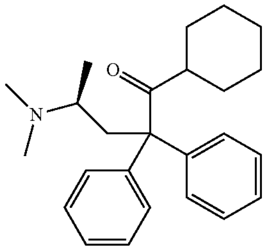 [SMILES: C[C@@H](CC(C(=O)C1CCCCC1)(c1ccccc1)c1ccccc1)N(C)C]
title: G51
glide gscore: −5.984
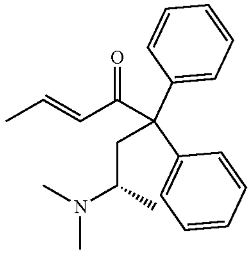 [SMILES: C/C=C/C(=O)C(C[C@H](C)N(C)C)(c1ccccc1)c1ccccc1]
title: G7
glide gscore: −5.964
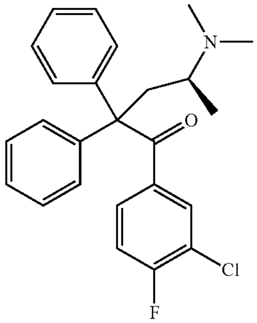 [SMILES: C[C@@H](CC(C(=O)c1ccc(F)c(Cl)c1)(c1ccccc1)c1ccccc1)N(C)C]
title: G38
glide gscore: −5.959
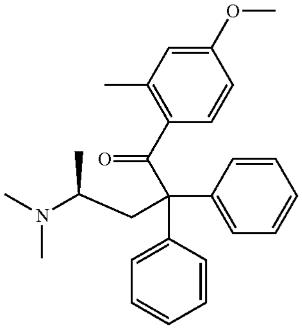 [SMILES: COc1ccc(C(=O)C(C[C@H](C)N(C)C)(c2ccccc2)c2ccccc2)c(C)c1]
title: G87
glide gscore: −5.931
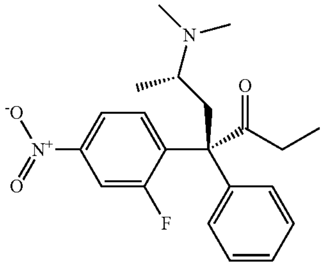
title: DMD36
glide gscore: −5.913
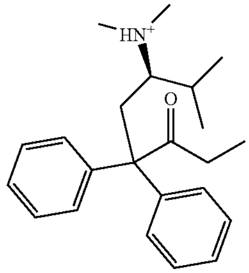 [SMILES: CCC(=O)C(C[C@H](C(C)C)[NH+](C)C)(c1ccccc1)c1ccccc1]
title: DMD-AA2
glide gscore: −5.901
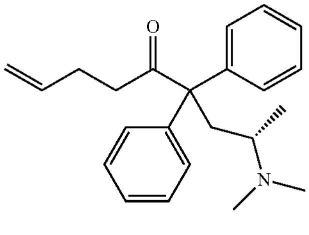 [SMILES: C=CCCC(=O)C(C[C@H](C)N(C)C)(c1ccccc1)c1ccccc1]
title: G19
glide gscore: −5.9
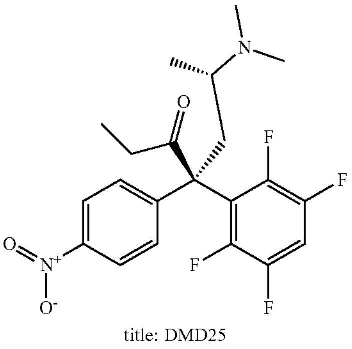
title: DMD25
glide gscore: −5.888

TABLE 2a-continued
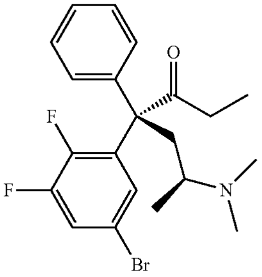
title: DMD35
glide gscore: −5.884
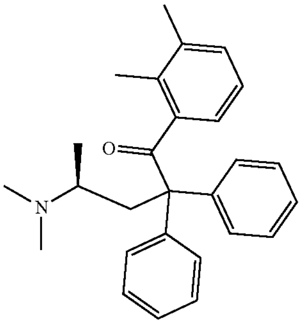 [SMILES: Cc1cccc(C(=O)C(C[C@H](C)N(C)C)(c2ccccc2)c2ccccc2)c1C]
title: G80
glide gscore: −5.865
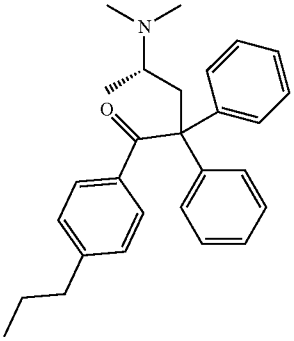 [SMILES: CCCc1ccc(C(=O)C(C[C@H](C)N(C)C)(c2ccccc2)c2ccccc2)cc1]
title: G103
glide gscore: −5.859
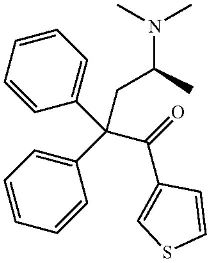 [SMILES: C[C@@H](CC(C(=O)c1ccsc1)(c1ccccc1)c1ccccc1)N(C)C]
title: G15
glide gscore: −5.854
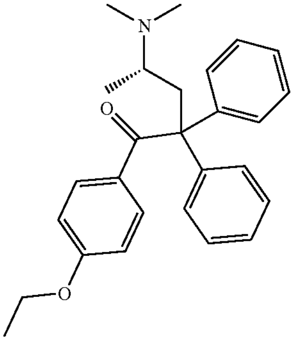 [SMILES: CCOc1ccc(C(=O)C(C[C@H](C)N(C)C)(c2ccccc2)c2ccccc2)cc1]
title: G86
glide gscore: −5.848
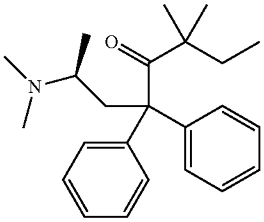 [SMILES: CCC(C)(C)C(=O)C(C[C@H](C)N(C)C)(c1ccccc1)c1ccccc1]
title: G33
glide gscore: −5.837
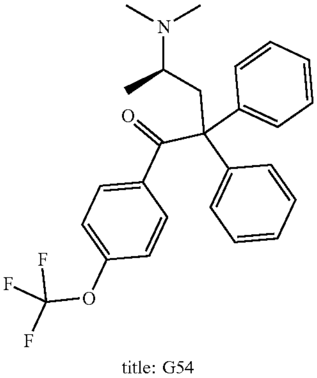
title: G54
glide gscore: −5.836
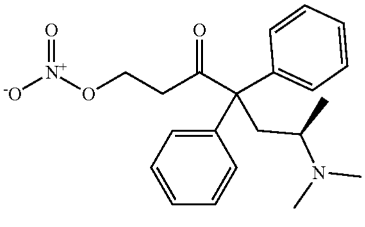
title: G122
glide gscore: −5.836

TABLE 2a-continued
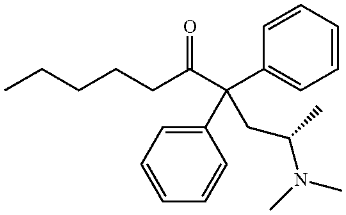 [SMILES: CCCCCC(=O)C(C[C@H](C)N(C)C)(c1ccccc1)c1ccccc1]
title: G32
glide gscore: −5.806
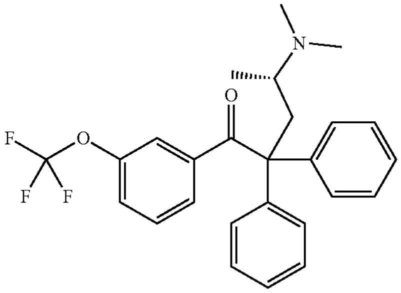 [SMILES: C[C@@H](CC(C(=O)c1cccc(OC(F)(F)F)c1)(c1ccccc1)c1ccccc1)N(C)C]
title: G53
glide gscore: −5.775
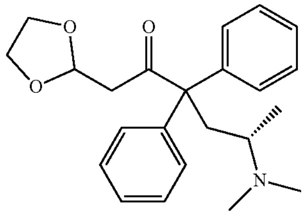 [SMILES: C[C@@H](CC(C(=O)CC1OCCO1)(c1ccccc1)c1ccccc1)N(C)C]
title: G20
glide gscore: −5.748
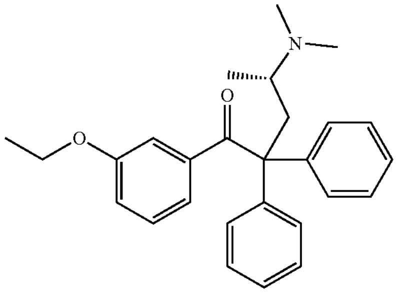 [SMILES: CCOc1cccc(C(=O)C(C[C@H](C)N(C)C)(c2ccccc2)c2ccccc2)c1]
title: G85
glide gscore: −5.738
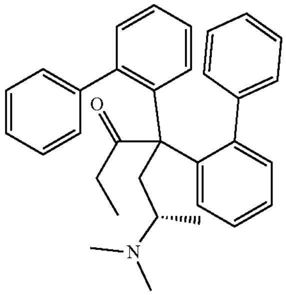 [SMILES: CCC(=O)C(C[C@H](C)N(C)C)(c1ccccc1-c1ccccc1)c1ccccc1-c1ccccc1]
title: DMD8
glide gscore: −5.711
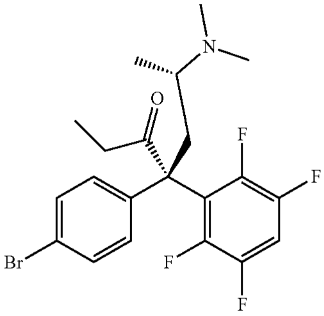 [SMILES: CCC(=O)[C@@](C[C@H](C)N(C)C)(c1ccc(Br)cc1)c1c(F)c(F)cc(F)c1F]
title: DMD22
glide gscore: −5.698
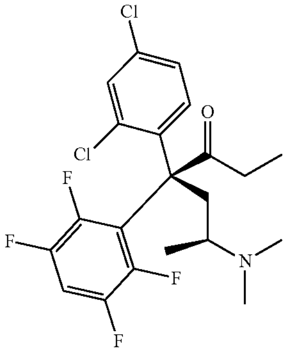 [SMILES: CCC(=O)[C@](C[C@H](C)N(C)C)(c1ccc(Cl)cc1Cl)c1c(F)c(F)cc(F)c1F]
title: DMD29
glide gscore: −5.695
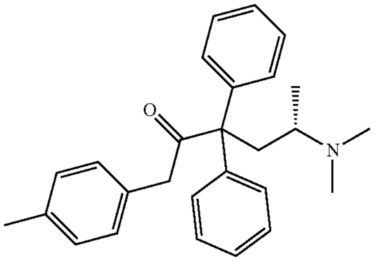
title: G94
glide gscore: −5.669

TABLE 2a-continued
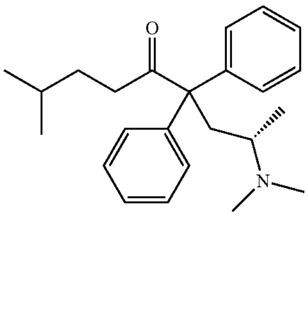 [SMILES: CC(C)CCC(=O)C(C[C@H](C)N(C)C)(c1ccccc1)c1ccccc1]
title: G31
glide gscore: −5.642
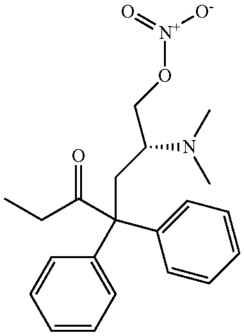 [SMILES: CCC(=O)C(C[C@H](CO[N+](=O)[O-])N(C)C)(c1ccccc1)c1ccccc1]
title: G123
glide gscore: −5.61
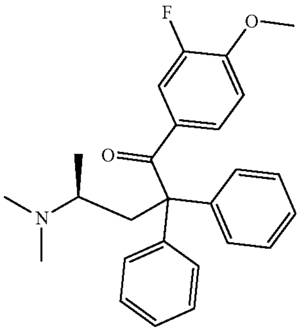 [SMILES: COc1ccc(C(=O)C(C[C@H](C)N(C)C)(c2ccccc2)c2ccccc2)cc1F]
title: G62
glide gscore: −5.595
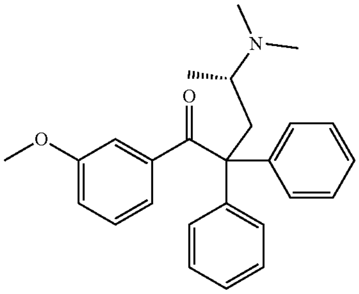 [SMILES: COc1cccc(C(=O)C(C[C@H](C)N(C)C)(c2ccccc2)c2ccccc2)c1]
title: G71
glide gscore: −5.584
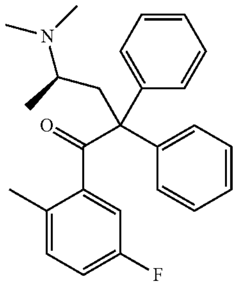 [SMILES: Cc1ccc(F)cc1C(=O)C(C[C@@H](C)N(C)C)(c1ccccc1)c1ccccc1]
title: G61
glide gscore: −5.578
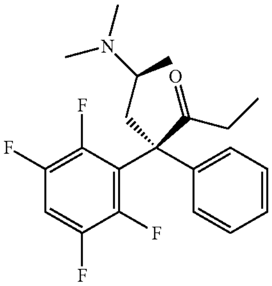 [SMILES: CCC(=O)[C@@](C[C@H](C)N(C)C)(c1ccccc1)c1c(F)c(F)cc(F)c1F]
title: DMD10
glide gscore: −5.557
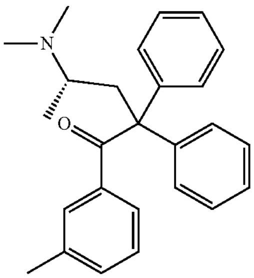 [SMILES: Cc1cccc(C(=O)C(C[C@H](C)N(C)C)(c2ccccc2)c2ccccc2)c1]
title: G75
glide gscore: −5.539
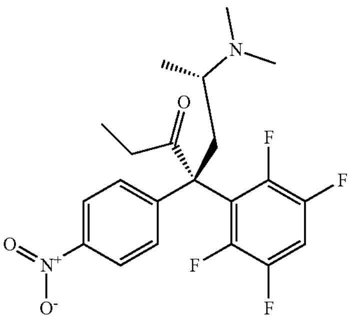 [SMILES: CCC(=O)[C@@](C[C@H](C)N(C)C)(c1ccc([N+](=O)[O-])cc1)c1c(F)c(F)cc(F)c1F]
title: DMD24
glide gscore: −5.524

TABLE 2a-continued
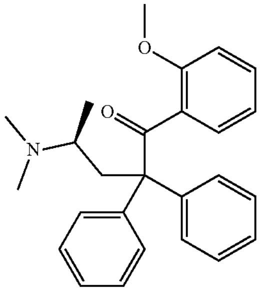 [SMILES: COc1ccccc1C(=O)C(C[C@H](C)N(C)C)(c1ccccc1)c1ccccc1]
title: G70
glide gscore: −5.511
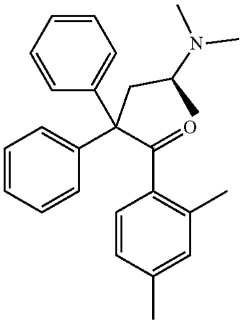 [SMILES: Cc1ccc(C(=O)C(C[C@H](C)N(C)C)(c2ccccc2)c2ccccc2)c(C)c1]
title: G81
glide gscore: −5.49
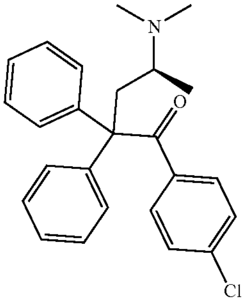 [SMILES: C[C@@H](CC(C(=O)c1ccc(Cl)cc1)(c1ccccc1)c1ccccc1)N(C)C]
title: G46
glide gscore: −5.469
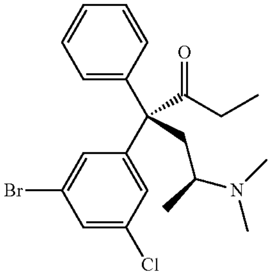 [SMILES: CCC(=O)[C@@](C[C@H](C)N(C)C)(c1ccccc1)c1cc(Cl)cc(Br)c1]
title: DMD38
glide gscore: −5.466
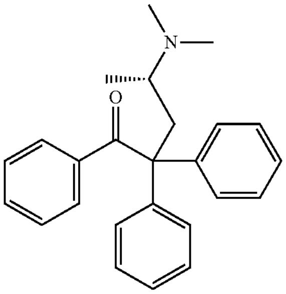 [SMILES: C[C@@H](CC(C(=O)c1ccccc1)(c1ccccc1)c1ccccc1)N(C)C]
title: G49
glide gscore: −5.452
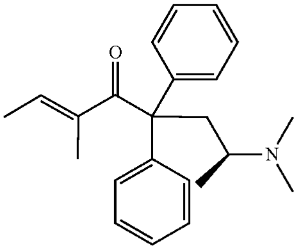 [SMILES: C/C=C(\C)C(=O)C(C[C@H](C)N(C)C)(c1ccccc1)c1ccccc1]
title: G16
glide gscore: −5.425
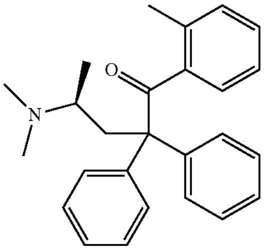 [SMILES: Cc1ccccc1C(=O)C(C[C@H](C)N(C)C)(c1ccccc1)c1ccccc1]
title: G68
glide gscore: −5.406
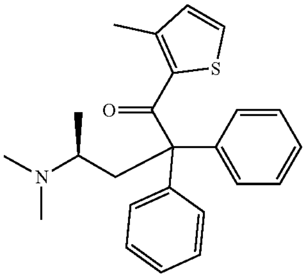 [SMILES: Cc1ccsc1C(=O)C(C[C@H](C)N(C)C)(c1ccccc1)c1ccccc1]
title: G26
glide gscore: −5.381

TABLE 2a-continued
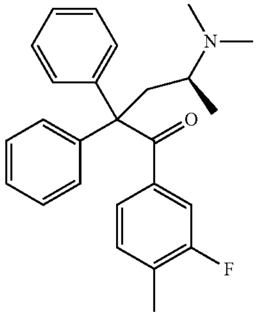 [SMILES: Cc1ccc(C(=O)C(C[C@H](C)N(C)C)(c2ccccc2)c2ccccc2)cc1F]
title: G58
glide gscore: −5.375
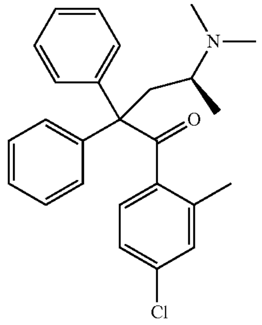 [SMILES: Cc1cc(Cl)ccc1C(=O)C(C[C@H](C)N(C)C)(c1ccccc1)c1ccccc1]
title: G57
glide gscore: −5.347
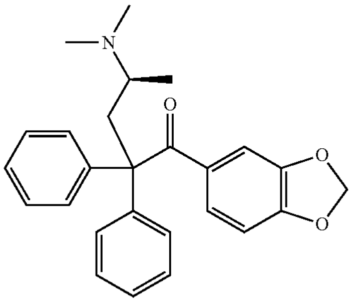 [SMILES: C[C@@H](CC(C(=O)c1ccc2c(c1)OCO2)(c1ccccc1)c1ccccc1)N(C)C]
title: G56
glide gscore: −5.293
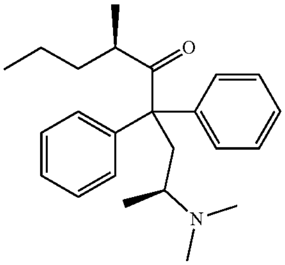 [SMILES: CCC[C@@H](C)C(=O)C(C[C@H](C)N(C)C)(c1ccccc1)c1ccccc1]
title: G29
glide gscore: −5.245
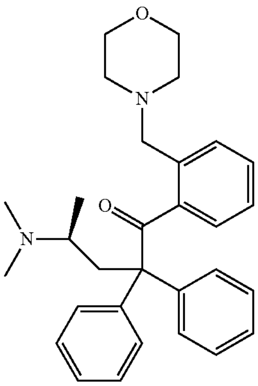 [SMILES: C[C@@H](CC(C(=O)c1ccccc1CN1CCOCC1)(c1ccccc1)c1ccccc1)N(C)C]
title: G113
glide gscore: −5.231
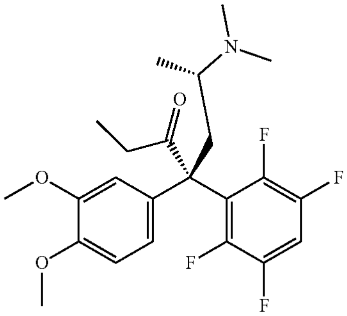 [SMILES: CCC(=O)[C@@](C[C@H](C)N(C)C)(c1ccc(OC)c(OC)c1)c1c(F)c(F)cc(F)c1F]
title: DMD16
glide gscore: −5.152
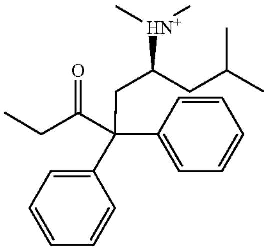 [SMILES: CCC(=O)C(C[C@H](CC(C)C)[NH+](C)C)(c1ccccc1)c1ccccc1]
title: DMD-AA3
glide gscore: −5.031
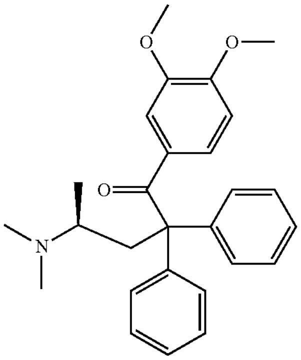 [SMILES: COc1ccc(C(=O)C(C[C@H](C)N(C)C)(c2ccccc2)c2ccccc2)cc1OC]
title: G90
glide gscore: −4.953

TABLE 2a-continued
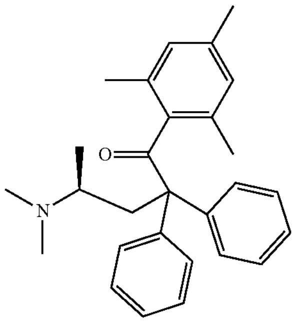 [SMILES: Cc1cc(C)c(C(=O)C(C[C@H](C)N(C)C)(c2ccccc2)c2ccccc2)c(C)c1]
title: G101
glide gscore: −4.917
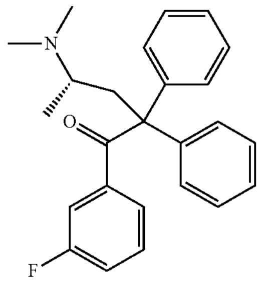 [SMILES: C[C@@H](CC(C(=O)c1cccc(F)c1)(c1ccccc1)c1ccccc1)N(C)C]
title: G47
glide gscore: −4.665
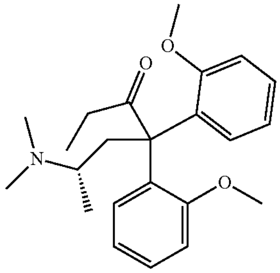 [SMILES: CCC(=O)C(C[C@H](C)N(C)C)(c1ccccc1OC)c1ccccc1OC]
title: DMD5
glide gscore: −3.594

TABLE 2b
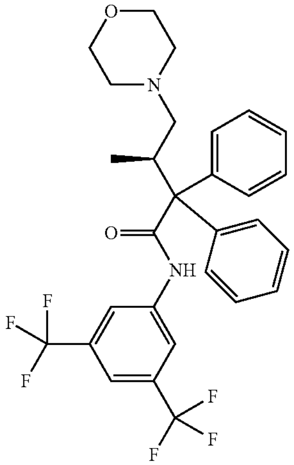
title: LMA9
docking score: -8.231
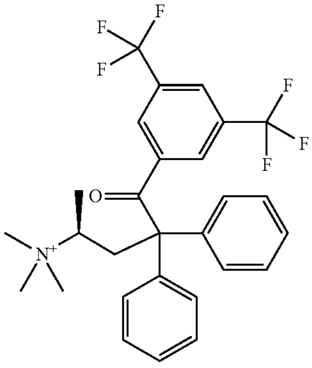
title: NMeDMD9
docking score: -7.788
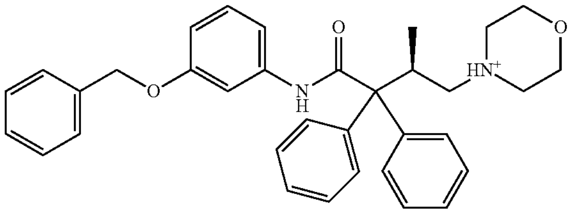
title: LMA1
docking score: -7.511
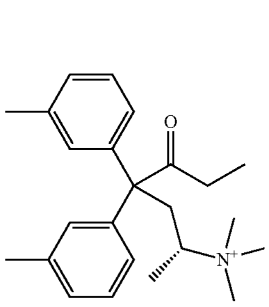
title: NMeDMD5
docking score: -7.439
TABLE 2b-continued
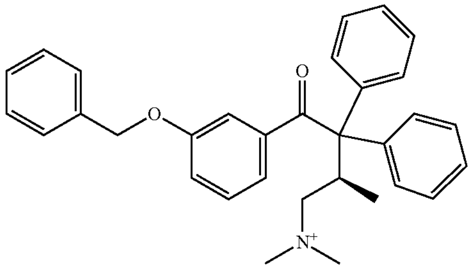
title: DIDM1
docking score: -7.341
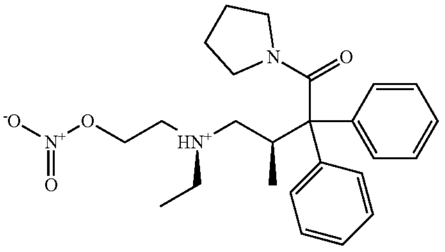
title: LMA8
docking score: -7.315
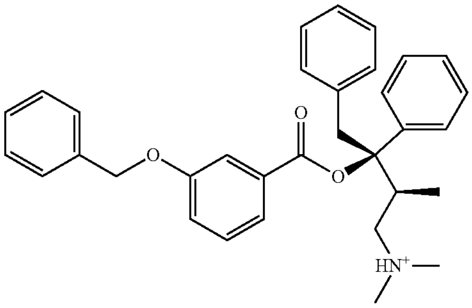
title: LPP1
docking score: -7.259
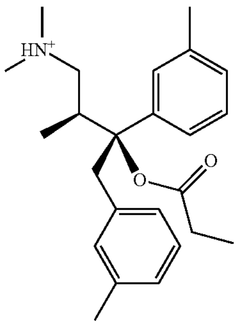
title: LPP5
docking score: -7.246

TABLE 2b-continued
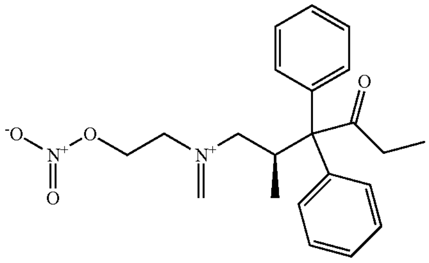
title: DIDM8
docking score: -7.221
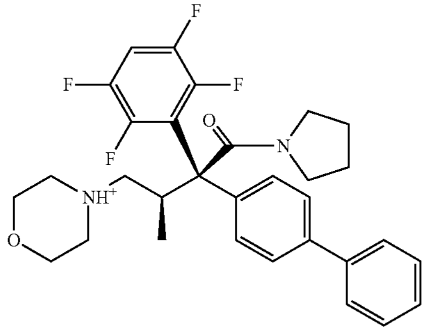
title: LMA6
docking score: -7.211
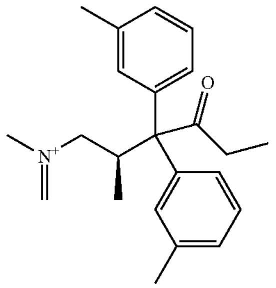
title: DIDM5
docking score: -7.078
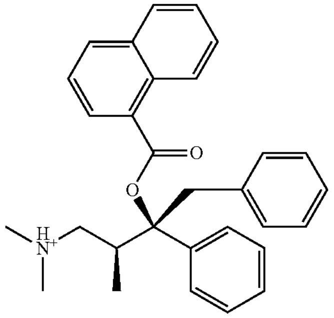
title: LPP4
docking score: -7.026
TABLE 2b-continued
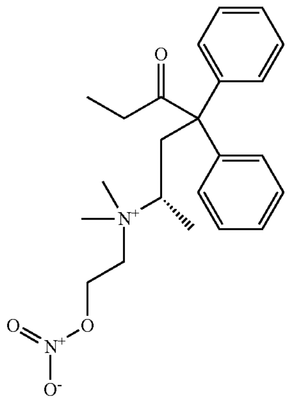
title: NMeDMD8
docking score: -6.982
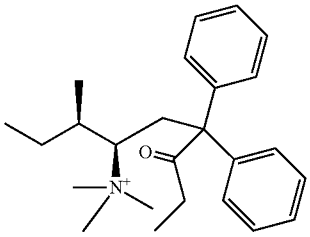
title: NMeDMD7
docking score: -6.974
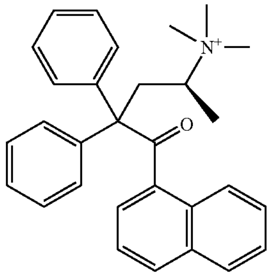
title: NMeDMD4
docking score: -6.965
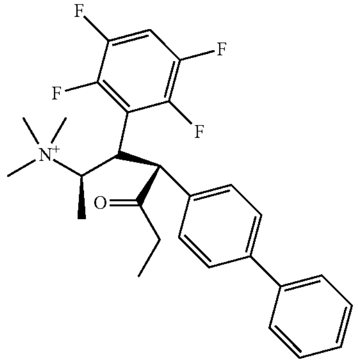
title: NMeDMD6
docking score: -6.947

TABLE 2b-continued
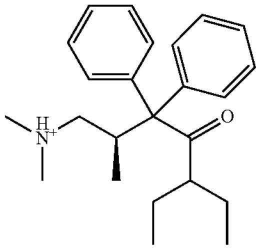
title: DIDM2
docking score: -6.922
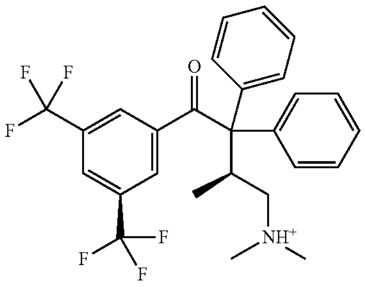
title: DIDM9
docking score: -6.871
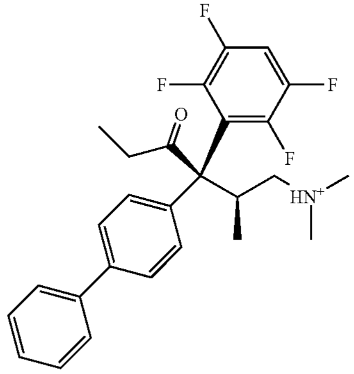
title: DIMD6
docking score: -6.851
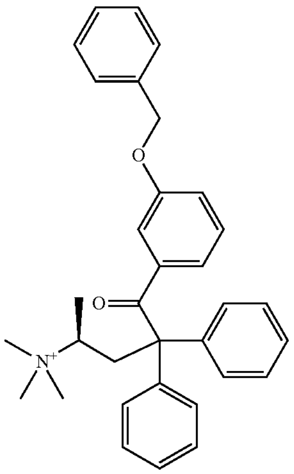
title: NMeDMD1
docking score: -6.747
TABLE 2b-continued
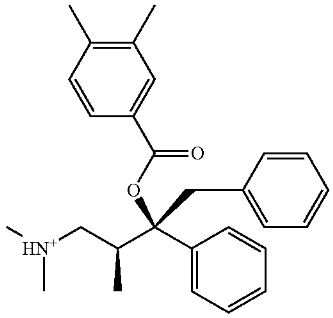
title: LPP3
docking score: -6.591
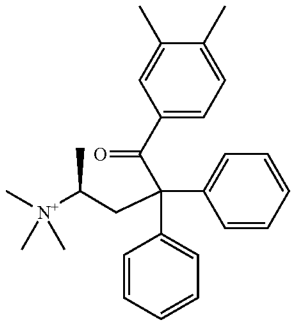
title: NMeDMD3
docking score: -6.579
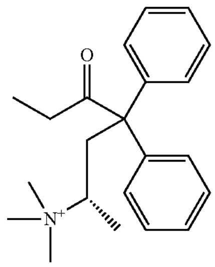
title: NMeDMetadone
docking score: -6.56
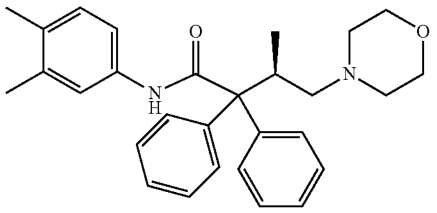
title: LMA3
docking score: -6.419

TABLE 2b-continued
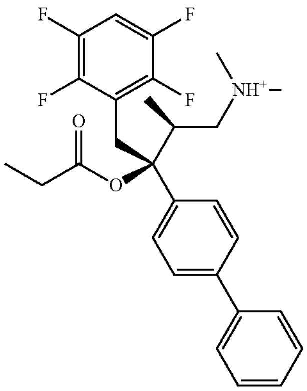
title: LPP6
docking score: -6.382
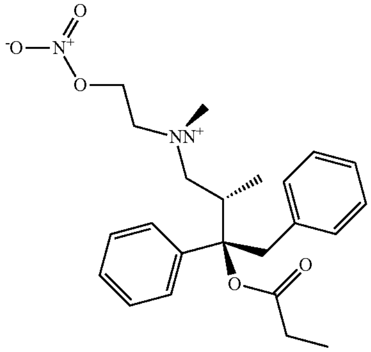
title: LPP8
docking score: -6.357
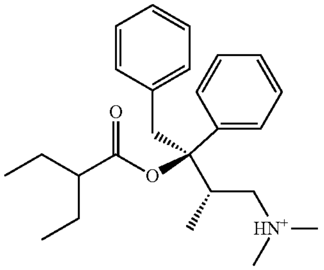
title: LPP2
docking score: -6.204
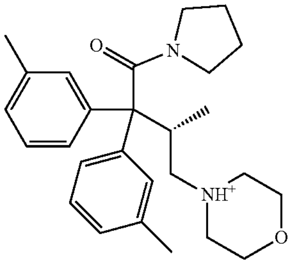
title: LMA5
docking score: -5.969
TABLE 2b-continued
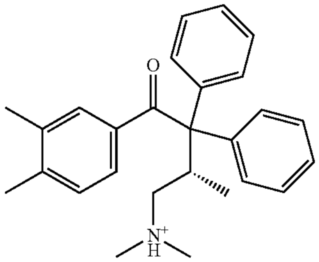
title: DIMD3
docking score: -5.958
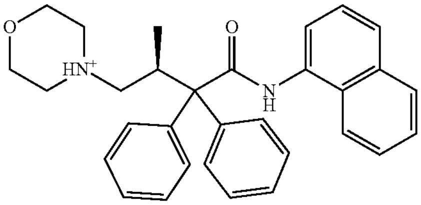
title: LMA4
docking score: -5.949
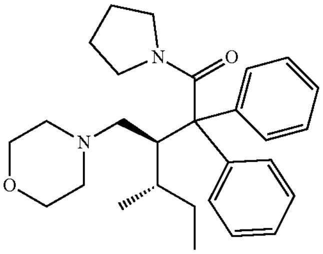
title: LMA7
docking score: -5.9
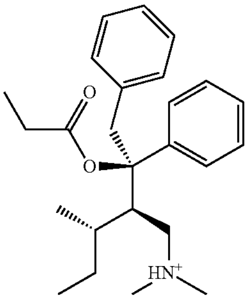
title: LPP7
docking score: -5.739
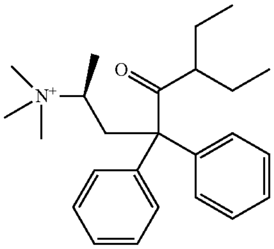
title: NMeDMD2
docking score: -5.535

TABLE 2b-continued

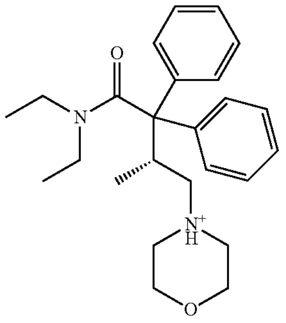

title: LMA2
docking score: -5.169

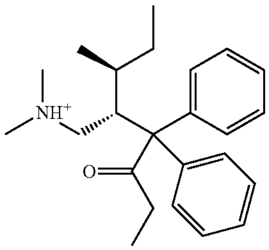

title: DIDM7
docking score: -4.962

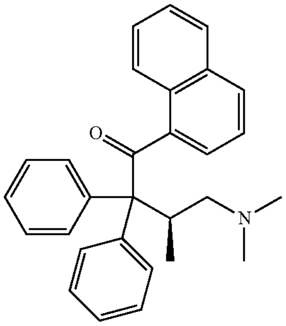

title: DIMD4
docking score: -4.557

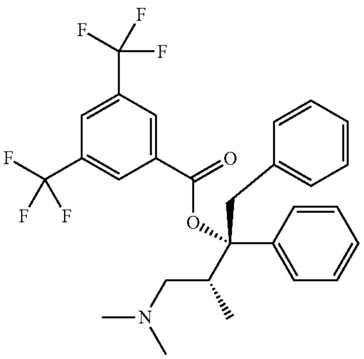

title: LPP9
docking score: -4.266

TABLE 2c

| Molecule code | Predicted affinity (Molecular dynamics) (Delta G, kcal/mol) | Predicted Affinity (Docking) (Delta G, kcal/mol) |
|---|---|---|
| MK-801 | −25.6 | −6.8 |
| PCP | −39.16 | −6 |
| Ketamine | −20 | −5.8 |
| Memantine | −27.3 | −5.8 |
| Amantadine | −25.6 | −5.23 |
| Dextromethorphan | −28.88 | −6.3 |
| d-methadone | −44.7 | −6.5 |
| d-isomethadone | −48.6 | −6.69 |
| Levomoramide | −63.13 | −7.32 |
| Levopropoxyphene | −52.3 | −5.6 |
| N-methyl-d-methadone | ND (simulation unstable) | −6.6 |
| Morphine | −42.6 | −6.6 |

The drug/receptor complexes that scored in the best 10% of the rank for the first set of SMOs were then simulated for 10 ns by MD simulation. Finally, their binding energy to the receptor was estimated by MM-GBSA and reported in Table 3.

Effective binding events are always characterized by a negative difference in free energy (Delta G) between the bound and the unbound state (i.e. the free energy of the complex is lower than that calculated for the isolated ligand and target).

In the present inventors' calculations, several molecules—including dextromethadone—were predicted to have a negative Delta G value. In particular, ligand/receptor binding affinity—expressed by Delta G values—of many of the new compounds tested was similar or more negative of the value obtained for ketamine, a drug known for its activity at the NMDAR with FDA approved clinical indications for anesthesia. The more negative Delta G values, with respect to ketamine and other reference molecules, obtained for the different compounds tested on the developed protein model, suggest potential differences in drug receptor interactions, different onset/offset and trapping values, and a more effective binding affinity with consequential different clinical effects, which ultimately may be better suited for one or more diseases. As the experimentation with SMOs advances, the present inventors are likely to be able to characterize each new molecule with unique PD and PK parameters which may prove advantageous for select diseases and conditions.

TABLE 3

Results of the computational evaluation of the first set of ligands expressed in Delta G values for the more active molecules in the docking pre-screening.

| Molecule Code | Predicted Affinity (Delta G, kcal/mol) |
|---|---|
| DMD119 (G121) | −66.65 |
| DMD29 (G30) | −57.09 |
| DMD90 (G92) | −55.26 |
| DMD106 (G108) | −54.08 |
| DAN-DMD7 (DMD-7) | −53.54 |
| DAN-DMD41 (DMD-41) | −50.08 |
| DMD-AA12 (DMD-AA10) | −48.3 |
| DMD-G53 (G55) | −48.29 |
| DMD-AA5 (DMD-AA4) | −47.8 |
| DAN-DMD37 (DMD-37) | −47.31 |
| DMD-AA14 (DMD-AA14) | −47.16 |
| DAN-DMD15 (DMD-15) | −46.08 |

TABLE 3-continued

Results of the computational evaluation of the first set of ligands expressed in Delta G values for the more active molecules in the docking pre-screening.

| Molecule Code | Predicted Affinity (Delta G, kcal/mol) |
|---|---|
| DMD-AA16 (DMD-AA16) | −46.06 |
| DMD-AA11 (DMD-AA9) | −44.39 |
| DMD-AA10 (DMD-AA8) | −44 |
| DMD-AA7 (DMD-AA12) | −40.99 |
| DMD-AA15 (DMD-AA15) | −40.13 |
| DMD-AA6 (DMD-AA5) | −38.8 |
| Dextromethadone | −44.7 |
| Isomethadone | −48.6 |
| Ketamine | −20 |

As mentioned above in order to select the new compounds for undergoing synthesis and testing in excitotoxicity protection models in vitro the present inventors developed a new in silico NMDAR model and performed a preliminary validation study with MK-801 (control), dextromethadone, and newly synthetized SMOs (including those described and shown above in Tables 1a, 1b, 2a, 2b, and 2c). The newly designed and tested in silico SMOs are now undergoing synthesis and further testing in vitro before in vivo experimental trials.

The contribution of other mechanisms of action, aside from NMDAR modulation, may also be also useful, as the present inventors discuss below for dextromethadone. As discussed above, absorption, distribution, metabolism, excretion (PK) and specific PD characteristics for differential actions at the NMDAR complex (including affinity for the binding site(s), "on set"-"off set" rates and trapping index,—receptor drug kinetics—and binding mechanism—non-competitive and/or uncompetitive), and other mechanisms of action of the drug, aside from NMDAR block, are likely to vary after even minimal molecular structure modifications of very similar drugs and thus these minor modifications might offer specific advantages within the same disease—including different stages of the disease—or for different diseases and conditions, including aging of cells. While this concept might hold true for most drugs, it is particularly relevant for NMDAR antagonists and modulators, because of the complexities outlined throughout this disclosure, including the complexities of drugs with multiple actions, such as dextromethadone (as outlined below) and other drugs in the same family (opioid drugs and opioid enantiomers, including SMOs), and including the multiplicity of diseases and conditions that involve malfunction of these ubiquitous and complex ion channels and the influence of other mechanisms regulated by dextromethadone and likely by SMOs on cellular processes, such as up-regulation of BDNF, as disclosed previously by the inventors. To underscore the importance of mechanisms other than NMDAR modulation, ketamine, a known NMDAR antagonist with demonstrated antidepressant activity in experimental models and in human studies, was recently found to be ineffective for depression when administered with an opioid antagonist, implying that ketamine may also modulate opioid receptors, aside from NMDARs and the dopamine system, and that the opioid system needs to be functioning in order for ketamine to exert its antidepressant effects.

Presently it appears that the ideal NMDAR modulator for the treatment of one or more diseases where NMDARs are dysregulated should provide an effective but short-lived open channel block, more prominent (or exclusively) when the receptor is over-stimulated and thus when the channel remains open for longer than a few tens of msec—in order to preserve receptor functioning under physiological conditions and thus should have low affinity, relatively slow "on rate" (so not to interfere with normal activity) and relatively rapid "off rate" to avoid trapping (so not to cause side effects, as is the case with MK-801). The ideal NMDAR modulator should act by uncompetitive antagonism (increasing channel blockade in the presence of increasing overstimulation of the receptor—in other words a constant level of drug will be more active in the presence of increasing levels of overstimulation of NMDARs, while minimally interfering with physiologic neurotransmission of NMDARs, for example during LTP, learning and memory formation). For certain diseases, a preferential activity for a specific receptor subtype may also be useful, as well as the cellular location of the receptor (synaptic, perisynaptic or extrasynaptic) or the location of the receptor along the neurotransmission path (presynaptic or postsynaptic). For other diseases, a specific drug might be particularly active on specific neuronal subpopulations or neuronal circuits, where NMDARs may be hyperactive because of disease, thus rendering the drug more disease selective. While dextromethadone appears to have the basic features that characterize an ideal NMDAR antagonist, including favorable PK and safety and tolerability, different diseases and different stages of the same disease might benefit from specific structural changes of the dextromethadone molecule or from structural changes of other opioids and their enantiomers, resulting in novel chemical entities with actions similar but not identical to the actions of dextromethadone: these structural changes might provide improved safety and efficacy profiles for select diseases and patient subpopulations.

It is therefore potentially useful to develop a platform of dextromethadone-like drugs (SMOs) with NMDAR modulating effects that might prove themselves better therapeutic agents than the currently approved NMDAR antagonists under some particular circumstance related to select disease and patient variables, as detailed above. It must be understood that while these novel molecules may share some structural features with dextromethadone or with other opioids and their enantiomers, they are de facto new molecular entities, with different PK and PD properties that will need to be characterized by a full drug development program, separate from the dextromethadone development program, starting from the design of the new chemical formulas, testing in novel molecular modeling assays, development of new synthetic methods and synthesis of the molecules and a new set of experimental work, in vitro and then in vivo and followed by complete clinical phases, starting from phase 1 safety studies.

As stated, NMDAR antagonists are increasingly recognized for their great potential as therapeutic agents for a multiplicity of diseases. It is known that amantadine is effective in Parkinson disease; memantine, structurally similar to amantadine, is effective for moderate to severe Alzheimer's disease; dextromethorphan is effective for controlling emotional lability in pseudobulbar palsy; ketamine is effective as an anesthetic and in experimental models of depression and esketamine has been approved by the FDA for patients with treatment resistant depression.

Ketamine and memantine were shown to influence synaptic protein synthesis and to increase the number of synapses in certain neuronal populations in experimental settings and thus these drugs are likely to play a role in neuronal plasticity. These effects may be beneficial for certain diseases: as an example, ketamine was recently proven effective in an experimental model of Rett syndrome, a severe developmental disorder (Patrizi A, Picard N, Simon A J, Gunner G, Centofante E, Andrews N A, Fagiolini M. Chronic Administration of the N-Methyl-D-Aspartate Receptor Antagonist Ketamine Improves Rett Syndrome Phenotype. Biol Psychiatry. 2016 May 1; 79(9):755-64. doi: 10.1016/j.biopsych.2015.08.018. Epub 2015 Aug. 24).

Dextromethadone was also found to increase the levels of GluR1 and PSD95 in rat models of depression (data for this is shown in the section below, titled "Development of the NMDAR Antagonist d-Methadone for the Treatment of Depression and other CNS Disorders") and these effects could potentially be shared, with different levels of activity, by select SMOs object of this disclosure.

Development of the NMDAR Antagonist d-Methadone for the Treatment of Depression and Other CNS Disorders In that regard, NMDA receptor (NMDAR) modulators are potential agents for the treatment of several central nervous system (CNS) disorders including major depressive disorder, as previously disclosed by the inventors in U.S. Pat. No. 9,468,611; International Patent Application No. PCT/US2018/016159. Further, racemic methadone and its stereoisomers, I-methadone and d-methadone, bind NMDARs with an affinity similar to that of established NMDAR antagonists, while only I-methadone and racemic methadone bind to opioid receptors with high affinity. D-methadone was found by the inventors to have no clinically significant opioid effects at therapeutic doses mediated by its NMDAR antagonism (SAD and MAD studies detailed below in the section titled Clinical Studies).

With that background in mind, the present inventors conducted several pre-clinical studies comparing the effect of d-methadone and ketamine in different behavioral animal models commonly used to assess antidepressant activity. These include the Forced Swim Test, the Female Urine Sniffing Test and the Novelty Suppressed Feeding Test. The present inventors also performed behavioral analysis of the effect of both d-methadone and ketamine on rats exposed to a Chronic Unpredictable Stress (CUS) protocol.

In all of the aforementioned tests, d-methadone, like ketamine, produced significant improvements in drug treated vs. vehicle treated animals. In addition, the present inventors observed positive effects on the expression of synaptic proteins and receptors critically involved in synaptic plasticity. These biochemical effects were also paralleled by favorable changes in electrophysiology.

FIG. 1 shows the effects of ketamine and d-methadone on immobility, climbing and swimming counts in the FST. Data represent mean±SEM. For immobility: *p=0.0034 for ketamine, 0.0007 for d-methadone 10 mg/kg, and <0.0001 for d-methadone 20 and 40 mg/kg compared to vehicle group, ANOVA. For climbing: *p<0.05 for d-methadone 40 mg/kg vs. vehicle. For swimming: *p<0.05 for ketamine and d-methadone 10 mg/kg, <0.0001 for d-methadone 20 mg/kg, and 0.0003 for d-methadone 40 mg/kg vs. vehicle, ANOVA.

Figure 2A:
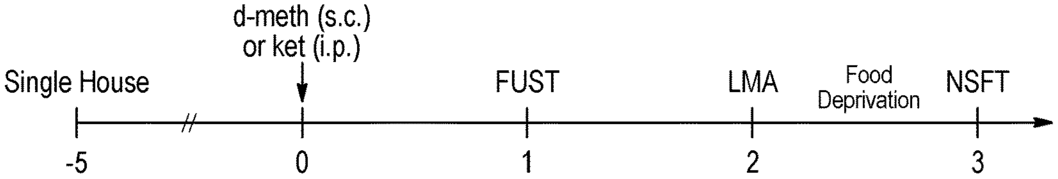
FIGS. 2A-2E show the influence of d-methadone and ketamine on a Female Urine Sniffing Test ("FUST") and Novelty Suppressed Feeding Test ("NSFT").
Figure 2B:
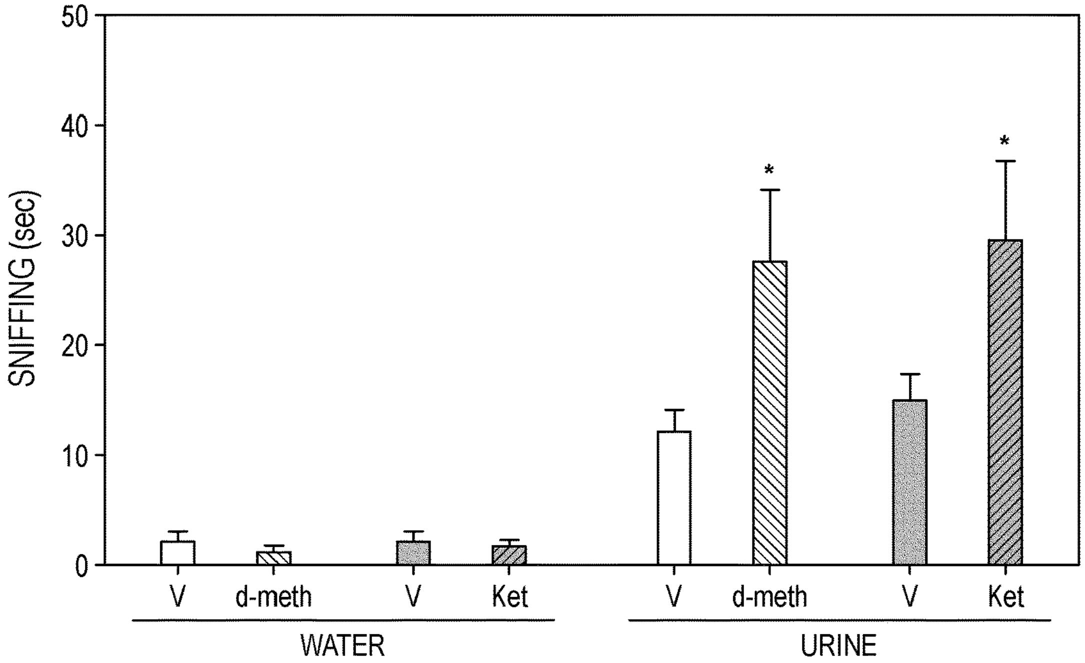
Figure 2C:
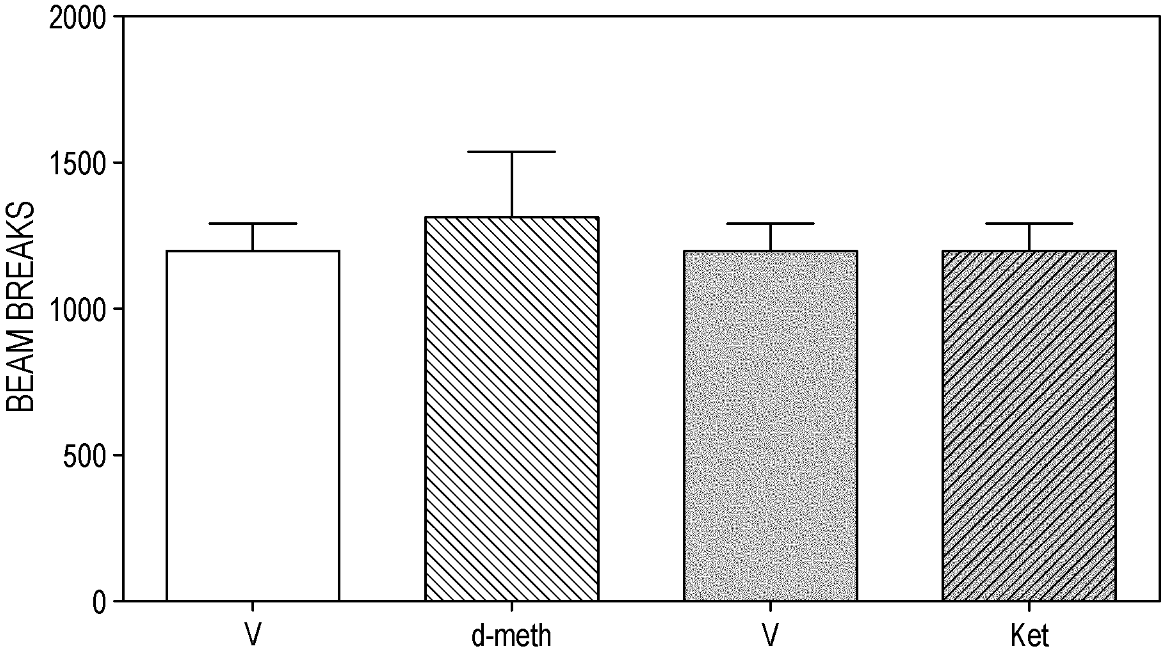
Figure 2D:
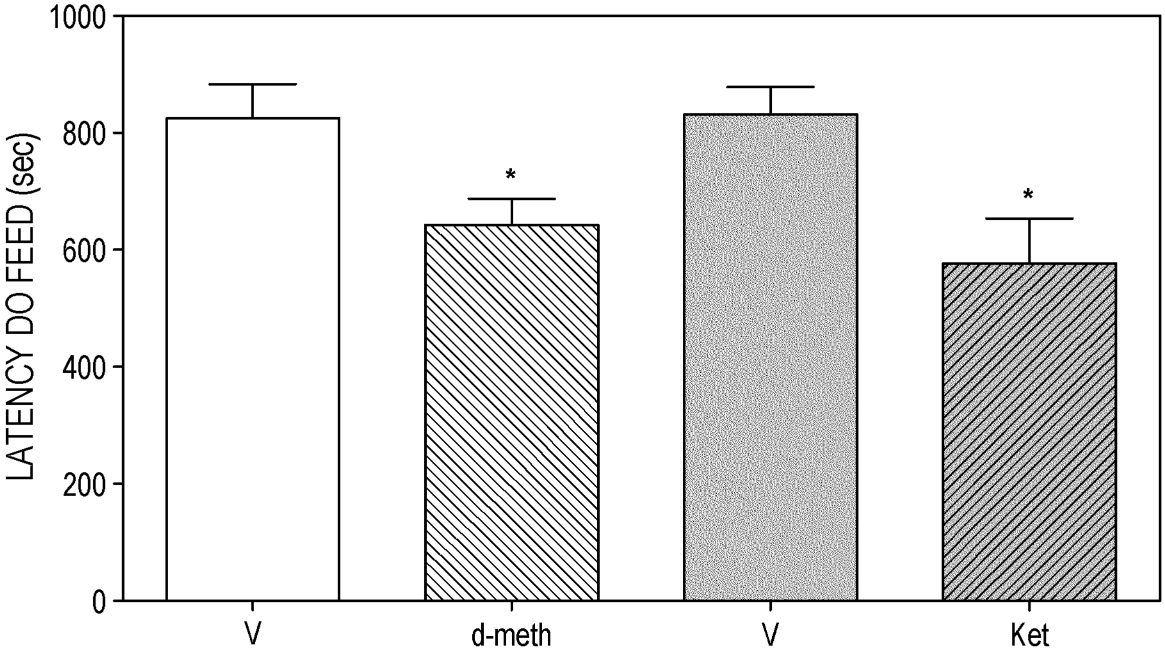
Figure 2E:
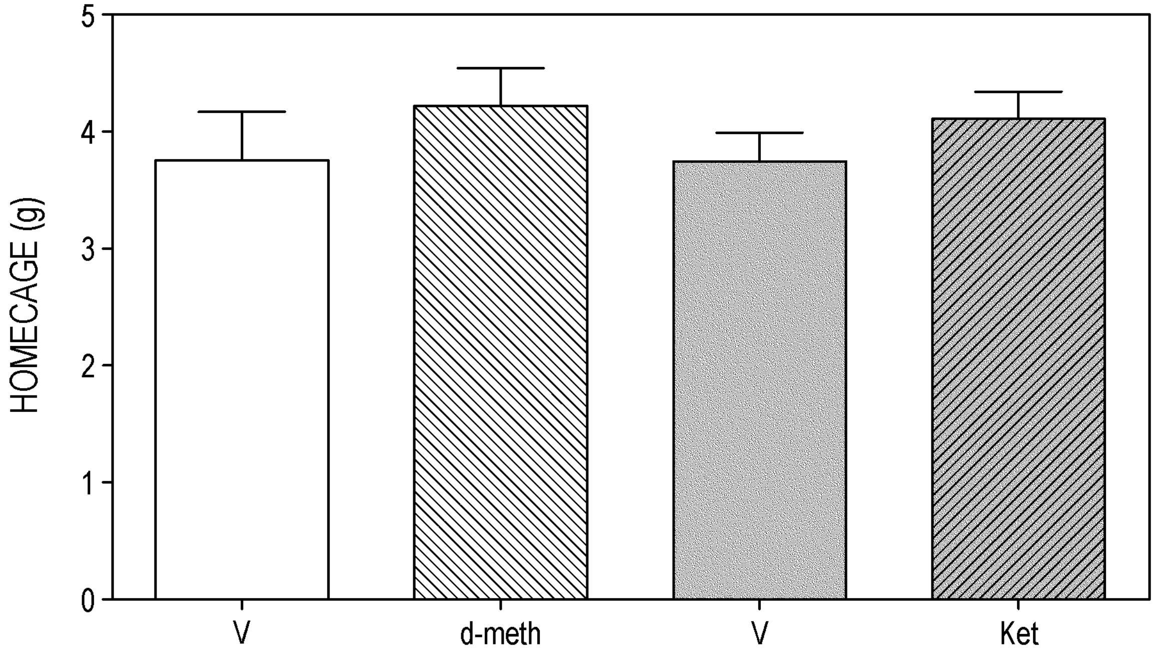

FIGS. 2A-2E show the influence of d-methadone and ketamine on a Female Urine Sniffing Test ("FUST") and Novelty Suppressed Feeding Test ("NSFT"). In FIG. 2A, a schedule for administration and testing rats is shown, where administered d-methadone or ketamine and then subjected to various tests. FIG. 2B shows rats tested in FUST 24 hr later. FIG. 2C shows rats tested for locomotor activity (LMA) 2 days later. FIG. 2D shows the rats tested for NSFT 72 hr later. And FIG. 2E represents home cage feeding. The results are the mean±S.E.M. FUST: One-way ANOVA, F3,42=3.26, p=0.031; Fisher's LSD: Veh x Met, p=0.025; Veh x Ket, p=0.046; n=9-12/group. NSFT: One-way ANOVA, F3,27=4.87, p=0.008; Fisher's LSD: Veh x Met, p=0.035; Veh x Ket, p=0.005; n=7-8/group.

Figure 3A:
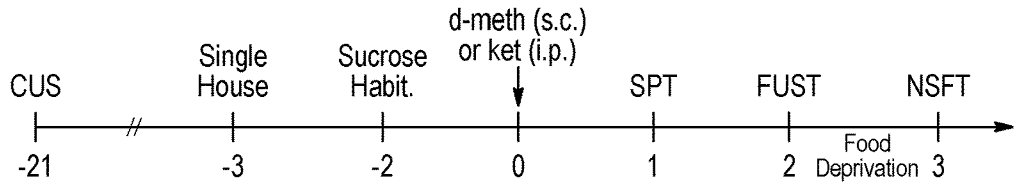
FIGS. 3A-3E show that a single dose D-methadone prevents depressive behaviors induced by Chronic Unpredictable Stress ("CUS") exposure.
Figure 3B:
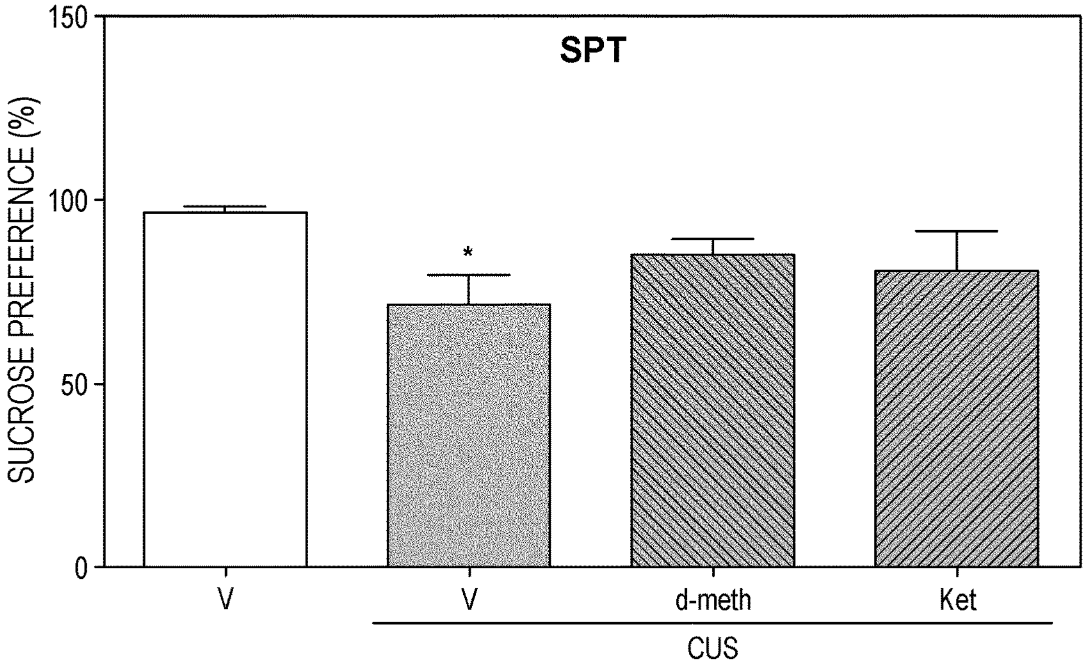
Figure 3C:
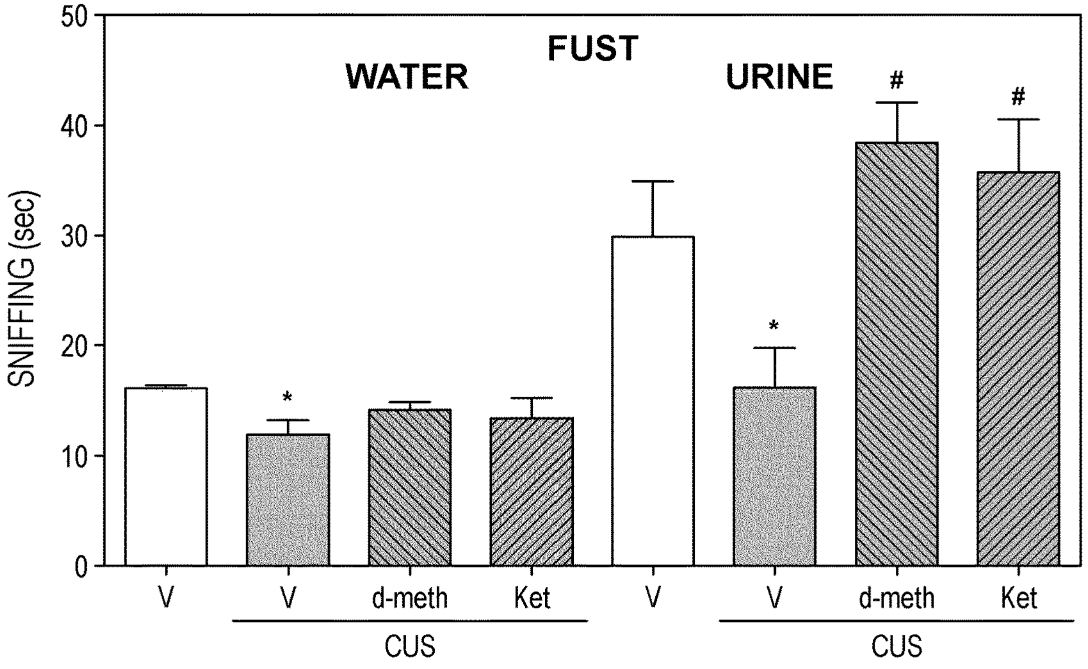
Figure 3D:
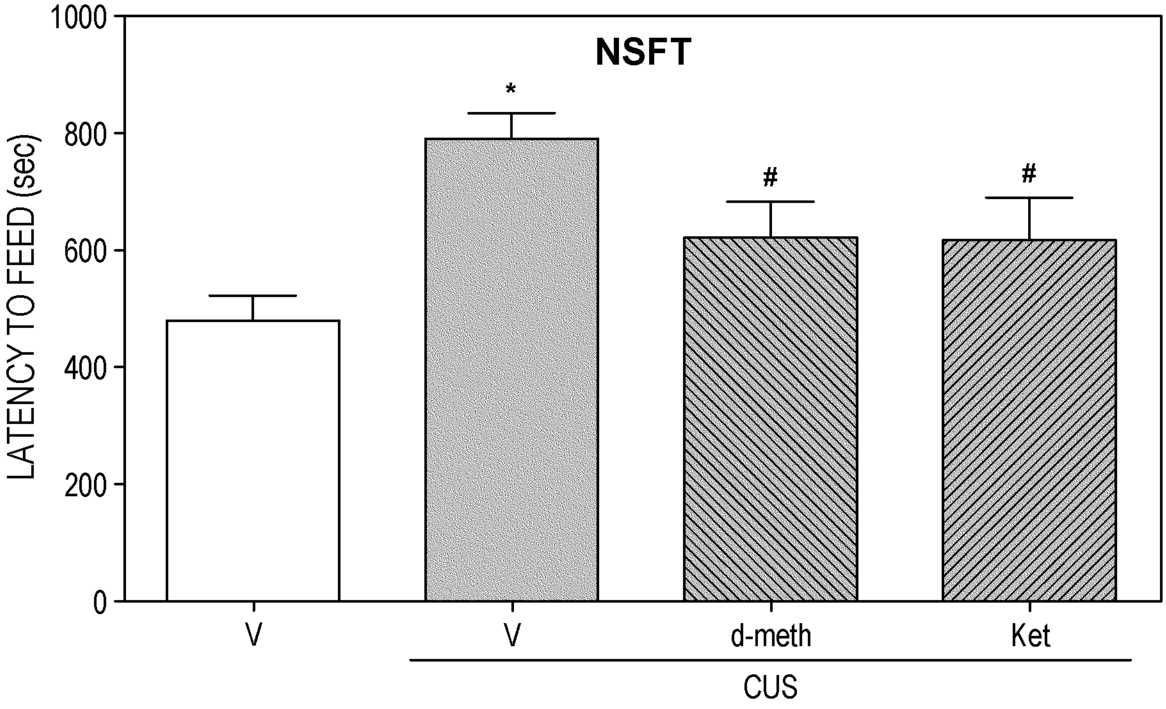
Figure 3E:
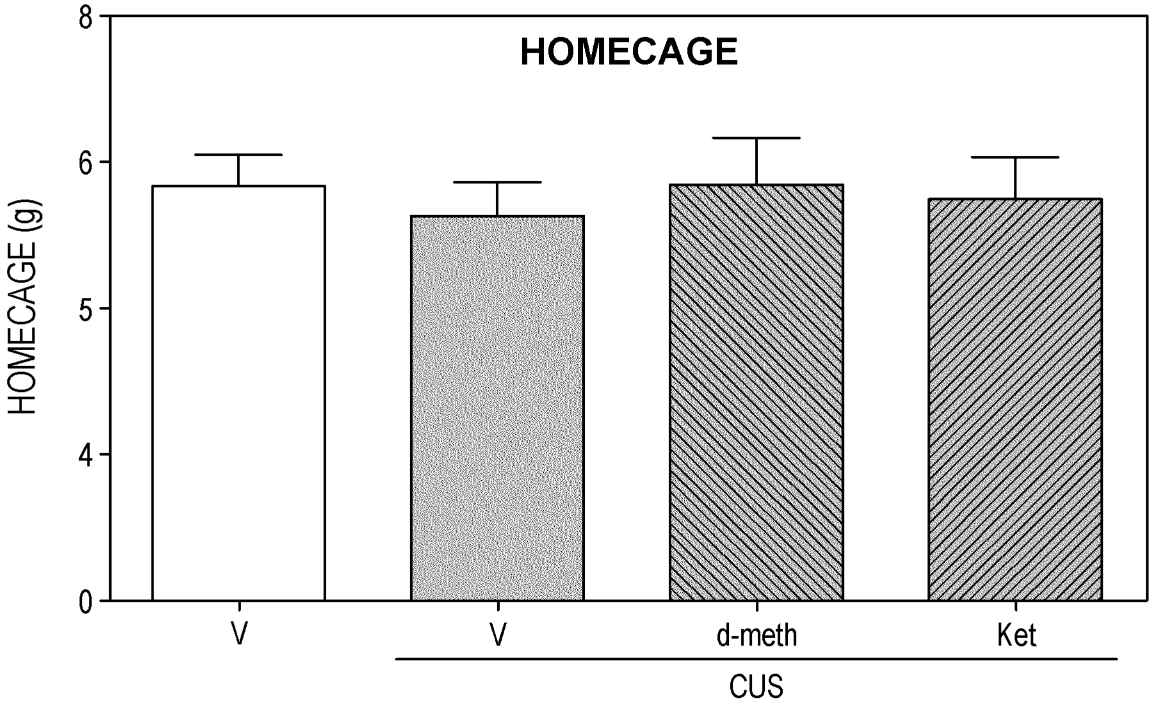

FIGS. 3A-3E show that a single dose D-methadone prevents depressive behaviors induced by Chronic Unpredictable Stress ("CUS") exposure. FIG. 3A shows time-course for the CUS protocol, drug dosing, and behavioral analysis. D-methadone and ketamine prevented the behavioral effects of CUS in FIG. 3B [sucrose preference test (SPT) (F3, 45=2.99)], FIG. 3C [FUST (F3,46=5.43)], and FIG. 3D [NSFT (F3,46=6.79)]. No difference was found for water sniffing or (FIG. 3E) home cage food consumption. Results are the mean±S.E.M., n=9-15/group. P<0.05, One-Way ANOVA and Duncan posthoc test.

Figure 4A:
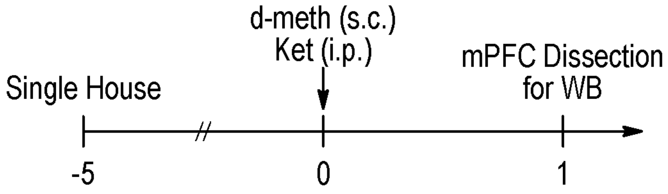
FIGS. 4A and 4B show influence of d-methadone on mTORC1 signaling and synaptic proteins. Rats were administered d-methadone and levels of mTORC1 signaling proteins and synaptic proteins were examined in the PFC and hippocampus.
Figure 4B:
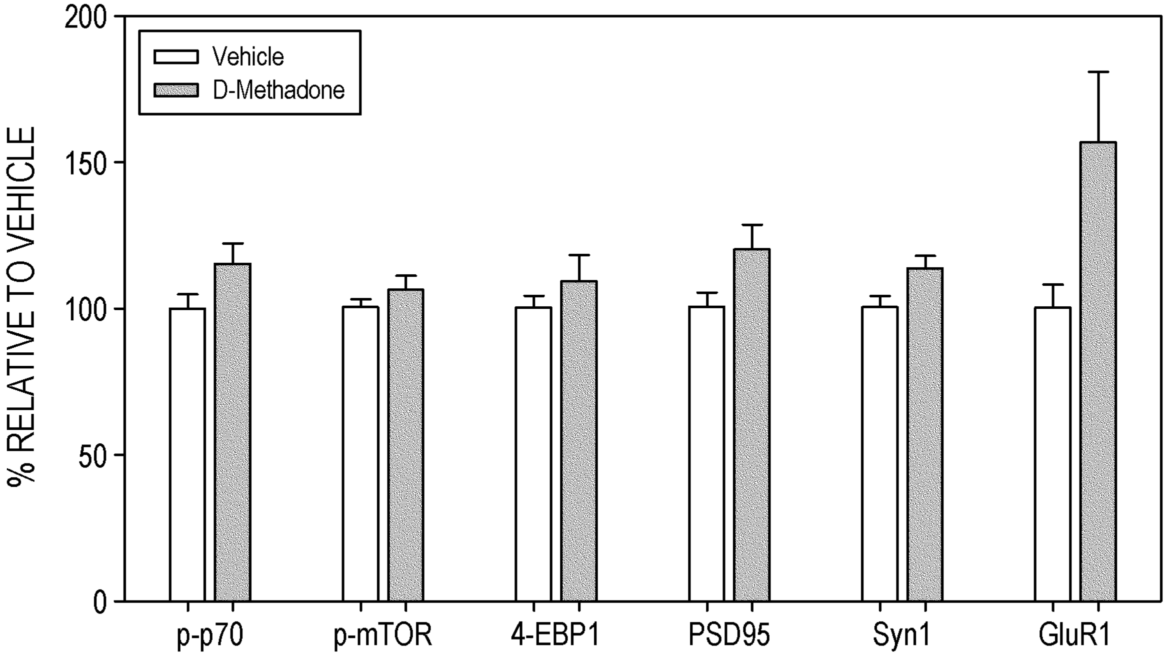

FIGS. 4A and 4B show influence of d-methadone on mTORC1 signaling and synaptic proteins. Rats were administered d-methadone and levels of mTORC1 signaling proteins and synaptic proteins were examined in the PFC and hippocampus.

Levels of phospho proteins were normalized to total proteins and levels of synaptic proteins were normalized the GAPDH. Results are the mean±S.E.M., n=10-12/group. P<0.05 compared to vehicle (Student's t-test).

Clinical Studies

As detailed in International Patent Application No. PCT/US2018/016159, the present inventors also investigated the safety, tolerability and pharmacokinetic (PK) profile of d-methadone in healthy opioid-naïve volunteers in two Phase 1, double-blind, randomized, placebo-controlled, single and multiple ascending dose (SAD and MAD) studies.

The Single Ascending Dose (SAD) study included a parallel group, double-blind, placebo-controlled design. The objectives of the study were to establish PK, PD, and safety of single dose administration. Administration involved cohorts of 5, 20, 60, 100, 150, 200 mg and N=42. SAD study conclusions were as follows: (1) Maximum tolerated dose (MTD)=150 mg (single dose); (2) PK demonstrated linear proportionality of $C_{max}$ and $AUC_{0\_,1if}$ vs. dose; and (3) no clinically significant opioid effects of dextromethadone up to 150 mg.

The objective of the Multiple Ascending Dose (MAD) study was to establish PK, PD, and safety of once daily, 10-day administration. Administration involved cohorts of 25, 50, 75 mg and N=24. MAD study conclusions were as follows: (1) Doses up to 75 mg per day were well tolerated, and (2) dose proportionality was demonstrated for the single-dose parameters $C_{max}$ and $AUC_{tau}$ on Day 1 and for the steady state parameters $C_{max}$, $AUC_{tau}$, and Css on Day 10.

Thus, d-methadone exhibited linear PK with dose proportionality for most single dose and multiple dose parameters. Single doses up to 150 mg and daily doses up to 75 mg for 10 days were well tolerated with mostly mild treatment emergent adverse events and no severe or serious adverse events. At the tested doses, d-methadone did not cause dissociative or psychotomimetic adverse events, no clinically relevant opioid effects and no signs or symptoms of withdrawal upon abrupt discontinuation.

Figure 5A:
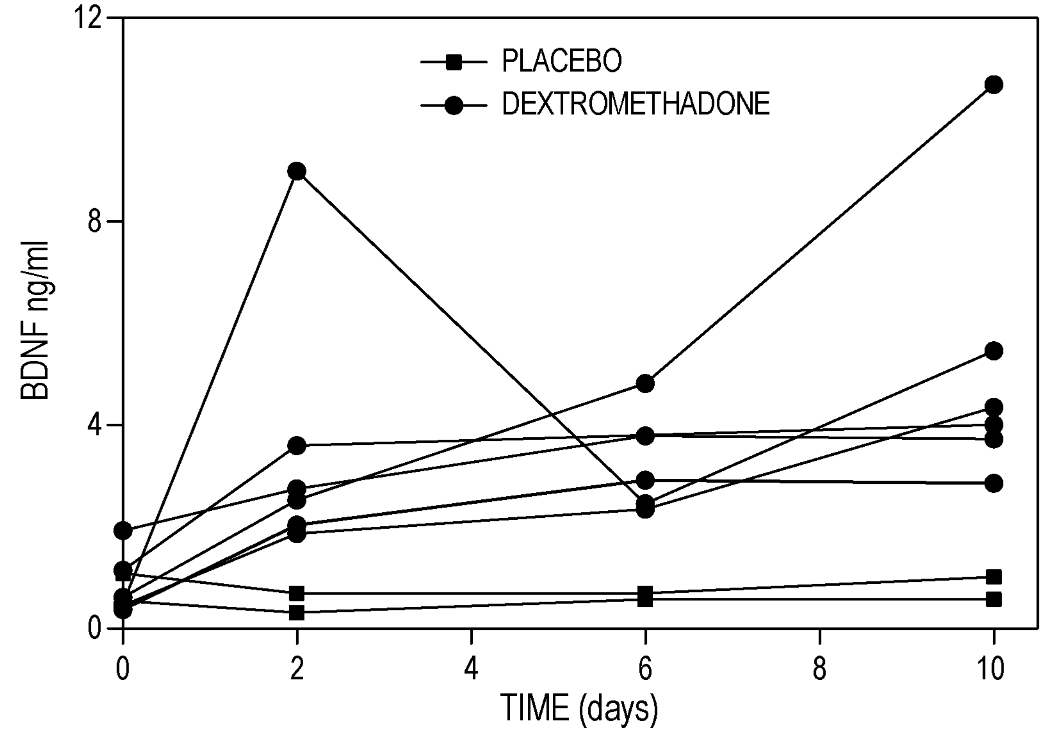
FIGS. 5A and 5B show brain derived neurotrophic factor (BDNF) plasma levels from a 25 mg cohort of a MAD study were tested before any treatment and 4 hours after administration of d-methadone 25 mg (six patients) or placebo (two patients) on days 2, 6 and 10. In the d-methadone treatment group, 6 of 6 subjects showed an increase in BDNF levels post d-methadone treatment compared to pre-treatment levels, with post-treatment day 10 BDNF plasma levels ranging from twice to 17 times the pre-treatment BDNF levels. By contrast, in the two placebo subjects, the BDNF plasma levels remained unchanged. Plasma BDNF levels measured at day 2 and day 10 were significantly correlated to the plasma levels of d-methadone when placebo subjects are included in the analysis. $p=0.028$ at day 2, $p=0.043$ at day 6, and $p=0.028$ at day 10; all vs BDNF plasma levels before treatment.
Figure 5B:
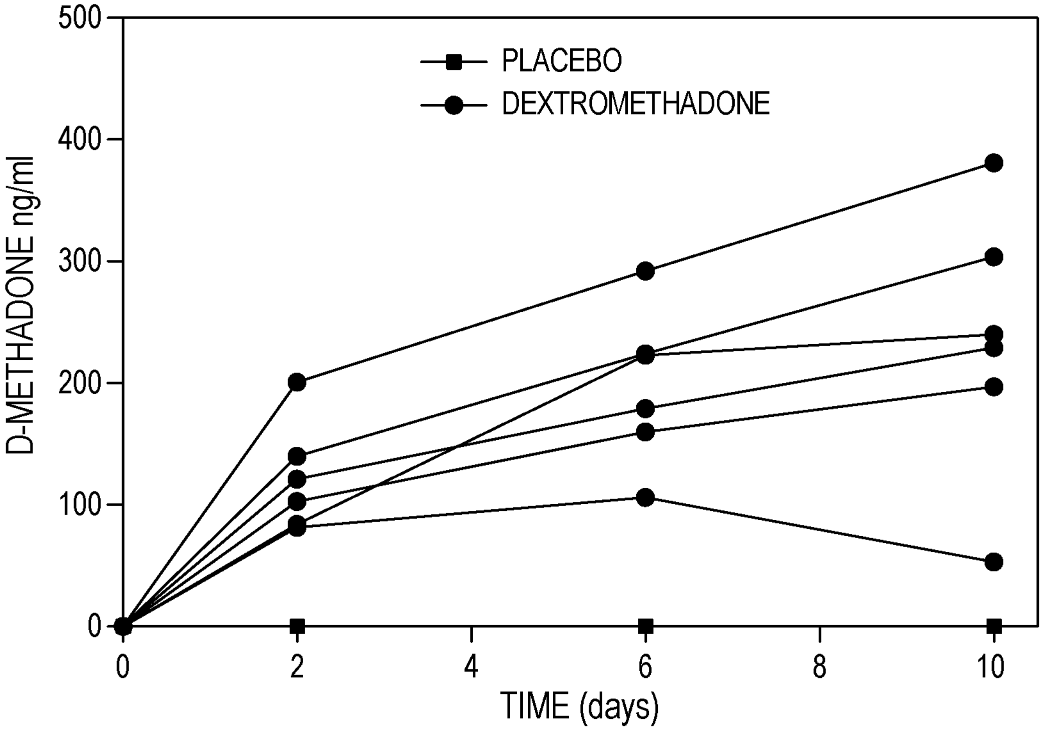

Brain derived neurotrophic factor (BDNF) plasma levels from the 25 mg cohort of the MAD study were tested before any treatment and 4 hours after administration of d-methadone 25 mg (six patients) or placebo (two patients) on days 2, 6 and 10. Referring to FIGS. 5A and 5B, in the d-methadone treatment group, 6 of 6 subjects showed an increase in BDNF levels post d-methadone treatment compared to pre-treatment levels, with post-treatment day 10 BDNF plasma levels ranging from twice to 17 times the pre-treatment BDNF levels. By contrast, in the two placebo subjects, the BDNF plasma levels remained unchanged. Plasma BDNF levels measured at day 2 and day 10 were significantly correlated to the plasma levels of d-methadone when placebo subjects are included in the analysis. These data were also presented in more detail in International Patent Application No. PCT/US2018/016159.

In summary, the evidence gathered so far continues to support the development of d-methadone in depression and other CNS conditions for which NMDAR modulation could be an effective mechanism of action for a potential treatment.

In addition to the information of "Development of the NMDAR Antagonist d-Methadone for the Treatment of Depression and other CNS Disorders" above, dextromethadone, but not MK-801, was found to increase the expression of mRNA coding for NMDAR1 (See the Example, below, and FIG. 10). While neuroplasticity events are likely downstream effects of the shared NMDAR antagonistic activity of these two drugs, ketamine and d-methadone, the extent and results and sites of neuroplasticity induced by different NMDAR antagonists derived from opioid drugs (SMOs) within the human brain is likely to differ between different chemical entities in this group and thus potentially only one specific NMDAR antagonist/modulator (and for the purpose of this disclosure, only one specific new chemical entity among many SMOs disclosed) may prove effective and complete development as an effective drug for one or more select diseases and conditions.

A recent paper (Frank RAW1, Zhu F2, Komiyama NH2, Grant SGN2.Hierarchical organization and genetically separable subfamilies of PSD95 postsynaptic supercomplexes. J Neurochem. 2017 August; 142(4):504-511. doi: 10.1111/jnc.14056. Epub 2017 Jul. 25) describes the supramolecular organization of NMDARs within the synaptic proteome, a postsynaptic density composed by approximately 1000 proteins. While NMDAR complexes are 0.8 MDa heterotetramers formed solely by its ion channel subunits, NMDAR supercomplexes are 1.5 MDa assemblies that include NMDAR receptors bound to approximately 50 different proteins, including other ion channels, receptors, adhesion proteins, signaling proteins, scaffolding proteins. Interestingly, while NMDAR complexes can be di-heterotetramers (GluN1-GluN2A and GluN1-GluN2B) or tri-heterotetramers (GluN1-GluN2A-GluN2B), NMDAR supercomplexes contain only GluN2B di-heterotetramers and tri-heterotetramers (the carboxy terminal intracytoplasmic tail of GluN2B is essential for NMDA supercomplex assembly, together with PD95-PD93 subunits). A drug that is more selective for NMDAR di-heterotetramers GluN1-GluN2A will be less likely to influence NMDA supercomplexes and thus will have differential PD effects compared to drugs more active on NMDAR assembled with GluN2B subunits, such as memantine compared to amantadine and deuterated dextromethadone compared to dextromethadone (International Patent Application No. PCT/US2018/016159).

Furthermore, the data described above in "Development of the NMDAR Antagonist d-Methadone for the Treatment of Depression and other CNS Disorders," showed that dextromethadone, aside from increasing GluR1, increases PSD95 in rat models of depression. These findings suggest that the actions of dextromethadone and possibly other SMOs are not limited to NMDAR complexes but also influence AMPA receptors and also involve NMDAR supercomplexes. PSD95, with PSD93 and GluN2B, is a player in the tripartite rule that explains the organization of a subset of NMDARs in supercomplexes (Frank RAW and Grant SGN, 2017) and thus this increase in PD95 seen in dextromethadone-treated rats disclosed by the inventors and the in vitro data on the increased expression of mRNA coding for NMDAR1 induced by dextromethadone (see the Example, below, and FIG. 10), provides additional insight into the biochemical consequences and neural plasticity potential of drugs like dextromethadone and the neural plasticity potential of new chemical entities in the group of SMOs object of this disclosure, and ultimately better defines the potential of this novel library of NMDAR antagonists (SMOs) for developing into drugs potentially effective the treatment of diseases and conditions as defined in this application.

Dextromethadone is presently undergoing pre-clinical and clinical trials for several indications including depression, Rett syndrome, restless leg syndrome, amyotrophic lateral sclerosis, eye diseases, and other potential indications. While dextromethadone might prove effective for one or more of these indications, it is possible that it will be effective for only one indication. Structural modifications of the dextromethadone molecule or structural modifications of another opioid or opioid enantiomer with NMDAR activity (SMO) is an option for potentially providing additional and differential effects at NMDARs or even at other sites (see below, "Other Therapeutic Targets for SMOs"), with potential therapeutic efficacy for different diseases and patient populations compared to dextromethadone.

Other Therapeutic Targets for SMOs

Apart from its activity at the NMDA receptor, already disclosed by the inventors in the listed patents and patent applications, and its downstream consequences, including up-regulation of synaptic proteins, including AMPA receptors, NMDAR1, PD95, as shown by the data presented with this application, dextromethadone also exerts other actions which may be therapeutic for select diseases: dextromethadone inhibits the norepinephrine transporter ("NET") system and the serotonin transporter ("SERT") system (Codd E E, Shank R P, Schupsky J J, Raffa R B. Serotonin and norepinephrine uptake inhibiting activity of centrally acting analgesics: structural determinants and role in antinociception. J Pharmacol Exp Ther. 1995 September; 274(3):1263-70); dextromethadone influences and up-regulates neurotrophic factors, such as brain derived neurotrophic factor ("BDNF") and it modulates reproductive hormones such as testosterone (International Patent Application No. PCT/US2018/016159); it exerts actions on $K^+$, $Ca^{2+}$ and $Na^+$ cellular currents (Horrigan FT1, Gilly W F. Methadone block of K+ current in squid giant fiber lobe neurons. J Gen Physiol. 1996 February; 107(2):243-60); it down-regulates blood pressure and potentially blood glucose in humans (International Patent Application No. PCT/US2018/016159). Thus, dextromethadone has a potential role in the treatment of one or more NS, endocrine, metabolic and trophic and aging processes. Finally, dextromethadone exerts mild opioidergic activity at different opioid receptor subtypes (Codd et al., 1995) and these effects, while they are mild and non-significant in terms of opioid side effects (Bernstein G, Davis K, Mills C, Wang L, McDonnell M; Oldenhof J, Inturrisi C, Manfredi P L, Vitolo O V. Characterization of the Safety and Pharmacokinetic Profile of D-Methadone, a Novel N-Methyl-D-Aspartate Receptor Antagonist in Healthy, Opioid-Naive Subjects: Results of Two Phase 1 Studies J Clin Psychopharmacol. 2019 May/June; 39(3):226-237), may instead offer disease specific advantages, for example opioid effects may be important for certain diseases such as depression, as was seen with ketamine, which fails to exerts its anti-depressant actions if administered with a concomitant opioid antagonists, or in the case of pain disorders, where even weak opioid effects may represent a therapeutic advantage.

SMOs might retain some but not others among the effects listed above for dextromethadone or might have different effects altogether, which will be completely uncovered as part of the drug development program, and these effects might be selectively beneficial for the treatment of one or more diseases.

In fact, there might also be other drugs already in clinical use for a multiplicity of clinical indications that could exert therapeutic effects by modulating the NMDAR complex but this mechanism of action is yet to be recognized for these drugs and their clinical effects might be attributed to other mechanisms. Amantadine is a NMDAR antagonist that is likely to exert its therapeutic actions with different mechanisms. As an example, for many years it was thought that the mechanism of action of amantadine in Parkinson disease was dopaminergic or anticholinergic; presently, NMDAR antagonism is recognized as an important mechanism for the anti-Parkinson effects of amantadine. While the NMDAR effects of amantadine may be crucial for its effectiveness in Parkinson disease, its "other" effects, dopaminergic or anticholinergic, cannot be discounted altogether, and it is possible that more than one mechanism of action contributes to the therapeutic benefits of amantadine for Parkinson disease.

Variables Affecting NMDARs as Therapeutic Targets

Below is a list of potentially favorable variables that might be preferentially targeted by one but not another SMO and thus result in a favorable therapeutic profile for one specific novel drug but not another for use against one or more diseases and conditions. This following list of variables underscores the unmet clinical need, addressed by the present application, for a library of potentially safe and effective NMDAR modulators derived from opioids and opioid enantiomers (the SMOs disclosed in this application):

(a) Presynaptic NMDAR block versus postsynaptic block: drugs more selective for one or the other will have very different effects (Banerjee A, Larsen R S, Philpot B D, Paulsen O. Roles of Presynaptic NMDA Receptors in Neurotransmission and Plasticity. Trends in Neurosciences, 2015, Volume 39, Issue 1).

(b) Synaptic versus extra synaptic block: preferential extra synaptic block may be advantageous over synaptic block as it may better prevent excitotoxicity with less interference with physiologic neuronal activity occurring at or in proximity to the synapse. As an example, memantine may preferably target extra synaptic NMDAR (Huei-Sheng Vincent Chen and Stuart A. Lipton. The chemical biology of clinically tolerated NMDA receptor antagonists. Journal of Neurochemistry, 2006, 97, 1611-1626).

(c) Mechanism of ion channel block: e.g., noncompetitive versus uncompetitive block: uncompetitive block allows for increasing blockade with increasing overstimulation while the drug remains at a stable concentration. As an example, memantine (Chen and Lipton, 2006) and dextromethadone are likely to exert this type of block.

(d) Number and position (expression) of NMDARs and other glutamate receptors, including AMPA receptors (dextromethadone increases GluR1 in rat models of depression and mRNA coding for NMDAR1 in retinal cells), on cell membrane and on different areas of the cell membrane of select neuronal populations: different drugs may be more selective for certain neuronal populations and certain neuronal circuits (Hansen et al., 2018).

(e) Relative numbers of open and closed ion channels in a particular moment and number and location of hyperactive (at risk for inducing excitotoxicity) NMDA channels (Hansen et al., 2018).

(f) Timing of the drug on and off the receptor (onset, offset, trapping and "foot in the door" concept), also in relation to the relative number of NMDARs and other glutamate inotropic receptors in the open or closed state.

(g) Affinity of the drug for the receptor. Improved affinity, when not, associated with trapping, may allow for lower and better tolerated doses.

(h) Selectivity of the drug for the receptor including NMDAR subtypes and even genetically and epigenetically determined variances within subtypes, such as NR1, NR2A-D and NR3A-B (Low and Wee, 2010). Modifications in the level of activity of a drug with NMDAR modulating activity based on receptor subunit composition, could be of importance in designing drugs effective during a particular age of the patient, changing its potential efficacy in ADHD in children versus adults. Furthermore, preferential block of NMDAR assembled in supercomplexes (NR2B is required for NMDAR assembled in supercomplexes—tripartite rule) could also be advantageous for select diseases. Approximately 3% of PD95 supercomplexes include NMDARs (Frank et al., 2017). The discovered dextromethadone-induced increase in PD95 (data from "Development of the NMDAR Antagonist d-Methadone for the Treatment of Depression and other CNS Disorders," above, and FIGS. 1-5 and in particular FIG. 4B) suggests a specific effect of dextromethadone on NMDARs which are part of supercomplexes. A drug's activity on NMDAR in super-complexes may also be a factor of its PK parameters, e.g., a drug with an advantageous partition coefficient (such as a fluoro-derivative of dextromethadone) might be more capable of reaching the NMDAR portion of super-complexes.

(i) Activity of the drug towards select neuronal populations and circuits with hyperactive NMDAR caused by genetic, environmental or genetic+ environmental triggers.

(j) Activity of the drug in select brain areas, neuronal sub-populations, brain circuits.

(k) Activity of the drug in select pathologic states, including different stages of the same disease as exemplified by memantine use for the treatment of moderate and severe Alzheimer's disease but not for early Alzheimer's disease.

(l) Modifications in absorption, distribution, metabolism, excretion that may prove beneficial for select diseases.

(m) Activity of the specific novel drug on targets other than the NMDAR might render it a better therapeutic option for one specific disease as exemplified by amantadine for Parkinson disease and potentially by dextromethadone for the treatment of depression.

(n) While only the advancement of properly designed and conducted drug development programs will be able to best characterize if a specific structural modification applied to an opioid drug with potentially therapeutic NMDAR modulatory effects will result in PK and PD advantages and more specifically will result in changes in the interaction between the new drug and NMDARs that may prove advantageous for specific diseases

[among other modifications, nitro-derivatives of drugs that target the NMDA channel pore, such as dextromethadone and potentially other SMOs, may exert additional NMDA modulation by mechanisms outside of the PCP site e.g., S-nitrosylation of NMDAR subunits (Tomohiro Nakamura and Stuart A. Lipton. Protein S-Nitrosylation as a Therapeutic Target for Neurodegenerative Diseases. Trends in Pharmacological Sciences, January 2016, Vol. 37, No. 1; Stamler et al., US patent number U.S. Pat. No. 5,593,876A; Inturrisi, CE. NMDA receptors, nitric oxide and opioid tolerance. Regulatory Peptides, 1994, Volume 54, Issue 1). However it should be considered that if a nitro-derivative of an NMDAR antagonist drug, including SMOs, should prove itself effective for a specific disease, this therapeutic effect might derive from the theoretical mechanism outlined above [protein channel (NMDAR subunit) S-nitrosylation of overactive NMDARs with NO induced channel closure] or it might be for another reason altogether, one of the multiple reasons outlined throughout this disclosure, including improved onset/offset at the NMDA receptor pore channel unrelated to S-nitrosylation. The present inventors already know that simply increasing the level of channel block is not necessarily therapeutic advantageous (MK-801, PCP and ketamine are examples of drugs providing a "stronger", "trapping" NMDAR block resulting in disadvantageous side effects); on the other hand, changes in molecular structure of select opioid drugs determining changes in their PK and PD functions might prove advantageous for select diseases and thus the synthesis of fluoro-derivatives and nitro-derivatives, among other possible structural modifications of opioids, may result in novel potentially effective NMDARs. Furthermore, while reactive radicals, reactive oxygen species (ROS) and RNS, are normal components of cellular metabolism, overproduction of these types of radicals leads to inability of the cell to regulate them, which leads to redox imbalance and formation of oxidative stress. A nitro-derivative of an opioid drug with NMDAR activity and thus tropism for the NMDAR may regulate production of these reactive radicals and prevent or decrease cellular damage.

(o) Activity on NMDARs outside of the CNS, as outlined above, and implications for the design of SMOs that do not cross the BBB and may be active on neurons in the PNS (e.g., sensory neurons or autonomic neuron) or on non-neuronal cells such as pancreatic cells or cardiac cells, where modulation of NMDAR may offer therapeutic or preventive benefits.

The present inventors disclose that select opioid drugs with baseline NMDAR modulating potential, after a structural modification, including structural modifications resulting in fluoro-derivatives and nitro-derivatives and fluoro-nitro-derivatives and deuterated forms thereof (SMOs), for one or more of the reasons and mechanisms listed above, are potential candidates for a drug development program for specific diseases and conditions worsened by NMDAR dysfunction. The design and PK and PD characterization of SMOs with potential modulating actions at the NMDAR, including at the transmembrane domain and or at the extracellular domain, is thus the object of this disclosure.

Astrocytes and NMDARs: Astrocyte morphology and gene expression vary greatly depending on location, local contacts, and microenvironment. Astrocytes provide critical regulation of synaptic glutamate concentrations through bi- and uni-directional transporters. Astrocytes also connect with neurons including glutamatergic and GABAergic interneurons and regulate the activity of neurons by regulating neurotransmitter levels. Furthermore, astrocytes connect with each other in networks via gap junctions. Complex brain activities such as the default mode network and the ultimately even the conscious mind may be related to astrocytic regulation of neuronal activity rather than the contrary. Furthermore, astrocytes express all seven subtypes of NMDARs (Ming-Chak Lee; Ka Ka Ting; Adams Seray. Characterisation of the Expression of NMDA Receptors in Human Astrocytes. PLoS One, November 2010, Volume 5, Issue 11). Calcium influx studies show that both glutamate and quinolinic acid could hyper-activate astrocytic NMDARs, resulting in $Ca^{2+}$ influx into the cell and dysfunction and even death of astrocytes. The excitotoxicity from glutamate and quinolinic acid was prevented with NMDAR antagonists (MK-801 and memantine). Astrocyte NMDARs may also play an important role in facilitating glial signaling in the CNS and therefore it is crucial that they are not dysfunctional. Modulation of dysfunctional astrocytic NMDARs including their subtypes potentially represents a therapeutic target with potential for treatment of a multiplicity of diseases. SMOs with their differential activity on NMDARs and on NMDAR subtypes, unique PK and PD, including differences in onset/offset/trapping of NMDAR block, and potentially differences in preferentially block of neuronal or astrocytic NMDARs and spatiotemporal differences in activity (cellular, cell population, circuit and brain area), provide a platform for the development of new drugs potentially useful for the treatment of a multiplicity of diseases and conditions caused by dysfunctional NMDARs not only on neurons but also on astrocytes.

Neural plasticity: Neural plasticity is essential for proper development, memory formation and learning, and ultimately determines the individual's cognitive functions, personality, behavior and mood. Genetic diseases, sporadic or hereditary, may be driven by abnormal neural plasticity generated by normal sensory stimuli and experiences. One example of abnormal neural plasticity is given by an experimental model of Rett syndrome. In this mouse model, early in development, normal visual stimuli have negative effects on vision (Patrizi et al., 2016) and ketamine, an NMDAR antagonist, may prevent these negative effects. Aside from genetic diseases of the neural system, hereditary or sporadic, it is likely that genetically determined predispositions to certain diseases, in association with one or more specific environmental factors, including different toxins (G+E concept described above), could drive abnormal CNS plasticity and cause neuropsychiatric illness. In the presence of a severe genetic disease (e.g., Rett syndrome animal model discussed above), the "toxic" environmental factor can be a normal sensory experience (visual stimuli). When instead subjects are genetically predisposed to display enhanced susceptibility to one or more environmental insults, these insults can be very diverse such as endogenous toxins (e.g., quinolinic acid); or food (e.g., polyamine rich foods, alcohol); or drugs (e.g., aminoglycosides and cisplatin), or excessive amounts of neurotransmitters, as is the case in excitotoxicity driven by glutamate, or even autoantibodies against the NMDAR. Furthermore, these environmental factors can be known, as those above, or even unknown, yet to be defined, factors that have an influence on neural plasticity via NMDARs only in the presence of a genetic predisposition. If the insult from the toxic substance is severe enough it will determine abnormal neural circuitry in most "normal" individuals. In the case of some neuropsychiatric disease the triggering factor in predisposed individuals may not be a chemical or physical factor but can also be a particularly stressful (toxic) "life experience", as is the case in patients with PTSD and in some patients with depression and anxiety.

Whatever the trigger of cellular dysfunction, when this dysfunction is mediated via NMDARs and/or NO pathways, nitro-dextromethadone like drugs may prove clinically useful. In his 1994 paper (Inturrisi, CE. NMDA receptors, nitric oxide and opioid tolerance. Regulatory Peptides, 1994, Volume 54, Issue 1), Charles Inturrisi, one of the inventors on the present application, anticipated how the administration of morphine results in tolerance and hyperalgesia and how NMDARs and the NO pathway are involved in the development of these side effects of morphine. The present inventors now present a library of new molecules (SMOs) with potential NMDAR antagonistic actions, based on novel in silico tests results shown in this disclosure, and because of the specific structural molecular modifications applied to opioids, such as NO or nitric ester substitution, these SMOs may have modulation actions on NMDARs and the NO pathway. Thus, these novel molecules potentially have a role in the treatment of diseases where the modulation of NMDAR activity and/or modulation of the NO pathways are involved in the pathophysiological mechanisms of diseases and conditions. These include all diseases and conditions disclosed International Patent Application No. PCT/US2018/016159, and all diseases and conditions as defined in the first paragraph of this application.

In light of the novel interpretation presented throughout this application, morphine tolerance and hyperalgesia can be viewed as manifestations of abnormal neural plasticity induced by a toxin (in this case morphine). Many other chemicals (e.g., aminoglycosides, cisplatin, domoic acid, polyamines, quinolinic acid, et cetera) or physical factors, including trauma or brain radiation therapy, or electroconvulsive therapy (ECT) or even sounds and other sensory stimuli and many diseases and conditions, including neuropsychiatric diseases caused or worsened by dysfunction at NMDARs or dysfunction at NO pathways could therefore be improved by a dextromethadone nitro derivative. "Toxic life experiences", resulting in abnormal neural plasticity and abnormal NS circuitry in susceptible individuals, may be also at the basis or may contribute to neuropsychiatric diseases such as depression, anxiety, PTSD, ADHD, schizophrenia et cetera (Chen and Baran, 2016).

New chemical entities with modulating activity at NMDARs and NO pathways, such as nitro-derivatives of opioids and their enantiomers (SMOs) may prevent or ameliorate these aberrant circuitries triggered or maintained by "toxic experiences" or any of the chemical or physical factors listed above, that may be at the basis of a multiplicity of neuropsychiatric disorders. The inventors have discovered previously that dextromethadone increases BDNF levels in humans (International Patent Application No. PCT/US2018/016159) and in this submission the inventors disclose that dextromethadone increases the expression of mRNA coding for NMDAR1 induced by dextromethadone (see the Example, below, and FIG. 10). A structural modification of the dextromethadone molecule, e.g., a dextromethadone nitro-derivative, with the potential for modulation of the NO pathway, may further enhance the potential for neuroplasticity of the parent molecule and thus expand the therapeutic potential of dextromethadone for the treatment of one or more diseases and conditions.

Furthermore, the novel compounds disclosed in this application, in particular dextromethadone nitro-derivatives, and NMDAR antagonists in general, including dextromethadone, may be of particular usefulness when administered to patients undergoing Electroconvulsive therapy (ECT). ECT may interrupt abnormal neural circuits, generated by aberrant neural plasticity, that express themselves in patients with the symptoms of depression or other neuro psychiatric diseases. These novel compounds, SMOs, may help restore and then preserve normal circuitry when administered as solo therapy or in combination with other drugs, ECT or even psychotherapy. In addition to SMOs, including opioid nitro-derivatives, and ECT, psychotherapy may be a third useful treatment arm because it might aid SMOs in the restoration and preservation of healthy neural circuits during and after ECT or other forms of therapy.

The 1994 statement by one of the applicants for the current disclosure, Charles Inturrisi, "Overall, these results suggest that mu tolerance may be modulated at either NMDA receptors or NOS (or both) and that these two systems may be targets used in the development of new drugs.", (Inturrisi, CE. NMDA receptors, nitric oxide and opioid tolerance. Regulatory Peptides, 1994, Volume 54, Issue 1), corroborated by new data presented throughout the application, can be now applied to SMOs, including opioid nitro-derivatives, and to a multiplicity of diseases and conditions, and not only to mu opioid tolerance caused by morphine induced aberrant neural plasticity. SMOs, including dextromethadone nitro-derivatives, may thus target NMDAR dysfunction and or aberrant neural plasticity from a multiplicity of causes.

On Target, Off Target and Mixed on/Off Target Effects of Opioids and SMOs

Aside from targeting the NMDARs and the multiplicity of their subtypes and variances as described in this application, and the nitric oxide pathways, and the actions at other receptors and systems as detailed throughout the application, the present inventors will also determine and characterize the actions at relevant off target sites for each SMO, when appropriate. In particular the present inventors are looking at SMOs from the standpoint of their opioid receptor activity, selecting molecules with lower affinity for these receptors or a molecules with a potentially favorable partial agonist or mixed agonist antagonist activity, including activity more specific for one or another opioid receptor subtype, pursuing a favorable clinical tolerability profile compared to strong mu opioid agonists and even possibly improved effectiveness: for example, if the new SMO, aside from acting as an NMDAR open channel blocker is also a kappa opioid antagonist, it may offer additional therapeutic effects for the treatment of depression (Lowe, Stephen L; Wong, Conrad J; Witcher, Jennifer. Safety, tolerability, and pharmacokinetic evaluation of single- and multiple-ascending doses of a novel kappa opioid receptor antagonist. The Journal of Clinical Pharmacology, September 2014, Volume 54, Issue 9).

Aside from opioid receptors, potassium channels represent another potential off target action site that will be studied during the development program: SMOs with less potential for blocking potassium channels associated with QT prolongation might be favored for the development program. However, like opioid receptors, potassium channels can also represent on target sites of action, for example if the potassium channel blocking effects do not cause cardiac morbidity and offer other therapeutic advantages instead, as outlined in International Patent Application No. PCT/US2018/016159 for dextromethadone and as described by Wulff et al., 2009 (Wulff H, Castle N A, Pardo L A. Voltage-gated potassium channels as therapeutic targets. Nat Rev Drug Discov 2009 December; 8(12):982-1001).

SMO Program

With the objective of developing a library of novel safe and effective NMDAR modulators with specific PK and PD characteristics that may be best suited for select indications, in collaboration with the University of Padova (Italy) and the Institute of Bioresearch the Swiss Italian University (Switzerland) the applicants implemented a drug development program that included the design of new chemical formulas derived from SMOs, including opioid enantiomers with low affinity for opioid receptors and with NMDAR antagonistic potential. A first set of new chemical entities designed for their potential activity at NMDARs and or for targeting the NO pathways is presented in this application (Table 1). The newly designed molecules (SMOs) were then tested in a novel static and dynamic in silico model of the trans-membrane domain of the NMDAR (Tables 2 a-c) and table 3).

After selecting the more promising molecules, and after completion of the synthetic work for select molecules, the present inventors are proceeding with in vitro and in vivo experimental work, in order to fully characterize and define the potential safety and PK and PD properties of the new molecules, with potentially clinically useful NMDAR actions and other target actions and off target actions potentially useful for the treatment of diseases. These new chemical entities and potential novel drugs include dextromethadone derivatives and other opioid derivatives (SMOs).

The structural modification resulting in potentially advantageous NMDAR subtype binding affinities in silico and in vitro are also informing on the structural-activity relationship (SAR), thus allowing for further in silico model improvements and improved selection of new molecules (SMOs). As this program progresses, while defining the differential actions at NMDARs subtypes with electrophysiological testing on cells transfected with specific NMDAR subtypes, the present inventors are confirming the biological activity of SMOs on cellular models of excitotoxicity and ion channel hyperactivity, including CNS cells and other cells, including retinal cells and other specialized cells). The present inventors are identifying specific diseases for preclinical in vitro testing for cell-specific effects relevant for those diseases (in vitro dextromethadone study on retinal cells treated with inflammatory mediators—see the Example, below), followed by preclinical disease models (see data from "Development of the NMDAR Antagonist d-Methadone for the Treatment of Depression and other CNS Disorders," above, and FIGS. 1-5) before finally arriving to the clinical phases of development for the more promising molecules (e.g., ongoing phase 2 clinical study of dextromethadone in treatment resistant depression). These SMOs might offer PK and PD advantages over dextromethadone and over other NMDAR antagonists currently available and they might offer improved selectiveness for NMDARs, NMDAR subtypes, brain areas, neuronal and astrocyte subpopulations and CNS circuits affected by diseases and conditions and they might offer spatial or temporal or overall receptor affinity advantages resulting ultimately in disease specific advantages, as detailed above. Aside from neuronal populations the effects of SMOs may be useful in extra-neuronal cellular populations and circuits as described in the application.

The present inventors have shown and previously disclosed (International Patent Application No. PCT/US2018/016159) that certain deuterated dextromethadone molecules potentially have affinity for NMDAR subtypes that differs from the affinities shown by dextromethadone and other NMDAR antagonists (International Patent Application No. PCT/US2018/016159), in particular the affinity of D9 for NR2B receptor subtype in the patch clamp study was double compared to the affinity for NR2A and thus, as outlined above, deuteration and other structural modifications may result in potentially advantageous drug profiles compared to dextromethadone and other NMDAR antagonists for specific indications. With this relatively minor modification of the dextromethadone molecule (deuteration) the present inventors were able to influence the relative affinity of dextromethadone for receptor subtypes (NR1-NR2A versus N1-NR2B tetrameric complexes) and the present inventors also were able to modify in vitro PK parameters: the present inventors tested dextromethadone and deuterated dextromethadone in In Vitro Metabolism Assays and showed how deuteration changes the results of the individual in vitro metabolism assays. The present inventors also compared these results with similar testing with dextromethorphan which showed significantly shorter half-life compared to dextromethadone and deuterated dextromethadone (D9, D10, D16) (International Patent Application No. PCT/US2018/016159). By further modifying the structure of dextromethadone and or its deuterated and tritium derivatives the present inventors are designing and testing molecules with potential for improved PK and PD characteristics that may prove beneficial for select diseases over dextromethadone and deuterated dextromethadone and over other opioid drugs and other NMDAR antagonists. This same principle (deuterated SMOs can produce new molecules with potential PK and PD advantages) is potentially even more relevant to the more substantial structural modifications disclosed below, including fluoro-derivatives and nitro-derivatives and fluoro-nitro-derivatives and deuterated fluoro-derivatives and nitro-derivatives and fluoro-nitro-derivatives.

Furthermore, the present inventors have shown that different NMDAR antagonists (ketamine, memantine, PCP) acting at the same site of the NMDA receptor as dextromethadone or in its proximity (PCP site), exert their actions with similar but different affinities compared to dextromethadone and its deuterated derivatives, including different affinities for different receptor subunit complexes (e.g., NR1-NR2A or NR1-NR2B and thus other possible combinations with other subunits) (International Patent Application No. PCT/US2018/016159).

Differences in "trapping", onset and offset of NMDAR block are also expected in SMOs, as shown with the structural modification of PCP resulting in ketamine a drug with lower trapping activity (Zanos et al., 2018) compared to PCP and as shown with the structural modifications of amantadine resulting in memantine a drug with lower affinity for NR1-NR2A compared to NR1-NR2B. This differential block of NMDARs is expected for each of the SMOs object of this disclosure. These differential affinities towards NMDARs among the different SMOs potentially carry therapeutic implications.

The burden of CNS diseases is enormous and treatments are few and often only partially effective. Novel safe and effective NMDAR modulators with potential therapeutic advantages for select diseases represent a highly unmet medical need.

While there are literally hundreds of diseases that might benefit from NMDAR modulators, as described above and illustrated by the inventors in some detail in International Patent Application No. PCT/US2018/016159 and throughout this application, there are only four FDA approved drugs targeting the trans-membrane domain of NMDARs for diseases that share NMDAR dysfunction as a common drug target, and one of them is a combination drug: amantadine, memantine, esketamine, and the combination drug dextromethorphan+quinidine. A fifth FDA approved NMDAR modulator, ketamine, is approved for anesthesia but not for the treatment of diseases and conditions.

The present inventors disclose that the newly designed SMOs have the potential for safety and effectiveness for one or more specific diseases and conditions, including for diseases and conditions where NMDAR block or modulation might be beneficial, including diseases and conditions disclosed in International Patent Application No. PCT/US2018/016159 and diseases and conditions as defined in this application.

Based on results from FST, FUST, NFST, CUS and immunohistochemical and morphologic and electrophysiologic data described above in "Development of the NMDAR Antagonist d-Methadone for the Treatment of Depression and other CNS Disorders"—suggesting antidepressant and neural plasticity effects for dextromethadone similar to ketamine, dextromethadone and SMOs may not only be useful for the treatment of psychiatric diseases and symptoms, including depression in all its-forms, anxiety in all its forms, PTSD, addictive behaviors and addiction to drugs, but may potentially prevent these diseases and symptoms when administered in anticipation of stress or during stress prior to the development of psychiatric diseases or symptoms. By promoting neural plasticity and by other mechanisms, such as modulating NMDARs, SERT, NET, and BDNF, dextromethadone and SMOs may increase resilience to developing psychiatric diseases and symptoms when administered during periods of life burdened by stressful events (CNS toxic experiences) or when a stressful event is anticipated and thus dextromethadone and SMOs may be useful for prevention of psychiatric diseases and symptoms, including those triggered by mental stress from a multiplicity of causes including, social stress, grief, disease, loss including financial loss and bereavement, marital and family related stress, war, natural disasters et cetera. This is also supported by the experimental findings for ketamine from Brachman et al. (Brachman R A, McGowan J C, Perusini J N, et al. Ketamine as a Prophylactic Against Stress-Induced Depressive-like Behavior. Biol Psychiatry. 2015; 79(9):776-786.

Several of the disclosed compounds were optimized with the aim of obtaining clinically tolerated NMDAR antagonists with activity at NO pathways and or for their potential for specific therapeutic actions for select diseases and conditions based on differential actions in select areas of the CNS and extra CNS because of particular PK parameters (e.g., lipo-solubility for fluoro-derivatives, e.g., DMD35, LMA9, DIMD6, LPP6, NMeDMD9 and other examples of compounds, above, and for halogen compounds, e.g., DAN-DMD38, DMD63, DMD41) or PD parameters (e.g., differential action and affinity for NMDARs, including potential differential action and affinity on receptor subtypes—e.g., SMOs disclosed herein including those with potential for additional blocking actions at the NMDAR and additional neuro-protective actions, as in the case of nitro-derivatives, e.g., Nitro-DMD1, LMA8, DIMD8, NMeDMD8, including deuterated fluoro and nitro-derivatives, or with the potential for additional actions at different receptors and transporters, including those resulting in changes in neurotransmitters such as serotonin and NE, opioid and DA and GABA pathways, or changes in neurotrophic factors such as BDNF, or changes in synaptic proteins, such as PD95, and thus differential actions at supercomplexes, or actions at GluR1 and NMDAR1 and consequential neuroplasticity effects.

The present inventors disclose the compounds outlined below, including salts thereof, for the treatment and prevention of human and veterinary diseases and conditions including those for improvement of cognitive and social functions and for anti-aging uses, including prevention and treatment of accelerated aging caused by environmental factors or medical treatments, in particular if caused by NMDAR dysfunction or dysfunction at NO pathways for which clinically tolerated and effective NMDAR modulators and NO pathway modulators, including actions on RNS, with specific PK and PD characteristics including differential affinities for NMDAR subtypes, may be beneficial.

The molecules shown in table 1 were designed for potential NMDAR modulating actions.

The molecules shown in tables 2a and 2b showed in silico NMDAR affinity in a static model to assess potential activity at NMDAR receptor NR2B subtype. Each of the designed molecules has unique PK and PD characteristics, including actions at NMDARs and other receptors potentially useful for the treatment of diseases. These compounds are shown in 2a, table 2b.

The molecules shown in table 3 showed in silico NMDAR affinity in a static and in a dynamic model to assess potential activity at NMDAR receptor NR2B subtype. Each of the designed molecules has unique PK and PD characteristics, including actions at NMDARs and other receptors potentially useful for the treatment of diseases. These compounds are shown in table 3.

Finally, the present inventors disclose the following compounds as examples of compounds in accordance with principles of various aspects of the present invention: Dextromethadone fluoro-derivatives (—F), including fluoro-dextromethadones; Dextromethadone nitro derivatives (—$NO_2$), including nitro-dextromethadones; Dextromethadone fluoro-nitro-derivatives, including fluoro-nitro-dextromethadones; and Deuterated dextromethadone derivatives modified as above for dextromethadone (Deuterated dextromethadone fluoro-derivatives (—F), including fluoro-dextromethadones; Deuterated dextromethadone nitro derivatives (—$NO_2$), including nitro-dextromethadones; and Deuterated dextromethadone fluoro-nitro-derivatives, including fluoro-nitro-dextromethadones).

General examples of such compounds may also include Dextroisomethadone derivatives, including: Dextroisomethadone fluoro derivatives, including fluoro-dextroisomethadones; Dextroisomethadone nitro derivative, including nitro-dextroisomethadones; Dextromethadone fluoro-nitro-derivatives, including fluoro-nitro-dextromethadones; and Deuterated dextroisomethadone derivatives modified as above for dextroisomethadone.

General examples of such compounds may also include N-methyl-dextromethadone derivatives, including: N-methyl-dextromethadone fluoro-derivatives, including fluoro-N-methyl-dextromethadones; N-methyl-dextromethadone nitro derivatives, including nitro-N-methyl-dextromethadones; N-methyl-dextromethadone fluoro-nitro-derivatives, including fluoro-nitro-N-methyl-dextromethadones; and Deuterated N-methyl-dextromethadone derivatives modified as above for N-methyl-dextromethadone.

General examples of such compounds may also include Levomoramide derivatives, including: Levomoramide fluoro-derivatives, including fluoro-levomoramides; Levomoramide nitro derivatives, including nitro-levomoramides; Levomoramide fluoro-nitro-derivatives, including fluoro-nitro-levomoramides; and Deuterated levomoramide derivatives modified as above for levomoramide General examples of such compounds may also include Levopropoxyphene derivatives, including: Levopropoxyphene fluoro-derivatives, including fluoro-levopropoxyphenes; Levopropoxyphene nitro derivatives, including nitro-levopropoxyphenes; Levopropoxyphene fluoro-nitro-derivatives, including fluoro-nitro-levopropoxyphenes; and Deuterated levopropoxyphene derivatives modified as above for levopropoxyphene.

General examples of such compounds may also include Levorphanol derivatives, including: Levorphanol-fluoro-derivatives, including fluoro-levorphanols; Levorphanol-nitro derivatives, including nitro-levorphanols; Levorphanol fluoro-nitro-derivatives, including fluoro-nitro-levorphanols; and Deuterated levorphanol derivatives modified as above for levorphanol.

General examples of such compounds may also include Dextromethorphan and dextrorphan derivatives, including: Dextromethorphan and dextrorphan-fluoro-derivatives, including fluoro-dextromethorphan and nitro-dextrorphan; Dextromethorphan and dextrorphan-nitro derivatives, including nitro-dextromethorphan and nitro-dextrorphan; Dextromethorphan and dextrorphan fluoro-nitro-derivatives, including fluoro dextromethorphan and fluoro-nitro-dextrorphan; and Deuterated dextromethorphan and deuterated dextrorphan derivatives modified as above for dextromethorphan and dextrorphan.

Example

Effect of NMDAR Antagonism on ARPE-19 Viability

Figure 6:
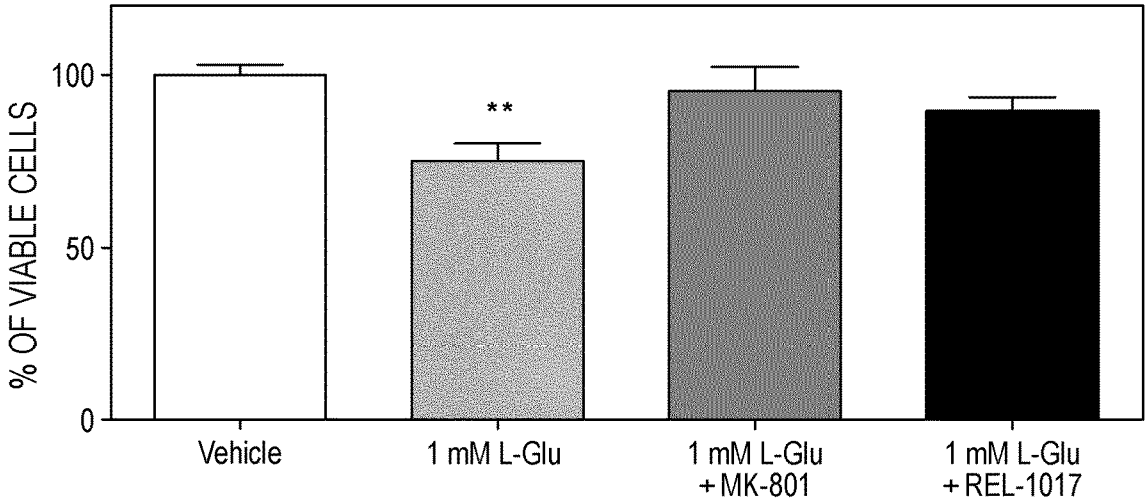
FIG. 6 shows cell viability of ARPE-19 cells after treatment with the NMDAR agonist L-glutamate alone, or in combination with the NMDAR antagonists MK-801 and dextromethadone. Dextromethadone may also be referred to herein as "REL-1017." More specifically.

With this experiment the present inventors ascertain whether inhibition of NMDAR receptor by MK-801 and dextromethadone (REL-1017) rescues the L-glutamate-induced cell viability decrease of ARPE-19. As shown in FIG. 6, there is a decrease in cell viability ($p<0.01$) in cells incubated with 1 mM L-glutamate, which is almost negligible when the cells are pretreated with the two NMDA receptor antagonists MK-801 and dextromethadone (REL-1017) before L-glutamate treatment, showing that these compounds have a protective effect on cell viability.

Effect of NMDAR Antagonism on the Production of Reactive Oxygen Species (ROS)

Figure 7:
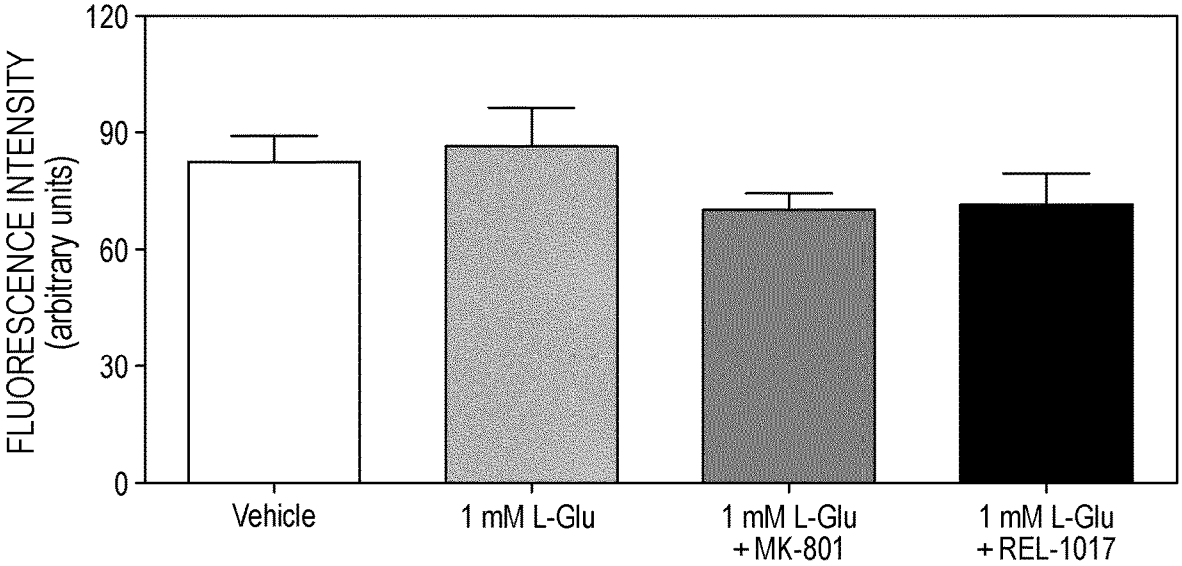
FIG. 7 shows ROS production in ARPE-19 cells. The treatment was performed with L-glutamate (1 mM L-Glu), and pretreatment was performed with MK-801 (1 mM L-Glu+MK-801) and REL-1017 (1 mM L-Glu+REL-1017).
Figure 8A:
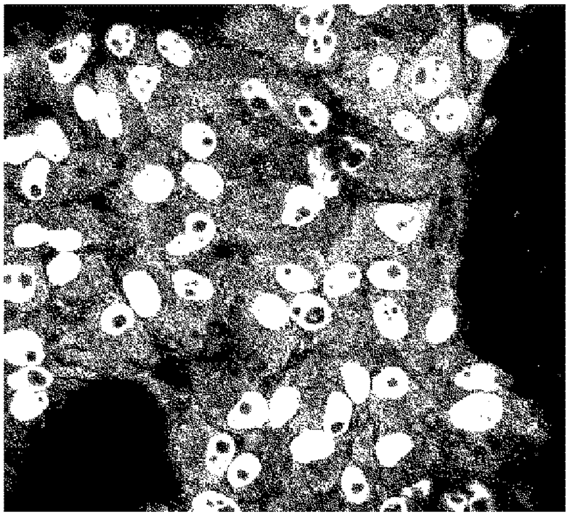
FIGS. 8A-8D shows immunofluorescence of p65 of ARPE-19 after treatment with L-glutamate (1 mM L-Glu), and pretreatment with MK-801 (1 mM L-Glu+MK-801) and REL-1017 (1 mM L-Glu+REL-1017). Cell nuclei are marked with DAPI.
Figure 8B:
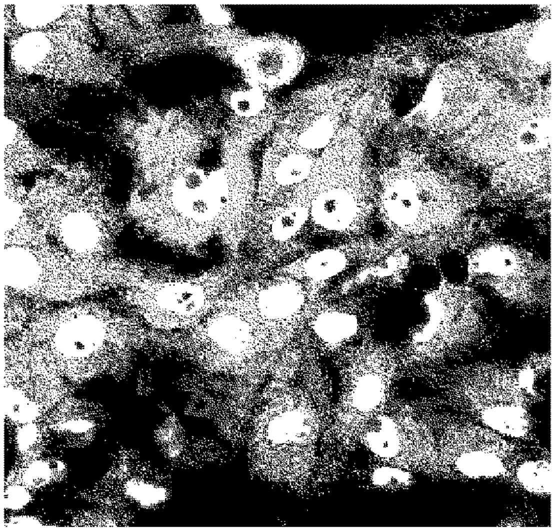
Figure 8C:
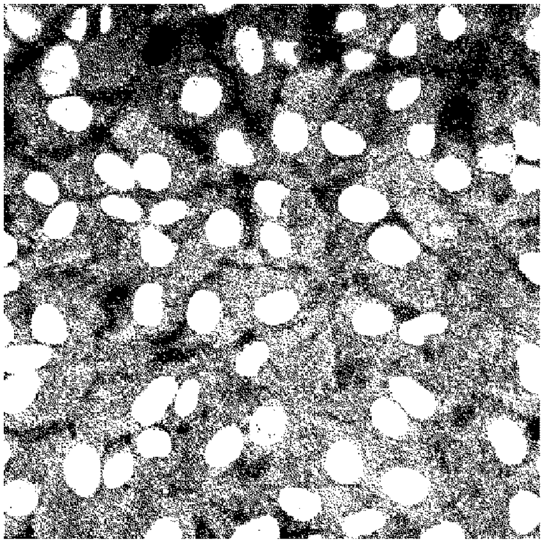
Figure 8D:
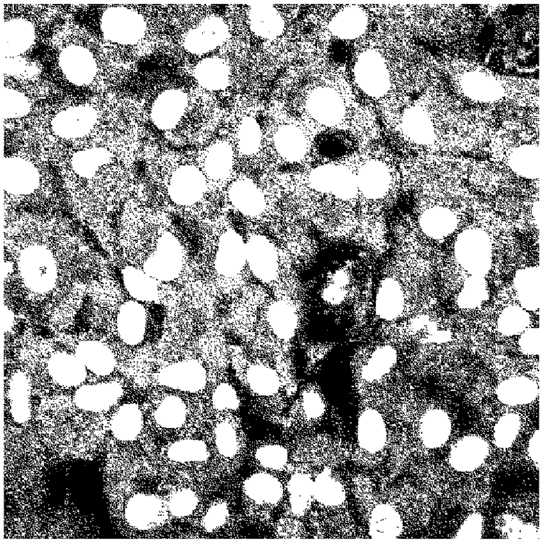

The increased production of ROS following NMDAR activation has been widely demonstrated in vitro in neuronal cells. This study was conducted also on the retinal cell line ARPE-19 in order to verify how NMDAR activation and blockade influence ROS production. As shown in FIG. 7, there is no significant increase in the production of ROS in the cells treated with 1 mM L-glutamate. A tendency to decrease could be observed in cells exposed to the NMDA receptor antagonists (1 mM L-Glu+30 μM MK-801, 1 mM L-Glu+30 μM REL-1017), whereas the statistical significance could not be reached.

Effect of NMDAR Antagonism on Expression and Nuclear Translocation of the Inflammatory Transcription Factor p65

To ascertain whether the excitotoxicity given by the glutaminergic stimulation of NMDAR receptor provokes or interferes with the activation of inflammatory mechanisms in retinal cells, the present inventors performed an immunofluorescence coupled to confocal microscopy by staining p65, a protein belonging to the NF-kB family. It is well known that the nuclear translocation of the transcription factor p65 leads to the increased synthesis of molecules involved in pro-inflammatory responses. Furthermore, the effect of the use of the receptor antagonists MK-801 and dextromethadone (REL-1017) on the expression and translocation of this protein was also evaluated.

Figure 9A:
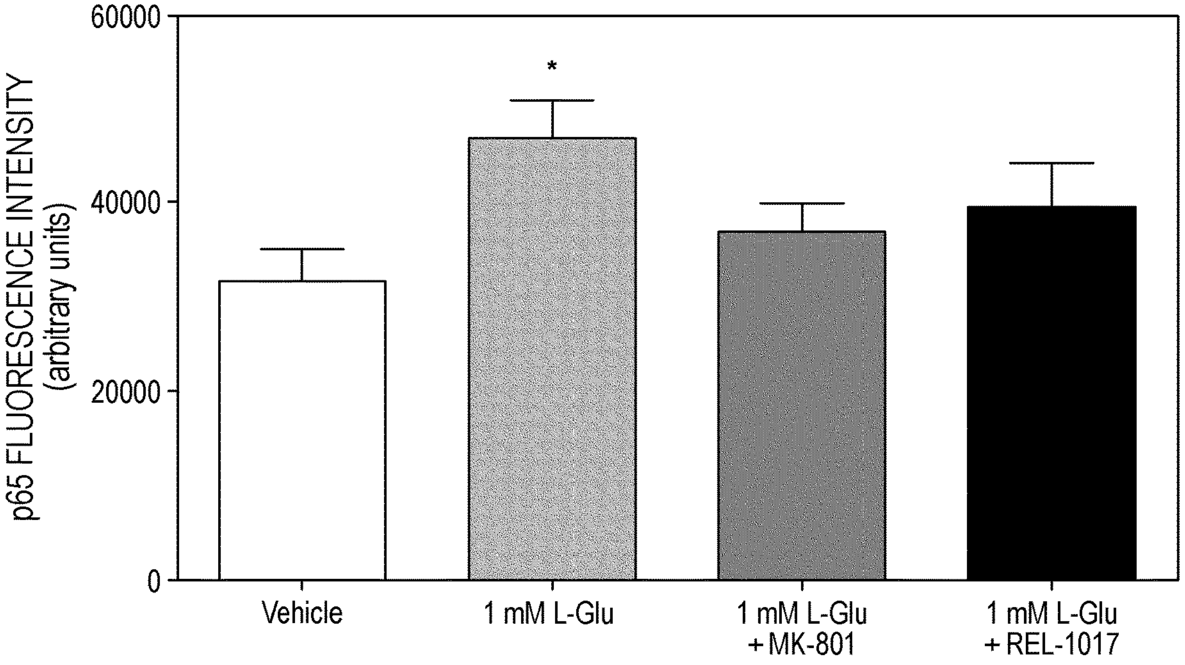
FIGS. 9A and 9B show a graphical representation of fluorescence intensity of p65 (A) and colocalization p65-DAPI (B) in immunocytochemistry experiments. The treatment was performed with L-glutamate (1 mM L-Glu), and pretreatment was performed with MK-801 (1 mM L-Glu+MK-801) and REL-1017 (1 mM L-Glu+REL-1017). The fluorescence intensity and the Pearson r indicating the degree of colocalization between p65 and the nuclear marker DAPI was calculated with the ImageJ Software. *$P<0.05$ vs vehicle (one-way ANOVA test followed by Dunnett's post hoc test).
Figure 9B:
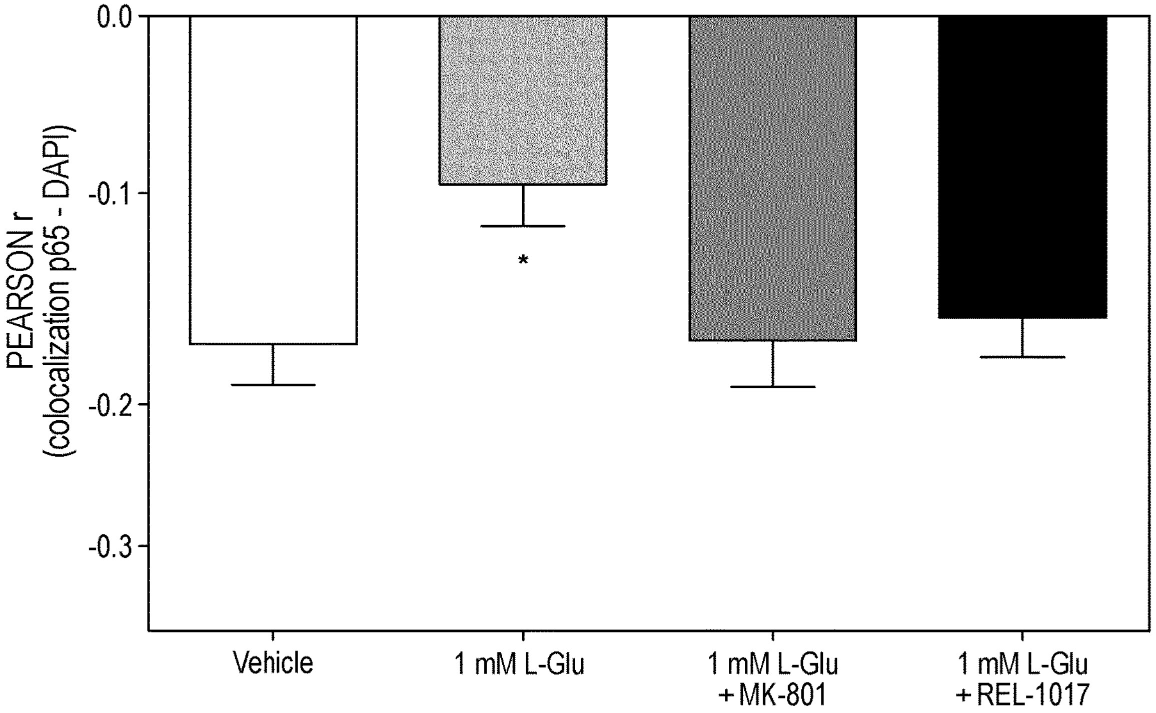

As shown in FIGS. 8A-8D, an increased expression of p65 in cells exposed to L-glutamate could be observed with respect to vehicle ($p<0.05$), while there is a decrease in p65-related fluorescence when cells are pre-treated with the two NMDAR receptor antagonists. The nuclear translocation of p65 in response to L-glutamate was also evaluated, since p65, when translocated to the nucleus, acts as a transcription factor and promotes the expression of pro-inflammatory genes. The degree of colocalization between p65 and the nuclear marker DAPI was determined by the Pearson r coefficient, which represents a correlation index between the two variables. This coefficient varies from −1 to 1, and the closer it gets to positive values, the more p65 and DAPI have the same (nuclear) localization. FIGS. 9A and 9B show that the nuclear expression of p65 protein increases following treatment with L-glutamate ($p<0.05$), and decreases after pretreating with the NMDAR antagonists, being comparable with that of vehicle-treated cells. This experiment demonstrates the involvement of NMDA receptor activation following glutaminergic stimulation in the establishment of an inflammatory response evidenced by the increased nuclear translocation of p65.

Effect of NMDAR Antagonism on the Expression of the Target Genes NMDAR1, p65, IL-6, TNF-α

Once the effect of NMDAR antagonists on nuclear translocation of p65 was verified, in order to confirm their anti-inflammatory effect, the present inventors investigated the changes of gene expression levels of the pro-inflammatory cytokines IL-6 (interleukin-6) and TNF-α, the transcription factor p65 and the NMDA receptor.

Quantification of Relative NMDAR mRNA Expression Levels

The first gene for which the level of gene expression was assessed is the 1A subunit of NMDAR receptor dimer (known as NMDAR1).

FIG. 10 shows that an NMDA receptor stimulation with L-glutamate leads to a slight decrease of the basal gene expression of this receptor, probably by a negative feedback mechanism, although this decrease was not statistically significant. Conversely, when receptor activation is blocked by the antagonist dextromethadone (REL-1017), the cells increase significantly its expression ($p<0.0001$) up to 9 times when compared to the expression level of vehicle-treated cells. This increase in NMDAR1 gene expression is only slightly evident when MK-801 was used as an antagonist.

Quantification of Relative p65 mRNA Expression Levels

Figure 11A:
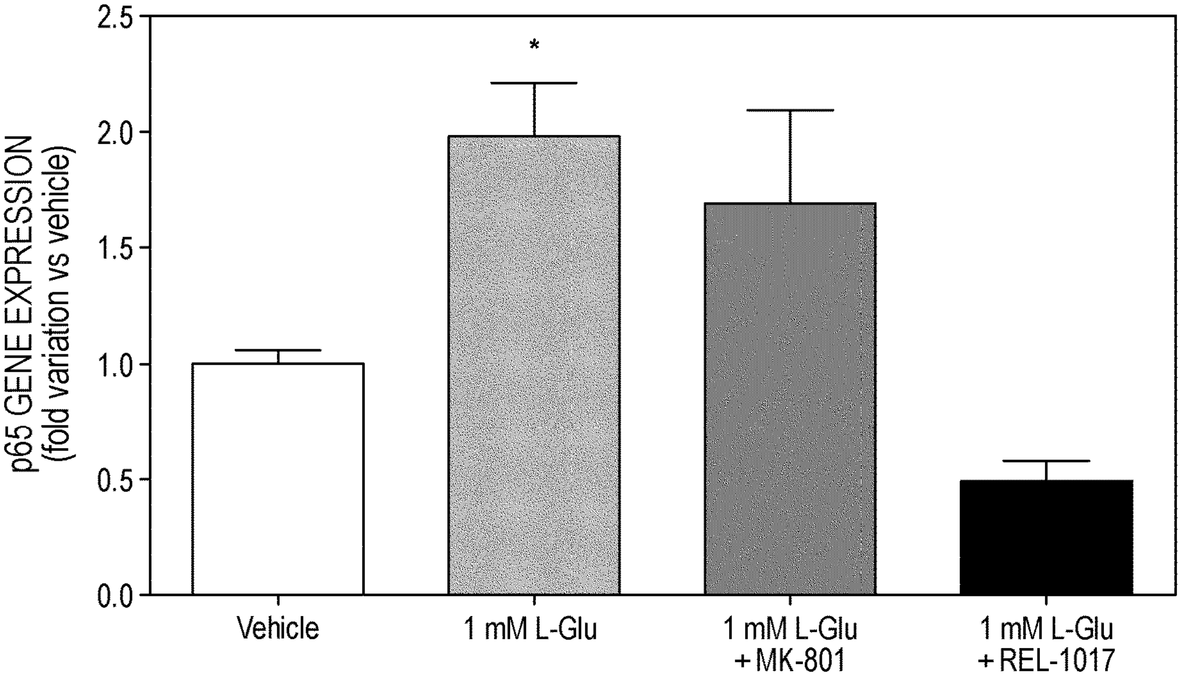
FIGS. 11A and 11B show relative quantification of p65 gene expression in ARPE-19 cells subjected to the following treatment conditions. The treatment was performed with L-glutamate (1 mM L-Glu), and pretreatment was performed with MK-801 (1 mM L-Glu+MK-801) and REL-1017 (1 mM L-Glu+REL-1017). * $P<0.05$ vs vehicle (one-way ANOVA test followed by Dunnett's post hoc test). In the scattered plot, comparison between vehicle-treated and REL-1017-treated cells. ** $p<0.01$ vs vehicle (Student' t test for unpaired data).
Figure 11B:
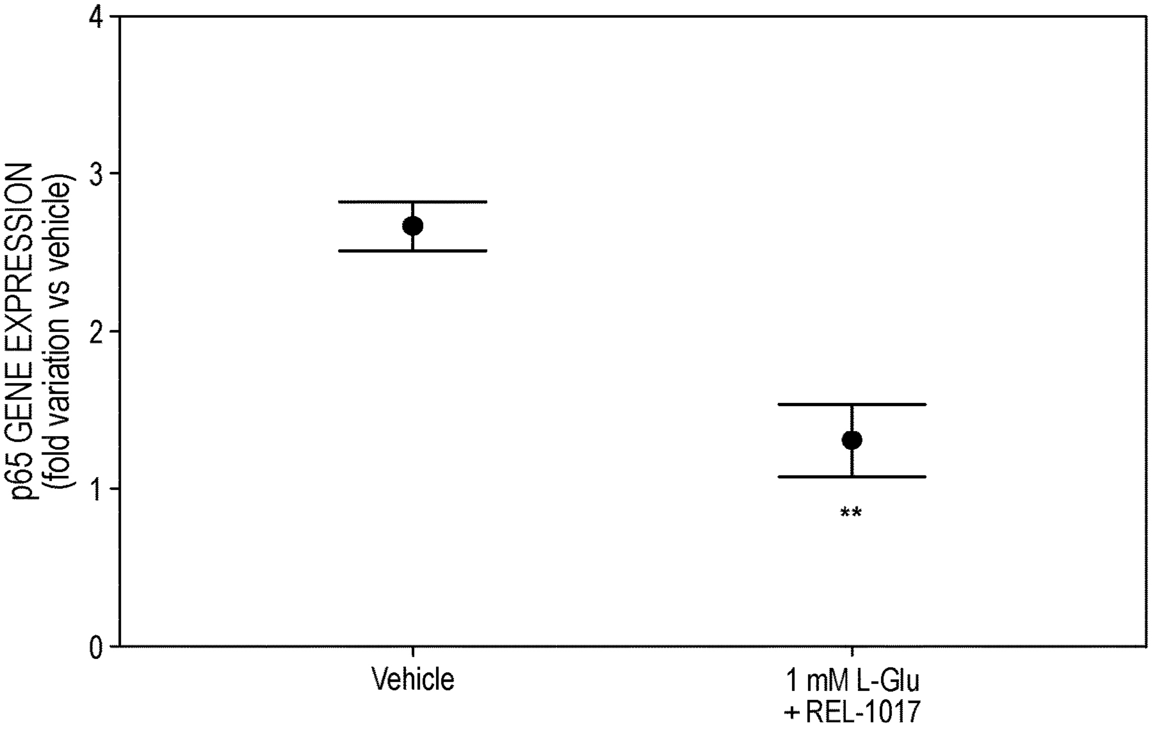

The gene expression analysis carried out on p65 (FIGS. 11A and 11B) demonstrates that the activation of the NMDA receptor by the agonist L-glutamate leads to a significant increase ($p<0.05$) of its gene expression, whereas in the cells pretreated with the receptor antagonist dextromethadone (REL-1017) there is a decrease in gene expression of p65 ($p<0.01$). These data are consistent with what was observed in the immunocytochemical analysis. Furthermore, the present inventors can conclude that L-glutamate triggers an inflammatory response against which dextromethadone (REL-1017) has a peculiar protective role.

Finally, the gene expression levels of pro-inflammatory cytokines have been investigated in the different experimental conditions.

Quantification of TNF-α and IL-6 mRNA Expression Levels

Figure 12:
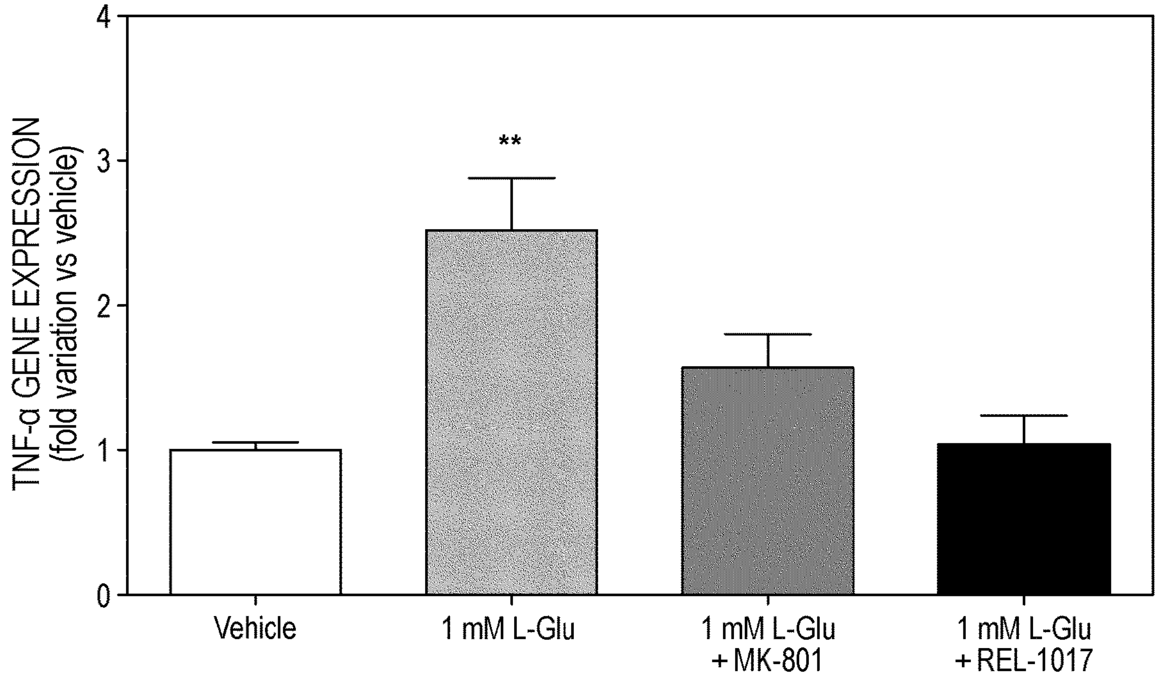
FIG. 12 shows relative quantification of TNF-α gene expression in ARPE-19 cells subjected to the following treatment conditions: L-glutamate (1 mM L-Glu), pretreatment with MK-801 (1 mM L-Glu+MK-801) and REL-1017 (1 mM L-Glu+REL-1017). ** $P<0.01$ vs vehicle (one-way ANOVA test followed by Dunnett's post hoc test).

FIG. 12 shows that there is a significant increase ($p<0.01$) of TNF-α gene expression cells treated with L-glutamate, whereas the expression of this pro-inflammatory cytokine is restored to normal levels when the receptor antagonists MK-801 and dextromethadone (REL-1017) are added. The decrease in TNF-α gene expression levels is slightly more evident in the samples pretreated with dextromethadone when compared to MK-801.

Figure 13:
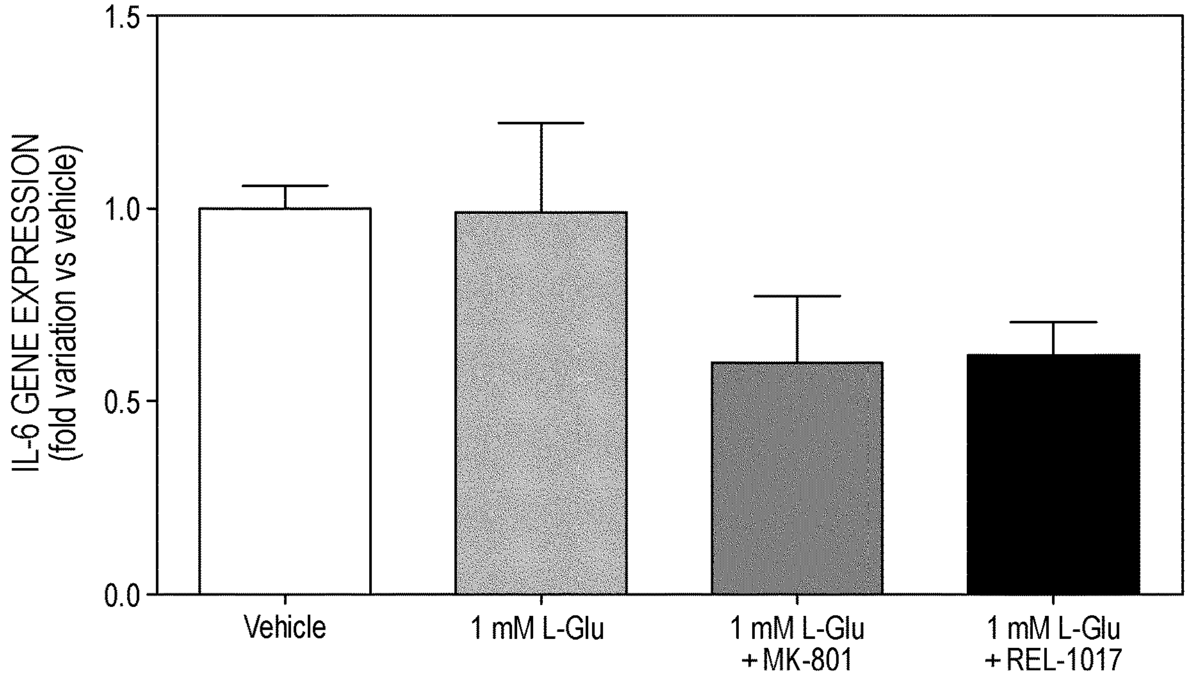
FIG. 13 shows relative quantification of IL-6 gene expression in ARPE-19 cells subjected to the following treatment conditions: L-glutamate (1 mM L-Glu), pretreatment with MK-801 (1 mM L-Glu+MK-801) and REL-1017 (1 mM L-Glu+REL-1017).

FIG. 13 shows that IL-6 gene expression tends to increase when the NMDA receptor are stimulated by glutamate; whereas there is a tendency to decrease when cells are pretreated with the receptor antagonists MK-801 and dextromethadone. There are no substantial differences between the decrease in expression in samples subjected to receptor antagonism by MK-801 and dextromethadone (REL-1017). In contrast, IL-6 does not undergo significant changes in gene expression levels after NMDA receptor activation by L-glutamate or inhibition by MK-801 and dextromethadone (REL-1017). These data indicate that TNF-α appears to be the main cytokine involved in cytotoxicity and inflammation after glutaminergic stimulation since the inhibition of NMDAR activation by MK-801 and dextromethadone (REL-1017) has a significant effect in the reduction of its gene expression. The increased level of TNF-α gene expression following NMDAR activation-related excitotoxicity is consistent with activation of the NF-κB transcriptional complex and the resulting translocation of p65 into the nucleus. Indeed, TNF-α demonstrates a role in promoting NF-κB activation in the retinal cells. These findings are also consistent with the observations that TNF-α induces optic nerve degeneration with possible delayed retinal neuronal cell death, and an increased expression of p65 in the optic nerve may be associated with a TNF-α-induced axonal degeneration.

The embodiments of the present invention recited herein are intended to be merely exemplary and those skilled in the art will be able to make numerous variations and modifications to it without departing from the spirit of the present invention. Notwithstanding the above, certain variations and modifications, while producing less than optimal results, may still produce satisfactory results. All such variations and modifications are intended to be within the scope of the present invention as defined by the claims appended hereto.

What is claimed is:

1. A compound having a structure analogue to dextromethadone, wherein the compound is selected from the group consisting of:

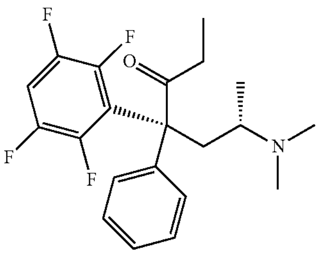

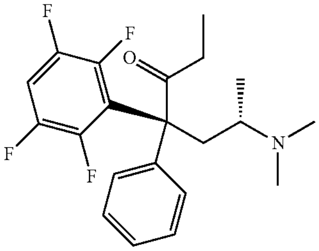

-continued

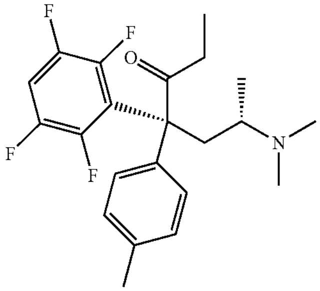

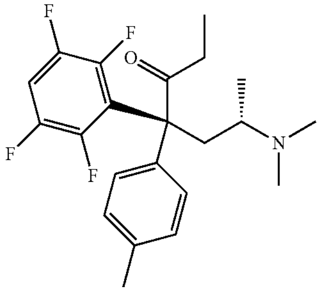

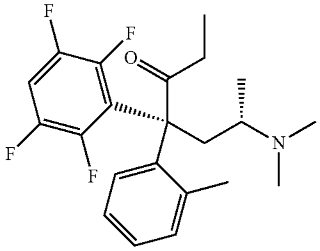

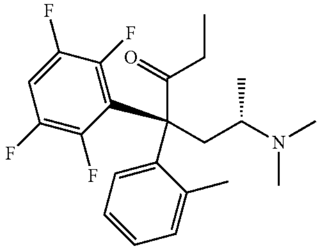

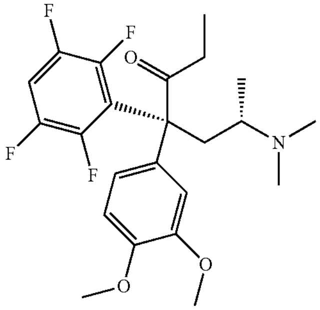

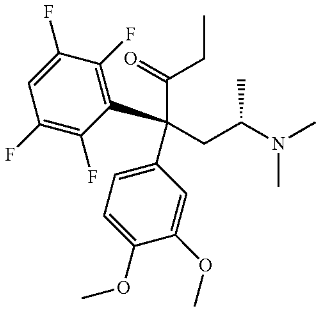

-continued
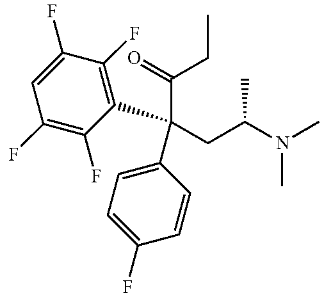
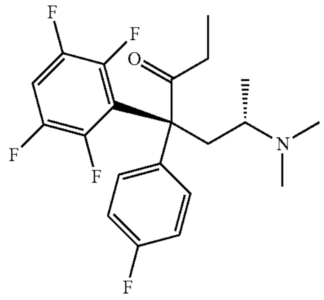
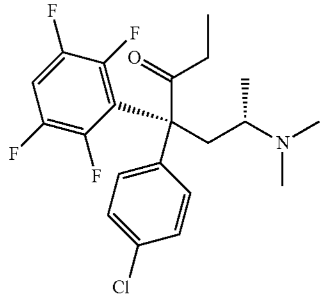
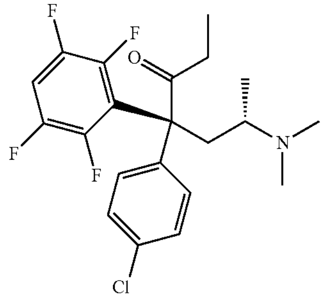
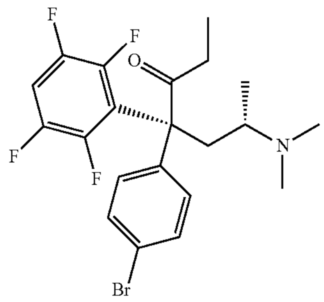
-continued
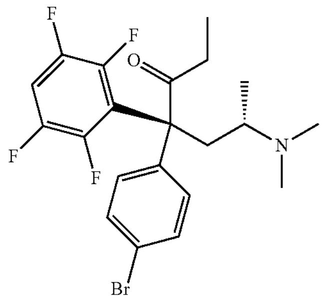
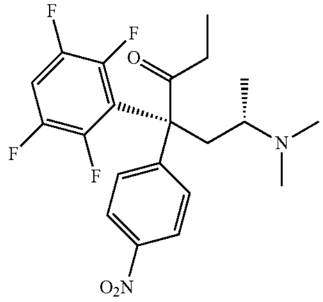
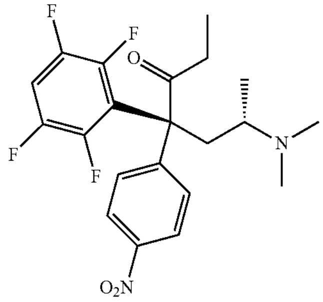
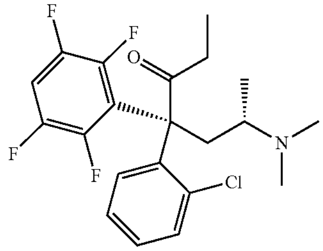
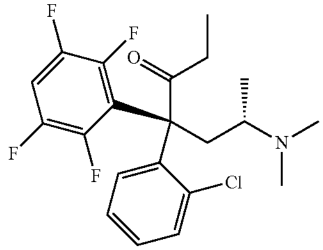
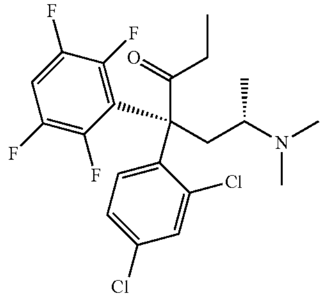

-continued
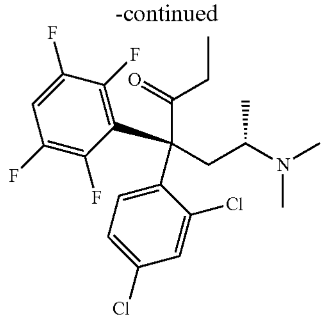
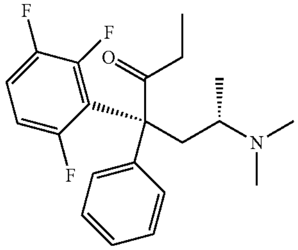
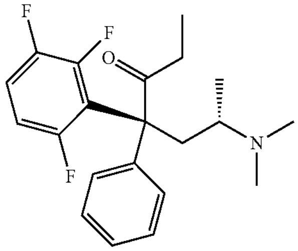
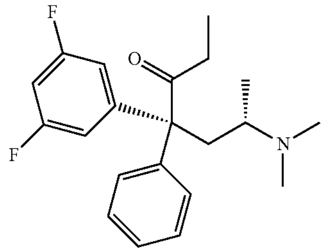
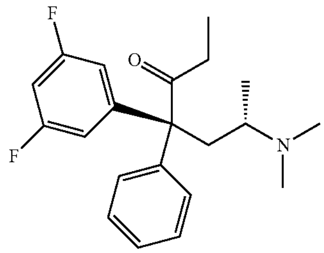
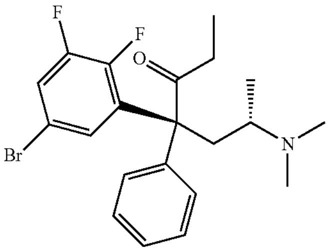
-continued
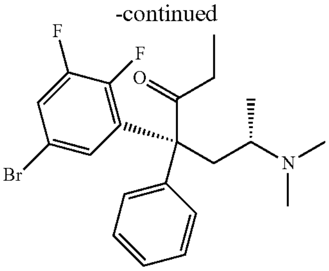
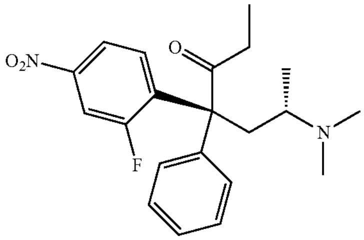
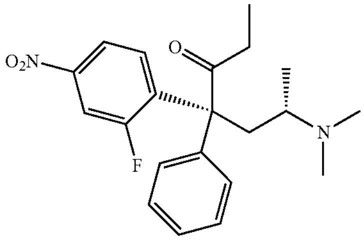
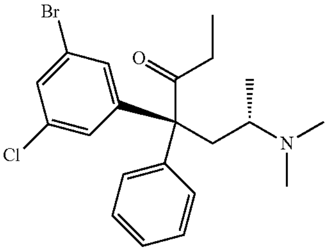
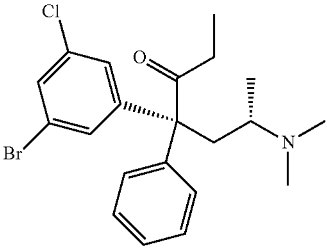
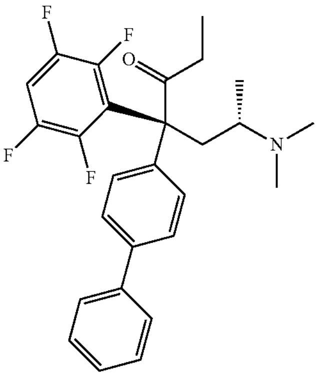

-continued
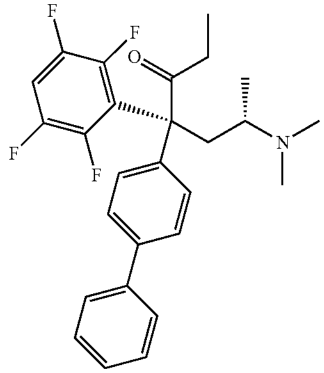
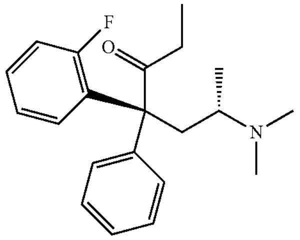
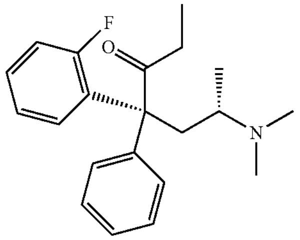
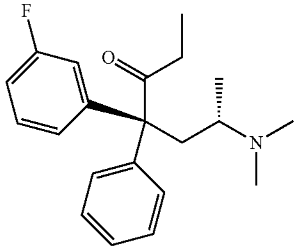
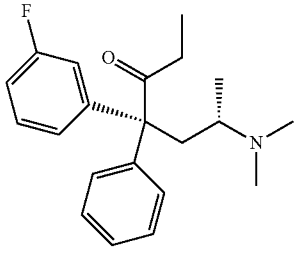
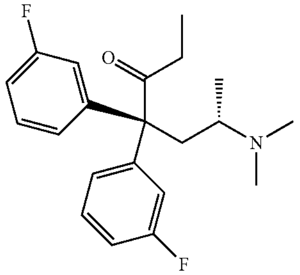
-continued
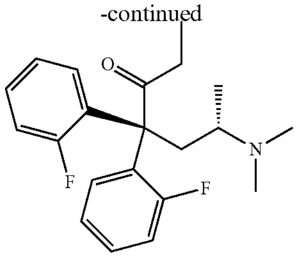
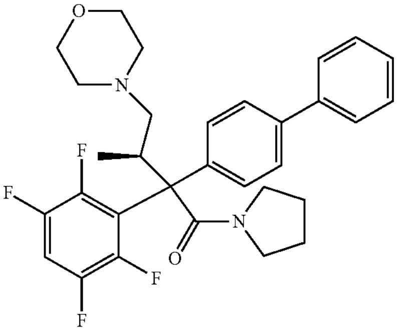
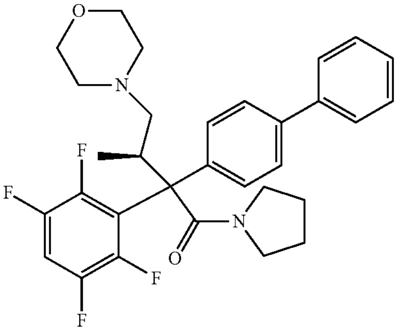
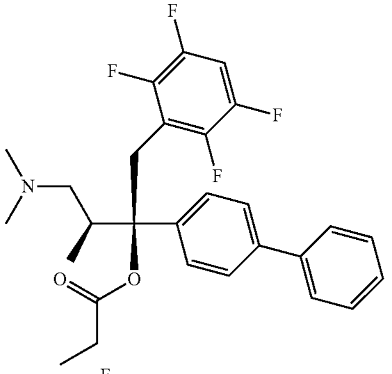
and
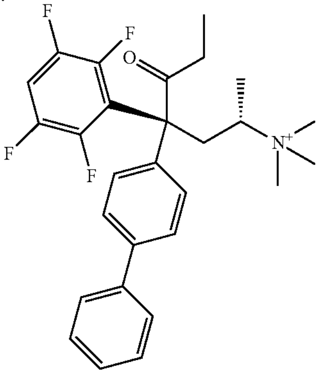
.
* * * * *